US012570988B2

(12) United States Patent
Guo et al.

(10) Patent No.: US 12,570,988 B2
(45) Date of Patent: Mar. 10, 2026

(54) APTAMERS THAT BIND THIAMINE ANALOGS AND DERIVATIVES

(71) Applicant: MeiraGTx Gene Regulation Limited, London (GB)

(72) Inventors: Xuecui Guo, Oyster Bay, NY (US); Alexandria Forbes, New York, NY (US); Kevin G. Liu, West Windsor, NJ (US); Ji-In Kim, Princeton, NJ (US)

(73) Assignee: MeiraGTx Gene Regulation Limited, London (GB)

( * ) Notice: Subject to any disclaimer, the term of this patent is extended or adjusted under 35 U.S.C. 154(b) by 669 days.

(21) Appl. No.: 17/907,189

(22) PCT Filed: Mar. 24, 2021

(86) PCT No.: PCT/IB2021/000163
§ 371 (c)(1),
(2) Date: Sep. 23, 2022

(87) PCT Pub. No.: WO2021/191680
PCT Pub. Date: Sep. 30, 2021

(65) Prior Publication Data

US 2023/0265441 A1     Aug. 24, 2023

Related U.S. Application Data

(60) Provisional application No. 62/994,135, filed on Mar. 24, 2020.

(51) Int. Cl.
| | |
|---|---|
| *C12N 15/115* | (2010.01) |
| *C12N 15/10* | (2006.01) |
| *C12N 15/11* | (2006.01) |
| *C12N 15/63* | (2006.01) |
| *C12N 15/86* | (2006.01) |

(52) U.S. Cl.
CPC ....... *C12N 15/635* (2013.01); *C12N 15/1086* (2013.01); *C12N 15/111* (2013.01); *C12N 15/115* (2013.01); *C12N 15/86* (2013.01); *C12N 2310/16* (2013.01); *C12N 2310/531* (2013.01); *C12N 2750/14143* (2013.01); *C12N 2830/002* (2013.01)

(58) Field of Classification Search
CPC .................................................. C12N 2310/16
See application file for complete search history.

(56) References Cited

FOREIGN PATENT DOCUMENTS

| | | |
|---|---|---|
| WO | 2012032522 A1 | 3/2012 |
| WO | 2016126747 A1 | 8/2016 |
| WO | 2017136608 A2 | 8/2017 |
| WO | 2018156658 A1 | 8/2018 |

OTHER PUBLICATIONS

Edwards, T. E., et al., "Crystal Structures of the Thi-Box Riboswitch Bound to Thiamine Pyrophosphate Analogs Reveal Adaptive RNA-Small Molecule Recognition" , Structure (2006); vol. 14, pp. 1459-1468.

*Primary Examiner* — Ekaterina Poliakova-Georgantas
(74) *Attorney, Agent, or Firm* — Fox Rothschild LLP

(57) ABSTRACT

The present disclosure relates to oligonucleotide aptamers that bind to certain small molecules including thiamine analogs and derivatives and methods of generating aptamers that bind to the small molecules. Also contemplated are riboswitches and polynucleotide cassettes comprising the aptamers disclosed herein. Further provided are methods of using said aptamers, riboswitches, and/or polynucleotide for the regulation of target genes, including therapeutic genes. Also provided herein are small molecules that are modulators of target gene expression where the target gene contains a riboswitch comprising an aptamer described herein.

37 Claims, 32 Drawing Sheets
Specification includes a Sequence Listing.

14G4 aptamer  ACAGGGGTCCGGCCTTTTCATTTGGCGCCGGTGAGAGCACACCCTTTGAACCTGTTTACGGATAATGCCGCCGCAGGGAGT Library A1    ACAGGGGTCCGGCCTTTTCATTTGGCGCCGGTGAGAGCACACCCTTTGAACCTGTTTACGGATAATGCCGNNNCAGGGAGT Library A2    ACNGGGGTCCGGCCTTTTCATTTGGCGCCGGTGAGAGCACACCCTNNNNNCCTGTTTACGGATAATGCCGCCGCAGGGAGT Library A3    ACAGGGGNCCGGCCTTTTCATTTGGCGCCGGTGAGANNNNNNCCCTTTGAACCTGTTTACGGATAATGCCGCCGCAGGGAGT

Fig. 3B

3H4 aptamer    ACAGGGGTCCGGCCCTTTTCATTTGGCGCCGGTGAGAGCACACCCCTTTGAACCTGTTCACGGATAATGCCGCTGCAGGGAGT Library A4    ACAGGGGTCCGGCCCTTTTCATTTGGCGCCGGTGAGANNANACCCCTTNNNACCTGTTCACGGATAATGCCGCTGCAGGGAGT

Fig. 5

No fursultiamine with fursultiamine

SEQUENCE LISTING

<160> NUMBER OF SEQ ID NOS: 98

<210> SEQ ID NO 1
<211> LENGTH: 81
<212> TYPE: DNA
<213> ORGANISM: Artificial Sequence
<220> FEATURE:
<223> OTHER INFORMATION: Aptamer motif

```
<220> FEATURE:
<221> NAME/KEY: misc_feature
<222> LOCATION: (3)..(3)
<223> OTHER INFORMATION: n is A or G
<220> FEATURE:
<221> NAME/KEY: misc_feature
<222> LOCATION: (14)..(14)
<223> OTHER INFORMATION: n is C or no nucleotide
<220> FEATURE:
<221> NAME/KEY: misc_feature
<222> LOCATION: (16)..(16)
<223> OTHER INFORMATION: n is T or no nucleotide
<220> FEATURE:
<221> NAME/KEY: misc_feature
<222> LOCATION: (27)..(27)
<223> OTHER INFORMATION: n is A or G
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (48)..(48)
<223> OTHER INFORMATION: n is C, G, or T
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (50)..(50)
<223> OTHER INFORMATION: n is A or T
<220> FEATURE:
<221> NAME/KEY: misc_feature
<222> LOCATION: (57)..(57)
<223> OTHER INFORMATION: n is C or T
<220> FEATURE:
<221> NAME/KEY: misc_feature
<222> LOCATION: (72)..(72)
<223> OTHER INFORMATION: n is C or T

<400> SEQUENCE: 1
acnggggtcc ggcntnttca tttggcnccg gtgagannan acccttnnnn cctgttnacg      60
gataatgccg cngcagggag t                                               81

<210> SEQ ID NO 2
<211> LENGTH: 81
<212> TYPE: DNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (3)..(3)
<223> OTHER INFORMATION: n is A or G
<220> FEATURE:
<221> NAME/KEY: misc_feature
<222> LOCATION: (14)..(14)
<223> OTHER INFORMATION: n is C or no nucleotide
<220> FEATURE:
<221> NAME/KEY: misc_feature
<222> LOCATION: (16)..(16)
<223> OTHER INFORMATION: n is T or no nucleotide
<220> FEATURE:
<221> NAME/KEY: misc_feature
<222> LOCATION: (37)..(37)
<223> OTHER INFORMATION: n is G or T
<220> FEATURE:
```

```
<221> NAME/KEY: misc_feature
<222> LOCATION: (38)..(38)
<223> OTHER INFORMATION: n is C or T
<220> FEATURE:
<221> NAME/KEY: misc_feature
<222> LOCATION: (40)..(40)
<223> OTHER INFORMATION: n is C or T
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (48)..(48)
<223> OTHER INFORMATION: n is G or T
<220> FEATURE:
<221> NAME/KEY: misc_feature
<222> LOCATION: (49)..(49)
<223> OTHER INFORMATION: n is A, G, or T
<220> FEATURE:
<221> NAME/KEY: misc_feature
<222> LOCATION: (50)..(50)
<223> OTHER INFORMATION: n is A or T
<220> FEATURE:
<221> NAME/KEY: misc_feature
<222> LOCATION: (57)..(57)
<223> OTHER INFORMATION: n is C or T
<220> FEATURE:
<221> NAME/KEY: misc_feature
<222> LOCATION: (72)..(72)
<223> OTHER INFORMATION: n is C or T

<400> SEQUENCE: 2
acnggggtcc ggcntnttca tttggcgccg gtgagannan acccttnnnn cctgttnacg      60
gataatgccg cngcagggag t                                               81

<210> SEQ ID NO 3
<211> LENGTH: 81
<212> TYPE: DNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (57)..(57)
<223> OTHER INFORMATION: n is C or T
<220> FEATURE:
<221> NAME/KEY: misc_feature
<222> LOCATION: (72)..(72)
<223> OTHER INFORMATION: n is C or T

<400> SEQUENCE: 3
acaggggtcc ggccttttca tttggcgccg gtgagagcac accctttgaa cctgttnacg      60
gataatgccg cngcagggag t                                               81

<210> SEQ ID NO 4
<211> LENGTH: 81
<212> TYPE: DNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (3)..(3)
<223> OTHER INFORMATION: n is A or G
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (48)..(48)
<223> OTHER INFORMATION: n is G or T
```

```
<220> FEATURE:
<221> NAME/KEY: misc_feature
<222> LOCATION: (49)..(49)
<223> OTHER INFORMATION: n is A, G, or T
<220> FEATURE:
<221> NAME/KEY: misc_feature
<222> LOCATION: (50)..(50)
<223> OTHER INFORMATION: n is A or T

<400> SEQUENCE: 4 acngggggtcc ggccttttca tttggcgccg gtgagagcac acccttnnnn cctgtttacg      60
gataatgccg ccgcagggag t                                                 81

<210> SEQ ID NO 5
<211> LENGTH: 81
<212> TYPE: DNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (37)..(37)
<223> OTHER INFORMATION: n is G or T
<220> FEATURE:
<221> NAME/KEY: misc_feature
<222> LOCATION: (38)..(38)
<223> OTHER INFORMATION: n is C or T
<220> FEATURE:
<221> NAME/KEY: misc_feature
<222> LOCATION: (40)..(40)
<223> OTHER INFORMATION: n is C or T

<400> SEQUENCE: 5
acaggggtcc ggccttttca tttggcgccg gtgagannan accctttgaa cctgtttacg      60
gataatgccg ccgcagggag t                                                 81

<210> SEQ ID NO 6
<211> LENGTH: 81
<212> TYPE: DNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (27)..(27)
<223> OTHER INFORMATION: n is A or G
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (48)..(48)
<223> OTHER INFORMATION: n is C or G
<220> FEATURE:
<221> NAME/KEY: misc_feature
<222> LOCATION: (49)..(49)
<223> OTHER INFORMATION: n is a, c, g, or t

<400> SEQUENCE: 6
acaggggtcc ggccttttca tttggcnccg gtgagannan acccttnnna cctgttcacg      60
gataatgccg ctgcagggag t                                                 81
```

```
<210> SEQ ID NO 7
<211> LENGTH: 81
<212> TYPE: DNA
<213> ORGANISM: Artificial Sequence
<220> FEATURE:
<223> OTHER INFORMATION: 14G4

<400> SEQUENCE: 7
acaggggtcc ggccttttca tttggcgccg gtgagagcac acccttgaa cctgtttacg      60 gataatgccg ccgcagggag t                                             81

<210> SEQ ID NO 8
<211> LENGTH: 81
<212> TYPE: DNA
<213> ORGANISM: Artificial Sequence
<220> FEATURE:
<223> OTHER INFORMATION: 1D10

<400> SEQUENCE: 8
acaggggtcc ggccttttca tttggcgccg gtgagattat acccttgaa cctgtttacg      60 gataatgccg ccgcagggag t                                             81

<210> SEQ ID NO 9
<211> LENGTH: 81
<212> TYPE: DNA
<213> ORGANISM: Artificial Sequence
<220> FEATURE:
<223> OTHER INFORMATION: 3H4

<400> SEQUENCE: 9
acaggggtcc ggccttttca tttggcgccg gtgagagcac acccttgaa cctgttcacg      60 gataatgccg ctgcagggag t                                             81

<210> SEQ ID NO 10
<211> LENGTH: 81
<212> TYPE: DNA
<213> ORGANISM: Artificial Sequence
<220> FEATURE:
<223> OTHER INFORMATION: 3F10

<400> SEQUENCE: 10 acggggtcc ggccttttca tttggcgccg gtgagagcac acccttcgga cctgtttacg      60
gataatgccg ccgcagggag t                                             81

<210> SEQ ID NO 11
<211> LENGTH: 80
<212> TYPE: DNA
<213> ORGANISM: Artificial Sequence
<220> FEATURE:
<223> OTHER INFORMATION: 3H9

<400> SEQUENCE: 11
acaggggtcc ggcttttcat ttggcgccgg tgagagcaca cccttatgac ctgtttacgg      60
ataatgccgc cgcagggagt                                               80

<210> SEQ ID NO 12
<211> LENGTH: 81
<212> TYPE: DNA
<213> ORGANISM: Artificial Sequence
<220> FEATURE:
<223> OTHER INFORMATION: 4G2

<400> SEQUENCE: 12
```

```
acgggggtcc ggccttttca tttggcgccg gtgagagcac accctttgga cctgtttacg    60
gataatgccg ccgcagggag t                                              81

<210> SEQ ID NO 13
<211> LENGTH: 81
<212> TYPE: DNA
<213> ORGANISM: Artificial Sequence
<220> FEATURE:
<223> OTHER INFORMATION: 6D2

<400> SEQUENCE: 13
acgggggtcc ggccttttca tttggcgccg gtgagagcac accctttgtt cctgtttacg    60
gataatgccg ccgcagggag t                                              81

<210> SEQ ID NO 14
<211> LENGTH: 81
<212> TYPE: DNA
<213> ORGANISM: Artificial Sequence
<220> FEATURE:
<223> OTHER INFORMATION: 6B4

<400> SEQUENCE: 14 acagggggtcc ggccttttca tttggcgccg gtgagagcac acccttgtga cctgtttacg    60
gataatgccg ccgcagggag t                                              81

<210> SEQ ID NO 15
<211> LENGTH: 81
<212> TYPE: DNA
<213> ORGANISM: Artificial Sequence
<220> FEATURE:
<223> OTHER INFORMATION: 4H2

<400> SEQUENCE: 15 acagggggtcc ggccttttca tttggcgccg gtgagagcac acccttcgga cctgtttacg    60
gataatgccg ccgcagggag t                                              81

<210> SEQ ID NO 16
<211> LENGTH: 81
<212> TYPE: DNA
<213> ORGANISM: Artificial Sequence
<220> FEATURE:
<223> OTHER INFORMATION: 6C4

<400> SEQUENCE: 16
acgggggtcc ggccttttca tttggcgccg gtgagagcac acccttcgaa cctgtttacg    60
gataatgccg ccgcagggag t                                              81

<210> SEQ ID NO 17
<211> LENGTH: 81
<212> TYPE: DNA
<213> ORGANISM: Artificial Sequence
<220> FEATURE:
<223> OTHER INFORMATION: 6G12

<400> SEQUENCE: 17 acagggggtcc ggccttttca tttggcgccg gtgagagcac accctttgga cctgtttacg    60
gataatgccg ccgcagggag t                                              81

<210> SEQ ID NO 18
<211> LENGTH: 80
<212> TYPE: DNA
```

-continued

```
<213> ORGANISM: Artificial Sequence
<220> FEATURE:
<223> OTHER INFORMATION: 8F1

<400> SEQUENCE: 18
acgggggtcc ggcctttcat ttggcgccgg tgagagcaca cccttcggac ctgtttacgg      60
ataatgccgc cgcagggagt                                                  80

<210> SEQ ID NO 19
<211> LENGTH: 81
<212> TYPE: DNA
<213> ORGANISM: Artificial Sequence
<220> FEATURE:
<223> OTHER INFORMATION: 10A7

<400> SEQUENCE: 19
acaggggtcc ggccttttca tttggcgccg gtgagatgat acccttttgga cctgttcacg     60 gataatgccg ctgcagggag t                                                81

<210> SEQ ID NO 20
<211> LENGTH: 81
<212> TYPE: DNA
<213> ORGANISM: Artificial Sequence
<220> FEATURE:
<223> OTHER INFORMATION: 12D5

<400> SEQUENCE: 20
acaggggtcc ggccttttca tttggcgccg gtgagagcac acccttttgga cctgttcacg     60 gataatgccg ctgcagggag t                                                81

<210> SEQ ID NO 21
<211> LENGTH: 81
<212> TYPE: DNA
<213> ORGANISM: Artificial Sequence
<220> FEATURE:
<223> OTHER INFORMATION: 12G7

<400> SEQUENCE: 21
acaggggtcc ggccttttca tttggcgccg gtgagattat acccttcgga cctgttcacg      60
gataatgccg ctgcagggag t                                                81

<210> SEQ ID NO 22
<211> LENGTH: 81
<212> TYPE: DNA
<213> ORGANISM: Artificial Sequence
<220> FEATURE:
<223> OTHER INFORMATION: 12H3

<400> SEQUENCE: 22
acaggggtcc ggccttttca tttggcgccg gtgagatcac acccttacta cctgttcacg      60
gataatgccg ctgcagggag t                                                81

<210> SEQ ID NO 23
<211> LENGTH: 81
<212> TYPE: DNA
<213> ORGANISM: Artificial Sequence
<220> FEATURE:
<223> OTHER INFORMATION: 13H7

<400> SEQUENCE: 23
acaggggtcc ggccttttca tttggcgccg gtgagaacag acccttttgca cctgttcacg     60 gataatgccg ctgcagggag t                                                81
```

-continued

```
<210> SEQ ID NO 24
<211> LENGTH: 81
<212> TYPE: DNA
<213> ORGANISM: Artificial Sequence
<220> FEATURE:
<223> OTHER INFORMATION: 13B6

<400> SEQUENCE: 24
acaggggtcc ggccttttca tttggcgccg gtgagaacac accctttgta cctgttcacg      60
gataatgccg ctgcagggag t                                               81

<210> SEQ ID NO 25
<211> LENGTH: 81
<212> TYPE: DNA
<213> ORGANISM: Artificial Sequence
<220> FEATURE:
<223> OTHER INFORMATION: 15A5

<400> SEQUENCE: 25
acaggggtcc ggccttttca tttggcgccg gtgagattat acccttacta cctgttcacg      60
gataatgccg ctgcagggag t                                               81

<210> SEQ ID NO 26
<211> LENGTH: 81
<212> TYPE: DNA
<213> ORGANISM: Artificial Sequence
<220> FEATURE:
<223> OTHER INFORMATION: 15D10

<400> SEQUENCE: 26
acaggggtcc ggccttttca tttggcaccg gtgagaacat acccttcgga cctgttcacg      60
gataatgccg ctgcagggag t                                               81

<210> SEQ ID NO 27
<211> LENGTH: 81
<212> TYPE: DNA
<213> ORGANISM: Artificial Sequence
<220> FEATURE:
<223> OTHER INFORMATION: 15F9

<400> SEQUENCE: 27
acaggggtcc ggccttttca tttggcgccg gtgagattac acccttagca cctgttcacg      60
gataatgccg ctgcagggag t                                               81

<210> SEQ ID NO 28
<211> LENGTH: 81
<212> TYPE: DNA
<213> ORGANISM: Artificial Sequence
<220> FEATURE:
<223> OTHER INFORMATION: 16E5

<400> SEQUENCE: 28
acaggggtcc ggccttttca tttggcgccg gtgagatcaa acccttggca cctgttcacg      60
gataatgccg ctgcagggag t                                               81

<210> SEQ ID NO 29
<211> LENGTH: 81
<212> TYPE: DNA
<213> ORGANISM: Artificial Sequence
<220> FEATURE:
<223> OTHER INFORMATION: 16G8
```

-continued

<400> SEQUENCE: 29
acaggggtcc ggccttttca tttggcgccg gtgagagtac acccttcgca cctgttcacg      60
gataatgccg ctgcagggag t      81

<210> SEQ ID NO 30
<211> LENGTH: 81
<212> TYPE: DNA
<213> ORGANISM: Artificial Sequence
<220> FEATURE:
<223> OTHER INFORMATION: 16G6

<400> SEQUENCE: 30
acaggggtcc ggccttttca tttggcgccg gtgagatcac acccttggta cctgttcacg      60
gataatgccg ctgcagggag t      81

<210> SEQ ID NO 31
<211> LENGTH: 81
<212> TYPE: DNA
<213> ORGANISM: Artificial Sequence
<220> FEATURE:
<223> OTHER INFORMATION: 17E2

<400> SEQUENCE: 31
acaggggtcc ggccttttca tttggcgccg gtgagattac acccttتgga cctgttcacg      60 gataatgccg ctgcagggag t      81

<210> SEQ ID NO 32
<211> LENGTH: 81
<212> TYPE: DNA
<213> ORGANISM: Artificial Sequence
<220> FEATURE:
<223> OTHER INFORMATION: 17G1

<400> SEQUENCE: 32
acaggggtcc ggccttttca tttggcgccg gtgagatcac acccttggaa cctgttcacg      60
gataatgccg ctgcagggag t      81

<210> SEQ ID NO 33
<211> LENGTH: 81
<212> TYPE: DNA
<213> ORGANISM: Artificial Sequence
<220> FEATURE:
<223> OTHER INFORMATION: 17D3

<400> SEQUENCE: 33
acaggggtcc ggccttttca tttggcgccg gtgagaggat acccttcgga cctgttcacg      60
gataatgccg ctgcagggag t      81

<210> SEQ ID NO 34
<211> LENGTH: 81
<212> TYPE: DNA
<213> ORGANISM: Artificial Sequence
<220> FEATURE:
<223> OTHER INFORMATION: 17F5

<400> SEQUENCE: 34
acaggggtcc ggccttttca tttggcgccg gtgagagtat acccttagta cctgttcacg      60
gataatgccg ctgcagggag t      81

<210> SEQ ID NO 35
<211> LENGTH: 81

```
<212> TYPE: DNA
<213> ORGANISM: Artificial Sequence
<220> FEATURE:
<223> OTHER INFORMATION: 17G3

<400> SEQUENCE: 35
acaggggtcc ggccttttca tttggcaccg gtgagacaat acccttggta cctgttcacg      60
gataatgccg ctgcagggag t                                               81

<210> SEQ ID NO 36
<211> LENGTH: 81
<212> TYPE: DNA
<213> ORGANISM: Artificial Sequence
<220> FEATURE:
<223> OTHER INFORMATION: 18G9

<400> SEQUENCE: 36
acaggggtcc ggccttttca tttggcgccg gtgagagaat acccttggta cctgttcacg      60
gataatgccg ctgcagggag t                                               81

<210> SEQ ID NO 37
<211> LENGTH: 563
<212> TYPE: DNA
<213> ORGANISM: Artificial Sequence
<220> FEATURE:
<223> OTHER INFORMATION: G17 riboswitch
<220> FEATURE:
<221> NAME/KEY: misc_feature
<222> LOCATION: (317)..(317)
<223> OTHER INFORMATION: n is aptamer encoding sequence

<400> SEQUENCE: 37
gtgagtctat gggacccttg atgttttctt tccccttctt ttctatggtt aagttcatgt     60
cataggaagg ggagaagtaa cagggtacac atattgacca aatcagggta attttgcatt     120
tgtaatttta aaaaatgctt tcttctttta atatactttt ttgtttatct tatttctaat     180
actttcccta atctctttct ttcagggcaa taatgataca atgtatcatg ccgagtaacg     240
ctgtttctct aacttgtagg aatgaattca gatatttcca gagaatgaaa aaaaaatctt     300
cagtagaagg taatgtnaca ttacgcacca ttctaaagaa taacagtgat aatttctggg     360
ttaaggcaat agcaatattt ctgcatataa atatttctgc atataaattg taactgatgt     420
aagaggtttc atattgctaa tagcagctac aatccagcta ccattctgct tttattttat     480
ggttgggata aggctggatt attctgagtc caagctaggc ccttttgcta atcatgttca     540
tacctcttat cttcctccca cag                                           563

<210> SEQ ID NO 38
<211> LENGTH: 95
<212> TYPE: RNA
<213> ORGANISM: Artificial Sequence
<220> FEATURE:
<223> OTHER INFORMATION: 14G4 with P1 stem

<400> SEQUENCE: 38
guaauguaca gggguccggc cuuuucauuu ggcgccggug agagcacacc cuuugaaccu     60
guuuacggau aaugccgccg cagggaguac auuac                               95

<210> SEQ ID NO 39
<211> LENGTH: 80
<212> TYPE: DNA
<213> ORGANISM: Artificial Sequence
<220> FEATURE:
```

-continued

```
<223> OTHER INFORMATION: Library A1
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t

<400> SEQUENCE: 39 acagggggtcc ggcctttttca tttggcgccg gtgagagcac acccctttgaa cctgnnncgg      60 ataatgccgn ngcagggagt                                                     80

<210> SEQ ID NO 40
<211> LENGTH: 81
<212> TYPE: DNA
<213> ORGANISM: Artificial Sequence
<220> FEATURE:
<223> OTHER INFORMATION: Library A2
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (46)..(50)
<223> OTHER INFORMATION: n is a, c, g, or t

<400> SEQUENCE: 40 acngggggtcc ggcctttttca tttggcgccg gtgagagcac acccctnnnnn cctgtttacg      60 gataatgccg ccgcagggag t                                                   81

<210> SEQ ID NO 41
<211> LENGTH: 81
<212> TYPE: DNA
<213> ORGANISM: Artificial Sequence
<220> FEATURE:
<223> OTHER INFORMATION: Library A3
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (37)..(41)
<223> OTHER INFORMATION: n is a, c, g, or t

<400> SEQUENCE: 41
acaggggncc ggcctttttca tttggcgccg gtgagannnn nccctttgaa cctgtttacg       60
gataatgccg ccgcagggag t                                                   81

<210> SEQ ID NO 42
<211> LENGTH: 81
<212> TYPE: DNA
<213> ORGANISM: Artificial Sequence
<220> FEATURE:
<223> OTHER INFORMATION: Library A4
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (47)..(49)
<223> OTHER INFORMATION: n is a, c, g, or t
```

-continued

<400> SEQUENCE: 42
acaggggtcc ggccttttca tttggcgccg gtgagannan acccttnnna cctgttcacg          60
gataatgccg ctgcagggag t                                                    81

<210> SEQ ID NO 43
<211> LENGTH: 81
<212> TYPE: RNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (3)..(3)
<223> OTHER INFORMATION: n is A or G
<220> FEATURE:
<221> NAME/KEY: misc_feature
<222> LOCATION: (14)..(14)
<223> OTHER INFORMATION: n is C or no nucleotide
<220> FEATURE:
<221> NAME/KEY: misc_feature
<222> LOCATION: (16)..(16)
<223> OTHER INFORMATION: n is U or no nucleotide
<220> FEATURE:
<221> NAME/KEY: misc_feature
<222> LOCATION: (27)..(27)
<223> OTHER INFORMATION: n is A or G
<220> FEATURE:
<221> NAME/KEY: misc_feature
<222> LOCATION: (37)..(38)
<223> OTHER INFORMATION: n is a, c, g, or u
<220> FEATURE:
<221> NAME/KEY: misc_feature
<222> LOCATION: (40)..(40)
<223> OTHER INFORMATION: n is a, c, g, or u
<220> FEATURE:
<221> NAME/KEY: misc_feature
<222> LOCATION: (47)..(47)
<223> OTHER INFORMATION: n is a, c, g, or u
<220> FEATURE:
<221> NAME/KEY: misc_feature
<222> LOCATION: (48)..(48)
<223> OTHER INFORMATION: n is C, G, or U
<220> FEATURE:
<221> NAME/KEY: misc_feature
<222> LOCATION: (49)..(49)
<223> OTHER INFORMATION: n is a, c, g, or u
<220> FEATURE:
<221> NAME/KEY: misc_feature
<222> LOCATION: (50)..(50)
<223> OTHER INFORMATION: n is A or U
<220> FEATURE:
<221> NAME/KEY: misc_feature
<222> LOCATION: (57)..(57)
<223> OTHER INFORMATION: n is C or U
<220> FEATURE:
<221> NAME/KEY: misc_feature
<222> LOCATION: (72)..(72)
<223> OTHER INFORMATION: n is C or U

<400> SEQUENCE: 43
acnggggucc ggcnunuuca uuuggcnccg gugagannan acccuunnnn ccuguunacg          60
gauaaugccg cngcagggag u                                                    81

<210> SEQ ID NO 44
<211> LENGTH: 81
<212> TYPE: RNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (3)..(3)

<220> FEATURE:
<221> NAME/KEY: misc_feature
<222> LOCATION: (14)..(14)
<223> OTHER INFORMATION: n is C or no nucleotide
<220> FEATURE:
<221> NAME/KEY: misc_feature
<222> LOCATION: (16)..(16)
<223> OTHER INFORMATION: n is U or no nucleotide
<220> FEATURE:
<221> NAME/KEY: misc_feature
<222> LOCATION: (37)..(37)
<223> OTHER INFORMATION: n is G or U
<220> FEATURE:
<221> NAME/KEY: misc_feature
<222> LOCATION: (38)..(38)
<223> OTHER INFORMATION: n is C or U
<220> FEATURE:
<221> NAME/KEY: misc_feature
<222> LOCATION: (40)..(40)
<223> OTHER INFORMATION: n is C or U
<220> FEATURE:
<221> NAME/KEY: misc_feature
<222> LOCATION: (47)..(47)
<223> OTHER INFORMATION: n is a, c, g, or u
<220> FEATURE:
<221> NAME/KEY: misc_feature
<222> LOCATION: (48)..(48)
<223> OTHER INFORMATION: n is G or U
<220> FEATURE:
<221> NAME/KEY: misc_feature
<222> LOCATION: (49)..(49)
<223> OTHER INFORMATION: n is A, G, or U
<220> FEATURE:
<221> NAME/KEY: misc_feature
<222> LOCATION: (50)..(50)
<223> OTHER INFORMATION: n is A or U
<220> FEATURE:
<221> NAME/KEY: misc_feature
<222> LOCATION: (57)..(57)
<223> OTHER INFORMATION: n is C or U
<220> FEATURE:
<221> NAME/KEY: misc_feature
<222> LOCATION: (72)..(72)
<223> OTHER INFORMATION: n is C or U

<400> SEQUENCE: 44
acnggggucc ggcnunuuca uuuggcgccg gugagannan acccuunnnn ccuguunacg      60
gauaaugccg cngcagggag u      81

<210> SEQ ID NO 45
<211> LENGTH: 81
<212> TYPE: RNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (57)..(57)
<223> OTHER INFORMATION: n is C or U
<220> FEATURE:
<221> NAME/KEY: misc_feature
<222> LOCATION: (72)..(72)
<223> OTHER INFORMATION: n is C or U

<400> SEQUENCE: 45
acagggguuc ggccuuuuca uuuggcgccg gugagagcac acccuuugaa ccuguunacg      60
gauaaugccg cngcagggag u      81

<210> SEQ ID NO 46
<211> LENGTH: 81
<212> TYPE: RNA
<213> ORGANISM: Artificial Sequence -continued

```
<220> FEATURE:
<223> OTHER INFORMATION: Aptamer motif
<220> FEATURE:
<221> NAME/KEY: misc_feature
<222> LOCATION: (3)..(3)
<223> OTHER INFORMATION: n is A or G
<220> FEATURE:
<221> NAME/KEY: misc_feature
<222> LOCATION: (47)..(47)
<223> OTHER INFORMATION: n is a, c, g, or u
<220> FEATURE:
<221> NAME/KEY: misc_feature
<222> LOCATION: (48)..(48)
<223> OTHER INFORMATION: n is G or U
<220> FEATURE:
<221> NAME/KEY: misc_feature
<222> LOCATION: (49)..(49)
<223> OTHER INFORMATION: n is A, G, or U
<220> FEATURE:
<221> NAME/KEY: misc_feature
<222> LOCATION: (50)..(50)
<223> OTHER INFORMATION: n is A or U

<400> SEQUENCE: 46
acnggggucc ggccuuuuca uuuggcgccg gugagagcac acccuunnnn ccuguuuacg        60
gauaaugccg ccgcagggag u                                               81

<210> SEQ ID NO 47
<211> LENGTH: 81
<212> TYPE: RNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (37)..(37)
<223> OTHER INFORMATION: n is G or U
<220> FEATURE:
<221> NAME/KEY: misc_feature
<222> LOCATION: (38)..(38)
<223> OTHER INFORMATION: n is C or U
<220> FEATURE:
<221> NAME/KEY: misc_feature
<222> LOCATION: (40)..(40)
<223> OTHER INFORMATION: n is C or U

<400> SEQUENCE: 47
acaggggucc ggccuuuuca uuuggcgccg gugagannan acccuuugaa ccuguuuacg        60
gauaaugccg ccgcagggag u                                               81

<210> SEQ ID NO 48
<211> LENGTH: 81
<212> TYPE: RNA
<213> ORGANISM: Artificial Sequence
<220> FEATURE:
<223> OTHER INFORMATION: Aptamer motif
<220> FEATURE:
<221> NAME/KEY: misc_feature
<222> LOCATION: (27)..(27)
<223> OTHER INFORMATION: n is A or G
<220> FEATURE:
<221> NAME/KEY: misc_feature
<222> LOCATION: (37)..(38)
<223> OTHER INFORMATION: n is a, c, g, or u
<220> FEATURE:
<221> NAME/KEY: misc_feature
<222> LOCATION: (40)..(40)
<223> OTHER INFORMATION: n is a, c, g, or u
<220> FEATURE:
<221> NAME/KEY: misc_feature
<222> LOCATION: (47)..(47)
<223> OTHER INFORMATION: n is a, c, g, or u
<220> FEATURE:
```

-continued

```
<221> NAME/KEY: misc_feature
<222> LOCATION: (48)..(48)
<223> OTHER INFORMATION: n is C or G
<220> FEATURE:
<221> NAME/KEY: misc_feature
<222> LOCATION: (49)..(49)
<223> OTHER INFORMATION: n is a, c, g, or u

<400> SEQUENCE: 48
acaggggucc ggccuuuuca uuuggcnccg gugagannan acccuunnna ccuguucacg     60
gauaaugccg cugcagggag u                                              81

<210> SEQ ID NO 49
<211> LENGTH: 81
<212> TYPE: RNA
<213> ORGANISM: Artificial Sequence
<220> FEATURE:
<223> OTHER INFORMATION: 14G4

<400> SEQUENCE: 49
acaggggucc ggccuuuuca uuuggcgccg gugagagcac acccuuugaa ccuguuuacg     60
gauaaugccg ccgcagggag u                                              81

<210> SEQ ID NO 50
<211> LENGTH: 81
<212> TYPE: RNA
<213> ORGANISM: Artificial Sequence
<220> FEATURE:
<223> OTHER INFORMATION: 1D10

<400> SEQUENCE: 50
acaggggucc ggccuuuuca uuuggcgccg gugagauuau acccuuugaa ccuguuuacg     60
gauaaugccg ccgcagggag u                                              81

<210> SEQ ID NO 51
<211> LENGTH: 81
<212> TYPE: RNA
<213> ORGANISM: Artificial Sequence
<220> FEATURE:
<223> OTHER INFORMATION: 3H4

<400> SEQUENCE: 51
acaggggucc ggccuuuuca uuuggcgccg gugagagcac acccuuugaa ccuguucacg     60
gauaaugccg cugcagggag u                                              81

<210> SEQ ID NO 52
<211> LENGTH: 81
<212> TYPE: RNA
<213> ORGANISM: Artificial Sequence
<220> FEATURE:
<223> OTHER INFORMATION: 3F10

<400> SEQUENCE: 52 acggggucc ggccuuuuca uuuggcgccg gugagagcac acccuucgga ccuguuuacg      60
gauaaugccg ccgcagggag u                                              81

<210> SEQ ID NO 53
<211> LENGTH: 80
<212> TYPE: RNA
<213> ORGANISM: Artificial Sequence
<220> FEATURE:
<223> OTHER INFORMATION: 3H9

<400> SEQUENCE: 53
```

-continued

```
acaggggucc ggcuuuucau uuggcgccgg ugagagcaca cccuuaugac cuguuuacgg      60
auaaugccgc cgcagggagu                                                  80

<210> SEQ ID NO 54
<211> LENGTH: 81
<212> TYPE: RNA
<213> ORGANISM: Artificial Sequence
<220> FEATURE:
<223> OTHER INFORMATION: 4G2

<400> SEQUENCE: 54 acggggggucc ggccuuuuca uuuggcgccg gugagagcac acccuuugga ccuguuuacg      60
gauaaugccg ccgcagggag u                                                81

<210> SEQ ID NO 55
<211> LENGTH: 81
<212> TYPE: RNA
<213> ORGANISM: Artificial Sequence
<220> FEATURE:
<223> OTHER INFORMATION: 6D2

<400> SEQUENCE: 55 acggggggucc ggccuuuuca uuuggcgccg gugagagcac acccuuuguu ccuguuuacg      60
gauaaugccg ccgcagggag u                                                81

<210> SEQ ID NO 56
<211> LENGTH: 81
<212> TYPE: RNA
<213> ORGANISM: Artificial Sequence
<220> FEATURE:
<223> OTHER INFORMATION: 6B4

<400> SEQUENCE: 56
acaggggucc ggccuuuuca uuuggcgccg gugagagcac acccuuguga ccuguuuacg       60
gauaaugccg ccgcagggag u                                                81

<210> SEQ ID NO 57
<211> LENGTH: 81
<212> TYPE: RNA
<213> ORGANISM: Artificial Sequence
<220> FEATURE:
<223> OTHER INFORMATION: 4H2

<400> SEQUENCE: 57
acaggggucc ggccuuuuca uuuggcgccg gugagagcac acccuucgga ccuguuuacg       60
gauaaugccg ccgcagggag u                                                81

<210> SEQ ID NO 58
<211> LENGTH: 81
<212> TYPE: RNA
<213> ORGANISM: Artificial Sequence
<220> FEATURE:
<223> OTHER INFORMATION: 6C4

<400> SEQUENCE: 58 acggggggucc ggccuuuuca uuuggcgccg gugagagcac acccuucgaa ccuguuuacg      60
gauaaugccg ccgcagggag u                                                81

<210> SEQ ID NO 59
<211> LENGTH: 81
<212> TYPE: RNA
```

-continued

```
<213> ORGANISM: Artificial Sequence
<220> FEATURE:
<223> OTHER INFORMATION: 6G12

<400> SEQUENCE: 59
acaggggucc ggccuuuuca uuuggcgccg gugagagcac acccuuugga ccuguuuacg      60
gauaaugccg ccgcagggag u                                               81

<210> SEQ ID NO 60
<211> LENGTH: 80
<212> TYPE: RNA
<213> ORGANISM: Artificial Sequence
<220> FEATURE:
<223> OTHER INFORMATION: 8F1

<400> SEQUENCE: 60
acggggaucc ggccuuucau uuggcgccgg ugagagcaca cccuucggac cuguuuacgg      60
auaaugccgc cgcagggagu                                                 80

<210> SEQ ID NO 61
<211> LENGTH: 81
<212> TYPE: RNA
<213> ORGANISM: Artificial Sequence
<220> FEATURE:
<223> OTHER INFORMATION: 10A7

<400> SEQUENCE: 61
acaggggucc ggccuuuuca uuuggcgccg gugagaugau acccuuugga ccuguucacg      60
gauaaugccg cugcagggag u                                               81

<210> SEQ ID NO 62
<211> LENGTH: 81
<212> TYPE: RNA
<213> ORGANISM: Artificial Sequence
<220> FEATURE:
<223> OTHER INFORMATION: 12D5

<400> SEQUENCE: 62
acaggggucc ggccuuuuca uuuggcgccg gugagagcac acccuuugga ccuguucacg      60
gauaaugccg cugcagggag u                                               81

<210> SEQ ID NO 63
<211> LENGTH: 81
<212> TYPE: RNA
<213> ORGANISM: Artificial Sequence
<220> FEATURE:
<223> OTHER INFORMATION: 12G7

<400> SEQUENCE: 63
acaggggucc ggccuuuuca uuuggcgccg gugagauuau acccuucgga ccuguucacg      60
gauaaugccg cugcagggag u                                               81

<210> SEQ ID NO 64
<211> LENGTH: 81
<212> TYPE: RNA
<213> ORGANISM: Artificial Sequence
<220> FEATURE:
<223> OTHER INFORMATION: 12H3

<400> SEQUENCE: 64
acaggggucc ggccuuuuca uuuggcgccg gugagaucac acccuuacua ccuguucacg      60
gauaaugccg cugcagggag u                                               81
```

-continued

```
<210> SEQ ID NO 65
<211> LENGTH: 81
<212> TYPE: RNA
<213> ORGANISM: Artificial Sequence
<220> FEATURE:
<223> OTHER INFORMATION: 13H7

<400> SEQUENCE: 65
acaggggucc ggccuuuuca uuuggcgccg gugagaacag acccuuugca ccuguucacg      60
gauaaugccg cugcagggag u                                                81

<210> SEQ ID NO 66
<211> LENGTH: 81
<212> TYPE: RNA
<213> ORGANISM: Artificial Sequence
<220> FEATURE:
<223> OTHER INFORMATION: 13B6

<400> SEQUENCE: 66
acaggggucc ggccuuuuca uuuggcgccg gugagaacac acccuuugua ccuguucacg      60
gauaaugccg cugcagggag u                                                81

<210> SEQ ID NO 67
<211> LENGTH: 81
<212> TYPE: RNA
<213> ORGANISM: Artificial Sequence
<220> FEATURE:
<223> OTHER INFORMATION: 15A5

<400> SEQUENCE: 67
acaggggucc ggccuuuuca uuuggcgccg gugagauuau acccuuacua ccuguucacg      60
gauaaugccg cugcagggag u                                                81

<210> SEQ ID NO 68
<211> LENGTH: 81
<212> TYPE: RNA
<213> ORGANISM: Artificial Sequence
<220> FEATURE:
<223> OTHER INFORMATION: 15D10

<400> SEQUENCE: 68
acaggggucc ggccuuuuca uuuggcaccg gugagaacau acccuucgga ccuguucacg      60
gauaaugccg cugcagggag u                                                81

<210> SEQ ID NO 69
<211> LENGTH: 81
<212> TYPE: RNA
<213> ORGANISM: Artificial Sequence
<220> FEATURE:
<223> OTHER INFORMATION: 15F9

<400> SEQUENCE: 69
acaggggucc ggccuuuuca uuuggcgccg gugagauuac acccuuagca ccuguucacg      60
gauaaugccg cugcagggag u                                                81

<210> SEQ ID NO 70
<211> LENGTH: 81
<212> TYPE: RNA
<213> ORGANISM: Artificial Sequence
<220> FEATURE:
<223> OTHER INFORMATION: 16E5
```

-continued

<400> SEQUENCE: 70
acaggggucc ggccuuuuca uuuggcgccg gugagaucaa acccuuggca ccuguucacg          60
gauaaugccg cugcagggag u                                                   81

<210> SEQ ID NO 71
<211> LENGTH: 81
<212> TYPE: RNA
<213> ORGANISM: Artificial Sequence
<220> FEATURE:
<223> OTHER INFORMATION: 16G8

<400> SEQUENCE: 71
acaggggucc ggccuuuuca uuuggcgccg gugagaguac acccuucgca ccuguucacg          60
gauaaugccg cugcagggag u                                                   81

<210> SEQ ID NO 72
<211> LENGTH: 81
<212> TYPE: RNA
<213> ORGANISM: Artificial Sequence
<220> FEATURE:
<223> OTHER INFORMATION: 16G6

<400> SEQUENCE: 72
acaggggucc ggccuuuuca uuuggcgccg gugagaucac acccuuggua ccuguucacg          60
gauaaugccg cugcagggag u                                                   81

<210> SEQ ID NO 73
<211> LENGTH: 81
<212> TYPE: RNA
<213> ORGANISM: Artificial Sequence
<220> FEATURE:
<223> OTHER INFORMATION: 17E2

<400> SEQUENCE: 73
acaggggucc ggccuuuuca uuuggcgccg gugagauuac acccuuugga ccuguucacg          60
gauaaugccg cugcagggag u                                                   81

<210> SEQ ID NO 74
<211> LENGTH: 81
<212> TYPE: RNA
<213> ORGANISM: Artificial Sequence
<220> FEATURE:
<223> OTHER INFORMATION: 17G1

<400> SEQUENCE: 74
acaggggucc ggccuuuuca uuuggcgccg gugagaucac acccuuggaa ccuguucacg          60
gauaaugccg cugcagggag u                                                   81

<210> SEQ ID NO 75
<211> LENGTH: 81
<212> TYPE: RNA
<213> ORGANISM: Artificial Sequence
<220> FEATURE:
<223> OTHER INFORMATION: 17D3

<400> SEQUENCE: 75
acaggggucc ggccuuuuca uuuggcgccg gugagaggau acccuucgga ccuguucacg          60
gauaaugccg cugcagggag u                                                   81

<210> SEQ ID NO 76
<211> LENGTH: 81

<212> TYPE: RNA
<213> ORGANISM: Artificial Sequence
<220> FEATURE:
<223> OTHER INFORMATION: 17F5

<400> SEQUENCE: 76
acaggggucc ggccuuuuca uuuggcgccg gugagaguau acccuuagua ccuguucacg        60
gauaaugccg cugcagggag u                                                  81

<210> SEQ ID NO 77
<211> LENGTH: 81
<212> TYPE: RNA
<213> ORGANISM: Artificial Sequence
<220> FEATURE:
<223> OTHER INFORMATION: 17G3

<400> SEQUENCE: 77
acaggggucc ggccuuuuca uuuggcaccg gugagacaau acccuugguia ccuguucacg       60 gauaaugccg cugcagggag u                                                  81

<210> SEQ ID NO 78
<211> LENGTH: 81
<212> TYPE: RNA
<213> ORGANISM: Artificial Sequence
<220> FEATURE:
<223> OTHER INFORMATION: 18G9

<400> SEQUENCE: 78
acaggggucc ggccuuuuca uuuggcgccg gugagagaau acccuugguia ccuguucacg       60 gauaaugccg cugcagggag u                                                  81

<210> SEQ ID NO 79
<211> LENGTH: 50
<212> TYPE: DNA
<213> ORGANISM: Artificial Sequence
<220> FEATURE:
<223> OTHER INFORMATION: modified DHFR exon 2

<400> SEQUENCE: 79
gaatgaattc agatatttcc agagaatgaa aaaaaaatct tcagtagaag                   50

<210> SEQ ID NO 80
<211> LENGTH: 10
<212> TYPE: DNA
<213> ORGANISM: Artificial Sequence
<220> FEATURE:
<223> OTHER INFORMATION: U1 snRNP binding site (consensus site)

<400> SEQUENCE: 80
caggtaagta                                                               10

<210> SEQ ID NO 81
<211> LENGTH: 10
<212> TYPE: RNA
<213> ORGANISM: Artificial Sequence
<220> FEATURE:
<223> OTHER INFORMATION: U1 snRNP binding site (consensus site)

<400> SEQUENCE: 81
cagguaagua                                                               10

<210> SEQ ID NO 82
<211> LENGTH: 2305
<212> TYPE: DNA

```
<213> ORGANISM: Artificial Sequence
<220> FEATURE:
<223> OTHER INFORMATION: TPPz riboswitch

<400> SEQUENCE: 82
atggaagacg ccaaaaacat aaagaaaggc ccggcgccat tctatccgct ggaagatgga     60
accgctggag agcaactgca taaggctatg aagagatacg ccctggttcc tggaacaatt    120
gcttttacag atgcacatat cgaggtggac atcacttacg ctgagtactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgggcatt    360
tcgcagccta ccgtggtgtt cgtttccaaa aaggggttgc aaaaaatttt gaacgtgcaa    420
aaaaagctcc caatcatcca aaaaattatt atcatggatt ctaaaacgga ttaccaggga    480
tttcagtcga tgtacacgtt cgtcacatct catctacctc ccggttttaa tgaatacgat    540
tttgtgccag agtccttcga tagggacaag acaattgcac tgatcatgaa ctcctctgga    600
tctactggtc tgcctaaagg tgtcgctctg cctcatagaa ctgcctgcgt gagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttc tgaggagcct tcaggattac    840
aagattcaaa gtgcgctgct ggtgccaacc ctattctcct tcttcgccaa aagcactctg    900
attgacaaat acgatttatc taatttacac gaaattgctt ctggtggcgc tcccctctct    960
aaggaagtcg gggaagcggt tgccaagagg ttccatctgc aggtatcag ggtgagtcta   1020 tgggacccct tgatgttttct ttccccttct tttctatggt taagttcatg tcataggaag   1080
gggagaagta acagggtaca catattgacc aaatcagggt aattttgcat ttgtaatttt   1140
aaaaaatgct tcttcttttt aatatacttt tttgtttatc ttatttctaa tactttccct   1200
aatctctttc tttcagggca ataatgatac aatgtatcat gccgagtaac gctgtttctc   1260
taacttgtag gaatgaattc agatatttcc agagaatgaa aaaaaaatct tcagtagaag   1320
gtaatgtgtc ggagtgcctt aggggattatt cccctaaagc tgagaccgca ttgcgggatc   1380
cgttgaacct gatcaggcta atacctgcga agggaacaca ttacgcacca ttctaaagaa   1440
taacagtgat aatttctggg ttaaggcaat agcaatattt ctgcatataa atatttctgc   1500
atataaattg taactgatgt aagaggtttc atattgctaa tagcagctac aatccagcta   1560
ccattctgct tttattttat ggttgggata aggctggatt attctgagtc caagctaggc   1620
ccttttgcta atcatgttca tacctcttat cttcctccca cagcaaggat atgggctcac   1680
tgagactaca tcagctattc tgattacacc cgaggggat gataaaccgg gcgcggtcgg   1740
taaagttgtt ccattttttg aagcgaaggt tgtggatctg gataccggga aaacgctggg   1800
cgttaatcaa agaggcgaac tgtgtgtgag aggtcctatg attatgtccg gttatgtaaa   1860
caatccggaa gcgaccaacg ccttgattga caaggatgga tggctacatt ctggagacat   1920
agcttactgg gacgaagacg aacacttctt catcgttgac cgcctgaagt ctctgattaa   1980
gtacaaaggc tatcaggtgg ctcccgctga attggaatcc atcttgctcc aacaccccaa   2040
catcttcgac gcaggtgtcg caggtcttcc cgacgatgac gccggtgaac ttcccgccgc   2100
cgttgttgtt ttggagcacg gaaagacgat gacggaaaaa gagatcgtgg attacgtcgc   2160
cagtcaagta acaaccgcga aaaagttgcg cggaggagtt gtgtttgtgg acgaagtacc   2220
```

-continued

```
gaaaggtctt accggaaaac tcgacgcaag aaaaatcaga gagatcctca taaaggccaa      2280
gaagggcgga aagatcgccg tgtaa                                            2305

<210> SEQ ID NO 83
<211> LENGTH: 2289
<212> TYPE: DNA
<213> ORGANISM: Artificial Sequence
<220> FEATURE:
<223> OTHER INFORMATION: TPPm riboswitch

<400> SEQUENCE: 83
atggaagacg ccaaaaacat aaagaaaggc ccggcgccat tctatccgct ggaagatgga        60
accgctggag agcaactgca taaggctatg aagagatacg ccctggttcc tggaacaatt       120
gcttttacag atgcacatat cgaggtggac atcacttacg ctgagtactt cgaaatgtcc       180
gttcggttgg cagaagctat gaaacgatat gggctgaata caaatcacag aatcgtcgta       240
tgcagtgaaa actctcttca attctttatg ccggtgttgg gcgcgttatt tatcggagtt       300
gcagttgcgc ccgcgaacga catttataat gaacgtgaat tgctcaacag tatgggcatt       360
tcgcagccta ccgtggtgtt cgtttccaaa aaggggttgc aaaaaatttt gaacgtgcaa       420
aaaaagctcc caatcatcca aaaaattatt atcatggatt ctaaaacgga ttaccaggga       480
tttcagtcga tgtacacgtt cgtcacatct catctacctc ccggttttaa tgaatacgat       540
tttgtgccag agtccttcga tagggacaag acaattgcac tgatcatgaa ctcctctgga       600
tctactggtc tgcctaaagg tgtcgctctg cctcatagaa ctgcctgcgt gagattctcg       660
catgccagag atcctatttt tggcaatcaa atcattccgg atactgcgat tttaagtgtt       720
gttccattcc atcacggttt tggaatgttt actacactcg gatatttgat atgtggattt       780
cgagtcgtct taatgtatag atttgaagaa gagctgtttc tgaggagcct tcaggattac       840
aagattcaaa gtgcgctgct ggtgccaacc ctattctcct tcttcgccaa aagcactctg       900
attgacaaat acgatttatc taatttacac gaaattgctt ctggtggcgc tcccctctct       960
aaggaagtcg gggaagcggt tgccaagagg ttccatctgc aggtatcag ggtgagtcta      1020 tgggacccct gatgttttct ttccccttct tttctatggt taagttcatg tcataggaag      1080
gggagaagta acagggtaca catattgacc aaatcagggt aattttgcat ttgtaatttt      1140
aaaaaatgct tcttcttttt aatatacttt tttgtttatc ttatttctaa tactttccct      1200
aatctctttc tttcagggca ataatgatac aatgtatcat gccgagtaac gctgtttctc      1260
taacttgtag gaatgaattc agatatttcc agagaatgaa aaaaaaatct tcagtagaag      1320
gtaatgtctc ggggtgccct tctgcgtgaa ggctgagaaa tacccgtatc acctgatctg      1380
gataatgcca gcgtagggaa gacattacgc accattctaa agaataacag tgataatttc      1440
tgggttaagg caatagcaat atttctgcat ataaatattt ctgcatataa attgtaactg      1500
atgtaagagg tttcatattg ctaatagcag ctacaatcca gctaccattc tgcttttatt      1560
ttatggttgg ataaggctg gattattctg agtccaagct aggcccttt gctaatcatg      1620 ttcatacctc ttatcttcct cccacagcaa ggatatgggc tcactgagac tacatcagct      1680
attctgatta cacccgaggg ggatgataaa ccgggcgcgg tcggtaaagt tgttccattt      1740
tttgaagcga aggttgtgga tctggatacc gggaaaacgc tgggcgttaa tcaaagaggc      1800
gaactgtgtg tgagaggtcc tatgattatg tccggttatg taaacaatcc ggaagcgacc      1860
aacgccttga ttgacaagga tggatggcta cattctggag acatagctta ctgggacgaa      1920
```

-continued

```
gacgaacact tcttcatcgt tgaccgcctg aagtctctga ttaagtacaa aggctatcag    1980
gtggctcccg ctgaattgga atccatcttg ctccaacacc ccaacatctt cgacgcaggt    2040
gtcgcaggtc ttcccgacga tgacgccggt gaacttcccg ccgccgttgt tgttttggag    2100
cacggaaaga cgatgacgga aaaagagatc gtggattacg tcgccagtca agtaacaacc    2160
gcgaaaaagt tgcgcggagg agttgtgttt gtggacgaag taccgaaagg tcttaccgga    2220
aaactcgacg caagaaaaat cagagagatc ctcataaagg ccaagaaggg cggaaagatc    2280
gccgtgtaa                                                           2289
```

```
<210> SEQ ID NO 84
<211> LENGTH: 2296
<212> TYPE: DNA
<213> ORGANISM: Artificial Sequence
<220> FEATURE:
<223> OTHER INFORMATION: 14G4 riboswitch

<400> SEQUENCE: 84
```

```
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgggcatt     360
tcgcagccta ccgtggtgtt cgtttccaaa aaggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt     720
gttccattcc atcacggttt tggaatgttt actacactcg atatttgat atgtggattt       780 cgagtcgtct taatgtatag atttgaagaa gagctgtttc tgaggagcct tcaggattac     840
aagattcaaa gtgcgctgct ggtgccaacc ctattctcct tcttcgccaa aagcactctg     900
attgacaaat acgatttatc taatttacac gaaattgctt ctggtggcgc tcccctctct     960
aaggaagtcg gggaagcggt tgccaagagg ttccatctgc caggtatcag ggtgagtcta    1020
tgggaccctt gatgttttct ttccccttct tttctatggt taagttcatg tcataggaag    1080
gggagaagta acagggtaca catattgacc aaatcagggt aattttgcat ttgtaatttt    1140
aaaaaatgct ttcttctttt aatatacttt tttgtttatc ttatttctaa tactttccct    1200
aatctctttc tttcagggca ataatgatac aatgtatcat gccgagtaac gctgtttctc    1260
taacttgtag gaatgaattc agatatttcc agagaatgaa aaaaaaatct tcagtagaag    1320
gtaatgtaca ggggtccggc cttttcattt ggcgccggtg agagcacacc ctttgaacct    1380
gtttacggat aatgccgccg cagggagtac attacgcacc attctaaaga ataacagtga    1440
taatttctgg gttaaggcaa tagcaatatt tctgcatata aatatttctg catataaatt    1500
gtaactgatg taagaggttt catattgcta atagcagcta caatccagct accattctgc    1560
ttttatttta tggttgggat aaggctggat tattctgagt ccaagctagg cccttttgct    1620
aatcatgttc atacctctta tcttcctccc acagcaagga tatgggctca ctgagactac    1680
```

-continued

```
atcagctatt ctgattacac ccgagggggga tgataaaccg ggcgcggtcg gtaaagttgt    1740 tccattttttt gaagcgaagg ttgtggatct ggataccggg aaaacgctgg gcgttaatca    1800
aagaggcgaa ctgtgtgtga gaggtcctat gattatgtcc ggttatgtaa acaatccgga    1860
agcgaccaac gccttgattg acaaggatgg atggctacat tctggagaca tagcttactg    1920
ggacgaagac gaacacttct tcatcgttga ccgcctgaag tctctgatta agtacaaagg    1980
ctatcaggtg gctcccgctg aattggaatc catcttgctc caacacccca acatcttcga    2040
cgcaggtgtc gcaggtcttc ccgacgatga cgccggtgaa cttcccgccg ccgttgttgt    2100
tttggagcac ggaaagacga tgacggaaaa agagatcgtg gattacgtcg ccagtcaagt    2160
aacaaccgcg aaaaagttgc gcggaggagt tgtgtttgtg gacgaagtac cgaaaggtct    2220
taccggaaaa ctcgacgcaa gaaaaatcag agagatcctc ataaaggcca agaagggcgg    2280
aaagatcgcc gtgtaa                                                     2296
```

<210> SEQ ID NO 85
<211> LENGTH: 579
<212> TYPE: DNA
<213> ORGANISM: Artificial Sequence
<220> FEATURE:
<223> OTHER INFORMATION: Con8-Epo

<400> SEQUENCE: 85

```
atgggggtgc ccgaacgtcc caccctgctg cttttactct ccttgctact gattcctctg      60
ggcctcccag tcctctgtgc tcccccacgc ctcatctgcg acagtcgagt tctggagagg     120
tacatcttag aggccaagga ggcagaaaat gtcacgatgg gttgtgcaga aggtcccaga     180
ctgagtgaaa atattacagt cccagatacc aaagtcaact ctatgcttg  aaaagaatg      240 gaggtggaag aacaggccat agaagtttgg caaggcctgt ccctgctctc agaagccatc     300
ctgcaggccc aggccctgct agccaattcc tcccagccac cagagaccct tcagcttcat     360
atagacaaag ccatcagtgg tctacgtagc ctcacttcac tgcttcgggt actgggagct     420
cagaaggaat tgatgtcgcc tccagatacc accccacctg ctccactccg aacactcaca     480
gtggatactt tctgcaagct cttccgggtc tacgccaact tcctccgggg gaaactgaag     540
ctgtacacgg agaggtctg  caggagaggg acaggtga                              579
```

<210> SEQ ID NO 86
<211> LENGTH: 1221
<212> TYPE: DNA
<213> ORGANISM: Artificial Sequence
<220> FEATURE:
<223> OTHER INFORMATION: Epo-3H4

<400> SEQUENCE: 86

```
atgggggtgc ccgaacgtcc caccctgctg cttttactct ccttgctact gattcctctg      60
ggcctcccag tcctctgtgc tcccccacgc ctcatctgcg acagtcgagt tctggagagg     120
tacatcttag aggccaagga ggcagaaaat gtcacgatgg gttgtgcaga aggtcccaga     180
ctgagtgaaa atattacagt cccagatacc aaagtcaact ctatgcttg  aaaagaatg      240 gaggtggaag aacaggccat agaagtttgg caaggcctgt ccctgctctc agaagccatc     300
ctgcagggtg agtctatggg acccttgatg ttttctttcc ccttctttc tatggttaag     360 ttcatgtcat aggaagggga gaagtaacag ggtacacata ttgaccaaat cagggtaatt     420
ttgcatttgt aatttttaaaa aatgctttct tcttttaata tacttttttg tttatcttat     480
```

-continued

```
ttctaatact ttccctaatc tctttctttc agggcaataa tgatacaatg tatcatgccg     540
agtaacgctg tttctctaac ttgtaggaat gaattcagat atttccagag aatgaaaaaa     600
aatcttcagt agaaggtaat gtacaggggt ccggcctttt catttggcgc cggtgagagc     660
acaccctttg aacctgttca cggataatgc cgctgcaggg agtacattac gcaccattct     720
aaagaataac agtgataatt tctgggttaa ggcaatagca atatttctgc atataaatat     780
ttctgcatat aaattgtaac tgatgtaaga ggtttcatat tgctaatagc agctacaatc     840
cagctaccat tctgctttta ttttatggtt gggataaggc tggattattc tgagtccaag     900
ctaggccctt ttgctaatca tgttcatacc tcttatcttc ctcccacagc ccaggccctg     960
ctagccaatt cctcccagcc accagagacc cttcagcttc atatagacaa agccatcagt    1020
ggtctacgta gcctcacttc actgcttcgg gtactgggag ctcagaagga attgatgtcg    1080
cctccagata ccacccccacc tgctccactc cgaacactca cagtggatac tttctgcaag    1140
ctcttccggg tctacgccaa cttcctccgg gggaaactga agctgtacac gggagaggtc    1200
tgcaggagag gggacaggtg a                                              1221
```

<210> SEQ ID NO 87
<211> LENGTH: 1221
<212> TYPE: DNA
<213> ORGANISM: Artificial Sequence
<220> FEATURE:
<223> OTHER INFORMATION: Epo-15D10

<400> SEQUENCE: 87

```
atggggggtgc ccgaacgtcc caccctgctg cttttactct ccttgctact gattcctctg      60
ggcctcccag tcctctgtgc tcccccacgc ctcatctgcg acagtcgagt tctggagagg     120
tacatcttag aggccaagga ggcagaaaat gtcacgatgg gttgtgcaga aggtcccaga     180
ctgagtgaaa atattacagt cccagatacc aaagtcaact ctatgcttg gaaaagaatg       240 gaggtggaag aacaggccat agaagtttgg caaggcctgt ccctgctctc agaagccatc     300
ctgcagggtg agtctatggg acccttgatg tttctttcc ccttctttc tatggttaag        360 ttcatgtcat aggaaggggga gaagtaacag ggtacacata ttgaccaaat cagggtaatt     420
ttgcatttgt aattttaaaa aatgctttct tcttttaata tactttttg tttatcttat        480 ttctaatact ttccctaatc tctttctttc agggcaataa tgatacaatg tatcatgccg      540
agtaacgctg tttctctaac ttgtaggaat gaattcagat atttccagag aatgaaaaaa      600
aatcttcagt agaaggtaat gtacaggggt ccggcctttt catttggcac cggtgagaac      660 ataccccttcg gacctgttca cggataatgc cgctgcaggg agtacattac gcaccattct     720
aaagaataac agtgataatt tctgggttaa ggcaatagca atatttctgc atataaatat      780
ttctgcatat aaattgtaac tgatgtaaga ggtttcatat tgctaatagc agctacaatc      840
cagctaccat tctgctttta ttttatggtt gggataaggc tggattattc tgagtccaag      900
ctaggccctt ttgctaatca tgttcatacc tcttatcttc ctcccacagc ccaggccctg      960
ctagccaatt cctcccagcc accagagacc cttcagcttc atatagacaa agccatcagt     1020
ggtctacgta gcctcacttc actgcttcgg gtactgggag ctcagaagga attgatgtcg     1080
cctccagata ccacccccacc tgctccactc cgaacactca cagtggatac tttctgcaag     1140
ctcttccggg tctacgccaa cttcctccgg gggaaactga agctgtacac gggagaggtc     1200
tgcaggagag gggacaggtg a                                              1221
```

-continued

```
<210> SEQ ID NO 88
<211> LENGTH: 1362
<212> TYPE: DNA
<213> ORGANISM: Artificial Sequence
<220> FEATURE:
<223> OTHER INFORMATION: EGFP-6B4

<400> SEQUENCE: 88
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgaccta cggcgtgcag tgcttcagcc gctacccccga ccacatgaag      240 cagcacgact tcttcaagtc cgccatgccc gaagggtgag tctatgggac ccttgatgtt       300
ttctttcccc ttcttttcta tggttaagtt catgtcatag aaggggggaga agtaacaggg      360 tacacatatt gaccaaatca gggtaatttt gcatttgtaa ttttaaaaaa tgctttcttc       420
ttttaatata cttttttgtt tatcttattt ctaatacttt ccctaatctc tttctttcag       480
ggcaataatg atacaatgta tcatgccgag taacgctgtt tctctaactt gtaggaatga       540
attcagatat ttccagagaa tgaaaaaaaa tcttcagtag aaggtaatgt acaggggtcc       600
ggccttttca tttggcgccg gtgagagcac acccttgtga cctgtttacg gataatgccg       660
ccgcagggag tacattacgc accattctaa agaataacag tgataatttc tgggttaagg       720
caatagcaat atttctgcat ataaatattt ctgcatataa attgtaactg atgtaagagg       780
tttcatattg ctaatagcag ctacaatcca gctaccattc tgctttcatt ttatggttgg       840
gataaggctg gattattctg agtccaagct aggcccctttt gctaatcatg ttcataccctc     900 ttatcttcct cccacagcta cgtccaggag cgcaccatct tcttcaagga cgacggcaac       960
tacaagaccc gcgccgaggt gaagttcgag ggcgacaccc tggtgaaccg catcgagctg      1020
aagggcatcg acttcaagga ggacggcaac atcctggggc acaagctgga gtacaactac      1080
aacagccaca cgtctatat catggccgac aagcagaaga cggcatcaa ggtgaacttc        1140 aagatccgcc acaacatcga ggacggcagc gtgcagctcg ccgaccacta ccagcagaac      1200
acccccatcg gcgacggccc cgtgctgctg cccgacaacc actacctgag cacccagtcc      1260
gccctgagca agacccccaa cgagaagcgc gatcacatgg tcctgctgga gttcgtgacc      1320
gccgccggga tcactctcgg catggacgag ctgtacaagt aa                         1362

<210> SEQ ID NO 89
<211> LENGTH: 1055
<212> TYPE: DNA
<213> ORGANISM: Artificial Sequence
<220> FEATURE:
<223> OTHER INFORMATION: Epo-Con1

<400> SEQUENCE: 89 atggggggtgc ccgaacgtcc caccctgctg cttttactct ccttgctact gattcctctg        60
ggcctcccag tcctctgtgc tcccccacgc ctcatctgcg acagtcgagt tctggagagg        120
tacatcttag aggccaagga ggcagaaaat gtcacgatgg gttgtgcaga aggtcccaga        180
ctgagtgaaa atattacagt cccagatacc aaagtcaact ctatgcttg gaaaagaatg        240 gaggtggaag aacaggccat agaagtttgg caaggcctgt ccctgctctc agaagccatc        300
ctgcagggtg agtctatggg acccttgatg ttttctttcc ccttcttttc tatggttaag        360
ttcatgtcat aggaaggggga gaagtaacag ggtacacata ttgaccaaat cagggtaatt        420
```

-continued

```
ttgcatttgt aattttaaaa aatgctttct tcttttaata tacttttttg tttatcttat      480
ttctaatact ttccctaatc tctttctttc agggcaataa tgatacaatg tatcatgcct      540
ctttgcacca ttctaaagaa taacagtgat aatttctggg ttaaggcaat agcaatattt      600
ctgcatataa atatttctgc atataaattg taactgatgt aagaggtttc atattgctaa      660
tagcagctac aatccagcta ccattctgct tttattttat ggttgggata aggctggatt      720
attctgagtc caagctaggc ccttttgcta atcatgttca tacctcttat cttcctccca      780
cagcccaggc cctgctagcc aattcctccc agccaccaga gacccttcag cttcatatag      840
acaaagccat cagtggtcta cgtagcctca cttcactgct tcgggtactg ggagctcaga      900
aggaattgat gtcgcctcca gataccaccc cacctgctcc actccgaaca ctcacagtgg      960
atactttctg caagctcttc cgggtctacg ccaacttcct ccggggggaaa ctgaagctgt     1020 acacgggaga ggtctgcagg agaggggaca ggtga                                 1055
```

<210> SEQ ID NO 90
<211> LENGTH: 2129
<212> TYPE: DNA
<213> ORGANISM: Artificial Sequence
<220> FEATURE:
<223> OTHER INFORMATION: luci-Con1

<400> SEQUENCE: 90

```
atggaagacg ccaaaaacat aaagaaaggc ccggcgccat tctatccgct ggaagatgga       60
accgctggag agcaactgca taaggctatg aagagatacg ccctggttcc tggaacaatt      120
gcttttacag atgcacatat cgaggtggac atcacttacg ctgagtactt cgaaatgtcc      180
gttcggttgg cagaagctat gaaacgatat gggctgaata caaatcacag aatcgtcgta      240
tgcagtgaaa actctcttca attctttatg ccggtgttgg gcgcgttatt tatcggagtt      300
gcagttgcgc ccgcgaacga catttataat gaacgtgaat tgctcaacag tatgggcatt      360
tcgcagccta ccgtggtgtt cgtttccaaa aaggggttgc aaaaaatttt gaacgtgcaa      420
aaaaagctcc caatcatcca aaaaattatt atcatggatt ctaaaacgga ttaccaggga      480
tttcagtcga tgtacacgtt cgtcacatct catctacctc ccggtttttaa tgaatacgat      540 tttgtgccag agtccttcga tagggacaag acaattgcac tgatcatgaa ctcctctgga      600
tctactggtc tgcctaaagg tgtcgctctg cctcatagaa ctgcctgcgt gagattctcg      660
catgccagag atcctatttt tggcaatcaa atcattccgg atactgcgat tttaagtgtt      720
gttccattcc atcacggttt tggaatgttt actacactcg atatttgat atgtggattt      780 cgagtcgtct taatgtatag atttgaagaa gagctgtttc tgaggagcct tcaggattac      840
aagattcaaa gtgcgctgct ggtgccaacc ctattctcct tcttcgccaa aagcactctg      900
attgacaaat acgatttatc taatttacac gaaattgctt ctggtggcgc tcccctctct      960
aaggaagtcg gggaagcggt tgccaagagg ttccatctgc caggtatcag ggtgagtcta     1020 tgggacccctt gatgttttct ttccccttct tttctatggt taagttcatg tcataggaag     1080
gggagaagta acagggtaca catattgacc aaatcagggt aattttgcat ttgtaatttt     1140
aaaaaatgct tcttcttttt aatatacttt tttgtttatc ttatttctaa tactttccct     1200
aatctctttc tttcagggca ataatgatac aatgtatcat gcctctttgc accattctaa     1260
agaataacag tgataatttc tgggttaagg caatagcaat atttctgcat ataaatattt     1320
ctgcatataa attgtaactg atgtaagagg tttcatattg ctaatagcag ctacaatcca     1380
gctaccattc tgctttttatt ttatggttgg gataaggctg gattattctg agtccaagct     1440
```

-continued

```
aggcccttt  gctaatcatg  ttcataccttc  ttatcttcct  cccacagcaa  ggatatgggc        1500
tcactgagac  tacatcagct  attctgatta  cacccgaggg  ggatgataaa  ccgggcgcgg        1560
tcggtaaagt  tgttccatttt  tttgaagcga  aggttgtgga  tctggatacc  gggaaaacgc       1620
tgggcgttaa  tcaaagaggc  gaactgtgtg  tgagaggtcc  tatgattatg  tccggttatg        1680
taaacaatcc  ggaagcgacc  aacgccttga  ttgacaagga  tggatggcta  cattctggag        1740
acatagctta  ctgggacgaa  gacgaacact  tcttcatcgt  tgaccgcctg  aagtctctga        1800
ttaagtacaa  aggctatcag  gtggctcccg  ctgaattgga  atccatcttg  ctccaacacc        1860
ccaacatctt  cgacgcaggt  gtcgcaggtc  ttcccgacga  tgacgccggt  gaacttcccg        1920
ccgccgttgt  tgttttggag  cacggaaaga  cgatgacgga  aaaagagatc  gtggattacg        1980
tcgccagtca  agtaacaacc  gcgaaaaagt  tgcgcggagg  agttgtgttt  gtggacgaag        2040
taccgaaagg  tcttaccgga  aaactcgacg  caagaaaaat  cagagagatc  ctcataaagg        2100
ccaagaaggg  cggaaagatc  gccgtgtaa                                            2129
```

<210> SEQ ID NO 91
<211> LENGTH: 2295
<212> TYPE: DNA
<213> ORGANISM: Artificial Sequence
<220> FEATURE:
<223> OTHER INFORMATION: luci-3H4

<400> SEQUENCE: 91

```
atggaagacg  ccaaaaacat  aaagaaaggc  ccggcgccat  tctatccgct  ggaagatgga          60
accgctggag  agcaactgca  taaggctatg  aagagatacg  ccctggttcc  tggaacaatt         120
gcttttacag  atgcacatat  cgaggtggac  atcacttacg  ctgagtactt  cgaaatgtcc         180
gttcggttgg  cagaagctat  gaaacgatat  gggctgaata  caaatcacag  aatcgtcgta         240
tgcagtgaaa  actctcttca  attctttatg  ccggtgttgg  gcgcgttatt  tatcggagtt         300
gcagttgcgc  ccgcgaacga  catttataat  gaacgtgaat  tgctcaacag  tatgggcatt         360
tcgcagccta  ccgtggtgtt  cgtttccaaa  aaggggttgc  aaaaaatttt  gaacgtgcaa         420
aaaaagctcc  caatcatcca  aaaaattatt  atcatggatt  ctaaaacgga  ttaccaggga         480
tttcagtcga  tgtacacgtt  cgtcacatct  catctacctc  ccggtttttaa  tgaatacgat        540 tttgtgccag  agtccttcga  tagggacaag  acaattgcac  tgatcatgaa  ctcctctgga        600
tctactggtc  tgcctaaagg  tgtcgctctg  cctcatagaa  ctgcctgcgt  gagattctcg        660
catgccagag  atcctattttt  tggcaatcaa  atcattccgg  atactgcgat  tttaagtgtt        720
gttccattcc  atcacggttt  tggaatgttt  actacactcg  gatatttgat  atgtggattt        780
cgagtcgtct  taatgtatag  atttgaagaa  gagctgtttc  tgaggagcct  tcaggattac        840
aagattcaaa  gtgcgctgct  ggtgccaacc  ctattctcct  tcttcgccaa  aagcactctg        900
attgacaaat  acgatttatc  taatttacac  gaaattgctt  ctggtggcgc  tcccctctct        960
aaggaagtcg  gggaagcggt  tgccaagagg  ttccatctgc  aggtatcag   ggtgagtcta       1020 tgggaccctt  gatgttttct  ttccccttct  tttctatggt  taagttcatg  tcataggaag       1080
gggagaagta  acagggtaca  catattgacc  aaatcagggt  aatttttgcat  ttgtaattttt     1140 aaaaaatgct  ttcttctttt  aatatacttt  tttgtttatc  ttatttctaa  tactttccct       1200
aatctctttc  tttcagggca  ataatgatac  aatgtatcat  gcccgagtaac gctgtttctc       1260 taacttgtag  gaatgaattc  agatatttcc  agagaatgaa  aaaaaatctt  cagtagaagg       1320
```

-continued

```
taatgtacag gggtccggcc ttttcatttg gcgccggtga gagcacaccc tttgaacctg      1380
ttcacggata atgccgctgc agggagtaca ttacgcacca ttctaaagaa taacagtgat      1440
aatttctggg ttaaggcaat agcaatattt ctgcatataa atatttctgc atataaattg      1500
taactgatgt aagaggtttc atattgctaa tagcagctac aatccagcta ccattctgct      1560
tttattttat ggttgggata aggctggatt attctgagtc caagctaggc ccttttgcta      1620
atcatgttca tacctcttat cttcctccca cagcaaggat atgggctcac tgagactaca      1680
tcagctattc tgattacacc cgagggggat gataaaccgg gcgcggtcgg taaagttgtt      1740 ccatttttg aagcgaaggt tgtggatctg gataccggga aaacgctggg cgttaatcaa      1800
agaggcgaac tgtgtgtgag aggtcctatg attatgtccg gttatgtaaa caatccggaa      1860
gcgaccaacg ccttgattga caaggatgga tggctacatt ctggagacat agcttactgg      1920
gacgaagacg aacacttctt catcgttgac cgcctgaagt ctctgattaa gtacaaaggc      1980
tatcaggtgg ctcccgctga attggaatcc atcttgctcc aacaccccaa catcttcgac      2040
gcaggtgtcg caggtcttcc cgacgatgac gccggtgaac ttcccgccgc cgttgttgtt      2100
ttggagcacg gaaagacgat gacggaaaaa gagatcgtgg attacgtcgc cagtcaagta      2160
acaaccgcga aaaagttgcg cggaggagtt gtgtttgtgg acgaagtacc gaaaggtctt      2220
accggaaaac tcgacgcaag aaaaatcaga gagatcctca taaaggccaa gaagggcgga      2280
aagatcgccg tgtaa                                                        2295
```

<210> SEQ ID NO 92
<211> LENGTH: 2295
<212> TYPE: DNA
<213> ORGANISM: Artificial Sequence
<220> FEATURE:
<223> OTHER INFORMATION: luci-6B4

<400> SEQUENCE: 92

```
atggaagacg ccaaaaacat aaagaaaggc ccggcgccat tctatccgct ggaagatgga        60
accgctggag agcaactgca taaggctatg aagagatacg ccctggttcc tggaacaatt       120
gcttttacag atgcacatat cgaggtggac atcacttacg ctgagtactt cgaaatgtcc       180
gttcggttgg cagaagctat gaaacgatat gggctgaata caaatcacag aatcgtcgta       240
tgcagtgaaa actctcttca attctttatg ccggtgttgg gcgcgttatt tatcggagtt       300
gcagttgcgc ccgcgaacga catttataat gaacgtgaat tgctcaacag tatgggcatt       360
tcgcagccta ccgtggtgtt cgtttccaaa aaggggttgc aaaaaatttt gaacgtgcaa       420
aaaaagctcc caatcatcca aaaaattatt atcatggatt ctaaaacgga ttaccaggga       480
tttcagtcga tgtacacgtt cgtcacatct catctacctc ccggtttttaa tgaatacgat       540 tttgtgccag agtccttcga tagggacaag acaattgcac tgatcatgaa ctcctctgga       600
tctactggtc tgcctaaagg tgtcgctctg cctcatagaa ctgcctgcgt gagattctcg       660
catgccagag atcctatttt tggcaatcaa atcattccgg atactgcgat tttaagtgtt       720
gttccattcc atcacggttt tggaatgttt actacactcg atatttgat atgtggattt       780 cgagtcgtct taatgtatag atttgaagaa gagctgtttc tgaggagcct tcaggattac       840
aagattcaaa gtgcgctgct ggtgccaacc ctattctcct tcttcgccaa aagcactctg       900
attgacaaat acgatttatc taatttacac gaaattgctt ctggtggcgc tcccctctct       960
aaggaagtcg gggaagcggt tgccaagagg ttccatctgc caggtatcag ggtgagtcta      1020
tgggaccctt gatgttttct ttccccttct tttctatggt taagttcatg tcataggaag      1080
```

```
gggagaagta acagggtaca catattgacc aaatcagggt aattttgcat ttgtaatttt     1140
aaaaaatgct ttcttctttt aatatacttt tttgtttatc ttatttctaa tactttccct     1200
aatctctttc tttcagggca ataatgatac aatgtatcat gccgagtaac gctgtttctc     1260
taacttgtag gaatgaattc agatatttcc agagaatgaa aaaaaatctt cagtagaagg     1320
taatgtacag gggtccggcc ttttcatttg gcgccggtga gagcacaccc ttgtgacctg     1380
tttacggata atgccgccgc agggagtaca ttacgcacca ttctaaagaa taacagtgat     1440
aatttctggg ttaaggcaat agcaatattt ctgcatataa atatttctgc atataaattg     1500
taactgatgt aagaggtttc atattgctaa tagcagctac aatccagcta ccattctgct     1560
tttattttat ggttgggata aggctggatt attctgagtc caagctaggc ccttttgcta     1620
atcatgttca tacctcttat cttcctccca cagcaaggat atgggctcac tgagactaca     1680
tcagctattc tgattacacc cgaggggggat dataaaccgg gcgcggtcgg taaagttgtt     1740
ccattttttg aagcgaaggt tgtggatctg dataccggga aaacgctggg cgttaatcaa     1800
agaggcgaac tgtgtgtgag aggtcctatg attatgtccg gttatgtaaa caatccggaa     1860
gcgaccaacg ccttgattga caaggatgga tggctacatt ctggagacat agcttactgg     1920
gacgaagacg aacacttctt catcgttgac cgcctgaagt ctctgattaa gtacaaaggc     1980
tatcaggtgg ctcccgctga attggaatcc atcttgctcc aacaccccaa catcttcgac     2040
gcaggtgtcg caggtcttcc cgacgatgac gccggtgaac ttcccgccgc cgttgttgtt     2100
ttggagcacg gaaagacgat gacggaaaaa gagatcgtgg attacgtcgc cagtcaagta     2160
acaaccgcga aaaagttgcg cggaggagtt gtgtttgtgg acgaagtacc gaaaggtctt     2220
accggaaaac tcgacgcaag aaaaatcaga gagatcctca taaaggccaa gaagggcgga     2280
aagatcgccg tgtaa                                                       2295
```

```
<210> SEQ ID NO 93
<211> LENGTH: 2295
<212> TYPE: DNA
<213> ORGANISM: Artificial Sequence
<220> FEATURE:
<223> OTHER INFORMATION: Luci-15D10

<400> SEQUENCE: 93
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgggcatt     360
tcgcagccta ccgtggtgtt cgtttccaaa aaggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt     720
gttccattcc atcacggttt tggaatgttt actacactcg gatatttgat atgtggattt     780
```

```
cgagtcgtct taatgtatag atttgaagaa gagctgtttc tgaggagcct tcaggattac     840
aagattcaaa gtgcgctgct ggtgccaacc ctattctcct tcttcgccaa aagcactctg     900
attgacaaat acgatttatc taatttacac gaaattgctt ctggtggcgc tccctctct      960 aaggaagtcg gggaagcggt tgccaagagg ttccatctgc caggtatcag ggtgagtcta     1020 tgggacccctt gatgttttct ttccccttct tttctatggt taagttcatg tcataggaag    1080
gggagaagta acagggtaca catattgacc aaatcagggt aattttgcat ttgtaatttt      1140
aaaaaatgct ttcttctttt aatatacttt tttgtttatc ttatttctaa tactttccct     1200
aatctctttc tttcagggca ataatgatac aatgtatcat gccgagtaac gctgtttctc      1260
taacttgtag gaatgaattc agatatttcc agagaatgaa aaaaaatctt cagtagaagg      1320
taatgtacag gggtccggcc ttttcatttg gcaccggtga aacataccc ttcggacctg       1380 ttcacggata atgccgctgc agggagtaca ttacgcacca ttctaaagaa taacagtgat      1440
aatttctggg ttaaggcaat agcaatattt ctgcatataa atatttctgc atataaattg      1500
taactgatgt aagaggtttc atattgctaa tagcagctac aatccagcta ccattctgct      1560
tttattttat ggttgggata aggctggatt attctgagtc caagctaggc ccttttgcta      1620
atcatgttca tacctcttat cttcctccca cagcaaggat atgggctcac tgagactaca      1680
tcagctattc tgattacacc cgagggggat gataaaccgg gcgcggtcgg taaagttgtt      1740
ccattttttg aagcgaaggt tgtggatctg gataccggga aaacgctggg cgttaatcaa      1800
agaggcgaac tgtgtgtgag aggtcctatg attatgtccg gttatgtaaa caatccggaa      1860
gcgaccaacg ccttgattga caaggatgga tggctacatt ctggagacat agcttactgg      1920
gacgaagacg aacacttctt catcgttgac cgcctgaagt ctctgattaa gtacaaaggc      1980
tatcaggtgg ctcccgctga attggaatcc atcttgctcc aacacccaa catcttcgac        2040 gcaggtgtcg caggtcttcc cgacgatgac gccggtgaac ttcccgccgc cgttgttgtt      2100
ttggagcacg aaagacgat gacgaaaaa gagatcgtgg attacgtcgc cagtcaagta         2160
acaaccgcga aaaagttgcg cggaggagtt gtgtttgtgg acgaagtacc gaaaggtctt      2220
accggaaaac tcgacgcaag aaaaatcaga gagatcctca taaaggccaa gaagggcgga      2280
aagatcgccg tgtaa                                                        2295

<210> SEQ ID NO 94
<211> LENGTH: 104
<212> TYPE: RNA
<213> ORGANISM: Artificial Sequence
<220> FEATURE:
<223> OTHER INFORMATION: thiC aptamer with stem

<400> SEQUENCE: 94
guaauguguc ggagugccuu agggauuauu ccccuaaagc ugagaccgca uugcgggauc      60
cguugaaccu gaucaggcua auaccugcga agggaacaca uuac                       104

<210> SEQ ID NO 95
<211> LENGTH: 88
<212> TYPE: RNA
<213> ORGANISM: Artificial Sequence
<220> FEATURE:
<223> OTHER INFORMATION: thiM aptamer with stem

<400> SEQUENCE: 95
guaaugucuc ggggugcccu ucugcgugaa ggcugagaaa uacccguauc accugaucug      60
gauaaugcca gcguagggaa gacauuac                                         88
```

```
<210> SEQ ID NO 96
<211> LENGTH: 90
<212> TYPE: DNA
<213> ORGANISM: Artificial Sequence
<220> FEATURE:
<223> OTHER INFORMATION: thiC aptamer encoding sequence

<400> SEQUENCE: 96
gtcggagtgc cttagggatt attcccctaa agctgagacc gcattgcggg atccgttgaa        60
cctgatcagg ctaatacctg cgaagggaac                                         90

<210> SEQ ID NO 97
<211> LENGTH: 74
<212> TYPE: DNA
<213> ORGANISM: Artificial Sequence
<220> FEATURE:
<223> OTHER INFORMATION: thiM aptamer encoding sequence

<400> SEQUENCE: 97
ctcggggtgc ccttctgcgt gaaggctgag aaatacccgt atcacctgat ctggataatg        60
ccagcgtagg gaag                                                          74

<210> SEQ ID NO 98
<211> LENGTH: 49
<212> TYPE: DNA
<213> ORGANISM: Artificial Sequence
<220> FEATURE:
<223> OTHER INFORMATION: modified DHFR exon 2

<400> SEQUENCE: 98
gaatgaattc agatatttcc agagaatgaa aaaaaatctt cagtagaag                    49
```

1

APTAMERS THAT BIND THIAMINE ANALOGS AND DERIVATIVES

CROSS REFERENCE TO RELATED APPLICATIONS

This application is a National Phase of PCT/IB2021/000163, filed Mar. 24, 2021, which claims priority to U.S. Application No. 62/994,135, filed Mar. 24, 2020, each of which is incorporated herein by reference in its entirety.

REFERENCE TO A SEQUENCE LISTING

This application contains a Squence Listing, which has been submitted electronically in txt format and is hereby incorporated by reference in its entirety. Said txt copy, created on Mar. 24, 2021, is named named 162027-48976_Sequence-Listing.txt, and is 59,067 bytes in size.

FIELD

The present disclosure relates to oligonucleotide aptamers that bind to certain small molecules and methods of generating aptamers that bind to the small molecules. Also contemplated are riboswitches and polynucleotide cassettes for regulating the expression of a target gene, wherein the polynucleotide cassettes comprise the aptamers disclosed herein. Further provided are small molecules that are modulators of target gene expression where the target gene contains a riboswitch comprising an aptamer described herein.

BACKGROUND

Aptamers are oligonucleotides that bind to a target ligand with high affinity and specificity. These nucleic acid sequences have proven to be of high therapeutic and diagnostic value with recent FDA approval of the first aptamer drug and additional ones in the clinical pipelines. Their high degree of specificity and versatility have established RNA aptamers as one of the pivotal tools of the emerging RNA nanotechnology field in the fight against human diseases including cancer, viral infections and other diseases.

In addition, aptamers may be utilized as part of a riboswitch that has certain effects in the presence or absence of an aptamer ligand. For example, riboswitches may be used to regulate gene expression in response to the presence or absence of the aptamer ligand.

However, aptamers derived from prokaryotic sources or generated using in vitro selection methods often fail to demonstrate the functionality required for the expression of therapeutic targets genes in eukaryotic systems. As such, novel aptamer sequences able to regulate gene expression in response to the presence or absence of a small molecule ligand are needed.

SUMMARY

Provided herein are aptamer sequences that bind to small molecules, such as thiamine pyrophosphate (TPP) and analogs or derivatives thereof. Also contemplated are riboswitches and polynucleotide cassettes for regulating the expression of a target gene, wherein the polynucleotide cassettes comprise the aptamers disclosed herein. Further provided are methods of using said aptamers, riboswitches, and/or polynucleotide cassettes for the regulation of target genes, including therapeutic genes. Also provided herein are small molecules that are modulators of target gene expression where the target gene contains a riboswitch comprising an aptamer described herein.

In one aspect, provided is a polynucleotide cassette for regulating the expression of a target gene, wherein the polynucleotide cassette comprises a sequence encoding an aptamer that binds to a small molecule, wherein the aptamer encoding sequence comprises:

$ACX_1GGGGTCCGGCX_2TX_3TTCATTTGGCX_4CCG$-$GTGAGAX_5X_6AX_7ACCCTTX_8X_9X_{10}X_{11}CCTGTT$-$X_{12}ACGGATAATGCCGCX_{13}GCAGGGAGT$ (SEQ ID NO:1), wherein $X_1$ is A or G;
$X_2$ is C or no nucleotide;
$X_3$ is T or no nucleotide;
$X_4$ is A or G;
$X_5$ is any nucleotide;
$X_6$ is any nucleotide;
$X_7$ is any nucleotide;
$X_8$ is any nucleotide;
$X_9$ is C, G, or T;
$X_{10}$ is any nucleotide;
$X_{11}$ is A or T;
$X_{12}$ is C or T; and
$X_{13}$ is C or T.

In one aspect, provided is a polynucleotide cassette for regulating the expression of a target gene, wherein the polynucleotide cassette comprises a sequence encoding an aptamer that binds to a small molecule, wherein the aptamer encoding sequence comprises $ACX_1GGGGTCCGGCX_2$ $TX_3TTCATTTGGCGCCGGTGAGAX_5X_6AX_7ACCCTT$-$X_8$ $X_9X_{10}X_{11}CCTGTTX_{12}ACGGATAATGCCGCX_{13}G$-$CAGGGAGT$ (SEQ ID NO:2), wherein $X_1$ is A or G;
$X_2$ is C or no nucleotide;
$X_3$ is T or no nucleotide;
$X_5$ is G or T;
$X_6$ is C or T;
$X_7$ is C or T;
$X_8$ is any nucleotide;
$X_9$ is G or T;
$X_{10}$ is A, G, or T;
$X_{11}$ is A or T;
$X_{12}$ is C or T; and
$X_{13}$ is C or T.

In one aspect, provided is a polynucleotide cassette for regulating the expression of a target gene, wherein the polynucleotide cassette comprises a sequence encoding an aptamer that binds to a small molecule, wherein the aptamer encoding sequence comprises $ACAGGGGTCCGG$-$CCTTTTCATTTGGCGCCGGTGAGAGCACACCCTTT$-$GAA$ $CCTGTTX_{12}ACGGATAATGCCGCX_{13}GCA$-$GGGAGT$ (SEQ ID NO:3), wherein $X_{12}$ is C or T; and
$X_{13}$ is C or T.

In one aspect, provided is a polynucleotide cassette for regulating the expression of a target gene, wherein the polynucleotide cassette comprises a sequence encoding an aptamer that binds to a small molecule, wherein the aptamer encoding sequence comprises $ACX_1GGGGTCCGGCCTT$-$TTCATTTGGCGCCGGTGAGAGCACACCCTTX_8X_9X_{10}$ $X_{11}CCTGTTTACGGATAATGCCGCCGCAGGGAGT$ (SEQ ID NO:4), wherein $X_1$ is A or G;
$X_8$ is any nucleotide;
$X_9$ is G or T;
$X_{10}$ is A, G, or T; and
$X_{11}$ is A or T.

In one aspect, provided is a polynucleotide cassette for regulating the expression of a target gene, wherein the polynucleotide cassette comprises a sequence encoding an aptamer that binds to a small molecule, wherein the aptamer encoding sequence comprises ACAGGGGTCCGGC-CTTTTCATTTGGCGCCGGTGAGAX$_5$X$_6$AX$_7$ACCCT-TTGA ACCTGTTTACGGATAATGCCGCCGCAGG-GAGT (SEQ ID NO:5), wherein X$_5$ is G or T;

X$_6$ is C or T; and

X$_7$ is C or T.

In one aspect, provided is a polynucleotide cassette for regulating the expression of a target gene, wherein the polynucleotide cassette comprises a sequence encoding an aptamer that binds to a small molecule, wherein the aptamer encoding sequence comprises ACAGGGGTCCGGCCTT-TTCATTTGGCX$_4$CCGGTGAGAX$_5$X$_6$AX$_7$ACCCTTX$_8$ X$_9$X$_{10}$ACCTGTTCACGGATAATGCCGCTGCAGGGAGT (SEQ ID NO:6), wherein X$_4$ is A or G;

X$_5$ is any nucleotide;

X$_6$ is any nucleotide;

X$_7$ is any nucleotide;

X$_8$ is any nucleotide;

X$_9$ is C or G; and

X$_{10}$ is any nucleotide.

In one aspect, provided is a polynucleotide cassette for regulating the expression of a target gene, wherein the polynucleotide cassette comprises a sequence encoding an aptamer that binds to a small molecule, wherein the aptamer encoding sequence comprises a sequence that is at least 95% identical to a sequence selected from the group consisting of SEQ ID NOs:7-36 (see Table 1). In one aspect, provided is a polynucleotide cassette for regulating the expression of a target gene, wherein the polynucleotide cassette comprises a sequence encoding an aptamer that binds to a small molecule, wherein the aptamer encoding sequence comprises a sequence selected from the group consisting of SEQ ID NOs:7-36 (see Table 1).

In one aspect, provided is a polynucleotide cassette for regulating the expression of a target gene, wherein the polynucleotide cassette comprises a sequence encoding an aptamer that binds to a small molecule, wherein the aptamer encoding sequence comprises a sequence that is at least 95% identical to a sequence selected from the group consisting of SEQ ID NOs:8, 9, 14-18, 21, 25, 26, and 30. In one aspect, provided is a polynucleotide cassette for regulating the expression of a target gene, wherein the polynucleotide cassette comprises a sequence encoding an aptamer that binds to a small molecule, wherein the aptamer encoding sequence comprises a sequence selected from the group consisting of SEQ ID NOs:8, 9, 14-18, 21, 25, 26, and 30.

In a preferred embodiment, provided is a polynucleotide cassette for regulating the expression of a target gene, wherein the polynucleotide cassette comprises a sequence encoding an aptamer that binds to a small molecule, wherein the aptamer encoding sequence comprises a sequence that is at least 95% identical to a sequence selected from the group consisting of SEQ ID NOs: 9, 14, and 26. In a even more preferred embodiment, provided is a polynucleotide cassette for regulating the expression of a target gene, wherein the polynucleotide cassette comprises a sequence encoding an aptamer that binds to a small molecule, wherein the aptamer encoding sequence comprises a sequence selected from the group consisting of SEQ ID NOs: 9, 14, and 26.

In one aspect, provided is a sequence encoding an aptamer that binds to a small molecule, wherein the aptamer encoding sequence comprises:

ACX$_1$GGGGTCCGGCX$_2$TX$_3$TTCATTTGGCX$_4$CCG-GTGAGAX$_5$X$_6$AX$_7$ACCCTTX$_8$X$_9$X$_{10}$X$_{11}$CCTGTT-X$_{12}$ACGGATAATGCCGCX$_{13}$GCAGGGAGT (SEQ ID NO:1), wherein X$_1$ is A or G;

X$_2$ is C or no nucleotide;

X$_3$ is T or no nucleotide;

X$_4$ is A or G;

X$_5$ is any nucleotide;

X$_6$ is any nucleotide;

X$_7$ is any nucleotide;

X$_8$ is any nucleotide;

X$_9$ is C, G, or T;

X$_{10}$ is any nucleotide;

X$_{11}$ is A or T;

X$_{12}$ is C or T; and

X$_{13}$ is C or T.

In embodiments, the aptamer encoding sequence has one or more of the following properties: X$_1$ is not A; X$_2$ is not C; X$_3$ is not T; X$_4$ is not G; X$_5$ is not G; X$_6$ is not C; X$_7$ is not C; X$_8$ is not T; X$_9$ is not G; X$_{10}$ is not A; X$_{11}$ is not A; X$_{12}$ is not T; and X$_{13}$ is not C.

In embodiments, all of the following are not simultaneously present in the aptamer encoding sequence: X$_1$ is A; X$_2$ is C; X$_3$ is T; X$_4$ is G; X$_5$ is G; X$_6$ is C; X$_7$ is C; X$_8$ is T; X$_9$ is G; X$_{10}$ is A; X$_{11}$ is A; X$_{12}$ is T; and X$_{13}$ is C.

In one aspect, provided is a sequence encoding an aptamer that binds to a small molecule, wherein the aptamer encoding sequence comprises:

ACX$_1$GGGGTCCGGCX$_2$TX$_3$TTCATTTGGCGCCGG-TGAGAX$_5$X$_6$AX$_7$ACCCTTX$_8$ X$_9$X$_{10}$X$_{11}$CCTGT-TX$_{12}$ACGGATAATGCCGCX$_{13}$GCAGGGAGT (SEQ ID NO:2), wherein X$_1$ is A or G;

X$_2$ is C or no nucleotide;

X$_3$ is T or no nucleotide;

X$_5$ is G or T;

X$_6$ is C or T;

X$_7$ is C or T;

X$_8$ is any nucleotide;

X$_9$ is G or T;

X$_{10}$ is A, G, or T;

X$_{11}$ is A or T;

X$_{12}$ is C or T; and

X$_{13}$ is C or T.

In embodiments, the aptamer encoding sequence has one or more of the following properties: X$_1$ is not A; X$_2$ is not C; X$_3$ is not T; X$_4$ is not G; X$_5$ is not G; X$_6$ is not C; X$_7$ is not C; X$_8$ is not T; X$_9$ is not G; X$_{10}$ is not A; X$_{11}$ is not A; X$_{12}$ is not T; and X$_{13}$ is not C. In embodiments, all of the following are not simultaneously present in the aptamer encoding sequence: X$_1$ is A; X$_2$ is C; X$_3$ is T; X$_5$ is G; X$_6$ is C; X$_7$ is C; X$_8$ is T; X$_9$ is G; X$_{10}$ is A; X$_{11}$ is A; X$_{12}$ is T; and X$_{13}$ is C.

In one aspect, provided is a sequence encoding an aptamer that binds to a small molecule, wherein the aptamer encoding sequence comprises: ACAGGGGTCCGGCCTTTT-CATTTGGCGCCGGTGAGAGCACACCCTTTGAA CCTGTTX$_{12}$ACGGATAATGCCGCX$_{13}$GCAGGGAGT (SEQ ID NO:3), wherein X$_{12}$ is C or T; and X$_{13}$ is C or T.

In embodiments, the aptamer encoding sequence has one or more of the following properties: X$_{12}$ is not T; and X$_{13}$ is not C. In embodiments, all of the following are not simultaneously present in the aptamer encoding sequence: $X_{12}$ is T and $X_{13}$ is C.

In one aspect, provided is a sequence encoding an aptamer that binds to a small molecule, wherein the aptamer encoding sequence comprises:

ACX$_1$GGGGTCCGGCCTTTTCATTTGGCGCCGGT-
GAGAGCACACCCTTX$_8$X$_9$X$_{10}$X$_{11}$CCTGTTTACG-
GATAATGCCGCCGCAGGGAGT (SEQ ID NO:4),
wherein $X_1$ is A or G;

$X_8$ is any nucleotide;

$X_9$ is G or T;

$X_{10}$ is A, G, or T; and $X_{11}$ is A or T.

In embodiments, the aptamer encoding sequence has one or more of the following properties: $X_1$ is not A; $X_8$ is not T; $X_9$ is not G; $X_{10}$ is not A; $X_{11}$ is not A. In embodiments, all of the following are not simultaneously present in the aptamer encoding sequence: $X_1$ is A; $X_8$ is T; $X_9$ is G; $X_{10}$ is A; $X_{11}$ is A; $X_2$ is T; and $X_{13}$ is C.

In one aspect, provided is a sequence encoding an aptamer that binds to a small molecule, wherein the aptamer encoding sequence comprises:

ACAGGGGTCCGGCCTTTTCATTTGGCGCCGGTG-
AGAX$_5$X$_6$AX$_7$ACCCTTTGA ACCTGTTTACGGA-
TAATGCCGCCGCAGGGAGT (SEQ ID NO:5),
wherein $X_5$ is G or T;

$X_6$ is C or T; and $X_7$ is C or T.

In embodiments, the aptamer encoding sequence has one or more of the following properties: $X_5$ is not G; $X_6$ is not C; and $X_7$ is not C. In embodiments, all of the following are not simultaneously present in the aptamer encoding sequence: $X_5$ is G; $X_6$ is C; and $X_7$ is C.

In one aspect, provided is a sequence encoding an aptamer that binds to a small molecule, wherein the aptamer encoding sequence comprises:

ACAGGGGTCCGGCCTTTTCATTTGGCX$_4$CCGGT-
GAGAGX$_5$X$_6$AX$_7$ACCCTTX$_8$X$_9$X$_{10}$ACCTGTTCA-
CGGATAATGCCGCTGCAGGGAGT (SEQ ID NO:6), wherein $X_4$ is A or G;

$X_5$ is any nucleotide;

$X_6$ is any nucleotide;

$X_7$ is any nucleotide;

$X_8$ is any nucleotide;

$X_9$ is C or G; and $X_{10}$ is any nucleotide.

In one aspect, provided is a sequence encoding an aptamer that binds to a small molecule, wherein the aptamer encoding sequence comprises a sequence that is at least 95% identical to a sequence selected from the group consisting of SEQ ID NOs:7-36 (see Table 1). In some embodiments, the aptamer encoding sequence comprises a sequence selected from the group consisting of SEQ ID NOs:8, 9, 14-18, 21, 25, 26, and 30. In one embodiment, the aptamer encoding sequence comprises a sequence selected from the group consisting of SEQ ID NOs: 9, 14, and 26.

In some embodiments, the aptamer binds to, or otherwise responds to the presence of, a small molecule disclosed herein including small molecules having the structure according to Formula I-VIII. In embodiments, the small molecule has the structure according to Formula I:

6

(I)

wherein:

$R^1$ is selected from the group consisting of OH, amino, F, Cl, Br, phosphate, pyrophosphate, —O—C(=O)—C$_1$-C$_6$ alkyl, —O—C(=O)—C$_2$-C$_6$ alkenyl, —O—C(=O)-phenyl, —O—C(=O)-heterocycle, —O—C(=O)—O—C$_1$-C$_6$ alkyl, —O—C(=O)—O—C$_2$-C$_6$ alkenyl, —O—C(=O)—O-phenyl, and —O—C(=O)—O-heterocycle.

In embodiments, the small molecule has the structure according to Formula II:

(II)

wherein:

$R^2$ is selected from the group consisting of H, C$_1$-C$_6$ alkyl, C$_2$-C$_6$ alkenyl, —(CH$_2$)$_n$—R$^6$, —C(=O)—R$^4$, —C(=O)—O—R$^4$, —CHR$^5$—O—C(=O)—R$^4$, —S—C$_1$-C$_6$ alkyl, —S—C$_2$-C$_6$ alkenyl, —S-heterocycle, and —S—CH$_2$-heterocycle;

or $R^2$ is —S-[Formula II] such that the compound forms a dimer of two molecules of Formula II connected through a disulfide (—S—S—) linkage;

$R^3$ is selected from the group consisting of OH, amino, F, Cl, Br, phosphate, pyrophosphate, —O—C(=O)—C$_1$-C$_6$ alkyl, —O—C(=O)—C$_1$-C$_6$ alkenyl, —O—C(=O)-phenyl, —O—C(=O)-heterocycle, —O—C(=O)—O—C$_1$-C$_6$ alkyl, —O—C(=O)—O—C$_1$-C$_6$ alkenyl, —O—C(=O)—O-phenyl, —O—C(=O)—O-heterocycle;

$R^4$ is selected from the group consisting of H, C$_1$-C$_6$ alkyl, C$_2$-C$_6$ alkenyl, C$_3$-C$_7$ cycloalkyl, C$_6$-C$_{10}$ bicyclyl, C$_9$-C$_{14}$ tricyclyl, —(C$_1$-C$_6$ alkyl)-aryl, —(C$_2$-C$_6$ alkenyl)-aryl, aryl, heteroaryl and hetercyclyl;

$R^5$ is selected from the group consisting of H, C$_1$-C$_6$ alkyl, C$_2$-C$_6$ alkenyl, C$_3$-C$_7$ cycloalkyl, aryl, heteroaryl and hetercyclyl;

$R^6$ is hydroxyl, amino, amido, C$_1$-C$_6$ alkoxy, C$_3$-C$_7$ cycloalkyl, C$_6$-C$_{10}$ bicyclyl, aryl, heteroaryl and hetercyclyl; and n is 1 to 8;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, C$_1$-C$_6$ alkyl, C$_2$-C$_6$ alkenyl, C$_3$-C$_7$ cycloalkyl, C$_6$-C$_{10}$ bicyclyl, C$_1$-C$_6$ haloalkyl, C$_1$-C$_6$ perhaloalkyl, —O—(C$_1$-C$_6$ alkyl), O—(C$_3$-C$_7$ cycloalkyl), —O—

7

8

(C_1-C_6 haloalkyl), —O—(C_1-C_6 perhaloalkyl), aryl, —O-aryl, —(C_1-C_6 alkyl)-aryl, —O—(C_1-C_6 alkyl)-aryl, —S—(C_1-C_6 alkyl), —S—(C_3-C_7 cycloalkyl), —S—(C_1-C_6 haloalkyl), —S—(C_1-C_6 perhaloalkyl), —S-aryl, —S—(C_1-C_6 alkyl)-aryl, heteroaryl and hetercyclyl.

In embodiments, the small molecule has the structure according to Formula III:

(III)

wherein:

$R^2$ is selected from the group consisting of H, $C_1$-$C_6$ alkyl, $C_2$-$C_6$ alkenyl, —$(CH_2)_n$—$R^6$, —$C(=O)$—$R^4$, —$C(=O)$—$O$—$R^4$, —$CHR^5$—$O$—$C(=O)$—$R^4$, —$S$—$C_1$-$C_6$ alkyl, —$S$—$C_2$-$C_6$ alkenyl, —S-heterocycle, and —$S$—$CH_2$-heterocycle;

$R^{31}$ is selected from the group consisting of OH and phosphate;

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

$R^5$ is selected from the group consisting of H, $C_1$-$C_6$ alkyl, $C_2$-$C_6$ alkenyl, $C_3$-$C_7$ cycloalkyl, aryl, heteroaryl and hetercyclyl;

$R^6$ is hydroxyl, amino, amido, $C_1$-$C_6$ alkoxy, $C_3$-$C_7$ cycloalkyl, $C_6$-$C_{10}$ bicyclyl, aryl, heteroaryl and hetercyclyl; and n is 1 to 8;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has the structure according to Formula IV:

(IV)

wherein:

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

$R^5$ is selected from the group consisting of H, $C_1$-$C_6$ alkyl, $C_2$-$C_6$ alkenyl, $C_3$-$C_7$ cycloalkyl, aryl, heteroaryl and hetercyclyl;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has the structure according to Formula V:

(V)

wherein:

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has the structure according to Formula VI:

(VI)

wherein:

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In some embodiments, the small molecule has the structure according to Formula VII:

(VII)

wherein each $R^7$ is independently selected from halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl;

additionally or alternatively, two adjacent $R^7$ groups may be taken together to form a fused 5- or 6-membered aromatic or non-aromatic ring, which contains 0 to 2 ring heteroatoms, and which is unsubstituted or is substituted by up to four substituents selected from halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl; and m is 0, 1, 2, 3 or 4.

In some embodiments, the small molecule has the structure according to Formula VIII:

(VIII)

wherein:

each $R^8$ is independently selected from halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl;

additionally or alternatively, two adjacent $R^8$ groups may be taken together to form a fused 5- or 6-membered aromatic or non-aromatic ring, which contains 0 to 2 ring heteroatoms, and which is unsubstituted or is substituted by up to four substituents selected from halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl;

each $R^9$ is independently selected from halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl;

additionally or alternatively, two adjacent $R^9$ groups may be taken together to form a fused 5- or 6-membered aromatic or non-aromatic ring, which contains 0 to 2 ring heteroatoms, and which is unsubstituted or is substituted by up to four substituents selected from halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—(C$_1$-C$_6$ haloalkyl), —S—(C$_1$-C$_6$ perhaloalkyl), —S-aryl, —S—(C$_1$-C$_6$ alkyl)-aryl, heteroaryl and hetercyclyl;

x is 0, 1, 2 or 3; and y is 0, 1, 2, 3, or 4.

In some embodiments, the aptamer binds to, or otherwise responds to the presence of, a small molecule selected from the group consisting of acefurtiamine, acetiamine, allithiamine, amprolium, beclotiamine, benfotiamine, bentiamine, bisbentiamine, cetotiamine, cycotiamine, fursultiamine, monophosphothiamine, octotiamine, oxythiamine, prosultiamine, sulbutiamine, thiamine, thiamine pyrophosphate, and vintiamol. In a preferred embodiment, the aptamer binds to, or otherwise responds to the presence of, a small molecule selected from the group consisting of benfotiamine, fursultiamine, and prosultiamine. In some embodiments, the aptamer binds to, or otherwise responds to the presence of, benfotiamine. In embodiments, the aptamer binds to, or otherwise responds to the presence of, fursultiamine. In embodiments, the aptamer binds to, or otherwise responds to the presence of, prosultiamine.

In some embodiments, the aptamer has reduced binding and/or shows a reduced response to thiamine pyrophosphate (TPP) compared to equimolar amounts of fursultiamine, benfotiamine or prosultiamine. In some embodiments where the aptamer is in the context of a riboswitch encoded as part of a polynucleotide cassette for regulating the expression of a target gene, the aptamer has reduced response to TPP compared to equimolar amounts of fursultiamine, benfotiamine or prosultiamine.

Also provided is a riboswitch for the regulation of target gene expression in response to a small molecule, wherein the riboswitch comprises an aptamer disclosed herein. In one embodiment, the riboswitch encoding sequence comprises the sequence of SEQ ID NO:37.

Also provided is a polynucleotide cassette for the regulation of the expression of a target gene in response to a small molecule, the polynucleotide cassette comprising:

(a) a riboswitch; and (b) an alternatively-spliced exon, flanked by a 5' intron and a 3' intron, wherein the riboswitch comprises (i) an effector region comprising a stem that includes the 5' splice site sequence of the 3' intron, and (ii) an aptamer disclosed herein; and wherein the alternatively-spliced exon comprises a stop codon that is in-frame with the target gene when the alternatively-spliced exon is spliced into the target gene mRNA.

In one embodiment, the polynucleotide cassette comprises a riboswitch encoding sequence comprising the sequence of SEQ ID NO:37 and further comprising an aptamer encoding sequence, wherein the aptamer sequence is selected from an aptamer sequence disclosed herein.

In one embodiment, provided is a nucleic acid molecule comprising an aptamer, riboswitch, and/or polynucleotide cassette disclosed herein. Also provided is a nucleic acid molecule comprising a target gene containing a riboswitch or a polynucleotide cassette disclosed herein. In one embodiment, the polynucleotide cassette is located in the protein coding sequence of the target gene. In one embodiment, the polynucleotide cassette is located in an untranslated region of the target gene or in an intron of the target gene.

Also provided is a vector comprising any of the nucleic acid molecules disclosed herein. In one embodiment, the vector is a viral vector. In some embodiments, the viral vector is selected from the group consisting of an adenoviral vector, an adeno-associated virus vector, and a lentiviral vector.

In one aspect, provided is a method for identifying an aptamer that modulates target gene expression in response to a compound of interest (e.g., a thiamine analog or derivate, such as a compound according to Formula I-VIII), the method comprising the steps of:

(i) selecting a parent aptamer sequence;

(ii) generating a riboswitch library comprising a sequences encoding all or part of the aptamer selected in step (i) wherein the aptamer encoding sequences comprise one or more randomly mutated nucleotides in one or more unpaired regions in the aptamer, wherein the mutated aptamer sequences are in the context of a riboswitch that controls the expression of a reporter gene;

(iii) screening the library from (ii) for aptamers having increased regulation (e.g., higher fold induction or repression) of the target gene expression in response to exposure to the compound of interest, compared to the parent aptamer sequence;

(iv) optionally repeating steps (ii) and (iii) (on an aptamer identified in step (iii) instead of an aptamer selected in step (i).

In embodiments, the parent aptamer sequence is a TTP aptamer (including a putative TPP aptamer or a known TPP aptamer). In embodiments, the parent aptamer sequence is selected from Rfam TPP riboswitch family RF00059. In embodiments, the one or more unpaired regions of the aptamer sequence are junction (J) regions. In addition or alternatively, the unpaired region may be a loop (L) region. In further embodiments, the sequence encoding the aptamer having one or more nucleotides in one or more unpaired regions that are randomly mutated, also has one or more nucleotides in a paired (P) region mutated, for example in one or more paired nucleotides adjacent to an unpaired region.

In embodiments, the compound of interest is a thiamine analog or derivative. In embodiments, the thiamine analog is fursultiamine, benfotiamine or prosultiamine. In one embodiment, the aptamer has reduced binding and/or shows a reduced response to thiamine pyrophosphate (TPP) compared to equimolar amounts of fursultiamine, benfotiamine or prosultiamine. In embodiments, the compound of interest is a compound according to Formulas I-VIII, In embodiments, the compound of interest is a compound according to Formulas I-III.

In aspects, the disclosure provides compounds of Formulas I-VIII. In embodiments, the disclosure provides compounds of Formulas I-VIII in a pharmaceutical composition.

BRIEF DESCRIPTION OF THE FIGURES

FIG. 4 illustrates the improvement of gene regulation activity through mutagenesis of the aptamers contained within riboswitches. Riboswitch constructs comprising randomly mutated aptamers (derived from aptamer libraries A1, A2, or A3) were screened for improved gene regulation activity in HEK cells. Transfected HEK cells were treated with 50 μM fursultiamine or left untreated. Examples of riboswitches comprising re-engineered aptamer sequences that were isolated in the screen and that demonstrated improved gene regulation activity as compared to riboswitch 14G4 are shown in FIG. 4A.

FIGS. 4A-4C: The fold induction was calculated as the quotient of the luciferase activity recorded for cells exposed to TPP or a thiamine analog divided by the luciferase activity recorded for cells that were not exposed to TPP or to a thiamine analog.

FIG. 5 shows the nucleotide sequence of the 3H4 aptamer encoding sequence (SEQ ID NO:9), which was obtained through mutagenesis of 14G4. Nucleotides that were randomly mutated to obtain aptamer library A4 (SEQ ID NO:42) are indicated with "N" in the aptamer encoding sequence.

FIG. 7 illustrates the ability of riboswitches comprising re-engineered aptamer sequences to induce expression of a variety of target genes in response to a ligand. FIGS. 7B and 7C illustrate that a riboswitch comprising 3H4 or 15D10, respectively, regulate mouse erythropoietin (mEpo) expression in response to fursultiamine treatment. AML12 cells were transfected with Epo-3H4 or Epo-15D10 constructs. The transfected cells were treated with fursultiamine at the indicated doses or left untreated. The expression of mEpo was detected and quantified using mEpo ELISA and was expressed as mean±S.D. (FIG. 7C). The fold induction was calculated as the quotient of the amount of mEpo produced from cells treated with fursultiamine divided by the amount of mEpo produced from cells without fursultiamine treatment (FIG. 7D).

FIG. 8 illustrates the inducible expression of luciferase by riboswitches comprising re-engineered aptamer sequences in vivo. Adeno-associated AAV2/8 viral particles were produced containing an intron-alternative exon-intron cassette with (1) a non-regulatable riboswitch without aptamer ("Control 1"), (2) a riboswitch cassette comprising aptamer 3H4 ("Switch 3H4" or "3H4"), or (3) a riboswitch cassette comprising aptamer 6B4 ("Switch 6B4" or "6B4"). Balb/c mice (n=5 each group) were injected with single tail vein injection of $1.0 \times 10^{11}$ (FIGS. 8A, 8B, and 8D) or $2.5 \times 10^{11}$ (FIGS. 8C and 8E) viral particles per mouse. Twenty-eight days after AAV delivery, mice were injected with 50 mg/kg prosultiamine intraperitoneally. Luciferase activity was measured the day prior to drug dosing, as well as 6 h, 24 h, 48 h, and 72 h after drug dosing. After the first administration of prosultiamine, the mice were subjected to three additional rounds of dosing and imaging cycles as follows: Day 36 (after AAV administration): 100 mg/kg; day 43: 200 mg/kg; and day 51: 400 mg/kg.

DETAILED DESCRIPTION

Figure 1A:
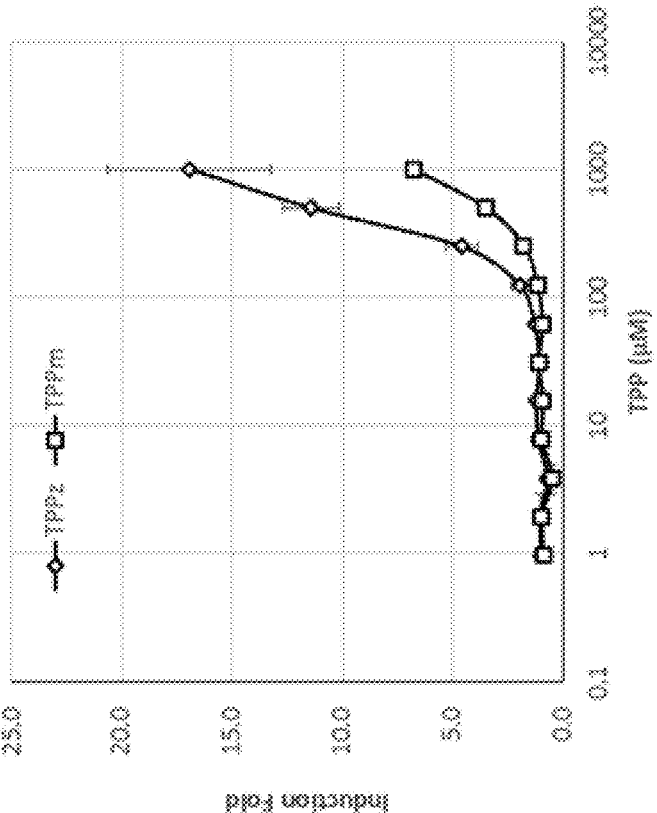
FIG. 1 illustrates that a synthetic riboswitch TPPz or TPPm comprising the thiC and thiM TPP aptamer, respectively, induce luciferase expression in response to treatment with thiamine pyrophosphate (TPP) or a thiamine analog. HEK 293 cells were transfected with constructs containing the luciferase gene containing the TPPz or TPPm riboswitch. Transfected cells were treated with TPP (FIG. 1A), fursultiamine (FIG. 1B), prosultiamine (FIG. 1C), bisbentiamine, beclotiamine or sulbutiamine (FIG. 1D), at the doses indicated or left untreated. The luciferase activity was expressed as mean arbitrary light units (ALU)±S.D., and fold induction was calculated as the quotient of the luciferase activity recorded for cells exposed to TPP or a thiamine analog divided by the luciferase activity recorded for cells that were not exposed to TPP or a thiamine analog.
Figure 1A:
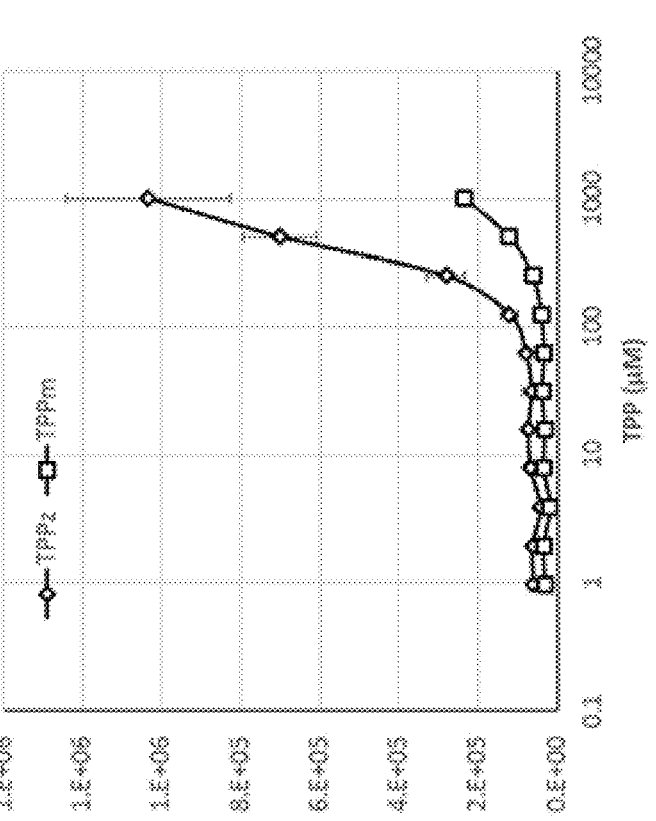

Provided herein are aptamer sequences that bind to, or otherwise respond to the presence of, small molecules, such as thiamine or TPP and analogs or derivatives of thiamine or TPP. In some embodiments, the aptamer sequences provided herein are useful for the regulation of the expression of a target gene in response to an analog or derivative of thiamine or TPP. Also contemplated are riboswitches comprising the aptamer sequences disclosed herein, as well as polynucleotide cassettes for regulating the expression of a target gene, wherein the polynucleotide cassettes comprise sequences encoding the riboswitches disclosed herein. Also provided herein are methods of using the aptamers, riboswitches, and/or polynucleotide cassettes for the regulation of target genes, including therapeutic genes, and for the treatment of subjects in need thereof.

Aptamers

Aptamers are single-stranded nucleic acid molecules that non-covalently bind to specific ligands with high affinity and specificity by folding into three-dimensional structures. Aptamer ligands include ions, small molecules, proteins, viruses, and cells. Aptamer ligands can be, for example, an organic compound, amino acid, steroid, carbohydrate, or nucleotide. Non-limiting examples of small molecule aptamer ligands include antibiotics, therapeutics, dyes, cofactors, metabolites, molecular markers, neurotransmitters, pollutants, toxins, food adulterants, carcinogens, drugs of abuse. As such, aptamers are useful for the detection of small molecules. Application of small-molecule detection by aptamers include environmental monitoring, food safety, medicine (including diagnostics), microbiology, analytical chemistry, forensic science, agriculture, and basic biology research.

The term "aptamer" as used herein refers to an RNA polynucleotide (or DNA sequence encoding the RNA polynucleotide) that specifically binds to a class of ligands. The term "ligand" refers to a molecule that is specifically bound by an aptamer. Aptamers have binding regions that are capable of forming complexes with an intended target molecule (i.e., the ligand). An aptamer will typically be between about 15 and about 200 nucleotides in length. More commonly, an aptamer will be between about 30 and about 100 nucleotides in length, for example, 70 to 90 nucleotides in length. Aptamers typically comprise multiple paired (P) regions in which the aptamer forms a stem and unpaired regions where the aptamer forms a joining (J) region or a loop (L) region. The paired regions can be numbered sequentially starting at the 5' end (P1) and numbering each stem sequentially (P2, P3, etc.). The loops (L1, L2, etc.) are numbered based on the adjacent paired region and the joining regions are numbered according to the paired regions that they link.

In one embodiment, the aptamer encoding sequence comprises $ACX_1GGGGTCCGGCX_2TX_3TTCATTTGGCX_4CCGGT$-$GAGAX_5X_6AX_7ACCCTTX_8X_9X_{10}$ $X_{11}CCTGTTX_{12}$ $ACGGATAATGCCGCX_{13}GCAGGGAGT$ (SEQ ID NO: 1), wherein $X_1$ is A or G;

$X_2$ is C or no nucleotide;

$X_3$ is T or no nucleotide;

$X_4$ is A or G;

$X_8$ is any nucleotide;

$X_6$ is any nucleotide;

$X_7$ is any nucleotide;

$X_8$ is any nucleotide;

$X_9$ is C, G, or T;

$X_{10}$ is any nucleotide;

$X_{11}$ is A or T;

$X_{12}$ is C or T; and $X_{13}$ is C or T.

In embodiments, the aptamer encoding sequence has one or more of the following properties: $X_1$ is not A; $X_2$ is not C; $X_3$ is not T; $X_4$ is not G; $X_8$ is not G; $X_6$ is not C; $X_7$ is not C; $X_8$ is not T; $X_9$ is not G; $X_{10}$ is not A; $X_{11}$ is not A; $X_{12}$ is not T; and $X_{13}$ is not C. In embodiments, all of the following are not simultaneously present in the aptamer encoding sequence: $X_1$ is A; $X_2$ is C; $X_3$ is T; $X_5$ is G; $X_6$ is C; $X_7$ is C; $X_8$ is T; $X_9$ is G; $X_{10}$ is A; $X_{11}$ is A; $X_{12}$ is T; and $X_{13}$ is C.

In one embodiment, the aptamer encoding sequence comprises $ACX_1GGGGTCCGGCX_2TX_3TTCATTTGGCG$-$CCGGTGAGAX_5X_6AX_7ACCCTTX_8X_9X_{10}$ $X_{11}CCTGT$-$TX_{12}$ $ACGGATAATGCCGCX_{13}GCAGGGAGT$ (SEQ ID NO:2), wherein $X_1$ is A or G;

$X_2$ is C or no nucleotide;

$X_3$ is T or no nucleotide;

$X_5$ is G or T;

$X_6$ is C or T;

$X_7$ is C or T;

$X_8$ is any nucleotide;

$X_9$ is G or T;

$X_{10}$ is A, G, or T;

$X_{11}$ is A or T;

$X_{12}$ is C or T; and $X_{13}$ is C or T.

In embodiments, the aptamer encoding sequence has one or more of the following properties: $X_1$ is not A; $X_2$ is not C; $X_3$ is not T; $X_4$ is not G; $X_8$ is not G; $X_6$ is not C; $X_7$ is not C; $X_8$ is not T; $X_9$ is not G; $X_{10}$ is not A; $X_{11}$ is not A; $X_{12}$ is not T; and $X_{13}$ is not C. In embodiments, all of the following are not simultaneously present in the aptamer sequence: $X_1$ is A; $X_2$ is C; $X_3$ is T; $X_8$ is G; $X_6$ is C; $X_7$ is C; $X_8$ is T; $X_9$ is G; $X_{10}$ is A; $X_{11}$ is A; $X_{12}$ is T; and $X_{13}$ is C.

In one embodiment, the aptamer encoding sequence comprises: $ACAGGGGTCCGGCCTTTTCATTTGGCGCC$-$GGTGAGAGCACACCCTTTGAACCTGT$ $TX_{12}AC$-$GGATAATGCCGCX_{13}GCAGGGAGT$ (SEQ ID NO:3), wherein $X_{12}$ is C or T; and $X_{13}$ is C or T.

In embodiments, the aptamer encoding sequence has one or more of the following properties: $X_{12}$ is not T; and $X_{13}$ is not C. In embodiments, all of the following are not simultaneously present in the aptamer sequence: $X_{12}$ is T and $X_{13}$ is C.

In one embodiment, the aptamer encoding sequence comprises: ACX$_1$GGGGTCCGGCCTTTTCATTTGGCGCC-GGTGAGAGCACACCCTTX$_8$X$_9$X$_{10}$X$_{11}$C CTGTTTACGG-GATAATGCCGCCGCAGGGAGT (SEQ ID NO:4), wherein $X_1$ is A or G;

$X_8$ is any nucleotide;

$X_9$ is G or T;

$X_{10}$ is A, G, or T; and $X_{11}$ is A or T.

In embodiments, the aptamer encoding sequence has one or more of the following properties: $X_1$ is not A; $X_8$ is not T; $X_9$ is not G; $X_{10}$ is not A; $X_{11}$ is not A. In embodiments, all of the following are not simultaneously present in the aptamer sequence: $X_1$ is A; $X_8$ is T; $X_9$ is G; $X_{10}$ is A; $X_{11}$ is A; $X_{12}$ is T; and $X_{13}$ is C.

In one embodiment, the aptamer encoding sequence comprises: ACAGGGGTCCGGCCTTTTCATTTGGCGCCG-GTGAGAX$_5$X$_6$AX$_7$ACCCTTTGAACCT GTTTACGGA-TAATGCCGCCGCAGGGAGT (SEQ ID NO:5), wherein $X_5$ is G or T;

$X_6$ is C or T; and $X_7$ is C or T.

In embodiments, the aptamer encoding sequence has one or more of the following properties: $X_5$ is not G; $X_6$ is not C; and $X_7$ is not C. In embodiments, all of the following are not simultaneously present in the aptamer sequence: $X_5$ is G; $X_6$ is C; and $X_7$ is C.

In one embodiment, the aptamer encoding sequence comprises: ACAGGGGTCCGGCCTTTTCATTTGGCX$_4$CCG-GTGAGAX$_5$X$_6$AX$_7$ACCCTTXX$_9$X$_{10}$AC CTGTTCACG-GATAATGCCGCTGCAGGGAGT (SEQ ID NO:6), wherein $X_4$ is A or G;

$X_5$ is any nucleotide;

$X_6$ is any nucleotide;

$X_7$ is any nucleotide;

$X_8$ is any nucleotide;

$X_9$ is C or G; and $X_{10}$ is any nucleotide.

In one embodiment, the aptamer encoding sequence comprises a sequence selected from the group consisting of SEQ ID NOs:7-36 (see Table 1). In one embodiment, the aptamer encoding sequence comprises a sequence that is at least 80%, at least 85%, at least 90%, at least 95%, at least 96%, at least 97%, at least 98%, or at least 99% identical to a sequence selected from the group consisting of SEQ ID NOs:7-36. "Percent sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity. Alignment for purposes of determining percent amino acid or nucleic acid sequence identity can be achieved in ways known to the ordinarily-skilled artisan, for example, using publicly available computer software programs including BLAST, BLAST-2, ALIGN or Megalign (DNASTAR) software.

TABLE 1

Aptamer coding sequences

| SEQ ID NO: | Aptamer | Aptamer encoding sequence |
|---|---|---|
| 7 | 14G4 (parent) | ACAGGGGTCCGGCCTTTTCATTTGGCGCCGGTGAGAGCACAC CCTTTGAACCTGTTTACGGATAATGCCGCCGCAGGGAGT |
| 8 | 1D10 | ACAGGGGTCCGGCCTTTTCATTTGGCGCCGGTGAGATTATACC CTTTGAACCTGTTTACGGATAATGCCGCCGCAGGGAGT |
| 9 | 3H4 | ACAGGGGTCCGGCCTTTTCATTTGGCGCCGGTGAGAGCACAC CCTTTGAACCTGTTCACGGATAATGCCGCTGCAGGGAGT |
| 10 | 3F10 | ACGGGGGTCCGGCCTTTTCATTTGGCGCCGGTGAGAGCACAC CCTTCGGACCTGTTTACGGATAATGCCGCCGCAGGGAGT |
| 11 | 3H9 | ACAGGGGTCCGGCCTTTTCATTTGGCGCCGGTGAGAGCACACC CTTATGACCTGTTTACGGATAATGCCGCCGCAGGGAGT |
| 12 | 4G2 | ACGGGGGTCCGGCCTTTTCATTTGGCGCCGGTGAGAGCACAC CCTTTGGACCTGTTTACGGATAATGCCGCCGCAGGGAGT |
| 13 | 6D2 | ACGGGGGTCCGGCCTTTTCATTTGGCGCCGGTGAGAGCACAC CCTTTGTTCCTGTTTACGGATAATGCCGCCGCAGGGAGT |
| 14 | 6B4 | ACAGGGGTCCGGCCTTTTCATTTGGCGCCGGTGAGAGCACAC CCTTGTGACCTGTTTACGGATAATGCCGCCGCAGGGAGT |
| 15 | 4H2 | ACAGGGGTCCGGCCTTTTCATTTGGCGCCGGTGAGAGCACAC CCTTCGGACCTGTTTACGGATAATGCCGCCGCAGGGAGT |
| 16 | 6C4 | ACGGGGGTCCGGCCTTTTCATTTGGCGCCGGTGAGAGCACAC CCTTCGAACCTGTTTACGGATAATGCCGCCGCAGGGAGT |
| 17 | 6G12 | ACAGGGGTCCGGCCTTTTCATTTGGCGCCGGTGAGAGCACAC CCTTTGGACCTGTTTACGGATAATGCCGCCGCAGGGAGT |
| 18 | 8F1 | ACGGGGGTCCGGCCTTTCATTTGGCGCCGGTGAGAGCACACC CTTCGGACCTGTTTACGGATAATGCCGCCGCAGGGAGT |
| 19 | 10A7 | ACAGGGGTCCGGCCTTTTCATTTGGCGCCGGTGAGATGATAC CCTTTGGACCTGTTCACGGATAATGCCGCTGCAGGGAGT |
| 20 | 12D5 | ACAGGGGTCCGGCCTTTTCATTTGGCGCCGGTGAGAGCACAC CCTTTGGACCTGTTCACGGATAATGCCGCTGCAGGGAGT |
| 21 | 12G7 | ACAGGGGTCCGGCCTTTTCATTTGGCGCCGGTGAGATTATACC CTTCGGACCTGTTCACGGATAATGCCGCTGCAGGGAGT |
| 22 | 12H3 | ACAGGGGTCCGGCCTTTTCATTTGGCGCCGGTGAGATCACAC CCTTACTACCTGTTCACGGATAATGCCGCTGCAGGGAGT |
| 23 | 13H7 | ACAGGGGTCCGGCCTTTTCATTTGGCGCCGGTGAGAACAGAC CCTTTGCACCTGTTCACGGATAATGCCGCTGCAGGGAGT |
| 24 | 13B6 | ACAGGGGTCCGGCCTTTTCATTTGGCGCCGGTGAGAACACAC CCTTTGTACCTGTTCACGGATAATGCCGCTGCAGGGAGT |
| 25 | 15A5 | ACAGGGGTCCGGCCTTTTCATTTGGCGCCGGTGAGATTATACC CTTACTACCTGTTCACGGATAATGCCGCTGCAGGGAGT |
| 26 | 15D10 | ACAGGGGTCCGGCCTTTTCATTTGGCACCGGTGAGAACATAC CCTTCGGACCTGTTCACGGATAATGCCGCTGCAGGGAGT |
| 27 | 15F9 | ACAGGGGTCCGGCCTTTTCATTTGGCGCCGGTGAGATTACACC CTTAGCACCTGTTCACGGATAATGCCGCTGCAGGGAGT |
| 28 | 16E5 | ACAGGGGTCCGGCCTTTTCATTTGGCGCCGGTGAGATCAAAC CCTTGGCACCTGTTCACGGATAATGCCGCTGCAGGGAGT |
| 29 | 16G8 | ACAGGGGTCCGGCCTTTTCATTTGGCGCCGGTGAGAGTACAC CCTTCGCACCTGTTCACGGATAATGCCGCTGCAGGGAGT |

TABLE 1-continued

Aptamer coding sequences

| SEQ ID NO: | Ap-tamer | Aptamer encoding sequence |
|---|---|---|
| 30 | 16G6 | ACAGGGGTCCGGCCTTTTCATTTGGCGCCGGTGAGATCACAC CCTTGGTACCTGTTCACGGATAATGCCGCTGCAGGGAGT |
| 31 | 17E2 | ACAGGGGTCCGGCCTTTTCATTTGGCGCCGGTGAGATTACACC CTTTGGACCTGTTCACGGATAATGCCGCTGCAGGGAGT |
| 32 | 17G1 | ACAGGGGTCCGGCCTTTTCATTTGGCGCCGGTGAGATCACAC CCTTGGAACCTGTTCACGGATAATGCCGCTGCAGGGAGT |
| 33 | 17D3 | ACAGGGGTCCGGCCTTTTCATTTGGCGCCGGTGAGAGGATAC CCTTCGGACCTGTTCACGGATAATGCCGCTGCAGGGAGT |
| 34 | 17F5 | ACAGGGGTCCGGCCTTTTCATTTGGCGCCGGTGAGAGTATAC CCTTAGTACCTGTTCACGGATAATGCCGCTGCAGGGAGT |
| 35 | 17G3 | ACAGGGGTCCGGCCTTTTCATTTGGCACCGGTGAGACAATAC CCTTGGTACCTGTTCACGGATAATGCCGCTGCAGGGAGT |
| 36 | 18G9 | ACAGGGGTCCGGCCTTTTCATTTGGCGCCGGTGAGAGAATAC CCTTGGTACCTGTTCACGGATAATGCCGCTGCAGGGAGT |

The ordinarily-skilled artisan would understand that the aptamers described herein may be ribonucleic acid (RNA) molecules. In embodiments, the aptamers described herein are part of a longer RNA polynucleotide, including, for example, hnRNA, mRNA, siRNA, or miRNA.

In one aspect, provided is an aptamer comprising the sequence: ACX$_1$GGGGUCCGGCX$_2$UX$_3$UUCAUUUGGCX$_4$ CCGGUGAGAX$_5$X$_6$AX$_7$ACCCUUX$_8$X$_9$ X$_{10}$X$_{11}$CCU-GUUX$_{12}$ACGGAUAAUGCCGCX$_{13}$GCAGGGAGU (SEQ ID NO:43), wherein X$_1$ is A or G;
X$_2$ is C or no nucleotide;
X$_3$ is U or no nucleotide;
X$_4$ is A or G;
X$_5$ is any nucleotide;
X$_6$ is any nucleotide;
X$_7$ is any nucleotide;
X$_8$ is any nucleotide;
X$_9$ is C, G, or U;
X$_{10}$ is any nucleotide;
X$_{11}$ is A or U;
X$_{12}$ is C or U; and
X$_{13}$ is C or U.

In embodiments, the aptamer sequence has one or more of the following properties: X$_1$ is not A; X$_2$ is not C; X$_3$ is not U; X$_4$ is not G; X$_5$ is not G; X$_6$ is not C; X$_7$ is not C; X$_8$ is not U; X$_9$ is not G; X$_{10}$ is not A; X$_{11}$ is not A; X$_{12}$ is not U; and X$_{13}$ is not C.

In embodiments, all of the following are not simultaneously present in the aptamer sequence: X$_1$ is A; X$_2$ is C; X$_3$ is U; X$_4$ is G; X$_5$ is G; X$_6$ is C; X$_7$ is C; X$_8$ is U; X$_9$ is G; X$_{10}$ is A; X$_{11}$ is A; X$_{12}$ is U; and X$_{13}$ is C.

In one aspect, provided is an aptamer comprising the sequence: ACX$_1$GGGGUCCGGCX$_2$UX$_3$UUCAUUUGG-CGCCGGUGAGAX$_5$X$_6$AX$_7$ACCCUUX$_8$X$_9$X$_{10}$X$_{11}$CCU-GUUX$_{12}$ACGGAUAAUGCCGCX$_{13}$GCAGGGAGU (SEQ ID NO:44), wherein X$_1$ is A or G;
X$_2$ is C or no nucleotide;
X$_3$ is U or no nucleotide;

X$_8$ is G or U;
X$_6$ is C or U;
X$_7$ is C or U;
X$_8$ is any nucleotide;
X$_9$ is G or U;
X$_{10}$ is A, G, or U;
X$_{11}$ is A or U;
X$_{12}$ is C or U; and
X$_{13}$ is C or U.

In embodiments, the aptamer sequence has one or more of the following properties: X$_1$ is not A; X$_2$ is not C; X$_3$ is not U; X$_4$ is not G; X$_8$ is not G; X$_6$ is not C; X$_7$ is not C; X$_8$ is not U; X$_9$ is not G; X$_{10}$ is not A; X$_{11}$ is not A; X$_{12}$ is not U; and X$_{13}$ is not C. In embodiments, all of the following are not simultaneously present in the aptamer sequence: X$_1$ is A; X$_2$ is C; X$_3$ is U; X$_5$ is G; X$_6$ is C; X$_7$ is C; X$_8$ is U; X$_9$ is G; X$_{10}$ is A; X$_1$ is A; X$_{12}$ is U; and X$_{13}$ is C.

In one aspect, provided is an aptamer comprising the sequence: ACAGGGGUCCGGCCUUUUCAUUUGGC-GCCGGUGAGAGCACACCCUUUGAACCU GUUX$_{12}$ ACGGAUAAUGCCGCX$_{13}$GCAGGGAGU (SEQ ID NO:45), wherein X$_{12}$ is C or U; and
X$_{13}$ is C or U.

In embodiments, the aptamer sequence has one or more of the following properties: X$_{12}$ is not U; and X$_{13}$ is not C. In embodiments, all of the following are not simultaneously present in the aptamer sequence: X$_{12}$ is U and X$_{13}$ is C.

In one aspect, provided is an aptamer comprising the sequence: ACX$_1$GGGGUCCGGCCUUUUCAUUUGG-CGCCGGUGAGAGCACACCCUUX$_8$X$_9$X$_{10}$ X$_{11}$CCU-GUUUACGGAUAAUGCCGCCGCAGGGAGU (SEQ ID NO:46), wherein X$_1$ is A or G;
X$_8$ is any nucleotide;
X$_9$ is G or U;
X$_{10}$ is A, G, or U; and
X$_{11}$ is A or U.

In embodiments, the aptamer sequence has one or more of the following properties: X$_1$ is not A; X$_8$ is not U; X$_9$ is not G; X$_{10}$ is not A; and X$_{11}$ is not A. In embodiments, all of the following are not simultaneously present in the aptamer sequence: X$_1$ is A; X$_8$ is U; X$_9$ is G; X$_{10}$ is A; X$_{11}$ is A; X$_{12}$ is U; and X$_{13}$ is C.

In one aspect, provided is an aptamer comprising the sequence: ACAGGGGUCCGGCCUUUUCAUUUGGC-GCCGGUGAGAX$_5$X$_6$AX$_7$ACCCUUUGAAC CUGUU-UACGGAUAAUGCCGCCGCAGGGAGU (SEQ ID NO:47), wherein X$_5$ is G or U;
X$_6$ is C or U; and
X$_7$ is C or U.

In embodiments, the aptamer sequence has one or more of the following properties: X$_5$ is not G; X$_6$ is not C; and X$_7$ is not C. In embodiments, all of the following are not simultaneously present in the aptamer sequence: X$_5$ is G; X$_6$ is C; and X$_7$ is C.

In one aspect, provided is an aptamer comprising the sequence: ACAGGGGUCCGGCCUUUUCAUUU-GGCX$_4$CCGGUGAGAX$_5$X$_6$AX$_7$ACCCUUXX$_9$X$_{10}$ ACC-UGUUCACGGAUAAUGCCGCUGCAGGGAGU (SEQ ID NO:48), wherein X$_4$ is A or G;
X$_5$ is any nucleotide;

$X_6$ is any nucleotide;

$X_7$ is any nucleotide;

$X_8$ is any nucleotide;

$X_9$ is C or G; and $X_{10}$ is any nucleotide.

In one aspect, provided is an aptamer that binds to a small molecule, wherein the aptamer comprises a sequence that is at least 95%, at least 96%, at least 97%, at least 98%, or at least 99%, identical to the sequence selected from the group consisting of SEQ ID NOs:49-78. In some embodiments, the aptamer sequence comprises a sequence selected from the group consisting of SEQ ID NOs:49-78. In embodiments, the aptamer sequence comprises a sequence selected from the group consisting of SEQ ID NOs:51, 56, and 68.

Aptamer Ligands

In one embodiment, the aptamer ligand is thiamine (vitamin B1) or is a thiamine analog and/or is a derivative of thiamine. As used herein, the term "thiamine analog" refers to a molecule that has similar physical, chemical, biochemical, or pharmacological properties compared to thiamine, and includes, for example, amprolium or cycotiamine. A thiamine analog may be a thiamine derivative. The term "thiamine derivative", as used herein, refers to a compound derived from thiamine, or its thiazole ring-opened form, by modification or substitution. Thiamine derivatives may include, for example, acefurtiamine, acetiamine, allithiamine, beclotiamine, benfotiamine, bentiamine, bisbentiamine, cetotiamine, fursultiamine, monophosphothiamine, octotiamine, prosultiamine, sulbutiamine, thiamine, thiamine pyrophosphate, or vintiamol.

In some embodiments, the aptamer binds to, or otherwise responds to the presence or addition of, a small molecule disclosed herein including small molecules having the structure according to Formula I-VIII. In embodiments, the small molecule has the structure according to Formula I:

wherein:

$R^1$ is selected from the group consisting of OH, amino, F, Cl, Br, phosphate, pyrophosphate, —O—C(=O)—$C_1$-$C_6$ alkyl, —O—C(=O)—$C_2$-$C_6$ alkenyl, —O—C(=O)-phenyl, —O—C(=O)-heterocycle, —O—C(=O)—O—$C_1$-$C_6$ alkyl, —O—C(=O)—O—$C_2$-$C_6$ alkenyl, —O—C(=O)—O-phenyl, and —O—C(=O)—O-heterocycle.

In embodiments, the small molecule has the structure according to Formula II:

wherein:

$R^2$ is selected from the group consisting of H, $C_1$-$C_6$ alkyl, $C_2$-$C_6$ alkenyl, —(CH$_2$)$_n$—$R^6$, —C(=O)—$R^4$, —C(=O)—O—$R^4$, —CHR$^5$—O—C(=O)—$R^4$, —S—$C_1$-$C_6$ alkyl, —S—$C_2$-$C_6$ alkenyl, —S-heterocycle, and —S—CH$_2$-heterocycle;

or $R^2$ is —S-[Formula II] such that the compound forms a dimer of two molecules of Formula II connected through a disulfide (—S—S—) linkage;

$R^3$ is selected from the group consisting of OH, amino, F, Cl, Br, phosphate, pyrophosphate, —O—C(=O)—$C_1$-$C_6$ alkyl, —O—C(=O)—$C_1$-$C_6$ alkenyl, —O—C(=O)-phenyl, —O—C(=O)-heterocycle, —O—C(=O)—O—$C_1$-$C_6$ alkyl, —O—C(=O)—O—$C_1$-$C_6$ alkenyl, —O—C(=O)—O-phenyl, —O—C(=O)—O-heterocycle;

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

$R^5$ is selected from the group consisting of H, $C_1$-$C_6$ alkyl, $C_2$-$C_6$ alkenyl, $C_3$-$C_7$ cycloalkyl, aryl, heteroaryl and hetercyclyl;

$R^6$ is hydroxyl, amino, amido, $C_1$-$C_6$ alkoxy, $C_3$-$C_7$ cycloalkyl, $C_6$-$C_{10}$ bicyclyl, aryl, heteroaryl and hetercyclyl; and n is 1 to 8;

and wherein each of the alkyl, alkenyl, cycloalkyl, bicyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has structure according to Formula III:

wherein:

$R^2$ is selected from the group consisting of H, $C_1$-$C_6$ alkyl, $C_2$-$C_6$ alkenyl, —(CH$_2$)$_n$—$R^6$, —C(=O)—$R^4$, —C(=O)—O—$R^4$, —CHR$^5$—O—C(=O)—$R^4$, —S—$C_1$-$C_6$ alkyl, —S—$C_2$-$C_6$ alkenyl, —S-heterocycle, and —S—CH$_2$-heterocycle;

$R^{31}$ is selected from the group consisting of OH and phosphate;

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and heterocyclyl;

23 24

$R^5$ is selected from the group consisting of H, $C_1$-$C_6$ alkyl, $C_2$-$C_6$ alkenyl, $C_3$-$C_7$ cycloalkyl, aryl, heteroaryl and hetercyclyl;

$R^6$ is hydroxyl, amino, amido, $C_1$-$C_6$ alkoxy, $C_3$-$C_7$ cycloalkyl, $C_6$-$C_{10}$ bicyclyl, aryl, heteroaryl and hetercyclyl; and n is 1 to 8;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has the structure according to Formula IV:

(IV)

wherein:

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

$R^5$ is selected from the group consisting of H, $C_1$-$C_6$ alkyl, $C_2$-$C_6$ alkenyl, $C_3$-$C_7$ cycloalkyl, aryl, heteroaryl and hetercyclyl;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has the structure according to Formula V:

(V)

wherein:

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has the structure according to Formula VI:

(VI)

wherein:

$R^4$ is selected from the group consisting of H, $C_1$-$C_6$ alkyl, $C_2$-$C_6$ alkenyl, $C_3$-$C_7$ cycloalkyl, $C_6$-$C_{10}$ bicyclyl, $C_9$-$C_{14}$ tricyclyl, —($C_1$-$C_6$ alkyl)-aryl, —($C_2$-$C_6$ alkenyl)-aryl, aryl, heteroaryl and hetercyclyl;

and wherein each of the alkyl, alkenyl, cycloalkyl, bicyclyl, tricyclyl, aryl, heteroaryl and hetercyclyl groups may be unsubstituted or substituted by 1 to 3 substituents selected from the group consisting of halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

In embodiments, the small molecule has the structure according to Formula VII:

25 | 26

(VII)

wherein each R$^7$ is independently selected from halogen, hydroxyl, amino, cyano, amido, sulfonamide, nitro, —SH, C$_1$-C$_6$ alkyl, C$_2$-C$_6$ alkenyl, C$_3$-C$_7$ cycloalkyl, C$_6$-C$_{10}$ bicyclyl, C$_1$-C$_6$ haloalkyl, C$_1$-C$_6$ perhaloalkyl, —O—(C$_1$-C$_6$ alkyl), O—(C$_3$-C$_7$ cycloalkyl), —O—(C$_1$-C$_6$ haloalkyl), —O—(C$_1$-C$_6$ perhaloalkyl), aryl, —O-aryl, —(C$_1$-C$_6$ alkyl)-aryl, —O—(C$_1$-C$_6$ alkyl)-aryl, —S—(C$_1$-C$_6$ alkyl), —S—(C$_3$-C$_7$ cycloalkyl), —S—(C$_1$-C$_6$ haloalkyl), —S—(C$_1$-C$_6$ perhaloalkyl), —S-aryl, —S—(C$_1$-C$_6$ alkyl)-aryl, heteroaryl and hetercyclyl;

additionally or alternatively, two adjacent R$^7$ groups may be taken together to form a fused 5- or 6-membered aromatic or non-aromatic ring, which contains 0 to 2 ring heteroatoms, and which is unsubstituted or is substituted by up to four substituents selected from halogen, hydroxyl, amino, cyano, amido, sulfonamide, nitro, —SH, C$_1$-C$_6$ alkyl, C$_2$-C$_6$ alkenyl, C$_3$-C$_7$ cycloalkyl, C$_6$-C$_{10}$ bicyclyl, C$_1$-C$_6$ haloalkyl, C$_1$-C$_6$ perhaloalkyl, —O—(C$_1$-C$_6$ alkyl), O—(C$_3$-C$_7$ cycloalkyl), —O—(C$_1$-C$_6$ haloalkyl), —O—(C$_1$-C$_6$ perhaloalkyl), aryl, —O-aryl, —(C$_1$-C$_6$ alkyl)-aryl, —O—(C$_1$-C$_6$ alkyl)-aryl, —S—(C$_1$-C$_6$ alkyl), —S—(C$_3$-C$_7$ cycloalkyl), —S—(C$_1$-C$_6$ haloalkyl), —S—(C$_1$-C$_6$ perhaloalkyl), —S-aryl, —S—(C$_1$-C$_6$ alkyl)-aryl, heteroaryl and hetercyclyl; and m is 0, 1, 2, 3 or 4.

In some embodiments, the small molecule has the structure according to Formula VIII:

(VIII)

wherein:

each R$^8$ is independently selected from halogen, hydroxyl, amino, cyano, amido, sulfonamide, nitro, —SH, C$_1$-C$_6$ alkyl, C$_2$-C$_6$ alkenyl, C$_3$-C$_7$ cycloalkyl, C$_6$-C$_{10}$ bicyclyl, C$_1$-C$_6$ haloalkyl, C$_1$-C$_6$ perhaloalkyl, —O—(C$_1$-C$_6$ alkyl), O—(C$_3$-C$_7$ cycloalkyl), —O—(C$_1$-C$_6$ haloalkyl), —O—(C$_1$-C$_6$ perhaloalkyl), aryl, —O-aryl, —(C$_1$-C$_6$ alkyl)-aryl, —O—(C$_1$-C$_6$ alkyl)-aryl, —S—(C$_1$-C$_6$ alkyl), —S—(C$_3$-C$_7$ cycloalkyl), —S—(C$_1$-C$_6$ haloalkyl), —S—(C$_1$-C$_6$ perhaloalkyl), —S-aryl, —S—(C$_1$-C$_6$ alkyl)-aryl, heteroaryl and hetercyclyl;

additionally or alternatively, two adjacent R$^8$ groups may be taken together to form a fused 5- or 6-membered aromatic or non-aromatic ring, which contains 0 to 2 ring heteroatoms, and which is unsubstituted or is substituted by up to four substituents selected from halogen, hydroxyl, amino, cyano, amido, sulfonamide, nitro, —SH, C$_1$-C$_6$ alkyl, C$_2$-C$_6$ alkenyl, C$_3$-C$_7$ cycloalkyl, C$_6$-C$_{10}$ bicyclyl, C$_1$-C$_6$ haloalkyl, C$_1$-C$_6$ perhaloalkyl, —O—(C$_1$-C$_6$ alkyl), O—(C$_3$-C$_7$ cycloalkyl), —O—(C$_1$-C$_6$ haloalkyl), —O—(C$_1$-C$_6$ perhaloalkyl), aryl, —O-aryl, —(C$_1$-C$_6$ alkyl)-aryl, —O—(C$_1$-C$_6$ alkyl)-aryl, —S—(C$_1$-C$_6$ alkyl), —S—(C$_3$-C$_7$ cycloalkyl), —S—(C$_1$-C$_6$ haloalkyl), —S—(C$_1$-C$_6$ perhaloalkyl), —S-aryl, —S—(C$_1$-C$_6$ alkyl)-aryl, heteroaryl and hetercyclyl;

each R$^9$ is independently selected from halogen, hydroxyl, amino, cyano, amido, sulfonamide, nitro, —SH, C$_1$-C$_6$ alkyl, C$_2$-C$_6$ alkenyl, C$_3$-C$_7$ cycloalkyl, C$_6$-C$_{10}$ bicyclyl, C$_1$-C$_6$ haloalkyl, C$_1$-C$_6$ perhaloalkyl, —O—(C$_1$-C$_6$ alkyl), O—(C$_3$-C$_7$ cycloalkyl), —O—(C$_1$-C$_6$ haloalkyl), —O—(C$_1$-C$_6$ perhaloalkyl), aryl, —O-aryl, —(C$_1$-C$_6$ alkyl)-aryl, —O—(C$_1$-C$_6$ alkyl)-aryl, —S—(C$_1$-C$_6$ alkyl), —S—(C$_3$-C$_7$ cycloalkyl), —S—(C$_1$-C$_6$ haloalkyl), —S—(C$_1$-C$_6$ perhaloalkyl), —S-aryl, —S—(C$_1$-C$_6$ alkyl)-aryl, heteroaryl and hetercyclyl;

additionally or alternatively, two adjacent R$^9$ groups may be taken together to form a fused 5- or 6-membered aromatic or non-aromatic ring, which contains 0 to 2 ring heteroatoms, and which is unsubstituted or is substituted by up to four substituents selected from halogen, hydroxyl, amino, cyano, amido, sulfonamide, nitro, —SH, C$_1$-C$_6$ alkyl, C$_2$-C$_6$ alkenyl, C$_3$-C$_7$ cycloalkyl, C$_6$-C$_{10}$ bicyclyl, C$_1$-C$_6$ haloalkyl, C$_1$-C$_6$ perhaloalkyl, —O—(C$_1$-C$_6$ alkyl), O—(C$_3$-C$_7$ cycloalkyl), —O—(C$_1$-C$_6$ haloalkyl), —O—(C$_1$-C$_6$ perhaloalkyl), aryl, —O-aryl, —(C$_1$-C$_6$ alkyl)-aryl, —O—(C$_1$-C$_6$ alkyl)-aryl, —S—(C$_1$-C$_6$ alkyl), —S—(C$_3$-C$_7$ cycloalkyl), —S—(C$_1$-C$_6$ haloalkyl), —S—(C$_1$-C$_6$ perhaloalkyl), —S-aryl, —S—(C$_1$-C$_6$ alkyl)-aryl, heteroaryl and hetercyclyl;

x is 0, 1, 2 or 3; and y is 0, 1, 2, 3, or 4.

The term "alkyl" refers to the radical of saturated aliphatic groups, including straight-chain alkyl groups and branched-chain alkyl groups. In preferred embodiments, a straight chain or branched chain alkyl has 6 or fewer carbon atoms in its backbone (e.g., C$_1$-C$_6$ for straight chain, C$_3$-C$_6$ for branched chain). Alkyl groups include methyl, ethyl, propyl, isopropyl, n-butyl, iso-butyl, tert-butyl, pentyl, isopentyl, hexyl, and the like.

The term "cycloalkyl" refers to saturated, carbocyclic groups having from 3 to 6 carbons in the ring. Cycloalkyl groups include cyclopropyl, cyclobutyl, cyclopentyl and cyclohexyl.

The term "bicyclyl" refers to saturated carbocyclic groups having two joined ring systems, which may be fused or bridged. Bicyclic groups include bicycle[2.1.1]hexane, bicycle[2.2.1]heptane, decalin, and the like. The term "tricyclyl" refers to saturated carbocyclic groups having three joined ring systems, which may be fused and/or bridged. Tricyclic groups include adamantane and the like.

The term "alkenyl" refers to unsaturated aliphatic groups, including straight-chain alkenyl groups and branched-chain alkenyl groups, having at least one carbon-carbon double bond. In preferred embodiments, the alkenyl group has two to six carbon atoms (e.g., $C_2$-$C_6$ alkenyl).

As used herein, the term "halogen" or "halo" designates —F, —Cl, —Br or —I, and preferably —F, —Cl or —Br.

The terms "alkoxyl" or "alkoxy" as used herein refers to an alkyl group, as defined above, that is attached through an oxygen atom. Representative alkoxyl groups include methoxy, ethoxy, propyloxy, tert-butoxy and the like.

The terms "amine" and "amino" refer to both unsubstituted and substituted amines, e.g., a moiety that can be represented by the general formula:

$$—N\begin{matrix} R \\ R' \end{matrix}$$

wherein R and R' are each independently selected from H and $C_1$-$C_3$ alkyl.

The terms "amido" refer to both unsubstituted and substituted amide substituents, e.g., a moiety that can be represented by the general formula:

$$—\underset{\underset{R'}{|}}{\overset{\overset{O}{\|}}{C}}—N—R$$

wherein R and R' are each independently selected from H and $C_1$-$C_3$ alkyl.

The terms "sulfonamide" or "sulfonamido" refer to both unsubstituted and substituted sulfonamide substituents, e.g., a moiety that can be represented by the general formula:

$$—\underset{\underset{O}{\|}}{\overset{\overset{O}{\|}}{S}}—\underset{\underset{R'}{|}}{N}—R$$

wherein R and R' are each independently selected from H and $C_1$-$C_3$ alkyl.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "aryl heterocycles" or "heteroaryl" groups. The term "aryl" also includes polycyclic ring systems having two or more cyclic rings in which two or more carbons are common to two adjoining rings (the rings are "fused rings") wherein at least one of the rings is aromatic. Accordingly, aryl includes 8- to 10-membered fused bicyclic aromatic groups that may include from zero to five heteroatoms, in which one or both rings are aromatic, for example napthylene, quinolone, isoquinoline, benzo[b] thiophene, tetrahydronapthelene, and the like. Each aryl group may be unsubstituted or may be substituted with 1 to 5 substituents selected from halogen, hydroxyl, amino, cyano, amido, sulfonamide, nitro, —SH, $C_1$-$C_6$ alkyl, $C_2$-$C_6$ alkenyl, $C_3$-$C_7$ cycloalkyl, $C_6$-$C_{10}$ bicyclyl, $C_1$-$C_6$ haloalkyl, $C_1$-$C_6$ perhaloalkyl, —O—($C_1$-$C_6$ alkyl), O—($C_3$-$C_7$ cycloalkyl), —O—($C_1$-$C_6$ haloalkyl), —O—($C_1$-$C_6$ perhaloalkyl), aryl, —O-aryl, —($C_1$-$C_6$ alkyl)-aryl, —O—($C_1$-$C_6$ alkyl)-aryl, —S—($C_1$-$C_6$ alkyl), —S—($C_3$-$C_7$ cycloalkyl), —S—($C_1$-$C_6$ haloalkyl), —S—($C_1$-$C_6$ perhaloalkyl), —S-aryl, —S—($C_1$-$C_6$ alkyl)-aryl, heteroaryl and hetercyclyl.

The term "heterocycle" of "heterocyclyl" refer to non-aromatic heterocycles having from 1 to 3 ring heteroatoms. Preferred heterocycles are 5- and 6-membered heterocyclic groups having from 1 to 3 heteroatoms selected from the group consisting of O, N and S.

The term "heteroatom" as used herein means an atom of any element other than carbon or hydrogen. Preferred heteroatoms are nitrogen, oxygen, and sulfur.

As used herein, the definition of each expression, e.g. alkyl, $R^1$, $R^2$, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The aptamer ligands disclosed herein may exist in particular geometric or stereoisomeric forms well as mixtures thereof. Such geometric or stereoisomeric forms include, but not limited to, cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group.

The compounds according to Formulas I to VIII may contain an acidic or basic functional group, and accordingly may be present in a salt form. Preferably, the salt form is a pharmaceutically acceptable salt. The term "pharmaceutically-acceptable salts" in this respect, refers to the relatively non-toxic, inorganic and organic acid and base addition salts of the compounds disclosed herein.

The compounds according to Formulas I to VIII may contain one or more basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or by separately reacting a purified compound disclosed herein in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds according to Formulas I to VIII may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, e.g., Berge et al., supra).

In embodiments, the aptamers provided herein bind to, or otherwise respond to the presence of, one or more thiamine or TPP analogs provided herein, and/or bind to, or otherwise respond to, a metabolite of the thiamine or TPP analog or derivative provided herein, including for example TPP and/or thiamine.

The specificity of the binding of an aptamer to its ligand can be defined in terms of the comparative dissociation constants ($K_d$) of the aptamer for its ligand as compared to the dissociation constant of the aptamer for unrelated molecules. Thus, the ligand is a molecule that binds to the aptamer with greater affinity than to unrelated material. Typically, the $K_d$ for the aptamer with respect to its ligand will be at least about 10-fold less than the $K_d$ for the aptamer with unrelated molecules. In other embodiments, the $K_d$ will be at least about 20-fold less, at least about 50-fold less, at least about 100-fold less, and at least about 200-fold less, at least about 500-fold less, at least about 1000-fold less, or at least about 10,000-fold less than the $K_d$ for the aptamer with unrelated molecules.

In one embodiment, the aptamer binds to TPP with an affinity that is least 5-fold, at least 10-fold, at least about 20-fold, at least 50-fold, at least 100-fold, at least 500-fold, at least 1000-fold, or at least 10,000-fold lower than the affinity of said aptamer to a compound of Formula I-VI1 or to acefurtiamine, acetiamine, allithiamine, beclotiamine, benfotiamine, bentiamine, bisbentiamine, cetotiamine, cycotiamine, fursultiamine, monophosphothiamine, octotiamine, prosultiamine, sulbutiamine, or vintiamol. In one embodiment, the aptamer binds to thiamine with an affinity that is least 5-fold, at least 10-fold, at least about 20-fold, at least 50-fold, at least 100-fold, at least 500-fold, at least 1000-fold, or at least 10,000 fold lower than the affinity of said aptamer a compound of Formula I-VI1 or to acefurtiamine, acetiamine, allithiamine, beclotiamine, benfotiamine, bentiamine, bisbentiamine, cetotiamine, cycotiamine, fursultiamine, monophosphothiamine, octotiamine, prosultiamine, sulbutiamine, or vintiamol.

Aptamers for the Regulation of Gene Expression

In some embodiments, the aptamers contemplated by the disclosure are used for the regulation of gene expression. Regulation of the expression of a target gene (e.g., a therapeutic transgene) is advantageous in a variety of situations. In the context of the therapeutic expression of genes, for example, techniques that enable regulated expression of transgenes in response to the presence of a small molecule can enhance safety and efficacy by allowing for the regulation of the level of target gene expression and its timing. In a research setting, the regulation of gene expression allows a systematic investigation of different experimental conditions.

In embodiments, the sequence encoding the aptamer is part of a gene regulation cassette that provides the ability to regulate the expression level of a target gene in response to the presence or absence of a small molecule described herein. In embodiments, the gene regulation cassette further comprises a target gene. As used herein, "target gene" refers to a transgene that is expressed in response to the presence or absence of the small molecule ligands disclosed herein due to the small molecule binding to the aptamers disclosed herein. In embodiments, the target gene comprises the coding sequence for a protein (e.g., a therapeutic protein), a miRNA, or a siRNA. The target gene is heterologous to the aptamer used for the regulation of target gene expression, is heterologous to the polynucleotide cassette used for the regulation of target gene and/or is heterologous to a portion of the polynucleotide cassette used for the regulation of target gene.

When used to regulate the expression of a target gene in response to the presence/absence of a ligand, the aptamers described herein can be part of a polynucleotide cassette that encodes the aptamer as part of a riboswitch. The terms "gene regulation cassette", "regulatory cassette", or "polynucleotide cassette" are used interchangeably herein.

In embodiments, the presence of a small molecule that binds to an aptamer disclosed herein leads to an increase in expression of a target gene as compared to the expression of the target gene in absence of the small molecule. In such an embodiment, the aptamer constitutes an "on" switch. In embodiments, the expression of the target gene is increased by at least 3-fold, by at least 5-fold, by at least 10-fold, by at least 15-fold, by at least 20-fold, by at least 25-fold, by at least 30-fold, by at least 40-fold, by at least 50-fold, by at least 100-fold, by at least 1000-fold, or by at least 10,000-fold in presence of the small molecule that binds to an aptamer disclosed herein as compared to in absence of the small molecule. In embodiments, the expression of the target gene is increased by between 2-fold and 10-fold, between 5-fold and 10-fold, between 5-fold and 15-fold, between 5-fold and 20-fold, between 5-fold and 25-fold, between 5-fold and 30-fold, between 10-fold and 20-fold, between 10-fold and 30-fold, between 10-fold and 40-fold, between 10-fold and 50-fold, between 10-fold and 100-fold, between 10-fold and 500-fold, between 10-fold and 1,000-fold, between 50-fold and 100-fold, between 50-fold and 500-fold, between 50-fold and 100-fold, between 50-fold and 1,000-fold, between 100-fold and 1,000-fold, or between 100-fold and 10,000-fold in presence of the small molecule that binds to an aptamer disclosed herein as compared to in absence of the small molecule.

In embodiments, the presence of a small molecule that binds to an aptamer disclosed herein leads to a decrease in expression of a target gene as compared to the expression of the target gene in the absence of the small molecule. In such embodiments, the aptamer constitutes an "off" switch. In embodiments, the expression of the target gene is decreased by at least 3-fold, by at least 5-fold, by at least 10-fold, by at least 15-fold, by at least 20-fold, by at least 25-fold, by at least 30-fold, by at least 40-fold, by at least 50-fold, by at least 100-fold, by at least 1000-fold, or by at least 10,000-fold in presence of the small molecule that binds to an aptamer disclosed herein as compared to in absence of the small molecule. In one embodiment, the expression of the target gene is decreased by between 2-fold and 10-fold, between 5-fold and 10-fold, between 5-fold and 15-fold, between 5-fold and 20-fold, between 5-fold and 25-fold, between 5-fold and 30-fold, between 10-fold and 20-fold, between 10-fold and 30-fold, between 10-fold and 40-fold, between 10-fold and 50-fold, between 10-fold and 100-fold, between 10-fold and 500-fold, between 10-fold and 1,000-fold, between 50-fold and 100-fold, between 50-fold and 500-fold, between 50-fold and 100-fold, between 50-fold and 1,000-fold, between 100-fold and 1,000-fold, or between 100-fold and 10,000-fold in presence of the small molecule that binds to an aptamer disclosed herein as compared to in absence of the small molecule.

In embodiments, the aptamer is part of a riboswitch. Riboswitches are regulatory segments of an RNA polynucle-otide that regulate the stability of the RNA polynucleotide and/or regulate the production of a protein from the RNA polynucleotide in response to the presence or absence of aptamer-specific ligand molecules. In embodiments, the riboswitch comprises a sensor region (e.g., the aptamer region) and an effector region that together are responsible for sensing the presence of a ligand (e.g., a small molecule) and causing an effect that leads to increased or decreased expression of the target gene. The riboswitches described herein are recombinant, utilizing polynucleotides from two or more sources. In embodiments, the sensor and effector regions are joined by a polynucleotide linker. In embodi-ments, the polynucleotide linker forms a RNA stem or paired region (i.e., a region of the RNA polynucleotide that is double-stranded). In embodiments, the paired region linking the aptamer to the effector region comprises all, or some of an aptamer stem (e.g., for example all, or some of the aptamer P1 stem.).

Riboswitches comprising aptamer sequences may be used, for example, to control the formation of rho-indepen-dent transcription termination hairpins leading to premature transcription termination. Riboswitches comprising aptamer sequences may also induce structural changes in the RNA, leading to sequestration for the ribosome binding site and inhibition of translation. Alternative riboswitch structures comprising the aptamer sequences disclosed herein can further affect the splicing of mRNA in response to the presence of the small molecule ligand.

Alternative Splicing Riboswitch

In one embodiment, the aptamers described herein are encoded as part of a gene regulation cassette for the regu-lation of a target gene by aptamer/ligand mediated alterna-tive splicing of the resulting RNA (e.g., pre-mRNA). In this context, the gene regulation cassette comprises a riboswitch comprising a sensor region (e.g., the aptamers described herein) and an effector region that together are responsible for sensing the presence of a small molecule ligand and altering splicing to an alternative exon. Splicing refers to the process by which an intronic sequence is removed from the nascent pre-messenger RNA (pre-mRNA) and the exons are joined together to form the mRNA. Splice sites are junctions between exons and introns, and are defined by different consensus sequences at the 5' and 3' ends of the intron (i.e., the splice donor and splice acceptor sites, respectively). Splicing is carried out by a large multi-component structure called the spliceosome, which is a collection of small nuclear ribonucleoproteins (snRNPs) and a diverse array of auxiliary proteins. By recognizing various cis regulatory sequences, the spliceosome defines exon/intron boundaries, removes intronic sequences, and splices together the exons into a final message (e.g., the mRNA). In the case of alternative splicing, certain exons can be included or excluded to vary the final coding message thereby changing the resulting expressed protein.

In one embodiment, the regulation of target gene expres-sion is achieved by using any of the DNA constructs disclosed in WO2016/126747, which is hereby incorporated by reference in its entirety. In embodiments of the present disclosure, the riboswitches and polynucleotide cassettes disclosed in WO2016/126747 comprise an aptamer encod-ing sequence described herein in place of the aptmer sequence disclosed in WO2016/126747.

In one embodiment, the polynucleotide cassette com-prises (a) a riboswitch and (b) an alternatively-spliced exon, flanked by a 5' intron and a 3' intron, wherein the riboswitch comprises (i) an effector region comprising a stem that includes the 5' splice site sequence of the 3' intron, and (ii) an aptamer disclosed herein. In embodiments, the effector region comprises the intronic 5' splice site ("5' ss") sequence of the intron that is immediately 3' of the alternative exon, as well as the sequence complimentary to the 5' ss sequence of the 3' intron. When the aptamer binds its ligand, the effector region forms a stem and thus prevents splicing to the splice donor site at the 3' end of the alternative exon. Under certain conditions (for example, when the aptamer is not bound to its ligand), the effector region is in a context that provides access to the splice donor site at the 3' end of the alternative exon, leading to inclusion of the alternative exon in the target gene mRNA. In some embodiments, the poly-nucleotide cassette is placed in the target gene to regulate expression of the target gene in response to a ligand. In one embodiment, the alternatively-spliced exon comprises a stop codon that is in-frame with the target gene when the alter-natively-spliced exon is spliced into the target gene mRNA.

In one embodiment, the gene regulation cassette com-prises the sequence of SEQ ID NO:37, wherein —X— represents an aptamer encoding sequence disclosed herein. Lower case letters indicate paired stem sequence linking the aptamer to the remainder of the riboswitch. In one embodi-ment, the alternative exon (underlined in SEQ ID NO:37, below) is replaced with another alternative exon sequence.

```
SEQ ID NO: 37 -
GTGAGTCTATGGGACCCTTGATGTTTTCTTTCCCCTTCTTTTCTATGGT

TAAGTTCATGTCATAGGAAGGGGAGAAGTAACAGGGTACACATATTGAC

CAAATCAGGGTAATTTTGCATTTGTAATTTTAAAAAATGCTTTCTTCTT

TTAATATACTTTTTTGTTTATCTTATTTCTAATACTTTCCCTAATCTCT

TTCTTTCAGGGCAATAATGATACAATGTATCATGCCGAGTAACGCTGTT

TCTCTAACTTGTAGGAATGAATTCAGATATTTCCAGAGAATGAAAAAAA

AATCTTCAGTAGAAGgtaatgt-X-acattacGCACCATTCTAAAGAAT

AACAGTGATAATTTCTGGGTTAAGGCAATAGCAATATTTCTGCATATAA

ATATTTCTGCATATAAATTGTAACTGATGTAAGAGGTTTCATATTGCTA

ATAGCAGCTACAATCCAGCTACCATTCTGCTTTTATTTTATGGTTGGGA

TAAGGCTGGATTATTCTGAGTCCAAGCTAGGCCCTTTTGCTAATCATGT

TCATACCTCTTATCTTCCTCCCACAG.
```

The alternative exon is flanked by 5' and 3' intronic sequences. The 5' and 3' intronic sequences that can be used in the gene regulation cassettes disclosed herein can be any sequence that can be spliced out of the target gene creating either the target gene mRNA or the target gene comprising the alternative exon in the mRNA, depending upon the presence or absence of a ligand that binds the aptamer. The 5' and 3' intronic sequences each have the sequences necessary for splicing to occur, i.e., splice donor, splice acceptor and branch point sequences. In one embodiment, the 5' and 3' intronic sequences of the gene regulation cassette are derived from one or more naturally occurring introns or portions thereof. In one embodiment, the 5' and 3' intronic sequences are derived from a truncated human beta-globin intron 2 (IVS2Δ), from intron 2 of the human 03-globin gene, from the SV40 mRNA intron (used in pCMV-LacZ vector from Clontech Laboratories, Inc.), from intron 6 of human triose phosphate isomerase (TPI) gene (Nott Ajit, et al. RNA. 2003, 9:6070617), from an intron from human factor IX (Sumiko Kurachi, et al. J. Bio. Chem. 1995, 270(10), 5276), from the target gene's own endogenous intron, or from any genomic fragment or synthetic introns (Yi Lai, et al. Hum Gene Ther. 2006:17(10): 1036) that contain elements that are sufficient for regulated splicing (Thomas A. Cooper, Methods 2005 (37):331).

In one embodiment, the alternative exon and riboswitch are engineered to be in an endogenous intron of a target gene. That is, the intron (or a substantially similar intronic sequence) naturally occurs at that position of the target gene. In this case, the intronic sequence immediately upstream of the alternative exon is referred to as the 5' intron or 5' intronic sequence, and the intronic sequence immediately downstream of the alternative exon is referred to as the 3' intron or 3' intronic sequence. In this case, the endogenous intron is modified to contain a splice acceptor sequence and splice donor sequence flanking the 5' and 3' ends of the alternative exon. In one embodiment, the 5' and/or 3' introns are exogenous to the target gene.

The splice donor and splice acceptor sites in the alternative splicing gene regulation cassette can be modified to be strengthened or weakened. That is, the splice sites can be modified to be closer to the consensus for a splice donor or acceptor by standard cloning methods, site directed mutagenesis, and the like. Splice sites that are more similar to the splice consensus tend to promote splicing and are thus strengthened. Splice sites that are less similar to the splice consensus tend to hinder splicing and are thus weakened. The consensus for the splice donor of the most common class of introns (U2) is A/C A G∥G T A/G A G T (where ∥ denotes the exon/intron boundary). The consensus for the splice acceptor is C A G∥G (where ∥ denotes the exon/intron boundary). The frequency of particular nucleotides at the splice donor and acceptor sites are described in the art (see, e.g., Zhang, M. Q., Hum Mol Genet. 1988. 7(5):919-932). The strength of 5' and 3' splice sites can be adjusted to modulate splicing of the alternative exon.

Additional modifications to 5' and 3' introns present in the alternative splicing gene regulation cassette that can be made to modulate splicing include modifying, deleting, and/or adding intronic splicing enhancer elements, intronic splicing suppressor elements and or splice sites, and/or modifying the branch site sequence.

In one embodiment, the 5' intron has been modified to contain a stop codon that will be in frame with the target gene. The 5' and 3' intronic sequences can also be modified to remove cryptic slice sites, which can be identified with publicly available software (see, e.g., Kapustin, Y. et al. Nucl. Acids Res. 2011. 1-8).

The lengths of the 5' and 3' intronic sequences can be adjusted in order to, for example, meet the size requirements for viral expression constructs. In one embodiment, the 5' and/or 3' intronic sequences are about 50 to about 300 nucleotides in length. In one embodiment, the 5' and/or 3' intronic sequences are about 125 to about 240 nucleotides in length.

The stem portion of the effector region should be of a sufficient length (and GC content) to substantially prevent alternative splicing of the alternative exon upon ligand binding the aptamer, while also allowing access to the splice site when the ligand is not present in sufficient quantities. In embodiments, the stem portion of the effector region comprises a stem sequence in addition to the 5' splice site sequence of the 3' intron and its complementary sequence of the 5' splice site sequence. In embodiments, this additional stem sequence comprises a sequence from the aptamer stem. The length and sequence of the stem portion can be modified using known techniques in order to identify stems that allow acceptable background expression of the target gene when no ligand is present and acceptable expression levels of the target gene when the ligand is present. In one embodiment, the effector region stem of the riboswitch is about 7 to about 20 base pairs in length. In one embodiment, the effector region stem is 8 to 11 base pairs in length. In addition to the length of the stem, the GC base pair content of the stem can be altered to modify the stability of the stem.

In one embodiment, the alternative exon that is part of the alternative splicing gene regulation cassettes disclosed herein is a polynucleotide sequence capable of being transcribed to a pre-mRNA and alternatively spliced into the mRNA of the target gene. In one embodiment, the alternative exon contains at least one sequence that inhibits translation such that when the alternative exon is included in the target gene mRNA, expression of the target gene from that mRNA is prevented or reduced. In a preferred embodiment, the alternative exon contains a stop codon (TGA, TAA, TAG) that is in frame with the target gene when the alternative exon is included in the target gene mRNA by splicing. In embodiments, the alternative exon comprises, in addition to a stop codon, or as an alternative to a stop codon, another sequence that reduces or substantially prevents translation when the alternative exon is incorporated by splicing into the target gene mRNA including, e.g., a microRNA binding site, which leads to degradation of the mRNA. In one embodiment, the alternative exon comprises a miRNA binding sequence that results in degradation of the mRNA. In one embodiment, the alternative exon encodes a polypeptide sequence which reduces the stability of the protein containing this polypeptide sequence. In one embodiment, the alternative exon encodes a polypeptide sequence which directs the protein containing this polypeptide sequence for degradation.

The basal or background level of splicing of the alternative exon can be optimized by altering exon splice enhancer (ESE) sequences and exon splice suppressor (ESS) sequences and/or by introducing ESE or ESS sequences into the alternative exon. Such changes to the sequence of the alternative exon can be accomplished using methods known in the art, including, but not limited to site directed mutagenesis. Alternatively, oligonucleotides of a desired sequence (e.g., comprising all or part of the alternative exon) can be obtained from commercial sources and cloned into the gene regulation cassette. Identification of ESS and ESE sequences can be accomplished by methods known in the art, including, for example using ESEfinder 3.0 (Cartegni, L. et al. ESEfinder: a web resource to identify exonic splicing enhancers. Nucleic Acid Research, 2003, 31(13): 3568-3571) and/or other available resources.

In one embodiment, the alternative exon is a naturally-occurring exon. In another embodiment, the alternative exon is derived from all or part of a known exon. In this context, "derived" refers to the alternative exon containing sequence that is substantially homologous to a naturally occurring exon, or a portion thereof, but may contain various mutations, such a mutations generated by altering exon splice enhancer (ESE) sequences and exon splice suppressor (ESS) sequences and/or by introducing ESE or ESS sequences into the alternative exon. "Homology" and "homologous" as used herein refer to the percent of identity between two polynucleotide sequences or between two polypeptide sequences. The correspondence between one sequence to another can be determined by techniques known in the art. For example, homology can be determined by a direct comparison of two polypeptide molecules by aligning their sequences and using readily available computer programs. Alternatively, homology can be determined by hybridization of polynucleotides under conditions which form stable duplexes between homologous regions, followed by digestion with single-stranded-specific nuclease(s), and size determination of the digested fragments. Two polynucleotide or two polypeptide sequences are "substantially homologous" to each other when, after optimally aligned with appropriate insertions or deletions, at least about 80%, at least about 85%, at least about 90%, and at least about 95% of the nucleotides or amino acids, respectively, match over a defined length of the molecules, as determined using the methods above.

In one embodiment, the alternative exon is exogenous to the target gene, although it may be derived from a sequence originating from the organism where the target gene will be expressed. As used herein, "exogenous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). In one embodiment, the alternatively-spliced exon is derived from exon 2 of the human dihydrofolate reductase gene (DHFR), mutant human Wilms tumor 1 exon 5, mouse calcium/calmodulin-dependent protein kinase II delta exon 16, or SIRT1 exon 6. In embodiments, the alternatively-spliced exon is, or comprises, the modified DHFR exon 2 in SEQ ID NO:79 (GAATGAATTCAGATATTTCCAGAGAATGAAAAA-AAAATCTTCAGTAGAAG). In embodiments, the alternatively-spliced exon is, or comprises, the modified DHFR exon 2 in SEQ ID NO:98 GAATGAATTCAGATAT-TTCCAGAGAATGAAAAAAAATCTTCAGTAGAAG.

Aptamer-Mediated Cleavage by Self-Cleaving Ribozymes

In one embodiment, the aptamer-mediated expression of the target gene is regulated by an aptamer-mediated modulation of small endonucleolytic ribozymes. A ribozyme is an RNA enzyme that catalyzes a chemical reaction. In the nucleic acids and methods disclosed herein, a ribozyme may be any small endonucleolytic ribozyme that will self-cleave in the target cell type including, but not limited to a hammerhead, hairpin, the hepatitis delta virus, the Varkud satellite, twister, twister sister, pistol or hatchet ribozyme. Accordingly, in one embodiment, provided is a riboswitch, and a gene expression cassette comprising the riboswitch that contains a ribozyme linked to an aptamer disclosed herein. WO2017/136608, which is incorporated in its entirety by reference herein, describes such riboswitches that activate ribozyme self-cleavage in the presence of aptamer ligand ("off" switch) or riboswitches that inhibit ribozyme self-cleavage in the presence of aptamer ("on" switch).

Figure 3A:
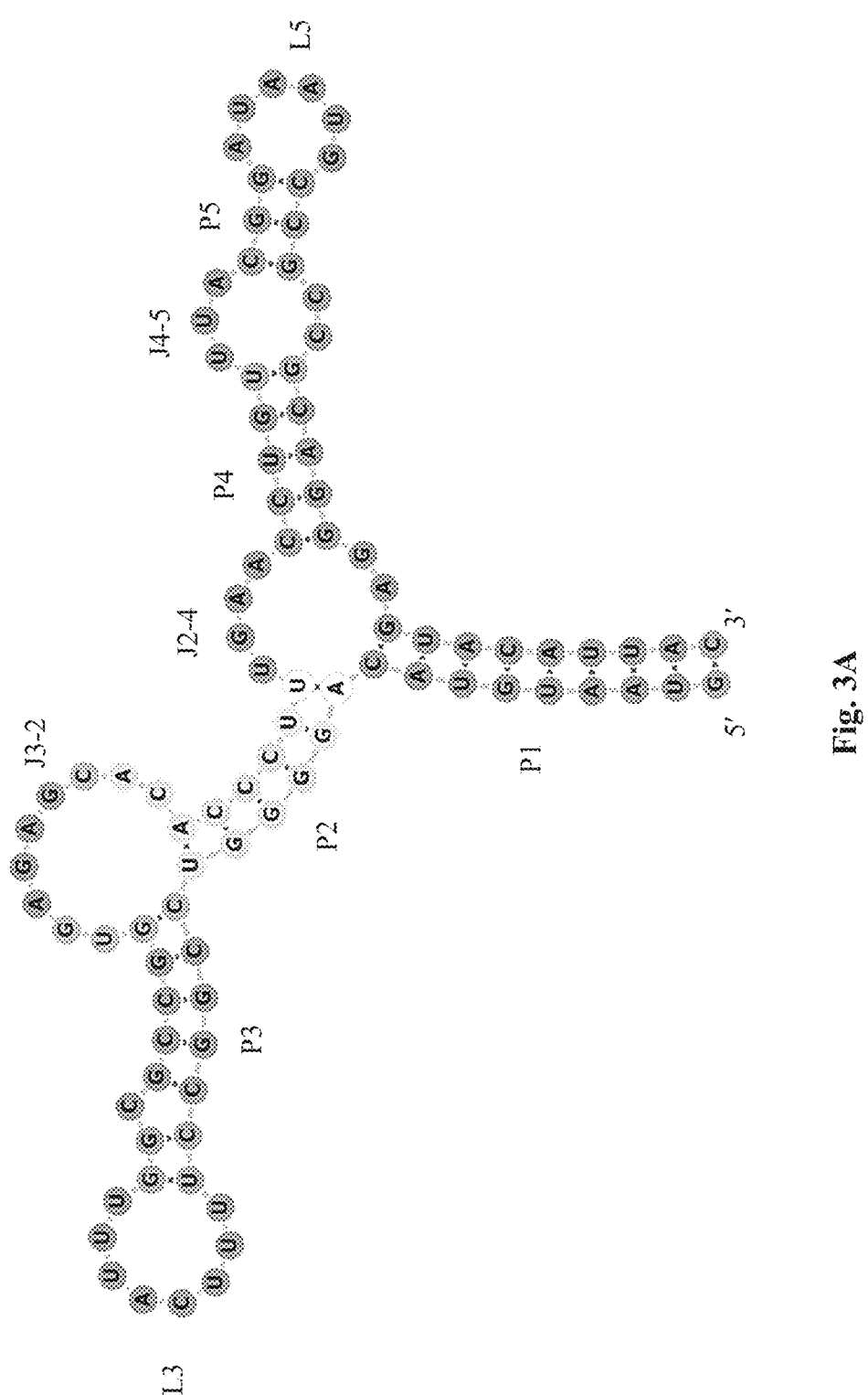
FIG. 3 shows the predicted structure of parent aptamer 14G4 with the native P1 stem (SEQ ID NO:38) (FIG. 3A) and the aptamer 14G4 encoding sequence (SEQ ID NO:7) and libraries derived therefrom (FIG. 3B). The predicted structure of the 14G4 aptamer, including positions of the stems and unpaired regions was determined as described herein. The structure shading around each base denotes its base-pairing probabilities with darker shading indicating higher probability. For unpaired regions the darker shading denotes the probability of being unpaired. The nucleotides that were randomly mutated to obtain aptamer libraries A1 (SEQ ID NO:39), A2 (SEQ ID NO:40), or A3 (SEQ ID NO:41), respectively are indicated with "N" in the aptamer coding sequences in FIG. 3B and correspond to nucleotides that are unpaired or adjacent to unpaired regions.

In an "off" switch scenario, aptamer/ligand binding increases the ribonuclease function of the ribozyme, leading to cleavage of the target gene RNA that contains the polynucleotide cassette, thereby reducing target gene expression. Examples of such an off switch include a polynucleotide cassette for the regulation of the expression of a target gene comprising a riboswitch that comprises a twister ribozyme linked by a stem to an aptamer, wherein the stem linking the twister ribozyme to the aptamer attaches to the ribozyme at the location of the P3 stem of the twister ribozyme and wherein the target gene is linked to the P1 stem of the twister ribozyme (see, e.g. FIGS. 1a, 1b, or 3a of WO2017/136608 and the associated text, incorporated herein by reference).

In an "on" switch scenario, aptamer/ligand binding inhibits the ribonuclease function of the ribozyme, decreasing cleavage of the target gene RNA that contains the polynucleotide cassette, thereby increasing target gene expression in the presence of ligand. Examples of an on switch include a riboswitch that comprises a twister ribozyme linked to an aptamer, wherein the aptamer is linked to the 3' or 5' end of the twister ribozyme P1 stem, wherein when the aptamer is linked to the 3' end of the twister ribozyme P1 stem, a portion of the 3' arm of the twister ribozyme P1 stem is alternatively the 5' arm of the aptamer P1 stem, and wherein when the aptamer is linked to the 5' end of the twister ribozyme P1 stem, a portion of the 5' arm of the twister ribozyme P1 stem is alternatively the 3' arm of the aptamer P1 stem (see, e.g., FIGS. 6a-6b of WO2017/136608 and the associated text, incorporated herein by reference).

Aptamer Modulation of Polyadenylation

In embodiments, the expression of a target gene is regulated by aptamer-modulated polyadenylation. The 3' end of almost all eukaryotic mRNAs comprises a poly(A) tail—a homopolymer of 20 to 250 adenosine residues. Because addition of the poly(A) tail to mRNA protects it from degradation, expression of a gene can be influenced by modulating the polyadenylation the corresponding mRNA.

In one embodiment, the expression of the target gene is regulated through aptamer-modulated accessibility of polyadenylation signals as described in and WO2018/156658, which is incorporated in its entirety by reference herein. In such embodiments, the riboswitch comprises an effector stem-loop and an aptamer described herein, wherein the effector stem-loop comprises a polyadenylation signal, and wherein the aptamer and effector stem-loop are linked by an alternatively shared stem arm comprising a sequence that is complementary to the unshared arm of the aptamer stem and to the unshared arm of the effector stem loop (see, e.g., FIGS. 1a, 1b, 2a, and 5a of WO2018/156658 and the associated text, incorporated herein by reference). In one embodiment, the effector stem-loop is positioned 3' of the aptamer such that the alternatively shared stem arm comprises all or a portion of the 3' aptamer stem arm and all or a portion of the 5' arm of the effector stem. In one embodiment, the effector stem-loop is positioned 5' of the aptamer such that the alternatively shared stem arm comprises all or a portion of the 5' aptamer stem arm and all or a portion of the 3' arm of the effector stem. In one embodiment, the polyadenylation signal is AATAAA or ATTAAA. In one embodiment, the polyadenylation signal is a downstream element (DSE). In one embodiment, the polyadenylation signal is an upstream sequence element (USE). In one embodiment, the polynucleotide cassette comprises two riboswitches, wherein the effector stem loop of the first riboswitch comprises all or part of the polyadenylation signal AATAAA or ATTAAA and the effector stem loop of the second riboswitch comprises all or part of the downstream element (DSE). In one embodiment, the two ribo-switches each comprise aptamers that bind the same ligand. In one embodiment, the two riboswitches comprise different aptamers that bind different ligands.

In some embodiments, the riboswitch comprises a sensing region (e.g., an aptamer described herein) and an effector region comprising a binding site for the small nuclear ribonucleoprotein (snRNP) U1, which is part of the spli-ceosome. WO2017/136591 describes riboswitches wherein the effector region comprises a U1 snRNP binding site, and is incorporated herein by reference in its entirety. When the aptamer binds its ligand, the effector region forms a stem and sequesters the U1 snRNP binding site from binding a U1 snRNP. Under certain conditions (for example, when the aptamer is not bound to its ligand), the effector region is in a context that provides access to the U1 snRNP binding site, allowing U1 snRNP to bind the mRNA and inhibit polyade-nylation leading to degradation of the message. The U1 snRNP binding site can be any polynucleotide sequence that is capable of binding the U1 snRNP, thereby recruiting the U1 snRNP to the 3' UTR of a target gene and suppressing polyadenylation of the target gene message. In one embodi-ment, the U1 snRNP binding site is the consensus site CAGGTAAGTA (SEQ ID NO:80) (CAGGUAAGUA, SEQ ID NO:81, when in the mRNA). In some embodiments, the U1 snRNP binding site is a variation of this consensus sequence, including for example sequences that are shorter or have one or more nucleotides changed from the consensus sequence. In one embodiment, the U1 snRNP binding site contains the sequence CAGGTAAG. In some embodiments, the binding site is encoded by the sequence selected from CAGGTAAGTA (SEQ ID NO:80), CAGGTAAGT, and CAGGTAAG. The U1 snRNP binding site can be any 5' splice site from a gene, e.g., the 5' splice site from human DHFR exon 2.

Aptamer-Mediated Modulation of Ribonuclease Cleavage

In one embodiment, the expression of the target gene is regulated through aptamer-modulated ribonuclease cleav-age. Ribonucleases (RNases) recognize and cleave specific ribonuclease substrate sequences. Provided herein are recombinant DNA constructs that, when incorporated into the DNA of a target gene, provide the ability to regulate expression of the target gene by aptamer/ligand mediated ribonuclease cleavage of the resulting RNA. In some embodiments, the aptamer encoding sequence described herein is part of a construct that contains or encodes a ribonuclease substrate sequence and a riboswitch compris-ing an effector region and the aptamer such that when the aptamer binds a ligand, target gene expression occurs (as described in WO2018/161053, which is incorporated in its entirety by reference herein). In embodiments, an RNase P substrate sequence is linked to a riboswitch wherein the riboswitch comprises an effector region and an aptamer described herein, wherein the effector region comprises a sequence complimentary to a portion of the RNase P sub-strate sequence. Binding of a suitable ligand to the aptamer induces structural changes in the aptamer and effector region, altering the accessibility of the ribonuclease sub-strate sequence for cleavage by the ribonuclease.

In one embodiment, the aptamer sequence is located 5' to the RNase P substrate sequence and the effector region comprises all or part of the leader sequence and all or part of the 5' acceptor stem sequence of the RNase P substrate sequence. See, e.g., FIGS. 1a, 1b, and 3b of WO2018/161053 and the associated text, incorporated herein by reference. In further embodiments, the acceptor stem of the RNase P substrate and the riboswitch effector region are separated by 0, 1, 2, 3, or 4 nucleotides. In other embodi-ments, the effector region stem includes, in addition to leader sequence (and its complement), one or more nucleotides of the acceptor stem of the RNase P substrate, and sequence complementary to the one or more nucleotides of the accep-tor stem.

In one embodiment, the aptamer sequence of the poly-nucleotide cassette is located 3' to the RNase P substrate sequence and the effector region comprises sequence com-plimentary to the all or part of the 3' acceptor stem of the RNase P substrate sequence. See, e.g., FIG. 3a of WO2018/161053 and the associated text, incorporated herein by reference. In further embodiments, the effector region sequence complimentary to the 3' acceptor stem of the RNase P substrate is 1 to 7 nucleotides. In other words, the effector region stem includes 1 to 7 nucleotides of the acceptor stem and includes sequence that is complementary to this 1 to 7 nucleotides of the acceptor stem. In embodi-ments, the riboswitch is located 3' of the RNase P substrate so the effector region stem and the acceptor stem of the RNase P substrate do not overlap. In embodiments, the effector region and the acceptor stem of the RNase P substrate are immediately adjacent (i.e., not overlapping). In other embodiments, the effector region and the acceptor stem of the RNase P substrate are separated by 1, 2, 3, 4, 5 or more nucleotides.

The aptamers and gene regulation cassettes disclosed herein can be used to regulate the expression of any target gene that can be expressed in a target cell, tissue or organ-ism. The term "target gene" refers to a polynucleotide that is introduced into a cell and is capable of being transcribed into RNA and translated and/or expressed under appropriate conditions. Alternatively, the target gene is endogenous to the target cell and the gene regulation cassette is positioned into the target gene (for example into an existing untrans-lated region or intron of the endogenous target gene). An example of a target gene is a polynucleotide encoding a therapeutic polypeptide. In one embodiment, the target gene is exogenous to the cell in which the recombinant DNA construct is to be transcribed. In another embodiment, the target gene is endogenous to the cell in which the recom-binant DNA construct is to be transcribed. The target gene may be a gene encoding a protein, or a sequence encoding a non-protein coding RNA. The target gene may be, for example, a gene encoding a structural protein, an enzyme, a cell signaling protein, a mitochondrial protein, a zinc finger protein, a hormone, a transport protein, a growth factor, a cytokine, an intracellular protein, an extracellular protein, a transmembrane protein, a cytoplasmic protein, a nuclear protein, a receptor molecule, an RNA binding protein, a DNA binding protein, a transcription factor, translational machinery, a channel protein, a motor protein, a cell adhe-sion molecule, a mitochondrial protein, a metabolic enzyme, a kinase, a phosphatase, exchange factors, a chaperone protein, and modulators of any of these. In embodiments, the target gene encodes erythropoietin (Epo), human growth hormone (hGH), transcription activator-like effector nucle-ases (TALEN), human insulin, CRISPR associated protein 9 (cas9), or an immunoglobulin (or portion thereof), includ-ing, e.g., a therapeutic antibody.

In embodiments, the aptamers and gene regulation cas-settes disclosed herein are used to regulate the expression of a target gene in eukaryotic cells for example, mammalian cells and more particularly human cells. In embodiments, the aptamers and gene regulation cassettes disclosed herein are used to regulate the expression of a target gene in the eye (including cornea and retina), central nervous system (including the brain), liver, kidney, pancreas, heart, airway, muscle, skin, lung, cartilage, testes, arteries, thymus, bone marrow, or in tumors.

In one aspect, provided are recombinant vectors and their use for the introduction of a polynucleotide comprising a target gene and a gene regulation cassette, wherein the gene regulation cassette comprises an aptamer disclosed herein. In some embodiments, the recombinant DNA constructs include additional DNA elements including DNA segments that provide for the replication of the DNA in a host cell and expression of the target gene in target cells at appropriate levels. The ordinarily skilled artisan appreciates that expression control sequences (promoters, enhancers, and the like) are selected based on their ability to promote expression of the target gene in the target cell. "Vector" means a recombinant plasmid, yeast artificial chromosome (YAC), mini chromosome, DNA mini-circle or virus (including virus derived sequences) that comprises a polynucleotide to be delivered into a host cell, either in vitro or in vivo. In one embodiment, the recombinant vector is a viral vector or a combination of multiple viral vectors.

Viral vectors for the expression of a target gene in a target cell, tissue, or organism are known in the art and include adenoviral (AV) vectors, adeno-associated virus (AAV) vectors, retroviral and lentiviral vectors, and Herpes simplex type 1 (HSV1) vectors.

Adenoviral vectors include, for example, those based on human adenovirus type 2 and human adenovirus type 5 that have been made replication defective through deletions in the E1 and E3 regions. The transcriptional cassette can be inserted into the E1 region, yielding a recombinant E1/E3-deleted AV vector. Adenoviral vectors also include helper-dependent high-capacity adenoviral vectors (also known as high-capacity, "gutless" or "gutted" vectors), which do not contain viral coding sequences. These vectors, contain the cis-acting elements needed for viral DNA replication and packaging, mainly the inverted terminal repeat sequences (ITR) and the packaging signal (CY). These helper-dependent AV vector genomes have the potential to carry from a few hundred base pairs up to approximately 36 kb of foreign DNA.

Recombinant adeno-associated virus "rAAV" vectors include any vector derived from any adeno-associated virus serotype, including, without limitation, AAV-1, AAV-2, AAV-3, AAV-4, AAV-5, AAV-7 and AAV-8, AAV-9, AAV-10, and the like. rAAV vectors can have one or more of the AAV wild-type genes deleted in whole or in part, preferably the Rep and/or Cap genes, but retain functional flanking ITR sequences. Functional ITR sequences are retained for the rescue, replication, packaging and potential chromosomal integration of the AAV genome. The ITRs need not be the wild-type nucleotide sequences, and may be altered (e.g., by the insertion, deletion or substitution of nucleotides) so long as the sequences provide for functional rescue, replication and packaging.

Alternatively, other systems such as lentiviral vectors can be used. Lentiviral-based systems can transduce nondividing as well as dividing cells making them useful for applications targeting, for examples, the nondividing cells of the CNS. Lentiviral vectors are derived from the human immunodeficiency virus and, like that virus, integrate into the host genome providing the potential for very long-term gene expression.

Polynucleotides, including plasmids, YACs, minichromosomes and minicircles, carrying the target gene containing the gene regulation cassette can also be introduced into a cell or organism by nonviral vector systems using, for example, cationic lipids, polymers, or both as carriers. Conjugated poly-L-lysine (PLL) polymer and polyethylenimine (PEI) polymer systems can also be used to deliver the vector to cells. Other methods for delivering the vector to cells includes hydrodynamic injection and electroporation and use of ultrasound, both for cell culture and for organisms. For a review of viral and non-viral delivery systems for gene delivery see Nayerossadat, N. et al. (Adv Biomed Res. 2012; 1:27) incorporated herein by reference.

In one aspect, this disclosure provides a method of modulating the expression of a target gene (e.g., a therapeutic gene) comprising (a) inserting the polynucleotide cassette comprising an aptamer disclosed herein into the target gene, (b) introducing the target gene comprising the polynucleotide cassette into a cell, and (c) exposing the cell to a small molecule ligand that specifically binds the aptamer in an amount effective to induce expression of the target gene. In aspects, expression of the target gene in target cells confers a desired property to a cell into which it was introduced, or otherwise leads to a desired therapeutic outcome.

In one embodiment, a gene regulation cassette comprising an aptamer disclosed herein is inserted into the protein coding sequence of the target gene (rather than in the 5' or 3' untranslated regions). In one embodiment, a single gene regulation cassette comprising an aptamer disclosed herein is inserted into the target gene. In other embodiments 2, 3, 4, or more gene regulation cassettes are inserted in the target gene, wherein one or more gene regulation cassettes comprise an aptamer disclosed herein. In one embodiment, two gene regulation cassettes are inserted into the target gene, wherein one or both gene regulation cassettes comprise an aptamer disclosed herein. When multiple gene regulation cassettes are inserted into a target gene, they each can contain the same aptamer such that a single ligand can be used to modulate target gene expression. In other embodiments, multiple gene regulation cassettes are inserted into a target gene, each can contain a different aptamer so that exposure to multiple different small molecule ligands modulates target gene expression.

Methods of Treatment and Pharmaceutical Compositions

In one aspect, provided is a method of regulating the level of a therapeutic protein delivered by gene therapy. The therapeutic gene sequence containing a regulatory cassette comprising an aptamer disclosed herein is delivered to the target cells in the body, e.g., by a vector. The cell specificity of the target gene expression may be controlled by a promoter and/or other elements within the vector and/or by the capsid of the viral vector. Delivery of the vector construct containing the target gene, and the transfection of the target tissues resulting in stable transfection of the regulated target gene, is the first step in producing the therapeutic protein. However, due to an aptamer within the target gene sequence, the target gene is not expressed at significant levels, i.e., it is in the "off state" in the absence of the specific ligand that binds to the aptamer contained within in the regulatory cassette riboswitch. Only when the aptamer specific ligand is administered is the target gene expression activated.

The delivery of the vector construct containing the target gene and the delivery of the activating ligand generally are separated in time. The delivery of the activating ligand will control when the target gene is expressed, as well as the level of protein expression. The ligand may be delivered by a number of routes including, but not limited to, intravitreal, intraocular, inhalation, subcutaneous, intramuscular, intradermal, intralesion, topical, intraperitoneal, intravenous (IV), intra-arterial, perivascular, intracerebral, intracerebroventricular, oral, sublingual, sublabial, buccal, nasal, intratho-racic, intracardiac, intrathecal, epidural, intraosseous, or intraarticular.

The timing of delivery of the ligand will depend on the requirement for activation of the target gene. For example, if the therapeutic protein encoded by the target gene is required constantly, an oral small molecule ligand may be delivered daily, or multiple times a day, to ensure continual activation of the target gene, and thus continual expression of the therapeutic protein. If the target gene has a long acting effect, the inducing ligand may be dosed less frequently, for example, once a week, every other week, once a month.

This aptamers described herein in the context of a gene regulation cassette comprising a riboswitch allow the expression of a therapeutic transgene to be controlled tem-porally, in a manner determined by the temporal dosing of the ligand specific to the aptamer. The expression of the therapeutic transgene only on ligand administration, increases the safety of a gene therapy treatment by allowing the target gene to be off in the absence of the ligand.

Different aptamers can be used in multiple riboswitches to allow different ligands to up-regulate or down-regulate the expression of a target gene. In certain embodiments, each therapeutic gene containing a regulatory cassette will have a specific aptamer within the cassette that will be activated by a specific small molecule. This means that each therapeutic gene can be activated only by the ligand specific to the aptamer housed within it. In these embodiments, each ligand will only activate one therapeutic gene. This allows for the possibility that several different "target genes" may be delivered to one individual and each will be activated on delivery of the specific ligand for the aptamer contained within the regulatory cassette housed in each target gene.

The aptamers disclosed herein in the context of a ribo-switch allow any therapeutic protein whose gene can be delivered to the body (such as erythropoietin (EPO) or a therapeutic antibody) to be produced by the body when the activating ligand is delivered. This method of therapeutic protein delivery may replace the manufacture of such thera-peutic proteins outside of the body which are then injected or infused, e.g., antibodies used in cancer or to block inflammatory or autoimmune disease. The body containing the regulated target gene becomes the biologics manufac-turing factory, which is switched on when the gene-specific ligand is administered.

In one embodiment, the target protein may be a nuclease that can target and edit a particular DNA sequence. Such nucleases include Cas9, zinc finger containing nucleases, or TALENs. In the case of these nucleases, the nuclease protein may be required for only a short period of time that is sufficient to edit the target endogenous genes. However, if an unregulated nuclease gene is delivered to the body, this protein may be present for the rest of the life of the cell. In the case of nucleases, there is an increasing risk of off-target editing the longer the nuclease is present. Regulation of expression of such proteins has a significant safety advan-tage. In this case, vector containing the nuclease target gene containing a regulatory cassette could be delivered to the appropriate cells in the body. The target gene is in the "off" state in the absence of the cassette-specific ligand, so no nuclease is produced. Only when the activating ligand is administered, is the nuclease produced. When sufficient time has elapsed allowing sufficient editing to occur, the ligand will be withdrawn and not administered again. Thus the nuclease gene is thereafter in the "off" state and no further nuclease is produced and editing stops. This approach may be used to correct genetic conditions, including a number of inherited retinopathies such as LCA10 caused by mutations in CEP290 and Stargardts disease caused by mutations in ABCA4.

Administration of a regulated target gene encoding a therapeutic protein which is activated only on specific ligand administration may be used to regulate therapeutic genes to treat many different types of diseases, e.g., cancer with therapeutic antibodies, immune disorders with immune modulatory proteins or antibodies, metabolic diseases, rare diseases such as PNH with anti-C5 antibodies or antibody fragments as the regulated gene, or ocular angiogenesis with therapeutic antibodies, and dry AMD with immune modu-latory proteins.

A wide variety of specific target genes, allowing for the treatment of a wide variety of specific diseases and condi-tions, are suitable for use as a target gene whose expression can be regulated using an aptamer/ligand described herein. For example, insulin or an insulin analog (preferably human insulin or an analog of human insulin) may be used as the target gene to treat type I diabetes, type II diabetes, or metabolic syndrome; human growth hormone may be used as the target gene to treat children with growth disorders or growth hormone-deficient adults; erythropoietin (preferably human erythropoietin) may be used as the target gene to treat anemia due to chronic kidney disease, anemia due to myelo-dysplasia, or anemia due to cancer chemotherapy. Additional target genes compatibles with the aptamers and gene expres-sion cassettes disclosed herein include, but are not limited to, cyclic nucleotide-gated cation channel alpha-3 (CNGA3) and cyclic nucleotide-gated cation channel beta-3 (CNGB3) for the treatment of achromatopsia, retinoid isomerohydro-lase (RPE65) for the treatment of retinitis pigmentosa or Leber's congenital amaurosis, X-linked retinitis pigmentosa GTPase regulator (RPGR) for the treatment of X-linked retinitis pigmentosa, glutamic acid decarboxylase (GAD) including for the treatment of Parkinson's disease, regulator of nonsense transcripts 1 (UPF1) for the treatment amyo-trophic lateral sclerosis, and aquaporin for the treatment of radiation-induced xerostomia and Sjogren's syndrome. Additional target genes include ArchT (archaerhodopsin from Halorubrum strain TP009), Jaws (cruxhalorhodopsin derived from *Haloarcula* (Halobacterium) *salinarum* (strain Shark)), iC1C2 (a variant of a C1C2 chimaera between channel rhodopsins ChR1 and ChR2 from *Chlamydomonas reinhardtii*), or Rgs9-anchor protein (R9AP), a critical com-ponent of GTPase complex that mediates the deactivation of phototransduction cascade.

The expression constructs comprising an aptamer dis-closed herein may be especially suitable for treating diseases caused by single gene defects such as cystic fibrosis, hemo-philia, muscular dystrophy, thalassemia, or sickle cell ane-mia. Thus, human β-, γ-, δ-, or ζ-globin may be used as the target gene to treat β-thalassemia or sickle cell anemia; human Factor VIII or Factor IX may be used as the target gene to treat hemophilia A or hemophilia B.

The small molecules described herein are generally com-bined with one or more pharmaceutically acceptable carriers to form pharmaceutical compositions suitable for adminis-tration to a patient. Pharmaceutically acceptable carriers include solvents, binders, diluents, disintegrants, lubricants, dispersion media, coatings, antibacterial and antifungal agents, isotonic and absorption delaying agents, and the like, generally used in the pharmaceutical arts. Pharmaceutical compositions may be in the form of tablets, pills, capsules, troches, and the like, and are formulated to be compatible with their intended route of administration. Examples of routes of administration include parenteral, e.g., intravenous, intradermal, intranasal, subcutaneous, oral, inhalation, transdermal (topical), transmucosal, The pharmaceutical compositions comprising thiamine analog or derivative are administered to a patient in a dosing schedule such that an amount of thiamine analog or derivative sufficient to desirably regulate the target gene is delivered to the patient. When the dosage form is a tablet, pill, or the like, preferably the pharmaceutical composition comprises from 0.1 mg to 10 g of thiamine analog or derivative; from 0.5 mg to 5 g of thiamine analog or derivative; from 1 mg to 1 g of thiamine analog or derivative; from 2 mg to 750 mg of thiamine analog or derivative; from 5 mg to 500 mg of thiamine analog or derivative; from 10 mg to 250 mg of thiamine analog or derivative; or from 150 mg to 300 mg of thiamine analog or derivative.

The pharmaceutical compositions may be dosed once per day or multiple times per day (e.g., 2, 3, 4, 5, or more times per day). Alternatively, pharmaceutical compositions may be dosed less often than once per day, e.g., once every 2, 3, 4, 5, 6, 7, 8, 9, 10, 11, 12, 13, or 14 days, or once a month or once every few months. In some embodiments, the pharmaceutical compositions may be administered to a patient only a small number of times, e.g., once, twice, three times, etc.

Provided herein is a method of treating a patient in need of increased expression of a therapeutic protein encoded by a target gene, the method comprising administering to the patient a pharmaceutical composition comprising a ligand, which an aptamer disclosed herein binds to or otherwise responds to, wherein the patient previously had been administered a recombinant DNA comprising the target gene, and where the target gene contains a gene regulation cassette disclosed herein that provides the ability to regulate expression of the target gene by the ligand of the aptamer. Provided herein is a pharmaceutical composition comprising a ligand, which an aptamer disclosed herein binds to or otherwise responds to, for use in a method of treating a patient in need of increased expression of a therapeutic protein encoded by a target gene, wherein the patient previously had been administered a recombinant DNA comprising the target gene, and where the target gene contains a gene regulation cassette disclosed herein that provides the ability to regulate expression of the target gene by the ligand of the aptamer.

Aptamers for Detection and/or Diagnostic Uses

A wide range of detection and diagnostic agents can be linked to aptamers through chimerical or physical conjugation. Further, aptamers can be incorporated in biosensors, microfluidic devices and other detection platforms. In some embodiments, the aptamer is conjugated to a polyalkylene glycol moiety, including, but not limited to, polyethylene glycol (PEG), polypropylene glycol (PPG), polyoxyethylated glycerol (POG) and other polyoxyethylated polyols, polyvinyl alcohol (PVA) and other polyalkylene oxides, polyoxyethylated sorbitol, or polyoxyethylated glucose.

In some embodiments, the aptamer is conjugated to a detectable moiety, including, but not limited to, fluorescent moieties or labels, imaging agents, radioisotopic moieties, radiopaque moieties, and the like, e.g. detectable labels such as biotin, fluorophores, chromophores, spin resonance probes, nanoparticles (including, but not limited to gold, magnetic, and superparamagnetic nanoparticles), quantum dots, radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}$C, $^{15}$N, $^{2}$H, $^{125}$I, $^{123}$I, $^{99}$Tc, $^{43}$K, $^{52}$Fe, $^{67}$Ga, $^{68}$Ga, $^{111}$In and the like). Other useful moieties are known in the art.

In some embodiments, the aptamer is conjugated to a therapeutic moiety, including, but not limited to, an anti-inflammatory agent, anti-cancer agent, anti-neurodegenerative agent, anti-infective agent, or generally a therapeutic agent.

Methods for Identifying an Aptamer That Binds to a Compound

Disclosed herein are methods for identifying an aptamer that binds to a compound of interest (such a small molecule including a thiamine analog, TPP analog, or derivatives thereof), or otherwise modulates target gene expression when part of a riboswitch in response to the addition of, or exposure to, the compound of interest. In one embodiment, the method comprises the steps of:

(i) selecting a parent aptamer sequence;

(ii) generating an aptamer library comprising sequence encoding the aptamer selected in (i), wherein one or more nucleotides in the aptamer encoding sequence are randomly mutated at one or more positions that correspond to one or more unpaired regions in the aptamer, wherein the mutated aptamer sequences are in the context of a riboswitch that controls the expression of a reporter gene;

(iii) screening the library from (ii) for aptamers having increased regulation (e.g., higher fold induction or repression) of the target gene expression in response to the thiamine analog compared to the parent aptamer sequence;

(iv) optionally repeating steps (ii) and (iii) on an aptamer identified in step (iii) rather than an aptamer selected in step (i).

The parent aptamer sequence may be a TPP aptamer, including known TPP aptamer sequence or may be a putative TPP aptamer identified by searching for homologous sequences in available databases. The parent aptamer sequence may be an aptamer sequence disclosed herein.

The step of selecting a parent aptamer sequence can involve, for example, (i) identifying a putative TPP aptamer; (ii) inserting the aptamer into a riboswitch that modulates the expression of a target gene (for example a reporter gene); and (iii) exposing the riboswitch/target gene construct to a thiamine or TPP analog or derivative (e.g., the compounds described herein).

Putative TPP aptamers can be identified from an appropriate sequence database such as the Rfam database, which is a collection of RNA families, each represented by multiple sequence alignments, consensus secondary structures and covariance models (CMs). In embodiments, the putative TPP aptamer is identified from the Rfam TPP riboswitch family RF00059. In embodiments, the putative TPP aptamer has a sequence that is at least 85%, at least 90%, at least 95%, at least 96%, at least 97% at least 98% or at least 99% identical to SEQ ID NO:94 or SEQ ID NO:95 (thiC or thiM aptamer with stems, respectively).

SEQ ID NO: 94:
GUAAUGUGUCGGAGUGCCUUAGGGAUUAUUCCCCUAAAGCUGAGACCGC

AUUGCGGGAUCCGUUGAACCUGAUCAGGCUAAUACCUGCGAAGGGAACA

CAUUAC

-continued

SEQ ID NO: 95:
GUAAUGUCUCGGGGUGCCCUUCUGCGUGAAGGCUGAGAAAUACCCGUAU

CACCUGAUCUGGAUAAUGCCAGCGUAGGGAAGACAUUAC

The putative TPP aptamer can be inserted into a ribo-switch using techniques known to the ordinarily skilled artisan. The responsiveness of the aptamer to the presence of TPP and one or more thiamine or TPP analogs or derivatives (e.g., the compounds described herein) can be tested in cell culture and/or in a cell-free system. In particular, the cell culture system is a eukaryotic cell culture including, e.g., a mammalian, a plant, or an insect cell culture.

In order to identify aptamers that respond to a thiamine or TPP analog or derivative (e.g., the compounds described herein), one or more nucleotide positions of the sequence encoding the aptamer (i.e., the parent aptamer) are random-ized. The nucleotide positions for randomization can be selected based on the structure of the parent aptamer sequence. The predicted secondary structure can be obtained using available programs such as RNAfold (http://rna.tbi-.univie.ac.at/cgi-bin/RNAWebSuite/RNAfold.cgi) and/or by comparison to the crystal structure of a related aptamer (e.g., the *E. coli* thiM riboswitch in Edwards, T E & Ferré-D'Amaré, AR, Structure. 2006 September; 14(9):1459-68). For example, unpaired regions of the aptamer, including loop (L) regions (e.g., L3 and/or L5) and joining (J) regions (e.g., J3-2 (joining paired regions P3 and P2), J2-4, and/or J4-5), can be identified, and one or more nucleotides in one or more unpaired regions can be randomized to generate a library of aptamers. In embodiments, one or more nucleo-tides adjacent to one or more unpaired regions are random-ized. Additionally, one or more nucleotides in a paired (P) region can be randomized. Further, one or more nucleotides in an unpaired or paired region can be added or deleted. The mutagenized aptamer sequences can be provided as a library of aptamer sequences in the context of a riboswitch. In embodiments, the aptamer library is provided in the context of a riboswitch as part of a gene expression cassette dis-closed herein.

The aptamer encoding sequences containing one or more mutations can be tested for responsiveness to the presence of TPP or one or more thiamine or TPP analogs or derivatives as described above. In embodiments, the aptamer containing one or more mutations is responsive to the analog or derivative, but has reduced responsiveness to thiamine and/or TPP than the parent aptamer from which it is derived (in the context of the same riboswitch/gene expression cas-sette).

Aptamers that are responsive to the desired compound, can be further mutagenized by randomizing nucleotides. The nucleotides at selected positions, for example unpaired regions, can be randomized and a library created as described above.

In some embodiments, the compound of interest is thia-mine analog, such as acefurtiamine, acetiamine, allithia-mine, amprolium, beclotiamine, benfotiamine, bentiamine, bisbentiamine, cetotiamine, cycotiamine, fursultiamine, monophosphothiamine, octotiamine, oxythiamine, prosul-tiamine, sulbutiamine, or vintiamol. In embodiments, the thiamine or TPP analog is a compound of Formula I-VIII, including, but not limited to the compounds M10-M99. In embodiments, the thiamine or TPP analog is one of M10, M16, M18, M19, M21, M26, M27, M28, M29, M30, M31, M32, M33, and M34.

Reporter proteins encoded by the reporter genes used in the methods disclosed herein are proteins that can be assayed by detecting characteristics of the reporter protein, such as enzymatic activity or spectrophotometric character-istics, or indirectly, such as with antibody-based assays. Examples of reporter gene products that are readily detect-able include, but are not limited to, puromycin resistance marker (pac), 3-galactosidase, luciferase, orotidine 5'-phos-phate decarboxylase (URA3), arginine permease CAN1, galactokinase (GAL1), beta-galactosidase (LacZ), or chloramphenicol acetyl transferase (CAT). Other examples of detectable signals include cell surface markers, including, but not limited to CD4. Reporter genes suitable for the use in the methods for identifying aptamers disclosed herein also include fluorescent proteins (e.g., green fluorescent protein (GFP) and its derivatives), or proteins fused to a fluorescent tag. Examples of fluorescent tags and proteins include, but are not limited to, (3-F)Tyr-EGFP, A44-KR, aacuGFP1, aacuGFP2, aceGFP, aceGFP-G222E-Y220L, aceGFP-h, AcGFP1, AdRed, AdRed-C148S, aeurGFP, afraGFP, alajGFP1, alajGFP2, alajGFP3, amCyanl, amFP486, amFP495, amFP506, amFP515, amilFP484, amilFP490, amilFP497, amilFP504, amilFP512, amilFP513, amilFP593, amilFP597, anm1GFP1, anm1GFP2, anm2CP, anobCFP1, anobCFP2, anobGFP, apulFP483, AQ14, AQ143, Aquama-rine, asCP562, asFP499, AsRed2, asulCP, atenFP, avGFP, avGFP454, avGFP480, avGFP509, avGFP510, avGFP514, avGFP523, AzamiGreen, Azurite, BDFP1.6, bfloGFPa1, bfloGFPc1, BFP, BFP.A5, BFP5, bsDronpa (On), ccalGFP1, ccalGFP3, ccalOFP1, ccalRFP1, ccalYFP1, cEGFP, cerFP505, Cerulean, CFP, cFP484, cfSGFP2, cgfmKate2, CGFP, cgfTagRFP, cgigGFP, cgreGFP, CheGFP1, CheGFP2, CheGFP4, Citrine, Citrine2, Clomeleon, Clover, cp-mKate, cpCitrine, cpT-Sapphire174-173, CyOFP1, CyPet, CyRFP1 (CyRFP1), d-RFP618, D10, dlEosFP (Green), dlEosFP (Red), d2EosFP (Green), d2EosFP (Red), deGFP1, deGFP2, deGFP3, deGFP4, dendFP (Green), dendFP (Red), Dendra (Green), Dendra (Red), Dendra2 (Green), Dendra2 (Red), Dendra2-M159A (Green), Den-dra2-M159A (Orange), Dendra2-T69A (Green), Dendra2-T69A (Orange), dfGFP, dimer1, dimer2, dis2RFP, dis3GFP, dKeima, dKeima570, dLanYFP, DrCBD, Dreiklang (On), Dronpa (On), Dronpa-2 (On), Dronpa-3 (On), dsFP483, DspR1, DsRed, DsRed-Express, DsRed-Express2, DsRed-Max, DsRed.M1, DsRed.T3, DsRed.T4, DsRed2, DstC1, dTFP0.1, dTFP0.2, dTG, dTomato, dVFP, E2-Crimson, E2-Orange, E2-Red/Green, EaGFP, EBFP, EBFP1.2, EBFP1.5, EBFP2, ECFP, ECFPH148D, ECGFP, eechGFP1, eechGFP2, eechGFP3, eechRFP, efasCFP, efasGFP, eforCP, EGFP, eGFP203C, eGFP205C, Emerald, Enhanced Cyan-Emitting GFP, EosFP (Green), EosFP (Red), eqFP578, eqFP611, eqFP611V124T, eqFP650, eqFP670, EYFP, EYFP-Q69K, fabdGFP, ffDronpa (On), FoldingRe-porterGFP, FP586, FPrfl2.3, FR-1, FusionRed, FusionRed-M, G1, G2, G3, Gamillus (On), Gamillus0.1, Gamillus0.2, Gamillus0.3, Gamillus0.4, GCaMP2, gfasGFP, GFP(S65T), GFP-151pyTyrCu, GFP-Tyrl51pyz, GFPmut2, GFPmut3, GFPxm16, GFPxm161, GFPxm162, GFPxm163, GFPxm18, GFPxm181uv, GFPxm18uv, GFPxm19, GFPxm19luv, GFPxm19uv, H9, HcRed, HcRed-Tandem, HcRed7, hcriGFP, hmGFP, HriCFP, HriGFP, iFP1.4, iFP2.0, iLov, iq-EBFP2, iq-mApple, iq-mCerulean3, iq-mEmerald, iq-mKate2, iq-mVenus, iRFP670, iRFP682, iRFP702, iRFP713, iRFP720, IrisFP (Green), IrisFP (Orange), IrisFP-M159A (Green), Jred, Kaede (Green), Kaede (Red), Katushka, Katushka-9-5, Katushka2S, KCY, KCY-G4219, KCY-G4219-38L, KCY—R1, KCY-R1-158A, KCY-R1-

38H, KCY-R1-38L, KFP1 (On), KikGR1 (Green), KikGR1 (Red), KillerOrange, KillerRed, KO, Kohinoor (On), laes-GFP, laGFP, LanFP1, LanFP2, lanRFP-AS831, LanYFP, laRFP, LSS-mKatel, LSS-mKate2, LSSmOrange, M355NA, mAmetrine, mApple, Maroon0.1, mAzamiGreen, mBanana, mBeRFP, mBlueberryl, mBlueberry2, mc1, mc2, mc3, mc4, mc5, mc6, McaG1, McaGlea, McaG2, mCardinal, mCarmine, mcavFP, mcavGFP, mcavRFP, mcCFP, mCerulean, mCerulean.B, mCerulean.B2, mCerulean.B24, mCerulean2, mCerulean2.D3, mCerulean2.N, mCerulean2.N(T65S), mCerulean3, mCherry, mCherry2, mCitrine, mClavGR2 (Green), mClavGR2 (Red), mClover3, mCyRFP1, mECFP, meffCFP, meffGFP, meffRFP, mEGFP, meleCFP, meleRFP, mEmerald, mEos2 (Green), mEos2 (Red), mEos2-A69T (Green), mEos2-A69T (Orange), mEos3.1 (Green), mEos3.1 (Red), mEos3.2 (Green), mEos3.2 (Red), mEos4a (Green), mEos4a (Red), mEos4b (Green), mEos4b (Red), mEosFP (Green), mEosFP (Red), mEosFP-F173S (Green), mEosFP-F173S (Red), mEosFP-M159A (Green), mEYFP, MfaGl, mGarnet, mGarnet2, mGeos-C(On), mGeos-E (On), mGeos-F (On), mGeos-L (On), mGeos-M (On), mGeos-S (On), mGingerl, mGinger2, mGrape1, mGrape2, mGrape3, mHoneydew, MiCy, mIFP, miniSOG, miniSOGQ103V, miniSOG2, miRFP, miRFP670, miRFP670nano, miRFP670-vl, miRFP703, miRFP709, miRFP720, mIrisFP (Green), mIrisFP (Red), mK-GO (Early), mK-GO (Late), mKalamal, mKate, mKateM41GS158C, mKateS158A, mKateS158C, mKate2, mKeima, mKellyl, mKelly2, mKG, mKikGR (Green), mKikGR (Red), mKillerOrange, mKO, mKO2, mKOx, mLumin, mMaple (Green), mMaple (Red), mMaple2 (Green), mMaple2 (Red), mMaple3 (Green), mMaple3 (Red), mMaroonl, mmGFP, mMiCy, mmilCFP, mNectarine, mNeonGreen, mNeptune, mNeptune2, mNeptune2.5, mNeptune681, mNeptune684, Montiporasp. #20-9115, mOrange, mOrange2, moxBFP, moxCerulean3, moxDendra2 (Green), moxDendra2 (Red), moxGFP, moxMaple3 (Green), moxMaple3 (Red), moxNeonGreen, moxVenus, mPapaya, mPapaya0.7, mPlum, mPlum-E16P, mRaspberry, mRed7, mRed7Q1, mRed7Q1S1, mRed7Q1S1BM, mRFP1, mRFP1-Q66C, mRFP1-Q66S, mRFP1-Q66T, mRFP1.1, mRFP1.2, mRojoA, mRojoB, mRouge, mRtms5, mRuby, mRuby2, mRuby3, mScarlet, mScarlet-H, mScarlet-I, mStable, mStrawberry, mT-Sapphire, mTagBFP2, mTangerine, mTFP0.3, mTFP0.7 (On), mTFP1, mTFP1-Y67W, mTurquoise, mTurquoise2, muGFP, mUkG, mVenus, mVenus-Q69M, mVFP, mVFP1, mWasabi, Neptune, NijiFP (Green), NijiFP (Orange), NowGFP, obeCFP, obeGFP, obeYFP, OFP, OFPxm, oxBFP, oxCerulean, oxGFP, oxVenus, P11, P4, P4-1, P4-3E, P9, PA-GFP (On), Padron (On), Padron(star) (On), Padron0.9 (On), PAmCherryl (On), PAmCherry2 (On), PAmCherry3 (On), PAmKate (On), PATagRFP (On), PATagRFP1297 (On), PATagRFP1314 (On), pcDronpa (Green), pcDronpa (Red), pcDronpa2 (Green), pcDronpa2 (Red), PdaC1, pdael-GFP, phiYFP, phiYFPv, pHluorin,ecliptic, pHluorin,ecliptic (acidic), pHluorin,ratiometric (acidic), pHluorin,ratiometric (alkaline), pHluorin2 (acidic), pHluorin2 (alkaline), pHuji, PlamGFP, pmeaGFP1, pmeaGFP2, pmimGFP1, pmimGFP2, Pp2FbFP, Pp2FbFPL30M, ppluGFP1, ppluGFP2, pporGFP, pporRFP, PS—CFP (Cyan), PS—CFP (Green), PS—CFP2 (Cyan), PS—CFP2 (Green), psamCFP, PSmOrange (Far-red), PSmOrange (Orange), PSmOrange2 (Far-red), PSmOrange2 (Orange), ptilGFP, R3-2+PCB, RCaMP, RDSmCherry0.1, RDSmCherry0.2, RDSmCherry0.5, RDSmCherryl, rfloGFP, rfloRFP, RFP611, RFP618, RFP630, RFP637, RFP639, roGFP1, roGFPI-R1, roGFPI-R8, roGFP2, rrenGFP, RRvT, rsCherry (On), rsCherryRev (On), rsCherryRev1.4 (On), rsEGFP (On), rsEGFP2 (On), rsFastLime (On), rsFolder (Green), rsFolder2 (Green), rsFusionRed1 (On), rsFusionRed2 (On), rsFusionRed3 (On), rsTagRFP (ON), Sandercyanin, Sapphire, sarcGFP, SBFP1, SBFP2, SCFP1, SCFP2, SCFP3A, SCFP3B, scubGFPl, scubGFP2, scubRFP, secBFP2, SEYFP, sgl1, sgl2, sg25, sg42, sg50, SGFP1, SGFP2, SGFP2(206A), SGFP2(E222Q), SGFP2(T65G), SHardonnay, shBFP, shBFP-N158S/L173I, ShG24, Sirius, SiriusGFP, Skylan-NS (On), Skylan-S(On), smURFP, SNIFP, SOPP, SOPP2, SOPP3, SPOON (on), stylGFP, SuperfolderGFP, SuperfoldermTurquoise2, SuperfoldermTurquoise2ox, SuperNovaGreen, SuperNovaRed, SYFP2, T-Sapphire, TagBFP, TagCFP, TagGFP, TagGFP2, TagRFP, TagRFP-T, TagRFP657, TagRFP675, TagYFP, td-RFP611, td-RFP639, tdimer2(12), tdKatushka2, TDsmURFP, tdTomato, tKeima, Topaz, TurboGFP, TurboGFP-V197L, TurboRFP, Turquoise-GL, Ultramarine, UnaG, usGFP, Venus, VFP, vsfGFP-0, vsfGFP-9, WiC, W2, W7, WasCFP, Wi-Phy, YPet, zFP538, zoan2RFP, ZsGreen, ZsYellowl, αGFP, 10B, 22G, 5B, 6C, Ala, aacuCP, acanFP, ahyaCP, amilCP, amilCP580, amilCP586, amilCP604, apulCP584, BFPsol, Blue102, CFP4, cgigCP, CheGFP3, Clover1.5, cpasCP, Cy11.5, dClavGR1.6, dClover2, dClover2A206K, dhorGFP, dhorRFP, dPapaya0.1, Dronpa-C62S, DsRed-Timer, echFP, echiFP, EYFP-F46L, fcFP, fcomFP, Fpaagar, Fpag_frag, Fpcondchrom, FPmann, FPmcavgr7.7, Gamillus0.5, gdjiCP, gfasCP, GFPhal, gtenCP, hcriCP, hfriFP, KikG, LEA, mcFP497, mcFP503, mcFP506, mCherry1.5, mClavGR1, mClavGR1.1, mClavGR1.8, mClover1.5, mcRFP, meffCP, mEos2-NA, meruFP, mKate2.5, mOFP.T.12, mOFP.T.8, montFP, moxEos3.2, mPA-GFP, mPapaya0.3, mPapaya0.6, mRFPl.3, mRFPl.4, mRFPl.5, mTFP0.4, mTFP0.5, mTFP0.6, mTFP0.8, mTFP0.9, mTFP1-Y67H, mTurquoise-146G, mTurquoise-146S, mTurquoise-DR, mTurquoise-GL, mTurquoise-GV, mTurquoise-RA, mTurquoise2-G, NpR3784g, PDM1-4, psupFP, Q80R, rfloGFP2, RpBphPl, RpBphP2, RpBphP6, rrGFP, RSGFP1, RSGFP2, RSGFP3, RSGFP4, RSGFP6, RSGFP7, Rtms5, scleFP1, scleFP2, spisCP, stylCP, sympFP, TeAPCa, tPapaya0.01, TrplessGFP, vsGFP, Xpa, yEGFP, YFP3, zGFP, and zRFP.

Methods for screening an aptamer library disclosed herein may include measuring the activity of the reporter gene under the control of the aptamer and/or comparing the activity of the reporter gene in presence of the thiamine or TPP analog used for the screen as compared to the activity of the reporter gene in absence of the thiamine or TPP analog used for the screen.

Articles of Manufacture and Kits

Also provided are kits or articles of manufacture for use in the methods described herein. In aspects, the kits comprise the compositions described herein (e.g., compositions for delivery of a vector comprising the target gene containing the gene regulation cassette) in suitable packaging. Suitable packaging for compositions (such as ocular compositions for injection) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

Also provided are kits comprising the compositions described herein. These kits may further comprise instruction(s) on methods of using the composition, such as uses described herein. The kits described herein may further include other materials desirable from a commercial and user standpoint, including buffers, diluents, filters, needles, syringes, and package inserts with instructions for performing the administration of the composition or performing any methods described herein. For example, in some embodiments, the kit comprises an rAAV for the expression of a target gene comprising a gene regulation cassette containing an aptamer sequence described herein, a pharmaceutically acceptable carrier suitable for injection, and one or more of: a buffer, a diluent, a filter, a needle, a syringe, and a package insert with instructions for performing the injections. In some embodiments, the kit is suitable for intraocular injection, intramuscular injection, intravenous injection and the like.

It is to be understood and expected that variations of the compositions of matter and methods herein disclosed can be made by one skilled in the art and it is intended that such modifications are to be included within the scope of the present disclosure. The following Examples further illustrate the invention, but should not be construed to limit the scope of the invention in any way.

All references cited herein are hereby incorporated by reference in their entirety. All nucleotide sequences provided herein are in a 5' to 3' orientation unless stated otherwise. A Sequence Listing is filed herewith, the contents of which are incorporated herein by reference in its entirety.

EXAMPLES

Example 1. Synthetic Riboswitch Comprising Thiamine Pyrophosphate (TPP)-Responsive Aptamers can Regulate Gene Expression in Response to TPP and Thiamine Analogs

Experimental Procedures

Riboswitch constructs: Aptamers were synthesized by Integrated DNA Technologies, Inc. and Golden Gate cloning strategy (New England Biolabs, NEB) was used to clone the synthesized aptamer sequences into intron-exon-intron cassette to replace the guanine aptamer in the G17 riboswitch cassette (see SEQ ID NO: 15 recited in WO 2016/126747, which is incorporated herein in its entirety) with a TPP aptamer from the *Alishewanella tabrizica* thiC gene (Microbiol Res. 2017 January; 195:71-80) or a TPP aptamer from the *Escherichia coli* thiM gene (Structure. 2006 September; 14(9):1459-68), generating riboswitch TPPz and TPPm, respectively.

SEQ ID NO: 82 was obtained by inserting the TPPz riboswitch into the luciferase reporter gene. Capital letters indicate the luciferase encoding sequence. Lower case letters indicate the intron/alternative exon/intron and riboswitch sequence. The thiC aptamer encoding sequence (SEQ ID NO: 96) is underlined. In one embodiment, provided is a riboswitch comprising SEQ ID NO: 82, wherein the aptamer encoding sequence (SEQ ID NO: 96) in SEQ ID NO:82 is replaced with another aptamer sequence disclosed herein.

```
                                      SEQ ID NO: 82
ATGGAAGACGCCAAAAACATAAAGAAAGGCCCGGCGCCATTCTATCCGC

TGGAAGATGGAACCGCTGGAGAGCAACTGCATAAGGCTATGAAGAGATA

CGCCCTGGTTCCTGGAACAATTGCTTTTACAGATGCACATATCGAGGTG

GACATCACTTACGCTGAGTACTTCGAAATGTCCGTTCGGTTGGCAGAAG

CTATGAAACGATATGGGCTGAATACAAATCACAGAATCGTCGTATGCAG
```

```
                    -continued
TGAAAACTCTCTTCAATTCTTTATGCCGGTGTTGGGCGCGTTATTTATC

GGAGTTGCAGTTGCGCCCGCGAACGACATTTATAATGAACGTGAATTGC

TCAACAGTATGGGCATTTCGCAGCCTACCGTGGTGTTCGTTTCCAAAAA

GGGGTTGCAAAAAATTTTGAACGTGCAAAAAAAGCTCCCAATCATCCAA

AAAATTATTATCATGGATTCTAAAACGGATTACCAGGGATTTCAGTCGA

TGTACACGTTCGTCACATCTCATCTACCTCCCGGTTTTAATGAATACGA

TTTTGTGCCAGAGTCCTTCGATAGGGACAAGACAATTGCACTGATCATG

AACTCCTCTGGATCTACTGGTCTGCCTAAAGGTGTCGCTCTGCCTCATA

GAACTGCCTGCGTGAGATTCTCGCATGCCAGAGATCCTATTTTTGGCAA

TCAAATCATTCCGGATACTGCGATTTTAAGTGTTGTTCCATTCCATCAC

GGTTTTGGAATGTTTACTACACTCGGATATTTGATATGTGGATTTCGAG

TCGTCTTAATGTATAGATTTGAAGAAGAGCTGTTTCTGAGGAGCCTTCA

GGATTACAAGATTCAAAGTGCGCTGCTGGTGCCAACCCTATTCTCCTTC

TTCGCCAAAAGCACTCTGATTGACAAATACGATTTATCTAATTTACACG

AAATTGCTTCTGGTGGCGCTCCCCTCTCTAAGGAAGTCGGGGAAGCGGT

TGCCAAGAGGTTCCATCTGCCAGGTATCAGGgtgagtctatgggaccct tgatgtttctttcccctctttctatggttaagttcatgtcatagga aggggagaagtaacagggtacacatattgaccaaatcagggtaattttg catttgtaattttaaaaaatgctttcttcttttaatatacttttttgtt tatcttatttctaatactttccctaatctctttctttcagggcaataat gatacaatgtatcatgccgagtaacgctgtttctctaacttgtaggaat gaattcagatatttccagagaatgaaaaaaaaatcttcagtagaaggta atgtgtcggagtgccttagggattattcccctaaagctgagaccgcatt gcgggatccgttgaacctgatcaggctaataacctgcgaagggaacacat tacgcaccattctaaagaataacagtgataatttctgggttaaggcaat agcaatatttctgcatataaatatttctgcatataaattgtaactgatg taagaggtttcatattgctaatagcagctacaatccagctaccattctg cttttattttatggttgggataaggctggattattctgagtccaagcta ggcccttttgctaatcatgttcatacctcttatcttcctcccacagCAA

GGATATGGGCTCACTGAGACTACATCAGCTATTCTGATTACACCCGAGG

GGGATGATAAACCGGGCGCGGTCGGTAAAGTTGTTCCATTTTTTGAAGC

GAAGGTTGTGGATCTGGATACCGGGAAAACGCTGGGCGTTAATCAAAGA

GGCGAACTGTGTGTGAGAGGTCCTATGATTATGTCCGGTTATGTAAACA

ATCCGGAAGCGACCAACGCCTTGATTGACAAGGATGGATGGCTACATTC

TGGAGACATAGCTTACTGGGACGAAGACGAACACTTCTTCATCGTTGAC

CGCCTGAAGTCTCTGATTAAGTACAAAGGCTATCAGGTGGCTCCCGCTG

AATTGGAATCCATCTTGCTCCAACACCCCAACATCTTCGACGCAGGTGT

CGCAGGTCTTCCCGACGATGACGCCGGTGAACTTCCCGCCGCCGTTGTT

GTTTTGGAGCACGGAAAGACGATGACGGAAAAAGAGATCGTGGATTACG

TCGCCAGTCAAGTAACAACCGCGAAAAAGTTGCGCGGAGGAGTTGTGTT

TGTGGACGAAGTACCGAAAGGTCTTACCGGAAAACTCGACGCAAGAAAA
```

-continued

ATCAGAGAGATCCTCATAAAGGCCAAGAAGGGCGGAAAGATCGCCGTGT

AA

SEQ ID NO: 83 was obtained by inserting the TPPm riboswitch into the luciferase reporter gene. Capital letters indicate the luciferase encoding sequence. Lower case letters indicate the intron/alternative exon/intron and riboswitch sequence. The thiM aptamer encoding sequence (SEQ ID NO:97) is underlined. In one embodiment, provided is a riboswitch comprising SEQ ID NO: 83, wherein the aptamer encoding sequence (SEQ ID NO: 97) in SEQ ID NO:83 is replaced with another aptamer sequence disclosed herein.

SEQ ID NO: 83
ATGGAAGACGCCAAAAACATAAAGAAAGGCCCGGCGCCATTCTATCCGC

TGGAAGATGGAACCGCTGGAGAGCAACTGCATAAGGCTATGAAGAGATA

CGCCCTGGTTCCTGGAACAATTGCTTTTACAGATGCACATATCGAGGTG

GACATCACTTACGCTGAGTACTTCGAAATGTCCGTTCGGTTGGCAGAAG

CTATGAAACGATATGGGCTGAATACAAATCACAGAATCGTCGTATGCAG

TGAAAACTCTCTTCAATTCTTTATGCCGGTGTTGGGCGCGTTATTTATC

GGAGTTGCAGTTGCGCCCGCGAACGACATTTATAATGAACGTGAATTGC

TCAACAGTATGGGCATTTCGCAGCCTACCGTGGTGTTCGTTTCCAAAAA

GGGGTTGCAAAAAATTTTGAACGTGCAAAAAAAGCTCCCAATCATCCAA

AAAATTATTATCATGGATTCTAAAACGGATTACCAGGGATTTCAGTCGA

TGTACACGTTCGTCACATCTCATCTACCTCCCGGTTTTAATGAATACGA

TTTTGTGCCAGAGTCCTTCGATAGGGACAAGACAATTGCACTGATCATG

AACTCCTCTGGATCTACTGGTCTGCCTAAAGGTGTCGCTCTGCCTCATA

GAACTGCCTGCGTGAGATTCTCGCATGCCAGAGATCCTATTTTTGGCAA

TCAAATCATTCCGGATACTGCGATTTTAAGTGTTGTTCCATTCCATCAC

GGTTTTGGAATGTTTACTACACTCGGATATTTGATATGTGGATTTCGAG

TCGTCTTAATGTATAGATTTGAAGAAGAGCTGTTTCTGAGGAGCCTTCA

GGATTACAAGATTCAAAGTGCGCTGCTGGTGCCAACCCTATTCTCCTTC

TTCGCCAAAAGCACTCTGATTGACAAATACGATTTATCTAATTTACACG

AAATTGCTTCTGGTGGCGCTCCCCTCTCTAAGGAAGTCGGGGAAGCGGT

TGCCAAGAGGTTCCATCTGCCAGGTATCAGGgtgagtctatgggaccct tgatgttttctttcccttcttttctatggttaagttcatgtcatagga aggggagaagtaacagggtacacatattgaccaaatcagggtaattttg catttgtaattttaaaaaatgctttcttcttttaatatacttttttgtt tatcttattctaatactttccctaatctctttctttcagggcaataat gatacaatgtatcatgccgagtaacgctgtttctctaacttgtaggaat gaattcagatatttccagagaatgaaaaaaaaatcttcagtagaaggta atgt<u>ctcggggtgcccttctgcgtgaaggctgagaaataccc</u>gtatcac <u>ctgatctggataatgccagcgtagggaagacatt</u>acgcaccattctaaa gaataacagtgataatttctgggttaaggcaatagcaatatttctgcat -continued ataaatatttctgcatatcaaattgtaactgatgtaagaggtttcatatt gctaatagcagctacaatccagctaccattctgcttttattttatggtt gggataaggctggattattctgagtccaagctaggcccttttgctaatc atgttcatacctcttatcttcctcccacagCAAGGATATGGGCTCACTG

AGACTACATCAGCTATTCTGATTACACCCGAGGGGGATGATAAACCGGG

CGCGGTCGGTAAAGTTGTTCCATTTTTTGAAGCGAAGGTTGTGGATCTG

GATACCGGGAAAACGCTGGGCGTTAATCAAAGAGGCGAACTGTGTGTGA

GAGGTCCTATGATTATGTCCGGTTATGTAAACAATCCGGAAGCGACCAA

CGCCTTGATTGACAAGGATGGATGGCTACATTCTGGAGACATAGCTTAC

TGGGACGAAGACGAACACTTCTTCATCGTTGACCGCCTGAAGTCTCTGA

TTAAGTACAAAGGCTATCAGGTGGCTCCCGCTGAATTGGAATCCATCTT

GCTCCAACACCCCAACATCTTCGACGCAGGTGTCGCAGGTCTTCCCGAC

GATGACGCCGGTGAACTTCCCGCCGCCGTTGTTGTTTTGGAGCACGGAA

AGACGATGACGGAAAAAGAGATCGTGGATTACGTCGCCAGTCAAGTAAC

AACCGCGAAAAAGTTGCGCGGAGGAGTTGTGTTTGTGGACGAAGTACCG

AAAGGTCTTACCGGAAAACTCGACGCAAGAAAAATCAGAGAGATCCTCA

TAAAGGCCAAGAAGGGCGGAAAGATCGCCGTGTAA

Transfection: $3.5 \times 10^4$ human embryonic kidney (HEK) 293 cells were plated in a 96-well flat bottom plate the day before transfection. Plasmid DNA (500 ng) was added to a tube or a 96-well U-bottom plate. Separately, TransIT-293 reagent (Mirus; 1.4 µL) was added to 50 µL Optimem I media (Life Technologies) and allowed to sit for 5 minutes at room temperature (RT). Then, 50 µL of this diluted transfection reagent was added to the DNA, mixed, and incubated at RT for 20 min. Finally, 7 µL of this solution was added to a well of cells in the 96-well plate. Four hours after transfection, medium containing transfection solution was replaced by medium containing either TPP, fursultiamine, prosultiamine, bisbentiamine, beclotiamine hydrochloride, or sulbutiamine as aptamer inducers.

Firefly luciferase assay of cultured cells: Twenty-four hours after media change, plates were removed from the incubator, and equilibrated to RT for several minutes on a lab bench, then aspirated. Glo-lysis buffer (Promega, 100 µL, RT) was added, and the plates allowed to remain at RT for at least 5 minutes. Then, the well contents were mixed by 50 µL trituration, and 20 µL of each sample was mixed with 20 µL of bright-glo reagent (Promega) that had been diluted to 10% in glo-lysis buffer. 96 wells were spaced on an opaque white 384-well plate. Following a 5 min incubation at RT, luminescence was measured using a Tecan machine with 500 ms read time. The luciferase activity was expressed as mean arbitrary light units (ALU)±S.D., and fold induction was calculated as the quotient of the luciferase activity obtained from cells with TPP or analog treatment divided by the luciferase activity obtained from cells without TPP or analog treatment.

Results

Gene expression cassettes comprising TPP-responsive riboswitches were generated by inserting TPP aptamers from either the A. tabrizica thiC riboswitch (for riboswitch TPPz) or E. coli thiM riboswitch (for riboswitch TPPm), respectively, into a synthetic riboswitch gene expression cassette. Here, the aptamer sequence was inserted into an intron downstream of an alternative exon containing an in-frame stop codon as described in WO2016/126747, incorporated herein by reference in its entirety. Ligand binding to the aptamer controls the accessibility of the 5' splice site of the 3' intron, therefore allowing for regulation of the expression of a target gene through modulating alternative splicing.

As shown in FIG. 1A, both synthetic riboswitches TPPz and TPPm regulate luciferase expression in response to TPP. TPPz induces target gene expression at even lower concentrations than TPPm, indicating that the *A. tabrizica* thiC aptamer has a higher TPP binding affinity in mammalian cells as compared to the *E. coli* thiM aptamer.

Figure 1B:
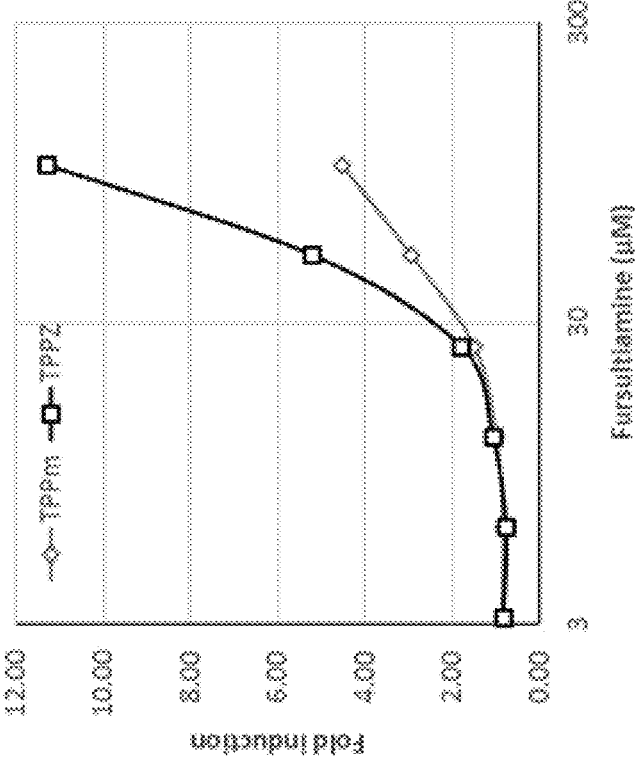
Figure 1B:
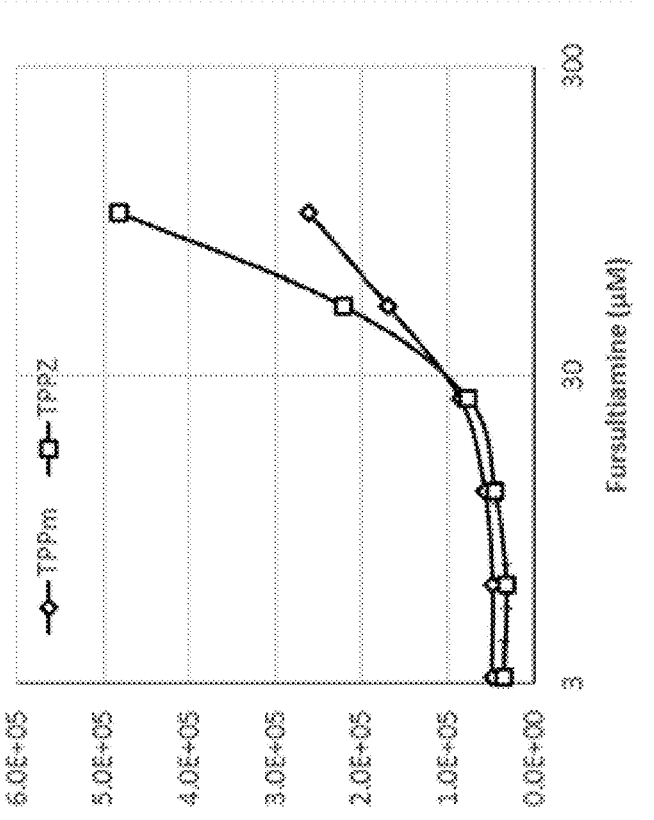
Figure 1C:
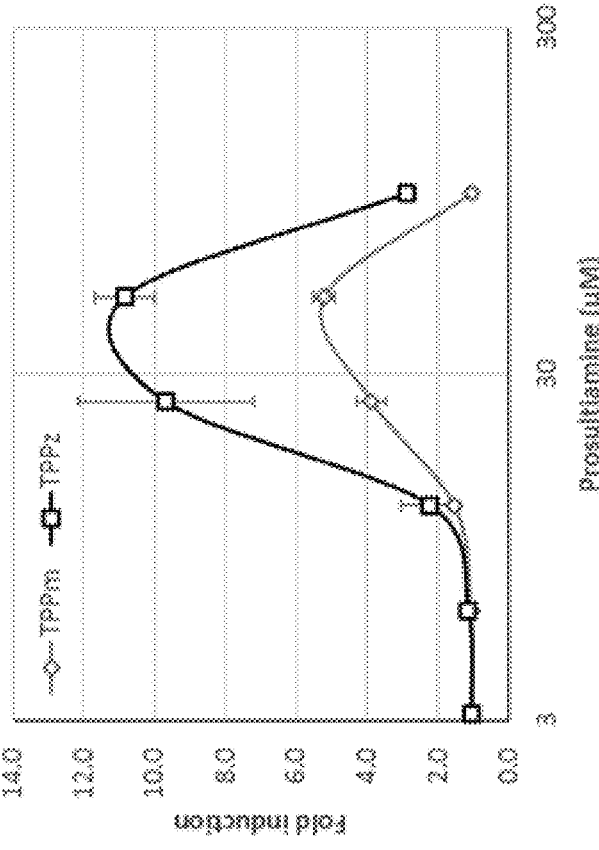
Figure 1C:
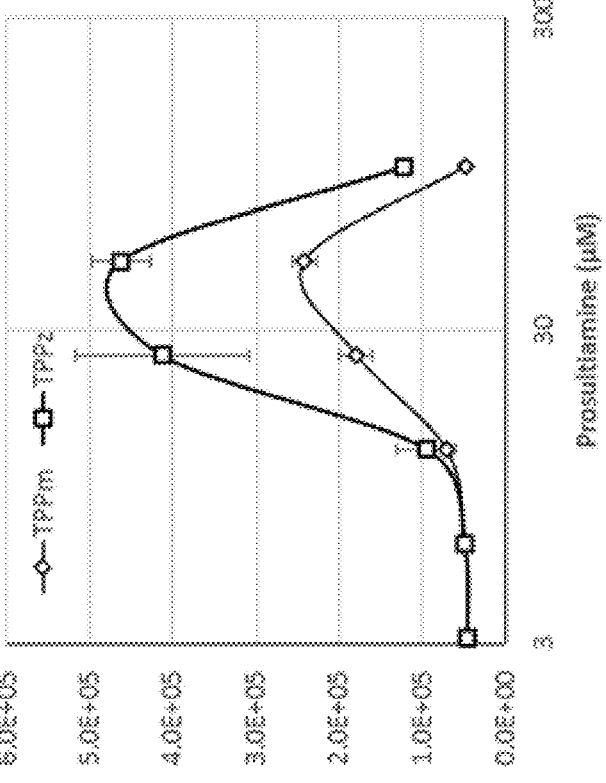
Figure 1D:
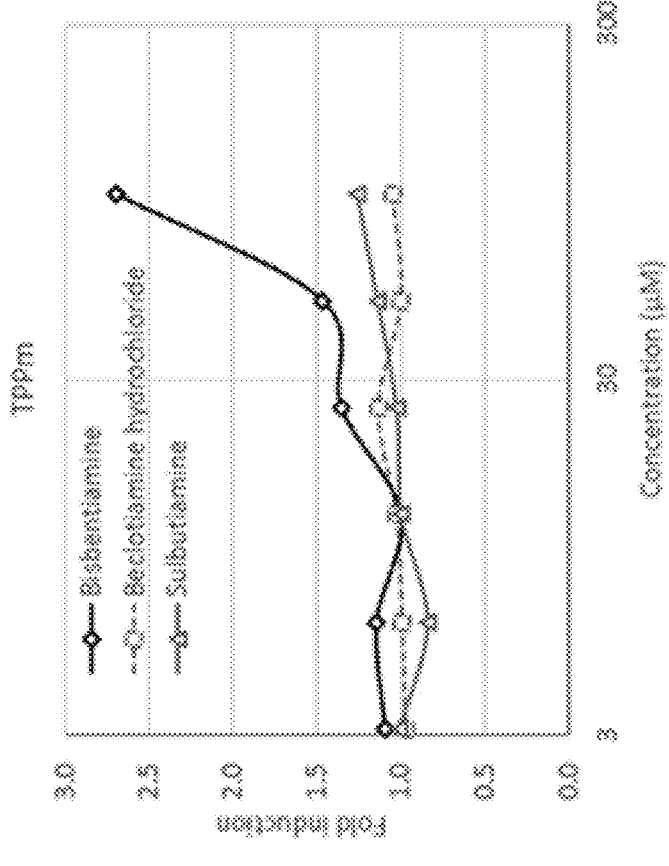
Figure 1D:
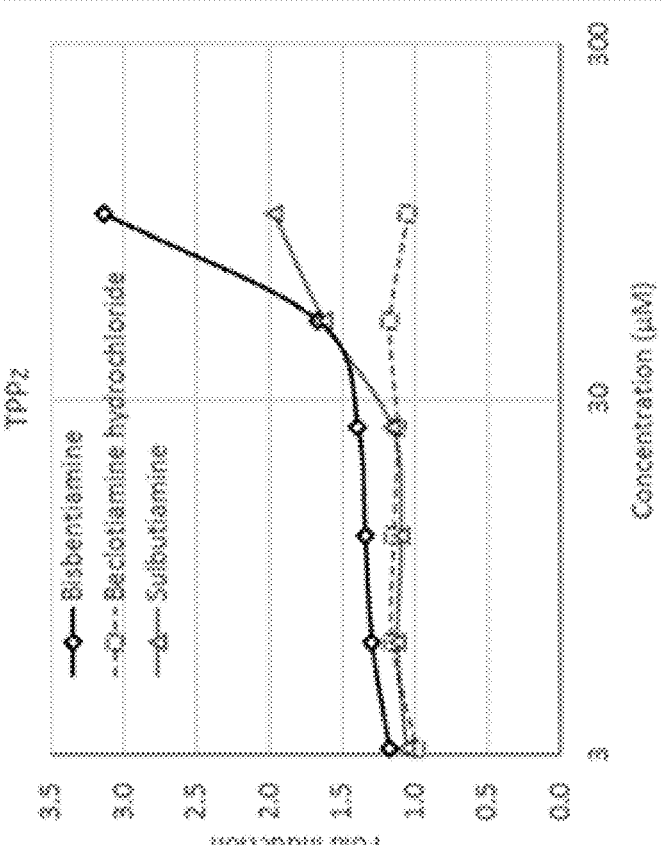
Figure 2A:
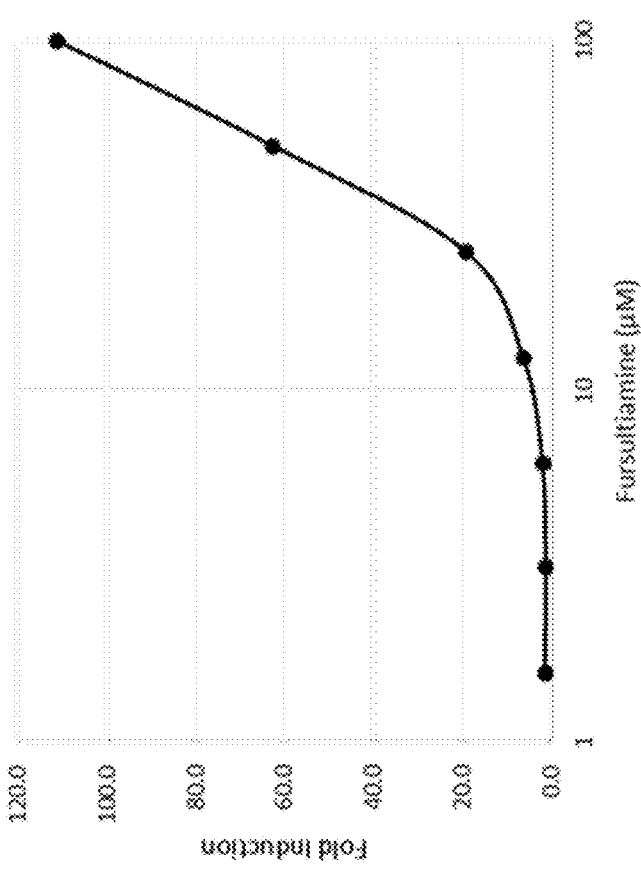
FIG. 2 illustrates that a putative aptamer sequence (14G4) subtracted from a family of TPP aptamers (Rfam family RF00059), regulates luciferase expression in response to fursultiamine. Cells were transfected with a luciferase-riboswitch construct comprising putative TPP aptamer, 14G4 (accession number AACY023654033.1/903-800 from Rfam RF00059). The transfected cells were treated with fursultiamine at the indicated doses in HEK 293 cells (FIG. 2A), or in other types of human and mouse cell lines (FIG. 2B). The fold induction was calculated as the quotient of the luciferase activity recorded for cells exposed to fursultiamine divided by the luciferase activity recorded for cells that were not exposed to fursultiamine.
Figure 2A:
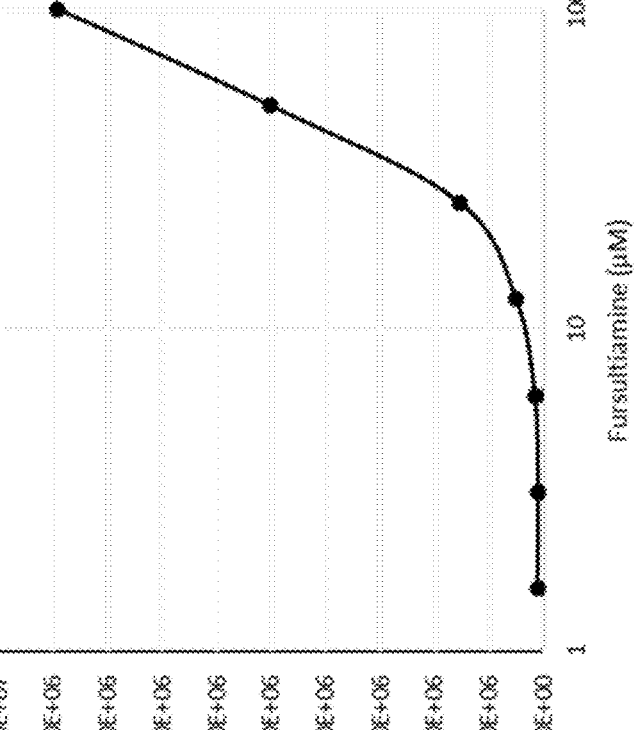
Figure 2B:
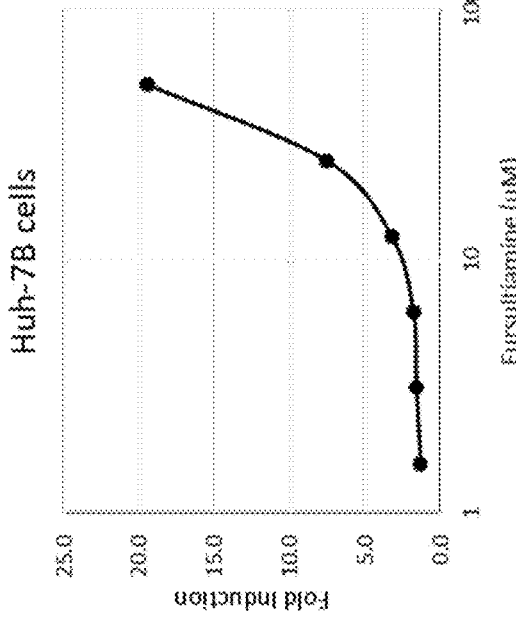
Figure 2B:
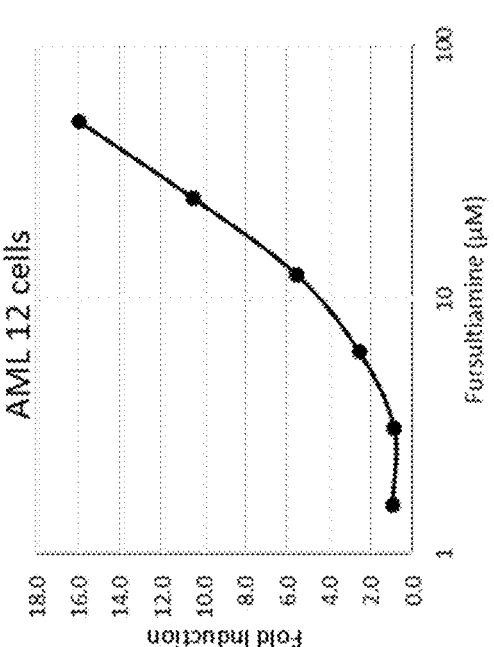
Figure 2B:
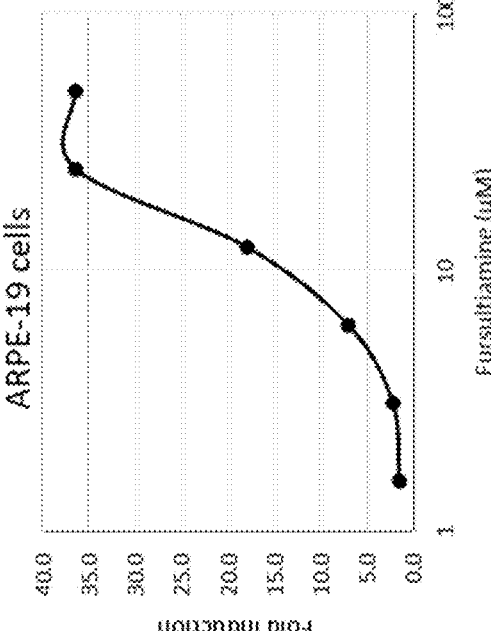
Figure 2B:
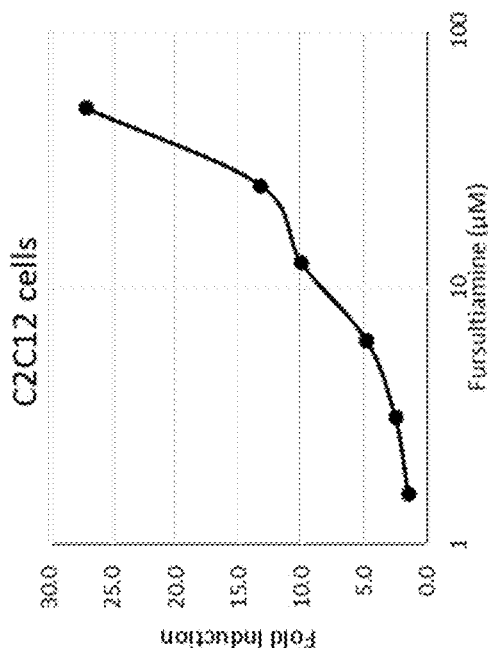

To determine whether the synthetic riboswitches TPPz and TPPm also respond to thiamine analogues, a group of thiamine analogs was surveyed. As shown in FIGS. 1B and 1C, both TPPz and TPPm induce luciferase expression in response to fursultiamine and prosultiamine treatment, while treatment with bisbentiamine, beclotiamine hydrochloride, and sulbutiamine resulted in weak or no effects on luciferase expression (see FIG. 1D). In all cases, riboswitch TPPz induced target gene expression at a lower concentration than TPPm.

These data indicate that synthetic riboswitches comprising heterologous aptamer sequences can effectively induce target gene expression in response to a variety of thiamine-related molecules in a dose dependent manner in mammalian cells.

Example 2. a TPP Aptamer Homologous Sequence Regulates Gene Expression in Mammalian Cells in Response to Thiamine Analogs

Experimental Procedures

Riboswitch construction: TPP aptamer homologous sequences were obtained from Rfam 12.0 (https://rfam.xfam.org/) and synthesized (Twister Biotech). To make riboswitch constructs containing TPP aptamer homologous sequences, the synthesized oligos were used as PCR templates and replaced the guanine aptamer in G17 riboswitch construct (WO 2016/126747) using Golden Gate cloning (NEB).

The transfection and firefly luciferase assay were performed as described in Example 1.

Results

For the regulation of genes for therapeutic purposes, e.g. in a human subject, the use of synthetic riboswitches in combination with synthetic compounds that naturally do not occur in the subject to be treated (such as fursultiamine) is particularly useful. This is because the absence of the regulatory compound in the patient allows for a stringently controlled expression of therapeutic genes.

To identify aptamers with increased gene regulation activity in response to thiamine analogs as compared to TPPz and TPPm, a putative TPP aptamer with homologous sequence was obtained from Rfam 12.0 (RNA family database RF00059, http://rfam.xfam.org/family/RF00059). This putative TPP aptamer (accession number AACY023654033.1, with the sequence starting at position 895 and ending at position 815; referred to herein as 14G4) was inserted into the alternative splicing-based gene regulation cassette as described in Example 1 to generate aptamer riboswitch 14G4.

SEQ ID NO: 84 was obtained by inserting the 14G4 riboswitch into the luciferase reporter gene. Capital letters indicate the luciferase encoding sequence. Lower case indicates the intron/alternative exon/intron and riboswitch sequence. The 14G4 aptamer encoding sequence (SEQ ID NO:7) is underlined. In one embodiment, provided is a riboswitch comprising SEQ ID NO: 84, wherein the aptamer encoding sequence (SEQ ID NO: 7) in SEQ ID NO:84 is replaced with another aptamer sequence disclosed herein.

```
                                          SEQ ID NO: 84
ATGGAAGACGCCAAAAACATAAAGAAAGGCCCGGCGCCATTCTATCCGC

TGGAAGATGGAACCGCTGGAGAGCAACTGCATAAGGCTATGAAGAGATA

CGCCCTGGTTCCTGGAACAATTGCTTTTACAGATGCACATATCGAGGTG

GACATCACTTACGCTGAGTACTTCGAAATGTCCGTTCGGTTGGCAGAAG

CTATGAAACGATATGGGCTGAATACAAATCACAGAATCGTCGTATGCAG

TGAAAACTCTCTTCAATTCTTTATGCCGGTGTTGGGCGCGTTATTTATC

GGAGTTGCAGTTGCGCCCGCGAACGACATTTATAATGAACGTGAATTGC

TCAACAGTATGGGCATTTCGCAGCCTACCGTGGTGTTCGTTTCCAAAAA

GGGGTTGCAAAAAATTTTGAACGTGCAAAAAAAGCTCCCAATCATCCAA

AAAATTATTATCATGGATTCTAAAACGGATTACCAGGGATTTCAGTCGA

TGTACACGTTCGTCACATCTCATCTACCTCCCGGTTTTAATGAATACGA

TTTTGTGCCAGAGTCCTTCGATAGGGACAAGACAATTGCACTGATCATG

AACTCCTCTGGATCTACTGGTCTGCCTAAAGGTGTCGCTCTGCCTCATA

GAACTGCCTGCGTGAGATTCTCGCATGCCAGAGATCCTATTTTTGGCAA

TCAAATCATTCCGGATACTGCGATTTTAAGTGTTGTTCCATTCCATCAC

GGTTTTGGAATGTTTACTACACTCGGATATTTGATATGTGGATTTCGAG

TCGTCTTAATGTATAGATTTGAAGAAGAGCTGTTTCTGAGGAGCCTTCA

GGATTACAAGATTCAAAGTGCGCTGCTGGTGCCAACCCTATTCTCCTTC

TTCGCCAAAAGCACTCTGATTGACAAATACGATTTATCTAATTTACACG

AAATTGCTTCTGGTGGCGCTCCCCTCTCTAAGGAAGTCGGGGAAGCGGT

TGCCAAGAGGTTCCATCTGCCAGGTATCAGGgtgagtctatgggaccct tgatgtttctttccccttcttttctatggttaagttcatgtcatagga aggggagaagtaacagggtacacatattgaccaaatcagggtaattttg catttgtaattttaaaaaatgctttcttcttttaatatacttttttgtt tatcttatttctaatactttccctaatctctttctttcagggcaataat gatacaatgtatcatgccgagtaacgctgtttctctaacttgtaggaat gaattcagatatttccagagaatgaaaaaaaaatcttcagtagaaggta atgtacaggggtccggcctttcatttggcgccggtgagagcacaccct ttgaacctgtttacggataatgccgccgcagggagtacattacgcacca ttctaaagaataacagtgataatttctgggttaaggcaatagcaatatt tctgcatataaatatttctgcatataaattgtaactgatgtaagaggtt tcatattgctaatagcagctacaatccagctaccattctgcttttattt tatggttgggataaggctggattattctgagtccaagctaggccctttt gctaatcatgttcatacctcttatcttcctcccacagCAAGGATATGGG

CTCACTGAGACTACATCAGCTATTCTGATTACACCCGAGGGGGATGATA
```

55
```
-continued
AACCGGGCGCGGTCGGTAAAGTTGTTCCATTTTTTGAAGCGAAGGTTGT

GGATCTGGATACCGGGAAAACGCTGGGCGTTAATCAAAGAGGCGAACTG

TGTGTGAGAGGTCCTATGATTATGTCCGGTTATGTAAACAATCCGGAAG

CGACCAACGCCTTGATTGACAAGGATGGATGGCTACATTCTGGAGACAT

AGCTTACTGGGACGAAGACGAACACTTCTTCATCGTTGACCGCCTGAAG

TCTCTGATTAAGTACAAAGGCTATCAGGTGGCTCCCGCTGAATTGGAAT

CCATCTTGCTCCAACACCCCAACATCTTCGACGCAGGTGTCGCAGGTCT

TCCCGACGATGACGCCGGTGAACTTCCCGCCGCCGTTGTTGTTTTGGAG

CACGGAAAGACGATGACGGAAAAGAGATCGTGGATTACGTCGCCAGTC

AAGTAACAACCGCGAAAAAGTTGCGCGGAGGAGTTGTGTTTGTGGACGA

AGTACCGAAAGGTCTTACCGGAAAACTCGACGCAAGAAAAATCAGAGAG

ATCCTCATAAAGGCCAAGAAGGGCGGAAAGATCGCCGTGTAA
```

This riboswitch was tested in HEK 293 cells for its ability to regulate luciferase gene expression. As shown in FIG. 2, luciferase expression increased 100-fold upon treatment with fursultiamine in a dose dependent manner. Further, the 14G4 riboswitch regulated luciferase gene expression in response to treatment with fursultiamine in multiple types of cells.

This experiment illustrates the successful generation of mammalian riboswitches comprising aptamers that are capable of significantly inducing target gene expression in mammalian cells in response to synthetic small molecules.

Example 3. Generation of Riboswitches Comprising Re-Engineered Aptamer Sequences that have Increased Sensitivity to Thiamine Analogs Riboswitch 14G4 was chosen for further improvement due to its selectivity for fursultiamine as compared to TPP. After comparing the predicted secondary structure (RNAfold, http://rna.tbi.univie.ac.at/cgi-bin/RNAWebSuite/RNAfold.cgi) of the 14G4 riboswitch with the crystallography structure of the E. coli thiM riboswitch, three regions in the 14G4 sequence were identified that do not appear to be involved in helical formation but may participate in tertiary structure upon ligand binding. These three regions were chosen for sequence randomization to generate riboswitches with re-engineered aptamer sequences with improved activity.

Figure 4A:
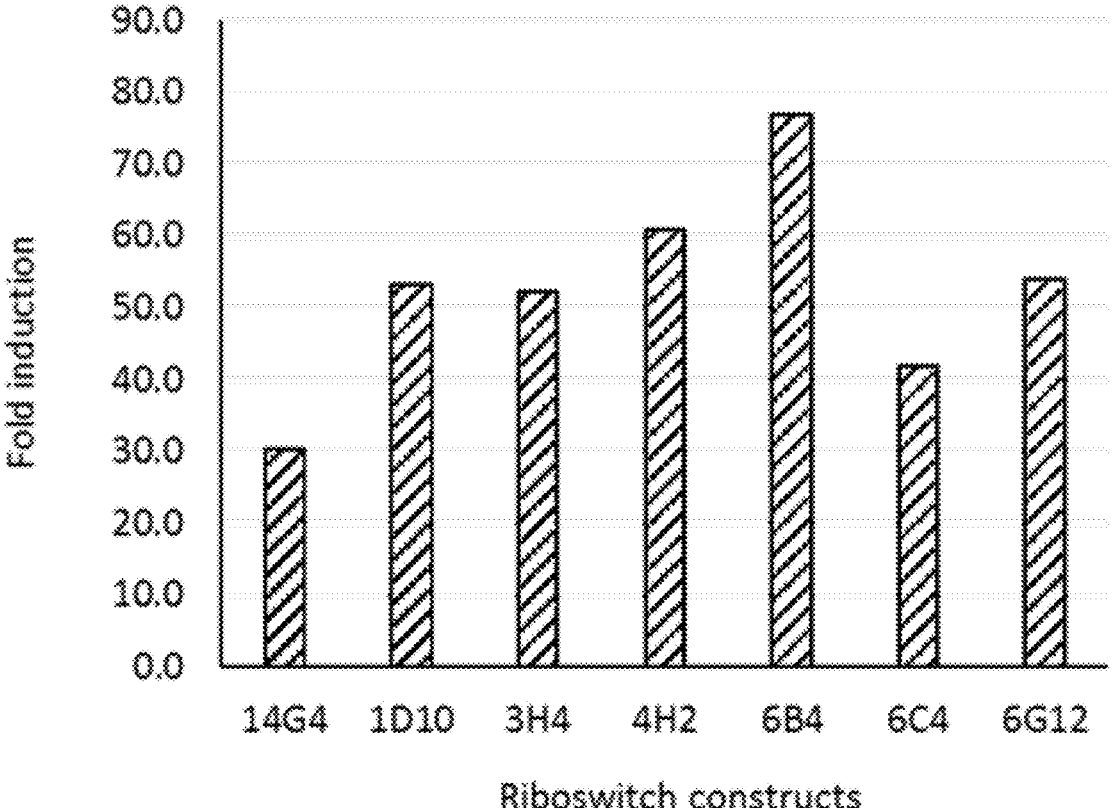
Figure 4B:
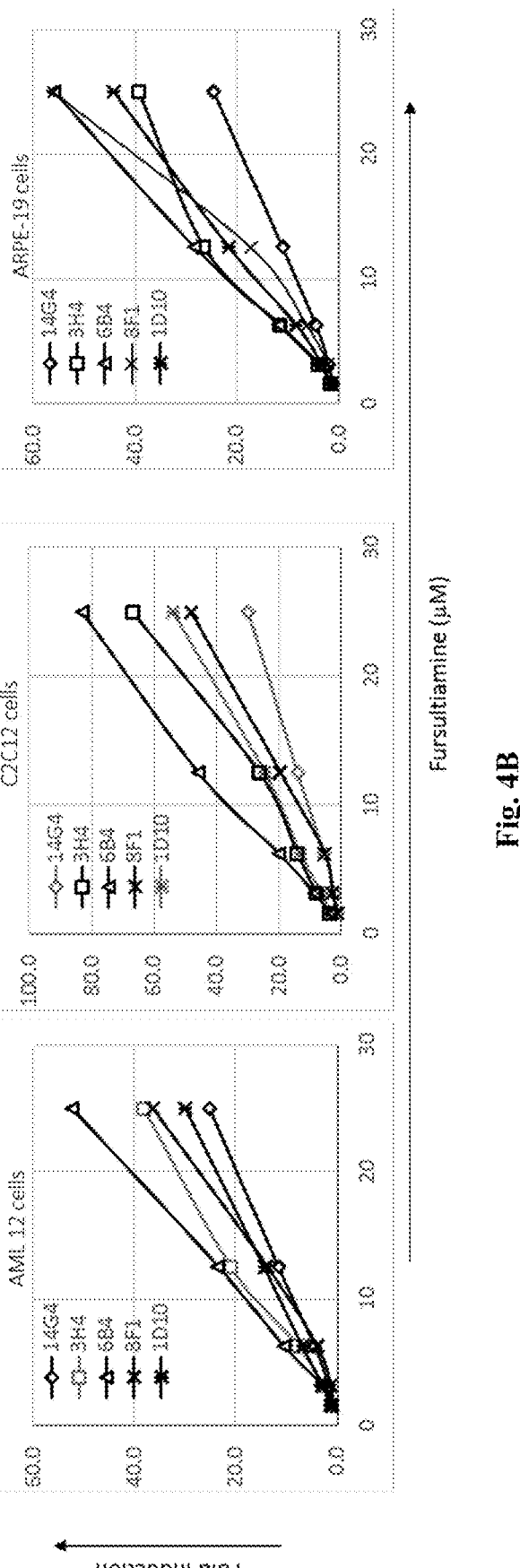
FIG. 4B illustrates that riboswitches comprising re-engineered aptamer sequences are useful for the dose-dependent induction of a target gene in different types of cells. AML12, C2C12 and ARPE-19 cells were transfected with re-engineered riboswitch constructs using TransIT-X2 reagent. The transfected cells were treated with fursultiamine at the indicated doses.

Three aptamer libraries A1, A2 and A3, were generated by randomizing nucleotides at 6 positions in, or adjacent to, regions J4-5, J2-4 and J3-2, respectively (see FIG. 3). Single bacterial colonies were picked and plasmids containing riboswitch constructs were screened in HEK 293 cells for improved gene regulation activity in response to 50 µM fursultiamine as compared to riboswitch 14G4. As shown in FIG. 4A, several of the aptamer constructs that were isolated, including 1D10, 3H4, 4H2, 6B4, 6C4, and 6G12, show an increase in fursultiamine-dependent induction as compared to the parent construct 14G4. These riboswitches comprising re-engineered aptamer sequences also lead to significant enhancements of target gene expression in other cells types, including alpha mouse liver 12 (AML12), C2C12 (murine myoblast cell line), and adult retinal pigment epithelial cell line-19 (ARPE-19) (see FIG. 4B). Further, the selected riboswitches comprising re-engineered aptamer sequences also increased target gene expression in

Figure 4C:
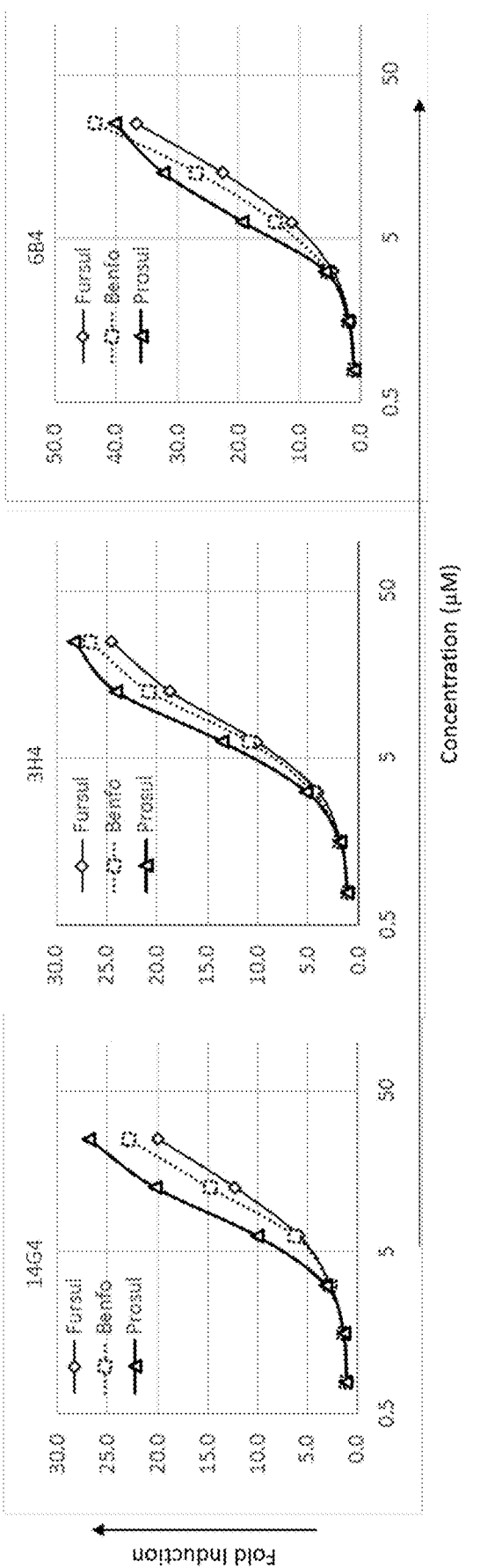
FIG. 4C illustrates that riboswitches comprising re-engineered aptamer sequences regulate luciferase expression in response to different TPP analogs. AML12 cells were transfected with riboswitches comprising re-engineered aptamer sequences and were treated with fursultiamine, benfotiamine, or prosultiamine at the indicated doses.

56 response to prosultiamine and benfotiamine (in AML 12 cells) treatment (see FIG. 4C).

This data demonstrates that the isolated riboswitches comprising re-engineered aptamer sequences are useful for inducing target gene expression in a variety of cell types in response to a variety of synthetic small molecules.

To further enhance gene regulation activity, a second round of mutagenesis was performed using library A4 (see FIG. 5). For this library, the aptamer sequence of the 3H4 variant riboswitch construct was randomized at six nucleotide positions, namely at three bases in the J3-2 region and three bases in the J2-4 region of the predicted secondary structure of 3H4 aptamer. Single bacterial colonies were picked and plasmids containing riboswitch constructs were screened in HEK 293 cells for improved gene regulation activities as compared to riboswitch 3H4, using 50 µM fursultiamine.

Figure 6A:
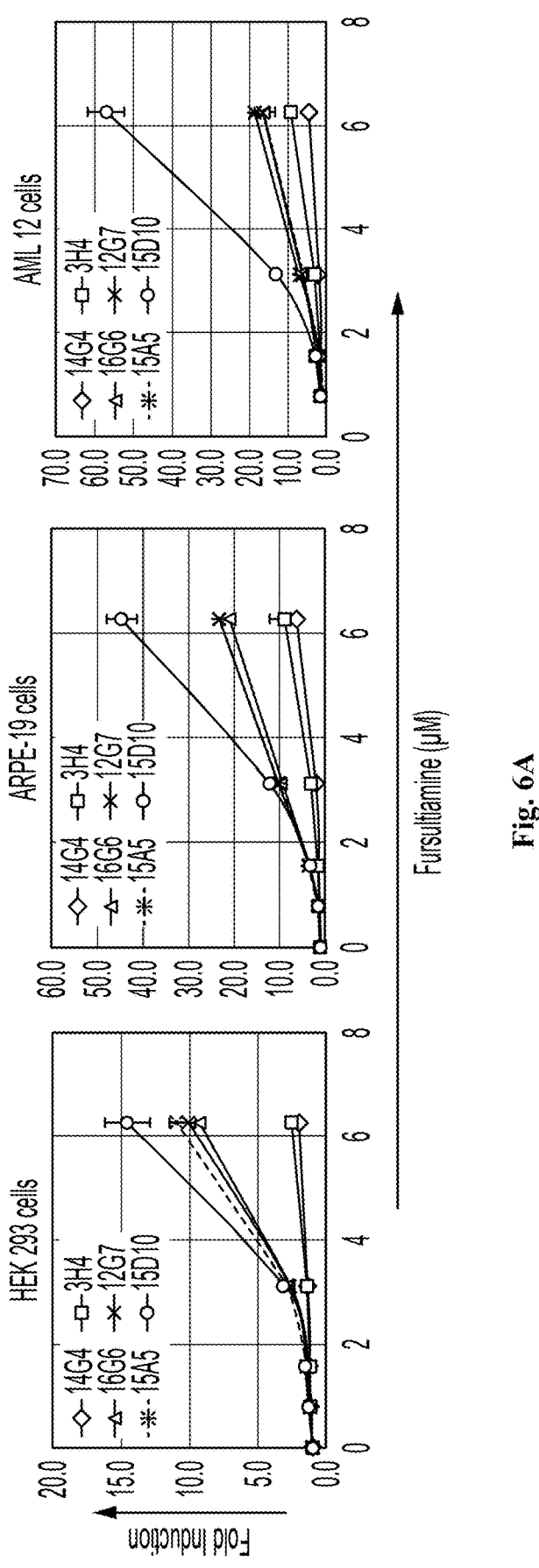
FIG. 6A illustrates that mutagenesis of select aptamer nucleotides involved in aptamer/ligand binding can improve the gene regulation activity of aptamer-based riboswitches in mammalian cells. HEK 293, ARPE-19 and AML12 cells were transfected with riboswitch constructs comprising re-engineered aptamer sequences isolated from aptamer library A4. The transfected cells were treated with fursultiamine at the doses indicated or left untreated.

Several riboswitches comprising different aptamer variants that were isolated from library A4 showed further improved sensitivity to fursultiamine as compared to both 14G4 and 3H4, demonstrating that mutagenesis of select nucleotides involved in aptamer/ligand binding can improve the gene regulation activity of aptamer-based riboswitches in mammalian cells (see FIG. 6A).

Figure 6B:
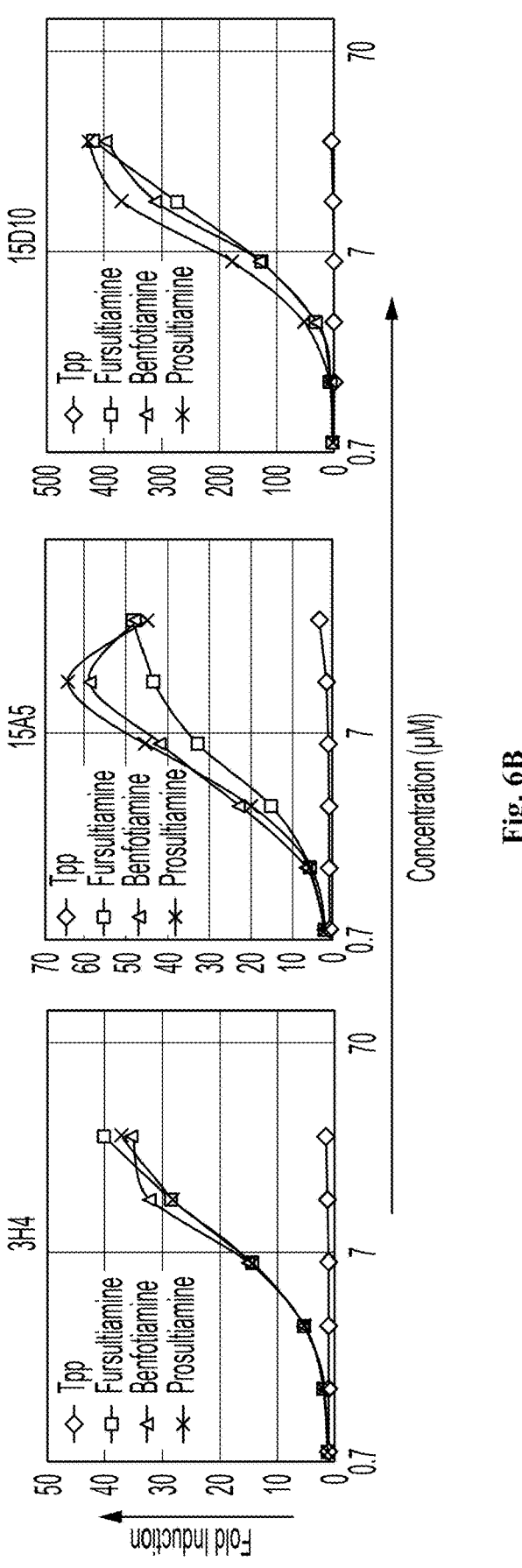
FIG. 6B illustrates the ability of riboswitches comprising re-engineered aptamer sequences to induce expression of luciferase in response to different thiamine derivatives that share chemical structural features with thiamine. AML12 cells were transfected with the indicated riboswitch constructs and treated with fursultiamine, benfotiamine, or prosultiamine at the doses indicated or left untreated. The fold induction was calculated as the quotient of the luciferase activity obtained from cells treated with thiamine analog compounds divided by the luciferase activity obtained from cells without thiamine analog treatment.

Next, the ability of the riboswitches comprising re-engineered aptamer sequences isolated from aptamer library A4 to respond to other thiamine analogs that share chemical structural features with thiamine was determined. As shown in FIG. 6B, 3H4-derived riboswitches comprising aptamers 15A5 and 15D10 robustly regulate luciferase expression in response to synthetic molecules fursultiamine, prosultiamine, and benfotiamine, but respond very poorly to naturally occurring TPP. Further, the riboswitches comprising re-engineered aptamer sequences 15A5 and 15D10 exhibit significantly improved dynamic ranges in response to fursultiamine, prosultiamine, and benfotiamine as compared to the parent riboswitch 3H4.

This example illustrates that, through multiple rounds of mutagenesis, improved riboswitches comprising re-engineered aptamer sequences can be generated that enhance target gene expression in response to treatment with several synthetic thiamine analogs.

Example 4. Synthetic Thiamine Analog Riboswitches can Regulate Expression of Various Target Genes in Response to Fursultiamine As discussed in Example 3, isolated riboswitches comprising re-engineered aptamer sequences efficiently induce expression of the reporter protein luciferase in response to various thiamine analogs. To test the ability of the isolated aptamers to regulate expression of other target genes, several of the riboswitches comprising re-engineered aptamer sequences were inserted into the cDNA sequence of murine erythropoietin (mEpo) and the cDNA sequence of enhanced green fluorescent protein (EGFP).

Experimental Procedures

Riboswitch constructs: Alternative splicing riboswitches containing aptamers 3H4 or 15D10, respectively, were inserted at position 308 into the mouse erythropoietin cDNA sequence in construct Con8-Epo (SEQ ID NO:85), resulting in constructs Epo-3H4 (SEQ ID NO:86) and Epo-15D10 (SEQ ID NO:87). Expression of the erythropoietin gene was driven by a cytomegalovirus (CMV) promoter. The riboswitch cassette containing aptamer 6B4 was inserted at position 276 into the cDNA sequence encoding enhanced green fluorescent protein (EGFP) in vector pEGFP-C1 to generate the EGFP-6B4 construct (SEQ ID NO:88). The intron-exon-intron cassette without aptamer sequence was inserted into Con8-Epo to create construct Epo-Con1 (SEQ ID NO:89), serving as a control for constitutive target gene expression.

SEQ ID NO: 86 was obtained by inserting the 3H4 riboswitch into the erythropoietin gene. Capital letters indicate the erythropoietin encoding sequence (see SEQ ID NO:85). Lower case letters indicate the intron/alternative exon/intron and riboswitch sequence. The 3H4 aptamer encoding sequence (SEQ ID NO:9) is underlined.

```
                                    SEQ ID NO: 86
ATGGGGGTGCCCGAACGTCCCACCCTGCTGCTTTTACTCTCCTTGCTAC

TGATTCCTCTGGGCCTCCCAGTCCTCTGTGCTCCCCCACGCCTCATCTG

CGACAGTCGAGTTCTGGAGAGGTACATCTTAGAGGCCAAGGAGGCAGAA

AATGTCACGATGGGTTGTGCAGAAGGTCCCAGACTGAGTGAAAATATTA

CAGTCCCAGATACCAAAGTCAACTTCTATGCTTGGAAAAGAATGGAGGT

GGAAGAACAGGCCATAGAAGTTTGGCAAGGCCTGTCCCTGCTCTCAGAA

GCCATCCTGCAGGgtgagtctatgggacccttgatgttttctttcccct tcttttctatggttaagttcatgtcataggaaggggagaagtaacaggg tacacatattgaccaaatcagggtaattttgcatttgtaattttaaaaa atgctttcttcttttaatatactttttgtttatcttatttctaatact ttccctaatctctttctttcagggcaataatgatacaatgtatcatgcc gagtaacgctgtttctctaacttgtaggaatgaattcagatatttccag agaatgaaaaaaatcttcagtagaaggtaatgtacaggggtccggcct tttcatttggcgccggtgagagcacaccctttgaacctgttcacggata atgccgctgcagggagtacattacgcaccattctaaagaataacagtga taatttctgggttaaggcaatagcaatatttctgcatataaatatttct gcatataaattgtaactgatgtaagaggtttcatattgctaatagcagc tacaatccagctaccattctgcttttattttatggttgggataaggctg gattattctgagtccaagctaggccctttttgctaatcatgttcatacct cttatcttcctcccacagCCCAGGCCCTGCTAGCCAATTCCTCCCAGCC

ACCAGAGACCCTTCAGCTTCATATAGACAAAGCCATCAGTGGTCTACGT

AGCCTCACTTCACTGCTTCGGGTACTGGGAGCTCAGAAGGAATTGATGT

CGCCTCCAGATACCACCCCACCTGCTCCACTCCGAACACTCACAGTGGA

TACTTTCTGCAAGCTCTTCCGGGTCTACGCCAACTTCCTCCGGGGGAAA

CTGAAGCTGTACACGGGAGAGGTCTGCAGGAGAGGGGACAGGTGA
```

SEQ ID NO: 87 was obtained by inserting the 15D10 riboswitch into the erythropoietin gene. Capital letters indicate the erythropoietin encoding sequence (see SEQ ID NO:85). Lower case letters indicate the intron/alternative exon/intron and riboswitch sequence. The 15D10 aptamer encoding sequence (SEQ ID NO:26) is underlined.

```
                                    SEQ ID NO: 87
ATGGGGGTGCCCGAACGTCCCACCCTGCTGCTTTTACTCTCCTTGCTAC

TGATTCCTCTGGGCCTCCCAGTCCTCTGTGCTCCCCCACGCCTCATCTG
```

-continued

```
CGACAGTCGAGTTCTGGAGAGGTACATCTTAGAGGCCAAGGAGGCAGAA

AATGTCACGATGGGTTGTGCAGAAGGTCCCAGACTGAGTGAAAATATTA

CAGTCCCAGATACCAAAGTCAACTTCTATGCTTGGAAAAGAATGGAGGT

GGAAGAACAGGCCATAGAAGTTTGGCAAGGCCTGTCCCTGCTCTCAGAA

GCCATCCTGCAGGgtgagtctatgggacccttgatgttttctttcccct tcttttctatggttaagttcatgtcataggaaggggagaagtaacaggg tacacatattgaccaaatcagggtaattttgcatttgtaattttaaaaa atgctttcttcttttaatatactttttgtttatcttatttctaatact ttccctaatctctttctttcagggcaataatgatacaatgtatcatgcc gagtaacgctgtttctctaacttgtaggaatgaattcagatatttccag agaatgaaaaaaatcttcagtagaaggtaatgtacaggggtccggcct tttcatttggcaccggtgagaacataccctttcggacctgttcacggata atgccgctgcagggagtacattacgcaccattctaaagaataacagtga taatttctgggttaaggcaatagcaatatttctgcatataaatatttct gcatataaattgtaactgatgtaagaggtttcatattgctaatagcagc tacaatccagctaccattctgcttttattttatggttgggataaggctg gattattctgagtccaagctaggccctttttgctaatcatgttcatacct cttatcttcctcccacagCCCAGGCCCTGCTAGCCAATTCCTCCCAGCC

ACCAGAGACCCTTCAGCTTCATATAGACAAAGCCATCAGTGGTCTACGT

AGCCTCACTTCACTGCTTCGGGTACTGGGAGCTCAGAAGGAATTGATGT

CGCCTCCAGATACCACCCCACCTGCTCCACTCCGAACACTCACAGTGGA

TACTTTCTGCAAGCTCTTCCGGGTCTACGCCAACTTCCTCCGGGGGAAA

CTGAAGCTGTACACGGGAGAGGTCTGCAGGAGAGGGGACAGGTGA
```

SEQ ID NO: 88 was obtained by inserting the 6B4 riboswitch into the EGFP gene. Capital letters indicate the EGFP encoding sequence. Lower case indicate the intron/alternative exon/intron and riboswitch sequence. The 6B4 aptamer encoding sequence (SEQ ID NO:14) is underlined.

```
                                    SEQ ID NO: 88
ATGGTGAGCAAGGGCGAGGAGCTGTTCACCGGGGTGGTGCCCATCCTGG

TCGAGCTGGACGGCGACGTAAACGGCCACAAGTTCAGCGTGTCCGGCGA

GGGCGAGGGCGATGCCACCTACGGCAAGCTGACCCTGAAGTTCATCTGC

ACCACCGGCAAGCTGCCCGTGCCCTGGCCCACCCTCGTGACCACCCTGA

CCTACGGCGTGCAGTGCTTCAGCCGCTACCCCGACCACATGAAGCAGCA

CGACTTCTTCAAGTCCGCCATGCCCGAAGGgtgagtctatgggacccctt gatgttttctttcccttcttttctatggttaagttcatgtcataggaa ggggagaagtaacagggtacacatattgaccaaatcagggtaattttgc atttgtaattttaaaaaatgctttcttcttttaatatactttttgttt atcttatttctaatactttccctaatctctttctttcagggcaataatg atacaatgtatcatgccgagtaacgctgtttctctaacttgtaggaatg aattcagatatttccagagaatgaaaaaaatcttcagtagaaggtaat
```

59

-continued gtacaggggtccggccttttcatttggcgccggtgagagcacacccttg tgacctgtttacggataatgccgccgcagggagtacattacgcaccatt ctaaagaataacagtgataatttctgggttaaggcaatagcaatatttc tgcatataaatatttctgcatatataaattgtaactgatgtaagaggtttc atattgctaatagcagctacaatccagctaccattctgcttttatttta tggttgggataaggctggattattctgagtccaagctaggcccttttgc taatcatgttcatacctcttatcttcctcccacagCTACGTCCAGGAGC

GCACCATCTTCTTCAAGGACGACGGCAACTACAAGACCCGCGCCGAGGT

GAAGTTCGAGGGCGACACCCTGGTGAACCGCATCGAGCTGAAGGGCATC

GACTTCAAGGAGGACGGCAACATCCTGGGGCACAAGCTGGAGTACAACT

ACAACAGCCACAACGTCTATATCATGGCCGACAAGCAGAAGAACGGCAT

CAAGGTGAACTTCAAGATCCGCCACAACATCGAGGACGGCAGCGTGCAG

CTCGCCGACCACTACCAGCAGAACACCCCCATCGGCGACGGCCCCGTGC

TGCTGCCCGACAACCACTACCTGAGCACCCAGTCCGCCCTGAGCAAAGA

CCCCAACGAGAAGCGCGATCACATGGTCCTGCTGGAGTTCGTGACCGCC

GCCGGGATCACTCTCGGCATGGACGAGCTGTACAAGTAA

SEQ ID NO: 89 was obtained by inserting the intron-exon-intron cassette without aptamer sequence into the erythropoietin gene. Capital letters indicate the erythropoietin encoding sequence (see SEQ ID NO:85). Lower case letters indicate the intron/alternative exon/intron sequence.

SEQ ID NO: 89

ATGGGGGTGCCCGAACGTCCCACCCTGCTGCTTTTACTCTCCTTGCTAC

TGATTCCTCTGGGCCTCCCAGTCCTCTGTGCTCCCCCACGCCTCATCTG

CGACAGTCGAGTTCTGGAGAGGTACATCTTAGAGGCCAAGGAGGCAGAA

AATGTCACGATGGGTTGTGCAGAAGGTCCCAGACTGAGTGAAAATATTA

CAGTCCCAGATACCAAAGTCAACTTCTATGCTTGGAAAAGAATGGAGGT

GGAAGAACAGGCCATAGAAGTTTGGCAAGGCCTGTCCCTGCTCTCAGAA

GCCATCCTGCAGGtgagtctatgggaccccttgatgtttttctttcccct tcttttctatggttaagttcatgtcataggaaggggagaagtaacaggg tacacatattgaccaaatcagggtaattttgcatttgtaattttaaaaa atgctttcttcttttaatatacttttttgtttatcttatttctaatact ttccctaatctctttctttcagggcaataatgatacaatgtatcatgcc tctttgcaccattctaaagaataacagtgataatttctgggttaaggca atagcaatatttctgcatataaatatttctgcatataaattgtaactga tgtaagaggtttcatattgctaatagcagctacaatccagctaccattc tgcttttattttatggttgggataaggctggattattctgagtccaagc taggcccttttgctaatcatgttcatacctcttatcttcctcccacagC

CCAGGCCCTGCTAGCCAATTCCTCCCAGCCACCAGAGACCCTTCAGCTT

CATATAGACAAAGCCATCAGTGGTCTACGTAGCCTCACTTCACTGCTTC

GGGTACTGGGAGCTCAGAAGGAATTGATGTCGCCTCCAGATACCACCCC

-continued

ACCTGCTCCACTCCGAACACTCACAGTGGATACTTTCTGCAAGCTCTTC

CGGGTCTACGCCAACTTCCTCCGGGGGAAACTGAAGCTGTACACGGGAG

AGGTCTGCAGGAGAGGGGACAGGTGA.

Enzyme-linked immunosorbent assay (ELISA) for mouse erythropoietin: AML12 cells were transfected as described in Example 1 with TransIT-X2 transfection reagent (Mirus Bio). Four hours after transfection, AML12 cells were treated with or without fursultiamine at the indicated doses. The supernatants from the transfected cells were collected 24 hours after fursultiamine treatment and were subjected to ELISA for the detection of mEpo in the supernatant following the manufacturer's instruction (R&D).

Generation of a cell line expressing EGFP-6B4: A stable cell line containing the EGFP-6B4 construct was generated by electroporating HEK 293 cells with 100 ng plasmid DNA using a Gene Pulser Xcell (Bio-Rad) and applying the default parameters for HEK 293 cells. 48 hours after electroporation, the cell culture was treated with 800 µg/ml of the antibiotic G418 for two weeks to select for cells that stably express the EGFP-6B4 cassette, which carries a G418 resistance gene. Cells were trypsinized. Intensity of EGFP fluorescence in the cell suspension was determined by flow cytometry using a Guava EasyCyte 8HT machine. The resulting data was analyzed using GuavaSoft 3.3. The fold increase in induction was calculated as the quotient of mean fluorescent intensity (MFI) obtained from cells after treated with fursultiamine divided by the MFI obtained from cells without fursultiamine treatment.

Flow cytometry analysis: $1.5 \times 10^5$ HEK 293 cells stably transduced with EGFP-6B4 construct were plated in 24-well plate one day before fursultiamine treatment. Cells were treated with fursultiamine for 24 hours. The intensity of EGFP fluorescence was determined by flow cytometry as described above.

Figure 7A:
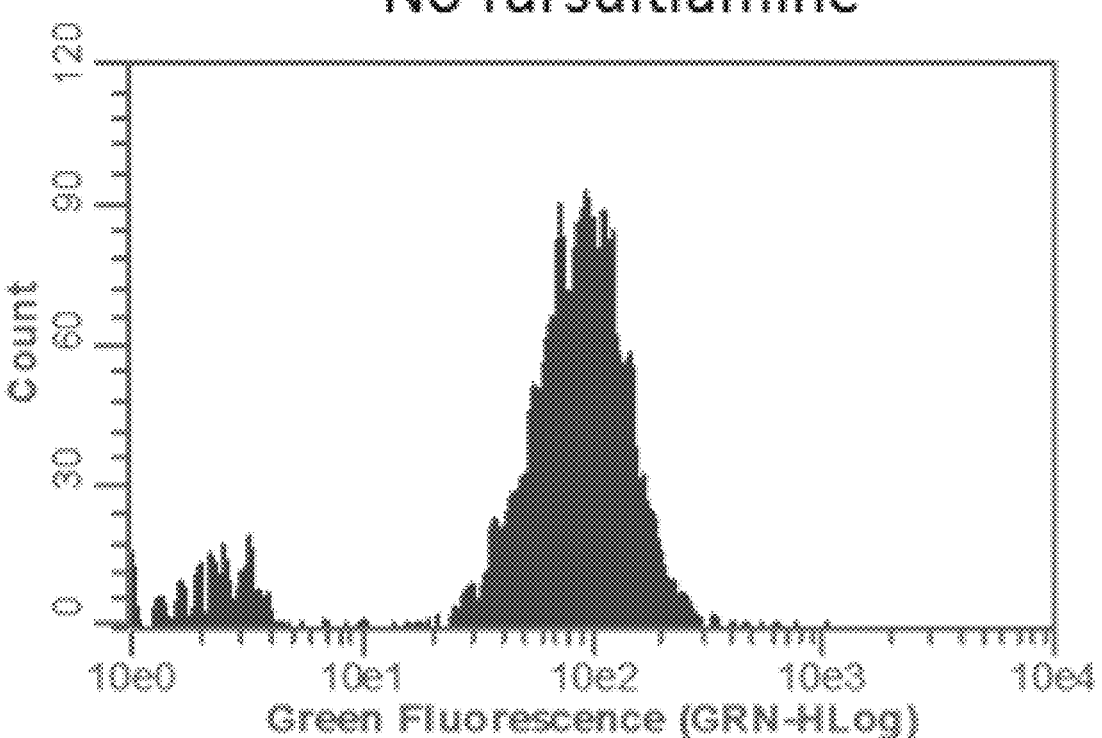
FIGS. 7A and 7B illustrate that a riboswitch comprising aptamer 6B4 regulates enhanced green fluorescent protein (EGFP) expression in response to fursultiamine treatment. Stably transfected HEK 293 cells containing the EGFP-6B4 construct were treated with fursultiamine at 50 μM (FIG. 7A) or at the indicated doses (FIG. 7B) for 24 hours or left untreated.
Figure 7A:
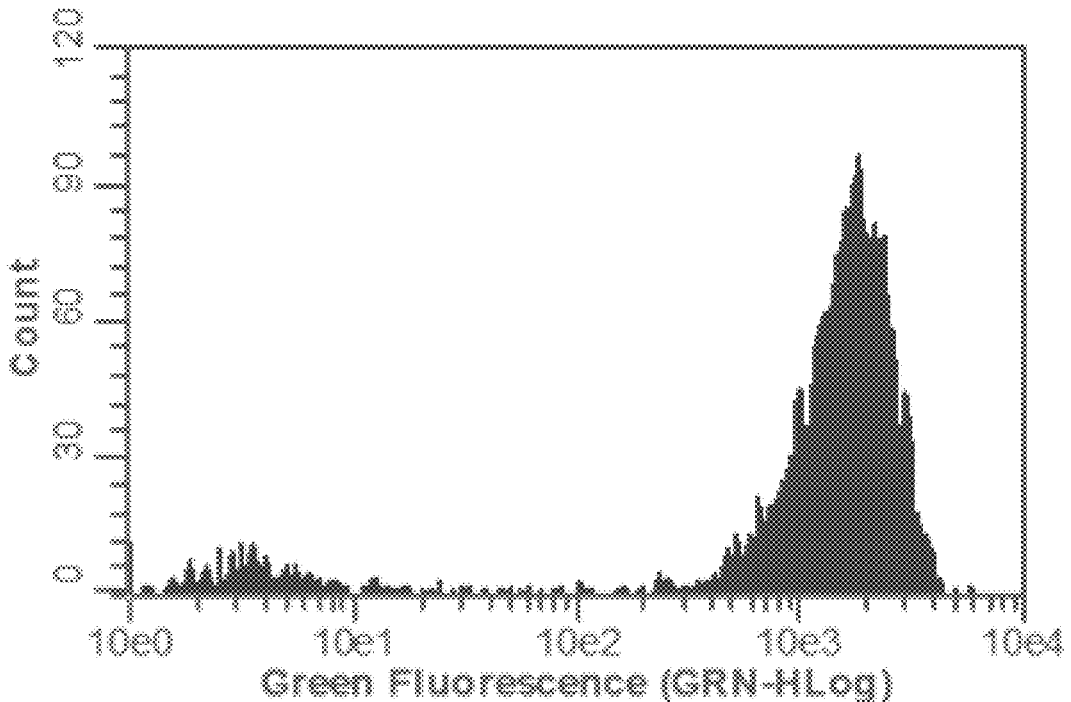
Figure 7B:
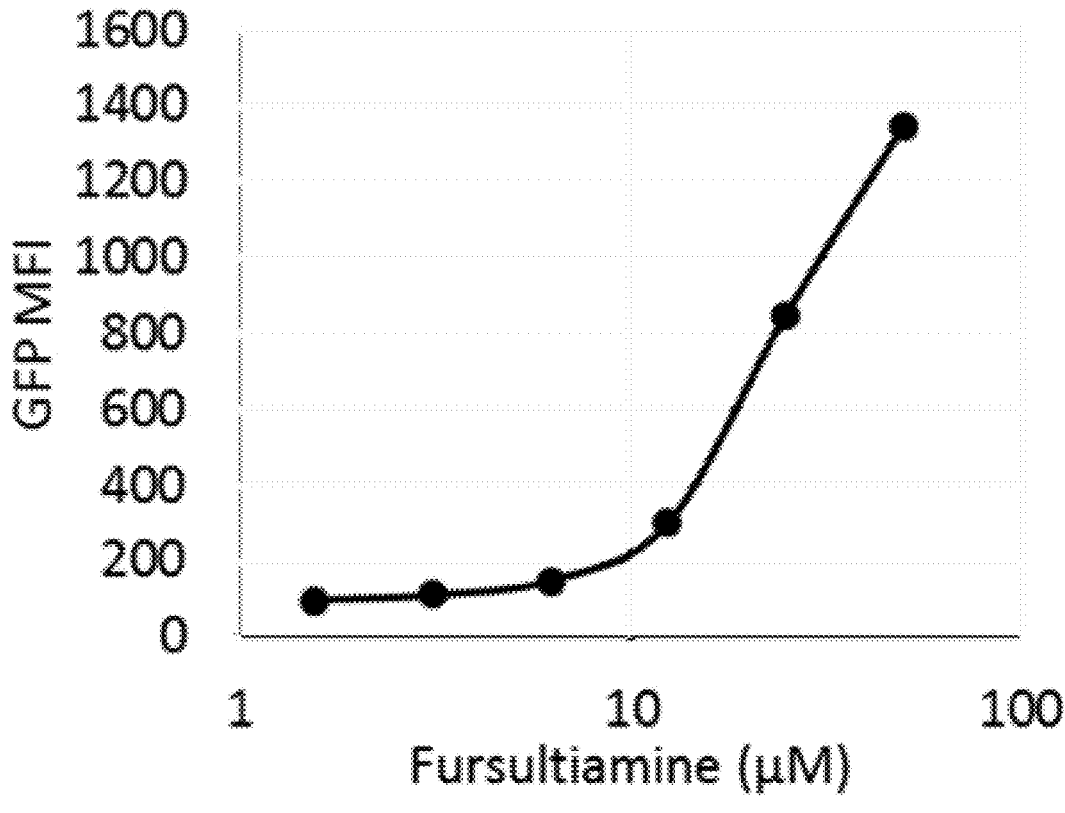

Results:

Cell expressing construct EGFP-6B4 exhibited low expression of the reporter protein EGFP in the absence of fursultiamine treatment, but showed a 14 fold increase in EGFP expression in the presence of fursultiamine (see FIG. 7A), illustrating the ability of the riboswitch comprising re-engineered aptamer 6B4 to induce expression of reporter proteins other than luciferase in response to the synthetic ligand fursultiamine. Further, the induction of EGFP expression in response to fursultiamine treatment was dose-dependent (see FIG. 7B).

Figure 7C:
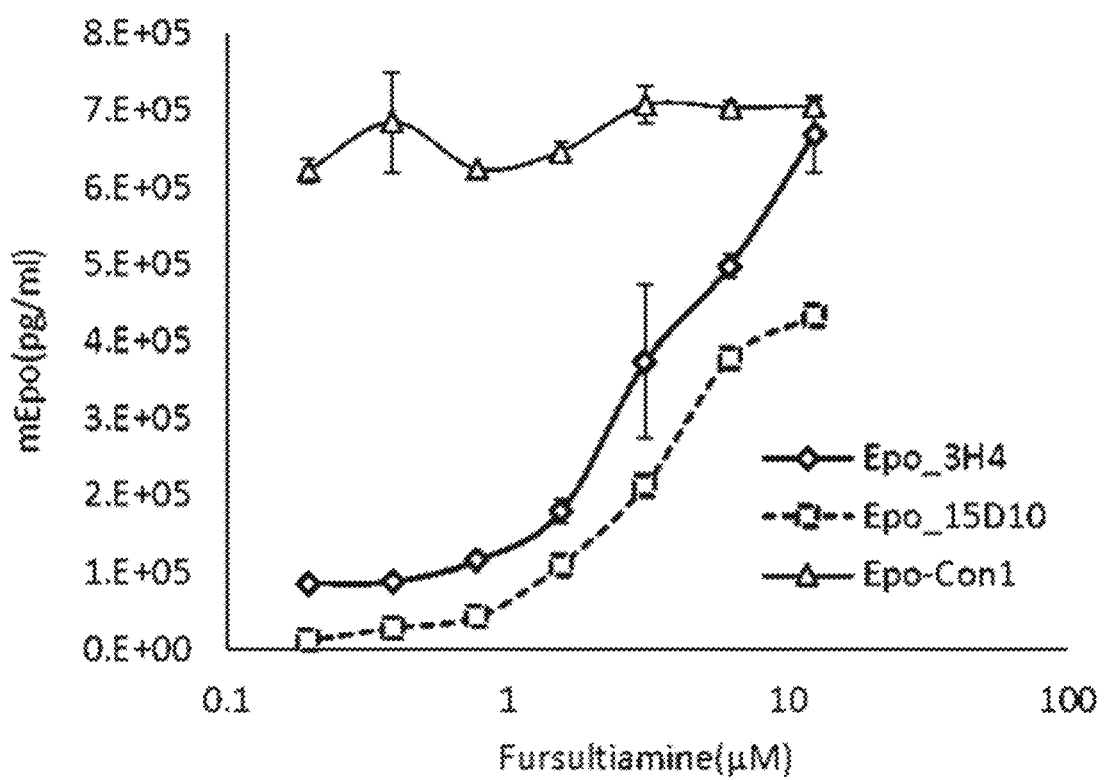
Figure 7D:
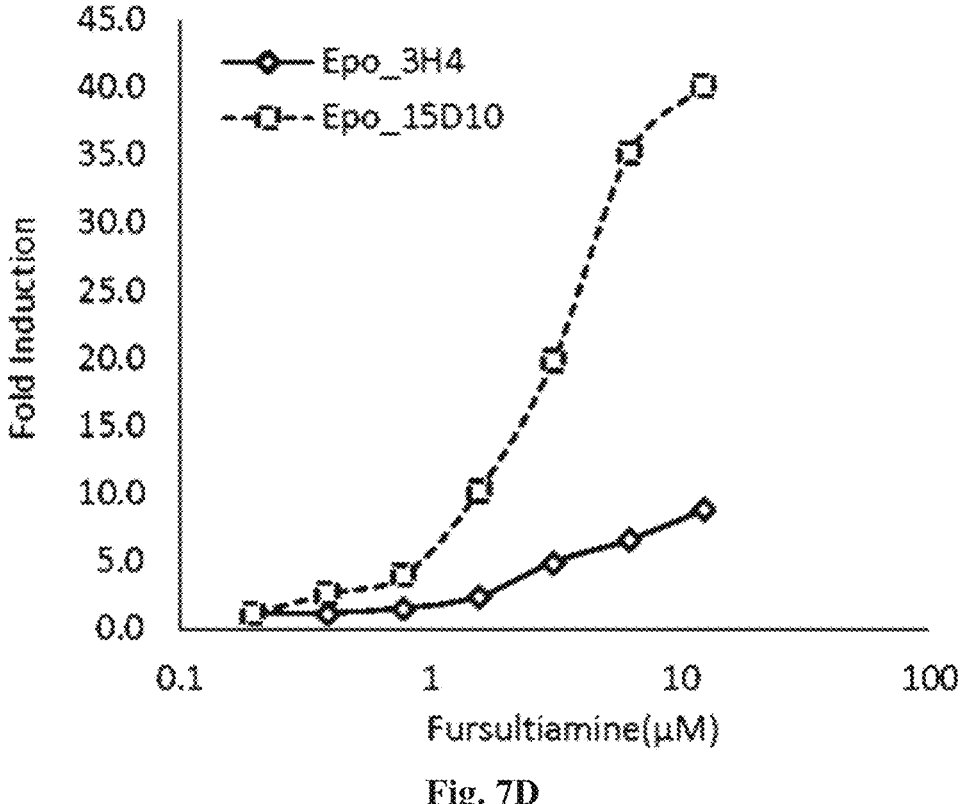
Figure 8A:
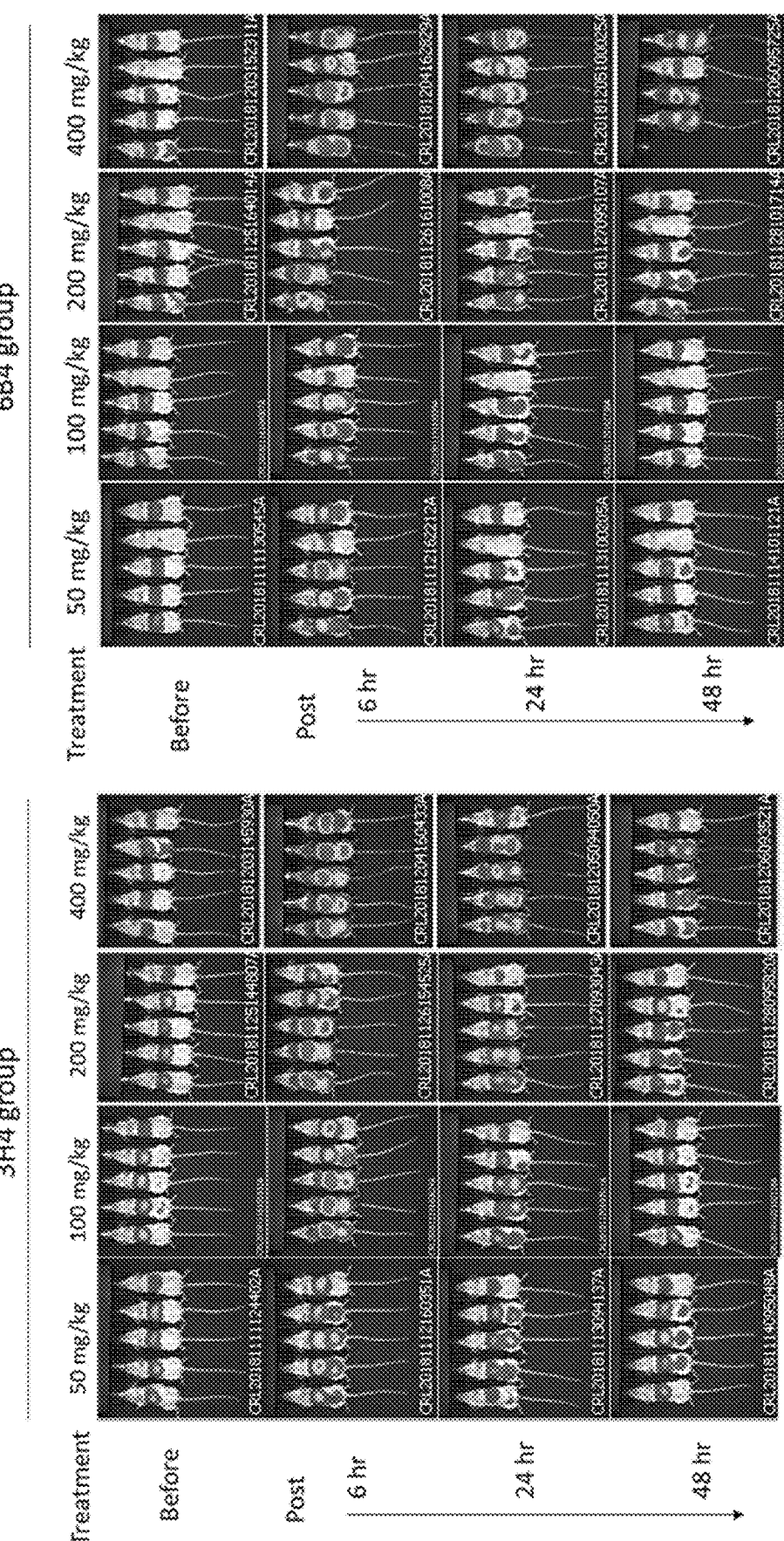
FIG. 8A shows luciferase expression at the time points and for the doses of prosultiamine indicated for mice transfected with AAV vectors comprising the luciferase gene with the re-engineered riboswitches 3H4 or 6B4.
Figure 8B:
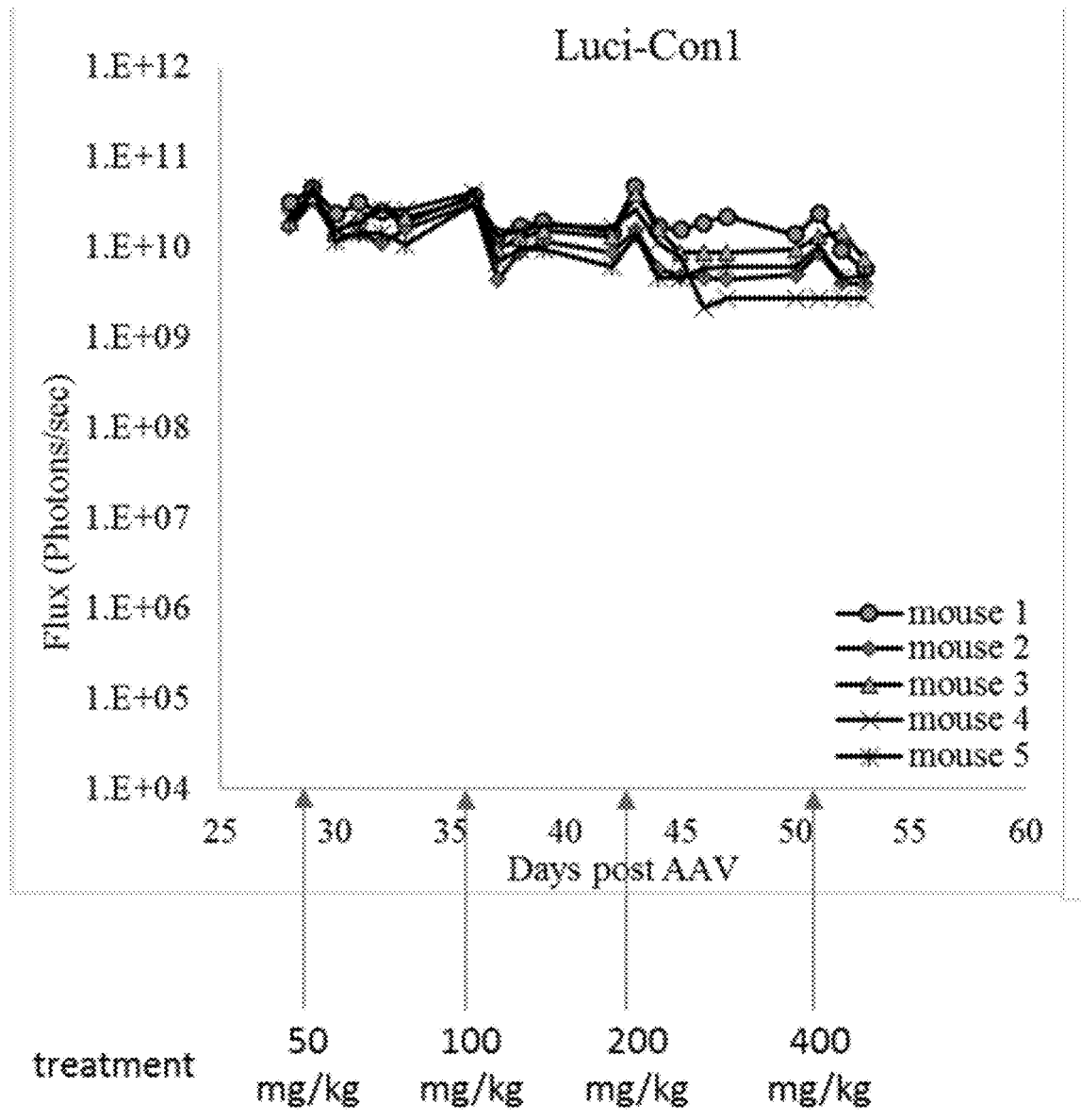
FIGS. 8B and 8C show the luciferase fluorescence intensity observed for the different groups the day prior to drug dosing, as well as 6 h, 24 h, 48 h and 72 after dosing.
Figure 8B:
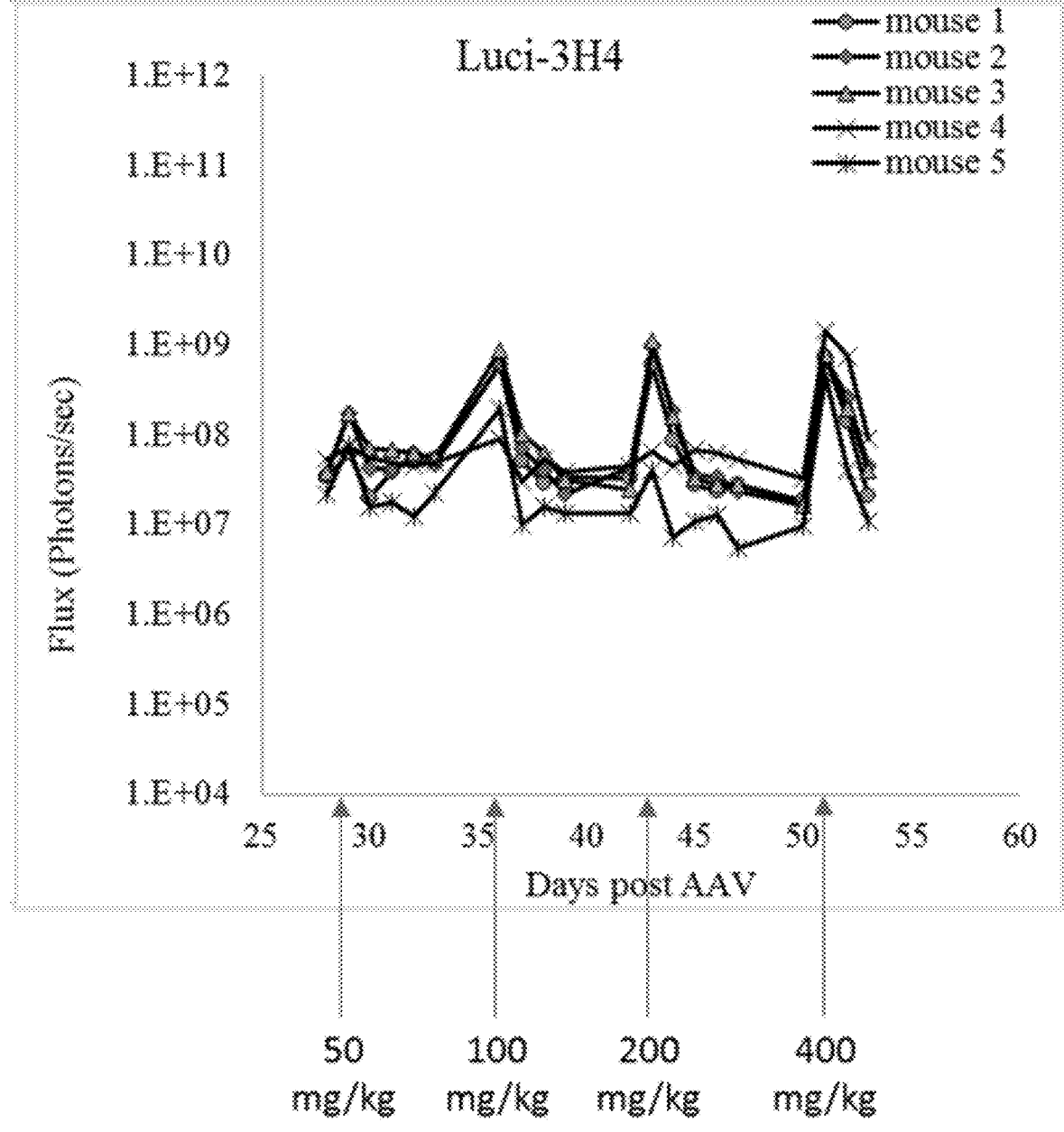
Figure 8B:
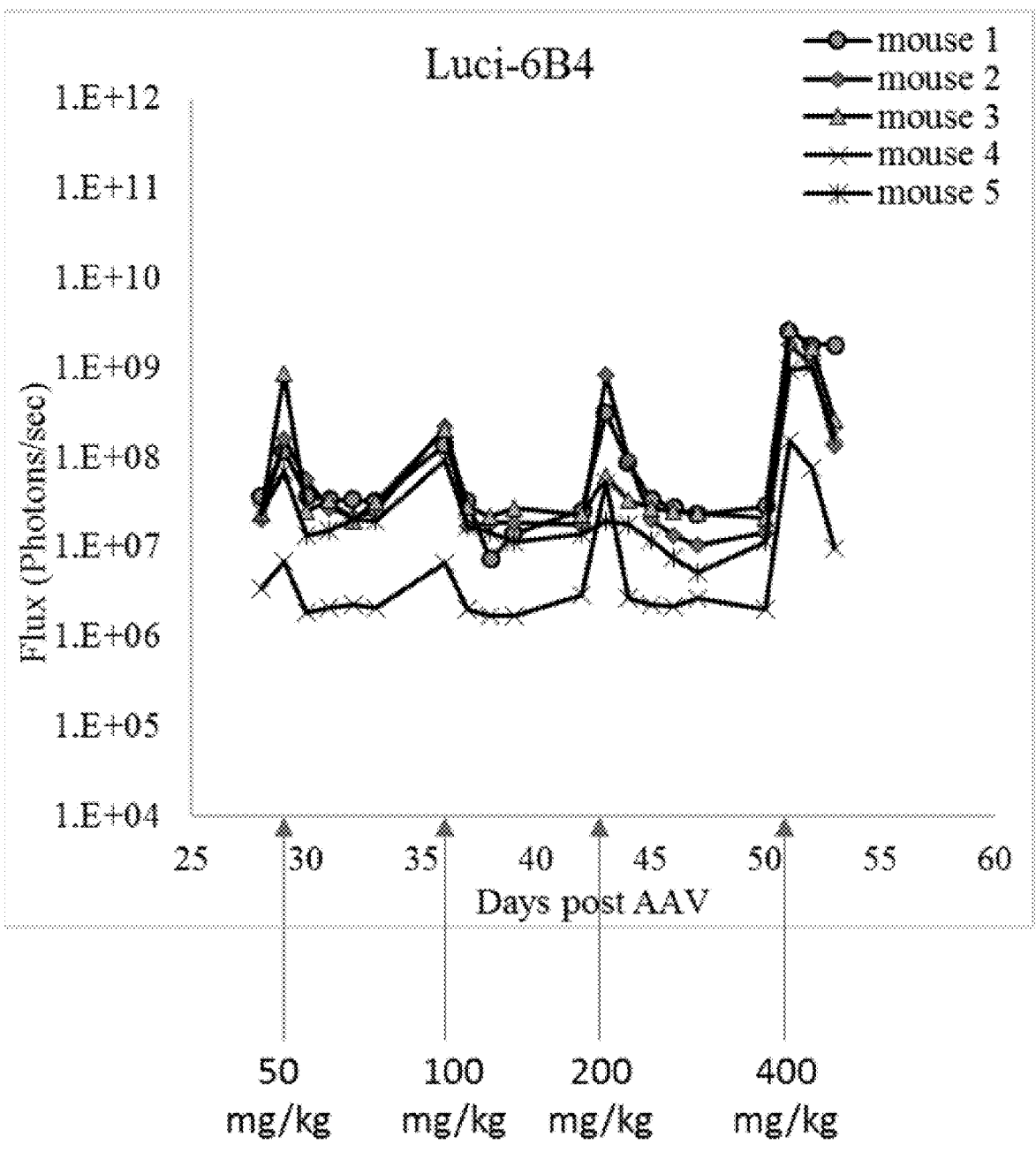
Figure 8C:
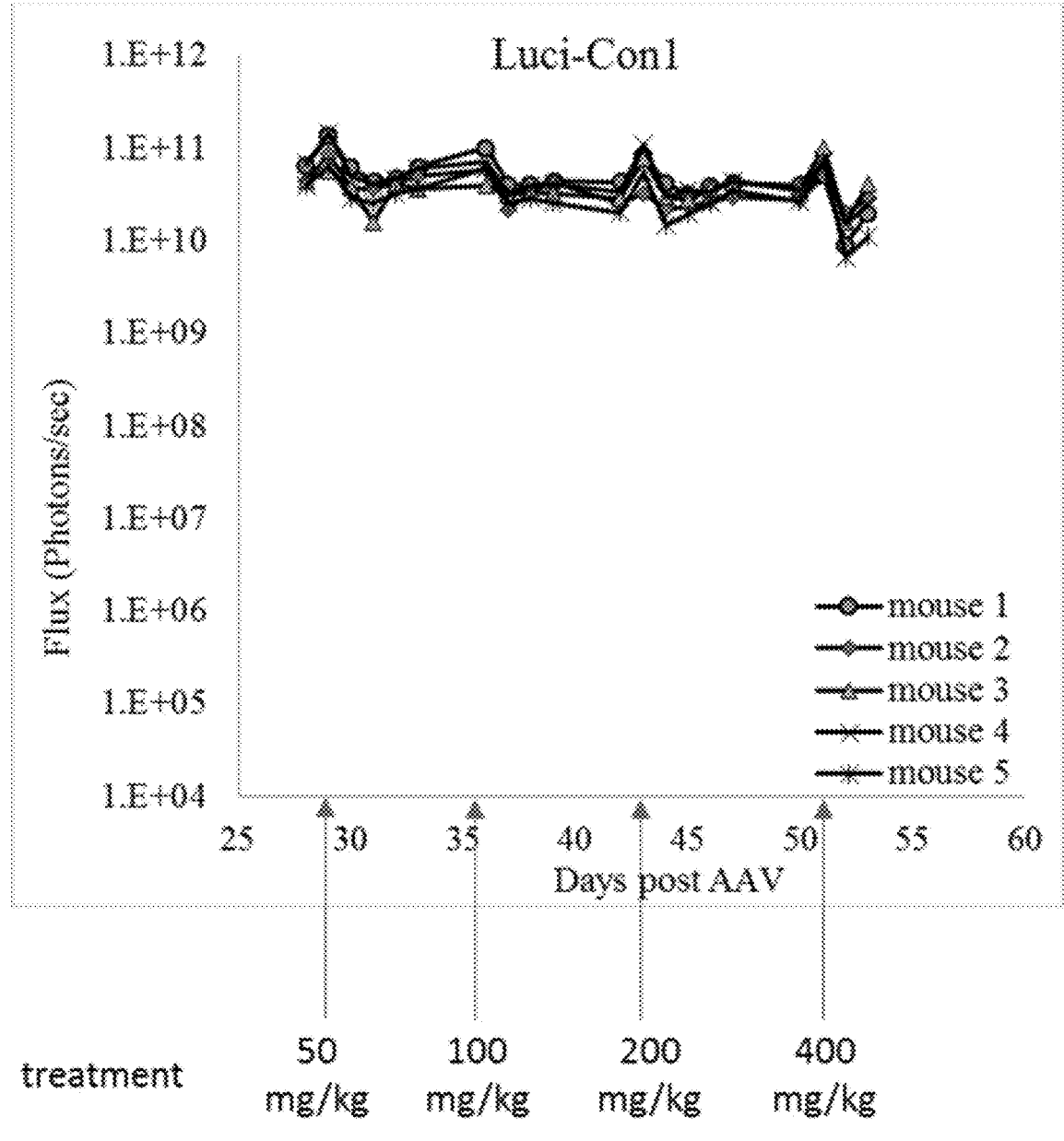
Figure 8C:
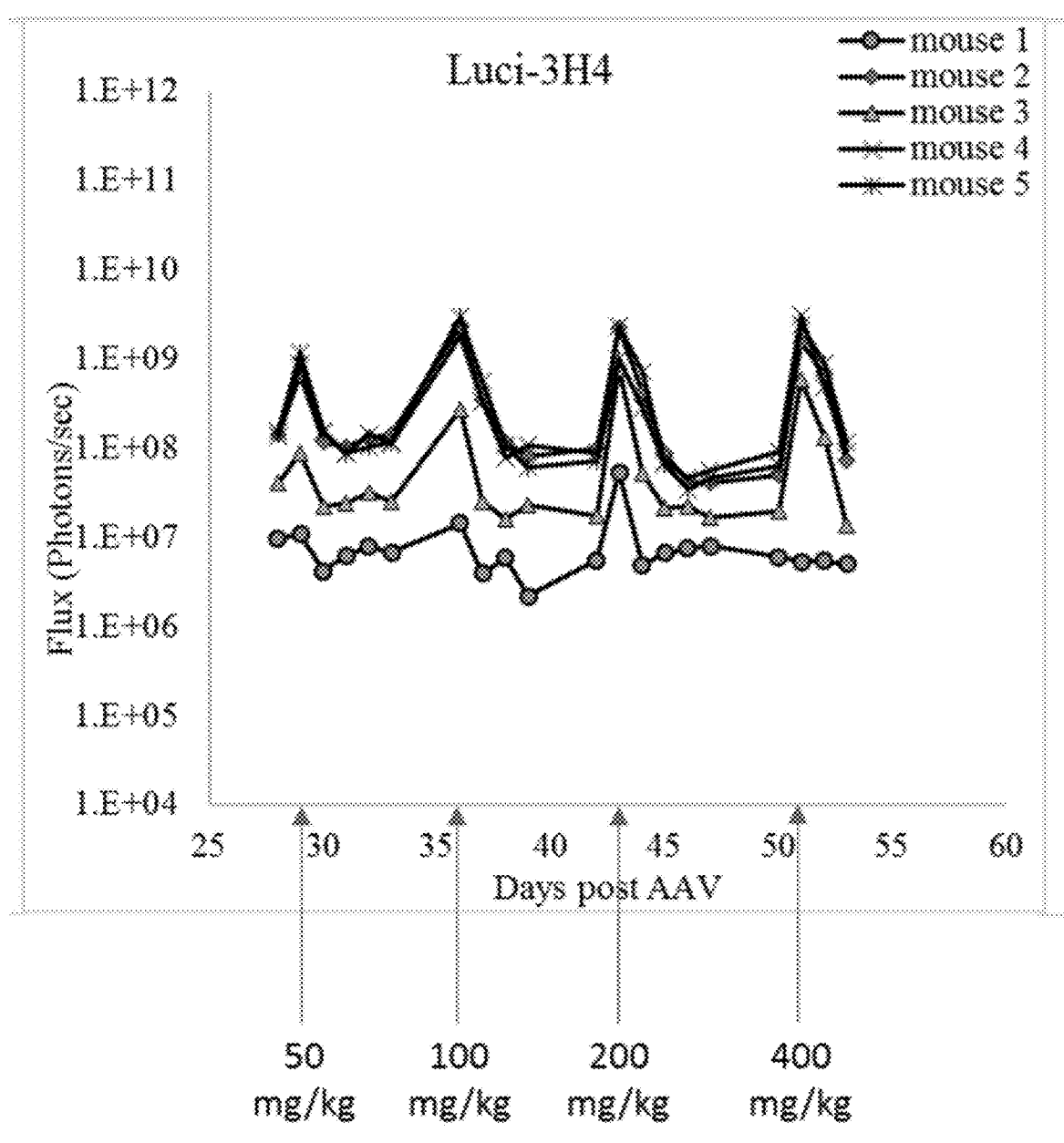
Figure 8C:
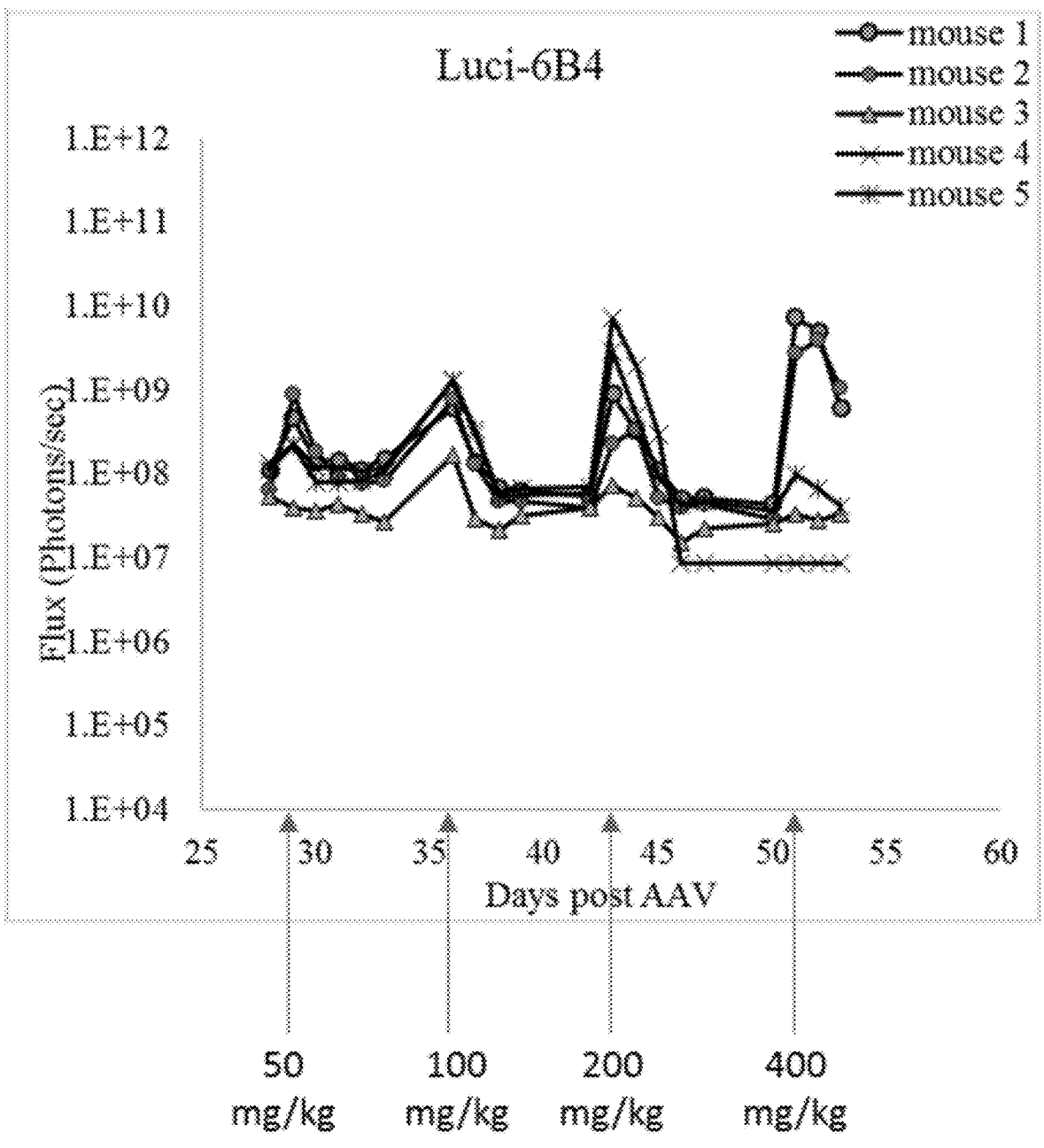
Figure 8D:
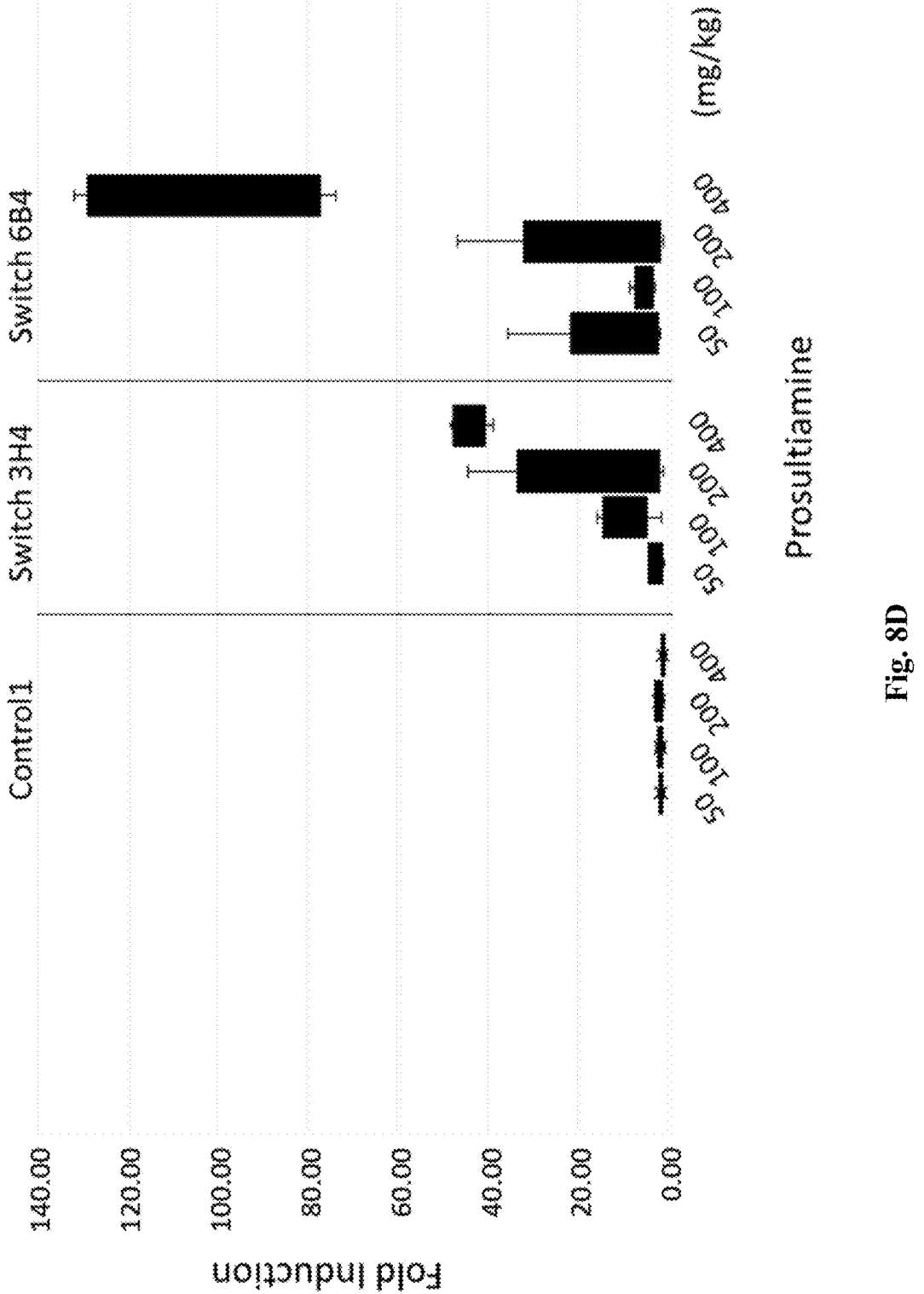
FIGS. 8D and 8E show the relative increase in luciferase expression upon prosultiamine treatment after drug dosing for the different drug doses and groups. The fold induction of luciferase expression was calculated as the quotient of photon/s obtained from mice treated with prosultiamine divided by the value obtained from mice one day before prosultiamine treatment.
Figure 8E:
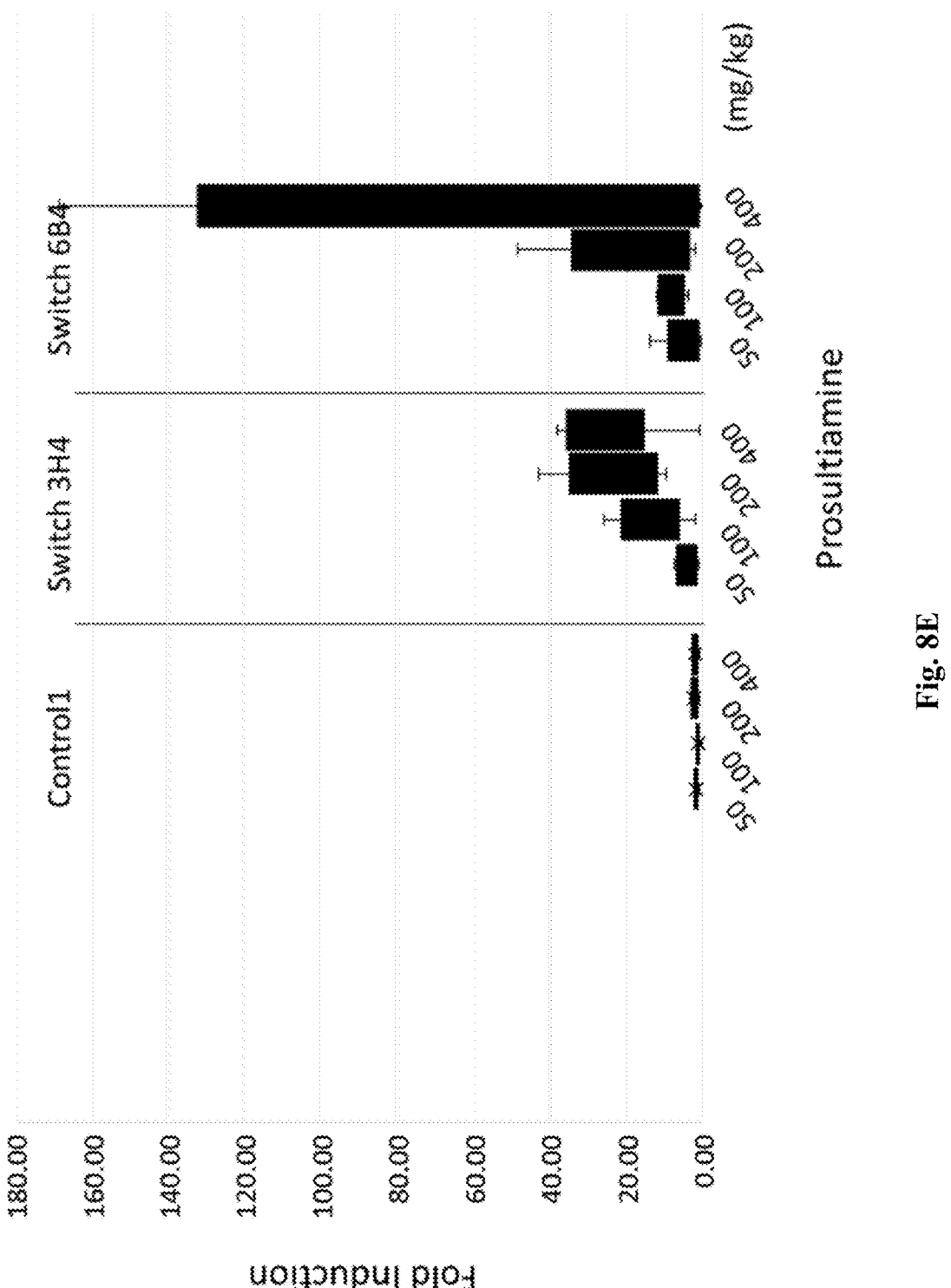

Next, the ability of riboswitches comprising aptamers 3H4 and 15D10 to regulate gene expression of mEpo was examined. In the absence of fursultiamine, cells containing mEpo-3H4 or the mEpo-15D10 expressed very low levels of mEpo. However, upon treatment with fursultiamine, expression of mEpo was enhanced in a dose-dependent manner in cells containing mEpo-3H4 or the mEpo-15D10 constructs. As expected, the control construct mEpo-Con1 expressed mEpo constitutively, irrespective of the presence or absence of fursultiamine (see FIG. 7C). In response to treatment with 12.5 µM fursultiamine, expression of mEpo was induced by about 40-fold (Epo-15D10) or 9-fold (Epo-3H4) as compared to expression in absence of fursultiamine (see FIG. 7D), the level of mEpo from mEpo-15D10 at 12.5 µM of inducer is approximately 61.3% of that from the constitutive and non-regulatable mEpo-Con1 construct.

These results demonstrate that the ability of riboswitches comprising re-engineered aptamer sequences to induce gene expression in response to small molecules is not restricted to specific target gene sequences, indicating a general applicability of these aptamer riboswitches in regulating target gene expression.

Example 5: Synthetic Riboswitches Regulate Gene Expression In Vivo in Mice

To assess the ability of re-engineered aptamers to induce gene expression in vivo, mice were transfected with an adeno-associated viral vector (AAV) carrying a re-engineered riboswitch, which was inserted into the gene for the reporter protein luciferase. Prosultiamine was used as the aptamer ligand to induce luciferase expression.

Experimental Procedures

AAV2.8 viral particle production: The AAV2.8 particles used for the transfection of mice comprised a viral genome derived from AAV2 and a capsid derived from AAV8. The luciferase gene containing an intron-exon-intron cassette with (1) a non-regulatable riboswitch without aptamer ("luci-Con1", SEQ ID NO:90), (2) a riboswitch cassette comprising aptamer 3H4 ("luci-3H4", SEQ ID NO:91), or (3) a riboswitch cassette comprising aptamer 6B4 ("luci-6B4", SEQ ID NO:92), respectively, was cloned into an AAV2 plasmid vector. Expression of the luciferase gene was controlled by a CASI promoter, which includes CMV and ubiquitin C enhancer elements and the chicken β-actin promoter. The viral vector was packaged into AAV8 capsid and produced following manufacture's protocol (Vigene Biosciences).

SEQ ID NO: 90 was obtained by inserting an intron-exon-intron cassette without aptamer sequence into the luciferase reporter gene. Capital letters indicate the luciferase encoding sequence. Lower case letters indicate the intron/alternative exon/intron sequence.

```
                                        SEQ ID NO: 90
ATGGAAGACGCCAAAAACATAAAGAAAGGCCCGGCGCCATTCTATCCGC

TGGAAGATGGAACCGCTGGAGAGCAACTGCATAAGGCTATGAAGAGATA

CGCCCTGGTTCCTGGAACAATTGCTTTTACAGATGCACATATCGAGGTG

GACATCACTTACGCTGAGTACTTCGAAATGTCCGTTCGGTTGGCAGAAG

CTATGAAACGATATGGGCTGAATACAAATCACAGAATCGTCGTATGCAG

TGAAAACTCTCTTCAATTCTTTATGCCGGTGTTGGGCGCGTTATTTATC

GGAGTTGCAGTTGCGCCCGCGAACGACATTTATAATGAACGTGAATTGC

TCAACAGTATGGGCATTTCGCAGCCTACCGTGGTGTTCGTTTCCAAAAA

GGGGTTGCAAAAAATTTTGAACGTGCAAAAAAAGCTCCCAATCATCCAA

AAAATTATTATCATGGATTCTAAAACGGATTACCAGGGATTTCAGTCGA

TGTACACGTTCGTCACATCTCATCTACCTCCCGGTTTTAATGAATACGA

TTTTGTGCCAGAGTCCTTCGATAGGGACAAGACAATTGCACTGATCATG

AACTCCTCTGGATCTACTGGTCTGCCTAAAGGTGTCGCTCTGCCTCATA

GAACTGCCTGCGTGAGATTCTCGCATGCCAGAGATCCTATTTTTGGCAA

TCAAATCATTCCGGATACTGCGATTTTAAGTGTTGTTCCATTCCATCAC

GGTTTTGGAATGTTTACTACACTCGGATATTTGATATGTGGATTTCGAG

TCGTCTTAATGTATAGATTTGAAGAAGAGCTGTTTCTGAGGAGCCTTCA
```

```
                                         -continued
GGATTACAAGATTCAAAGTGCGCTGCTGGTGCCAACCCTATTCTCCTTC

TTCGCCAAAAGCACTCTGATTGACAAATACGATTTATCTAATTTACACG

AAATTGCTTCTGGTGGCGCTCCCCTCTCTAAGGAAGTCGGGGAAGCGGT

TGCCAAGAGGTTCCATCTGCCAGGTATCAGGgtgagtctatgggaccct tgatgttttctttccccttcttttctatggttaagttcatgtcatagga aggggagaagtaacagggtacacatattgaccaaatcagggtaattttg catttgtaattttaaaaaatgctttcttcttttaatatactttttgtt tatcttatttctaatactttccctaatctctttctttcagggcaataat gatacaatgtatcatgcctctttgcaccattctaaagaataacagtgat aatttctgggttaaggcaatagcaatatttctgcatataaatatttctg catataaattgtaactgatgtaagaggtttcatattgctaatagcagct acaatccagctaccattctgcttttattttatggttgggataaggctgg attattctgagtccaagctaggccctttgctaatcatgttcatacctc ttatcttcctcccacagCAAGGATATGGGCTCACTGAGACTACATCAGC

TATTCTGATTACACCCGAGGGGGATGATAAACCGGGCGCGGTCGGTAAA

GTTGTTCCATTTTTTGAAGCGAAGGTTGTGGATCTGGATACCGGGAAAA

CGCTGGGCGTTAATCAAAGAGGCGAACTGTGTGTGAGAGGTCCTATGAT

TATGTCCGGTTATGTAAACAATCCGGAAGCGACCAACGCCTTGATTGAC

AAGGATGGATGGCTACATTCTGGAGACATAGCTTACTGGGACGAAGACG

AACACTTCTTCATCGTTGACCGCCTGAAGTCTCTGATTAAGTACAAAGG

CTATCAGGTGGCTCCCGCTGAATTGGAATCCATCTTGCTCCAACACCCC

AACATCTTCGACGCAGGTGTCGCAGGTCTTCCCGACGATGACGCCGGTG

AACTTCCCGCCGCCGTTGTTGTTTTGGAGCACGGAAAGACGATGACGGA

AAAAGAGATCGTGGATTACGTCGCCAGTCAAGTAACAACCGCGAAAAAG

TTGCGCGGAGGAGTTGTGTTTGTGGACGAAGTACCGAAAGGTCTTACCG

GAAAACTCGACGCAAGAAAAATCAGAGAGATCCTCATAAAGGCCAAGAA

GGGCGGAAAGATCGCCGTGTAA
```

SEQ ID NO: 91 was obtained by inserting the 3H4 riboswitch into the luciferase reporter gene. Capital letters indicate the luciferase encoding sequence. Lower case letters indicate the intron/alternative exon/intron and riboswitch sequence. The 3H4 aptamer encoding sequence (SEQ ID NO:9) is underlined.

```
                                        SEQ ID NO: 91
ATGGAAGACGCCAAAAACATAAAGAAAGGCCCGGCGCCATTCTATCCGC

TGGAAGATGGAACCGCTGGAGAGCAACTGCATAAGGCTATGAAGAGATA

CGCCCTGGTTCCTGGAACAATTGCTTTTACAGATGCACATATCGAGGTG

GACATCACTTACGCTGAGTACTTCGAAATGTCCGTTCGGTTGGCAGAAG

CTATGAAACGATATGGGCTGAATACAAATCACAGAATCGTCGTATGCAG

TGAAAACTCTCTTCAATTCTTTATGCCGGTGTTGGGCGCGTTATTTATC

GGAGTTGCAGTTGCGCCCGCGAACGACATTTATAATGAACGTGAATTGC

TCAACAGTATGGGCATTTCGCAGCCTACCGTGGTGTTCGTTTCCAAAAA
```

-continued

GGGGTTGCAAAAAATTTTGAACGTGCAAAAAAAGCTCCCAATCATCCAA

AAAATTATTATCATGGATTCTAAAACGGATTACCAGGGATTTCAGTCGA

TGTACACGTTCGTCACATCTCATCTACCTCCCGGTTTTAATGAATACGA

TTTTGTGCCAGAGTCCTTCGATAGGGACAAGACAATTGCACTGATCATG

AACTCCTCTGGATCTACTGGTCTGCCTAAAGGTGTCGCTCTGCCTCATA

GAACTGCCTGCGTGAGATTCTCGCATGCCAGAGATCCTATTTTTGGCAA

TCAAATCATTCCGGATACTGCGATTTTAAGTGTTGTTCCATTCCATCAC

GGTTTTGGAATGTTTACTACACTCGGATATTTGATATGTGGATTTCGAG

TCGTCTTAATGTATAGATTTGAAGAAGAGCTGTTTCTGAGGAGCCTTCA

GGATTACAAGATTCAAAGTGCGCTGCTGGTGCCAACCCTATTCTCCTTC

TTCGCCAAAAGCACTCTGATTGACAAATACGATTTATCTAATTTACACG

AAATTGCTTCTGGTGGCGCTCCCCTCTCTAAGGAAGTCGGGGAAGCGGT

TGCCAAGAGGTTCCATCTGCCAGGTATCAGGgtgagtctatgggaccct tgatgttttctttccccttctttctatggttaagttcatgtcatagga aggggagaagtaacagggtacacatattgaccaaatcagggtaattttg catttgtaattttaaaaaatgctttcttcttttaatatactttttgtt tatcttatttctaatactttccctaatctctttctttcagggcaataat gatacaatgtatcatgccgagtaacgctgtttctctaacttgtaggaat gaattcagatatttccagagaatgaaaaaaatcttcagtagaaggtaa tgt<u>acaggggtccggccttttcatttggcgccggtgagagcacaccctt</u>

<u>tgaacctgttcacggataatgccgctgcaggga</u>gtacattacgcaccat tctaaagaataacagtgataaatttctgggttaaggcaatagcaatattt ctgcatataaatatttctgcatataaaattgtaactgatgtaagaggttt catattgctaatagcagctacaatccagctaccattctgcttttatttt atggttgggataaggctggattattctgagtccaagctaggccctttg ctaatcatgttcatacctcttatcttcctcccacagCAAGGATATGGGC

TCACTGAGACTACATCAGCTATTCTGATTACACCCGAGGGGGATGATAA

ACCGGGCGCGGTCGGTAAAGTTGTTCCATTTTTTGAAGCGAAGGTTGTG

GATCTGGATACCGGGAAAACGCTGGGCGTTAATCAAAGAGGCGAACTGT

GTGTGAGAGGTCCTATGATTATGTCCGGTTATGTAAACAATCCGGAAGC

GACCAACGCCTTGATTGACAAGGATGGATGGCTACATTCTGGAGACATA

GCTTACTGGGACGAAGACGAACACTTCTTCATCGTTGACCGCCTGAAGT

CTCTGATTAAGTACAAAGGCTATCAGGTGGCTCCCGCTGAATTGGAATC

CATCTTGCTCCAACACCCCAACATCTTCGACGCAGGTGTCGCAGGTCTT

CCCGACGATGACGCCGGTGAACTTCCCGCCGCCGTTGTTGTTTTGGAGC

ACGGAAAGACGATGACGGAAAAAGAGATCGTGGATTACGTCGCCAGTCA

AGTAACAACCGCGAAAAAGTTGCGCGGAGGAGTTGTGTTTGTGGACGAA

GTACCGAAAGGTCTTACCGGAAAACTCGACGCAAGAAAAATCAGAGAGA

TCCTCATAAAGGCCAAGAAGGGCGGAAAGATCGCCGTGTAA

SEQ ID NO: 92 was obtained by inserting the 6B4 riboswitch into the luciferase reporter gene. Capital letters indicate the luciferase encoding sequence. Lower case letters indicate the intron/alternative exon/intron and riboswitch sequence. The 6B4 aptamer encoding sequence (SEQ ID NO:14) is underlined.

SEQ ID NO: 92

ATGGAAGACGCCAAAAACATAAAGAAAGGCCCGGCGCCATTCTATCCGC

TGGAAGATGGAACCGCTGGAGAGCAACTGCATAAGGCTATGAAGAGATA

CGCCCTGGTTCCTGGAACAATTGCTTTTACAGATGCACATATCGAGGTG

GACATCACTTACGCTGAGTACTTCGAAATGTCCGTTCGGTTGGCAGAAG

CTATGAAACGATATGGGCTGAATACAAATCACAGAATCGTCGTATGCAG

TGAAAACTCTCTTCAATTCTTTATGCCGGTGTTGGGCGCGTTATTTATC

GGAGTTGCAGTTGCGCCCGCGAACGACATTTATAATGAACGTGAATTGC

TCAACAGTATGGGCATTTCGCAGCCTACCGTGGTGTTCGTTTCCAAAAA

GGGGTTGCAAAAAATTTTGAACGTGCAAAAAAAGCTCCCAATCATCCAA

AAAATTATTATCATGGATTCTAAAACGGATTACCAGGGATTTCAGTCGA

TGTACACGTTCGTCACATCTCATCTACCTCCCGGTTTTAATGAATACGA

TTTTGTGCCAGAGTCCTTCGATAGGGACAAGACAATTGCACTGATCATG

AACTCCTCTGGATCTACTGGTCTGCCTAAAGGTGTCGCTCTGCCTCATA

GAACTGCCTGCGTGAGATTCTCGCATGCCAGAGATCCTATTTTTGGCAA

TCAAATCATTCCGGATACTGCGATTTTAAGTGTTGTTCCATTCCATCAC

GGTTTTGGAATGTTTACTACACTCGGATATTTGATATGTGGATTTCGAG

TCGTCTTAATGTATAGATTTGAAGAAGAGCTGTTTCTGAGGAGCCTTCA

GGATTACAAGATTCAAAGTGCGCTGCTGGTGCCAACCCTATTCTCCTTC

TTCGCCAAAAGCACTCTGATTGACAAATACGATTTATCTAATTTACACG

AAATTGCTTCTGGTGGCGCTCCCCTCTCTAAGGAAGTCGGGGAAGCGGT

TGCCAAGAGGTTCCATCTGCCAGGTATCAGGgtgagtctatgggaccct tgatgttttctttccccttctttctatggttaagttcatgtcatagga aggggagaagtaacagggtacacatattgaccaaatcagggtaattttg catttgtaattttaaaaaatgctttcttcttttaatatactttttgtt tatcttatttctaatactttccctaatctctttctttcagggcaataat gatacaatgtatcatgccgagtaacgctgtttctctaacttgtaggaat gaattcagatatttccagagaatgaaaaaaatcttcagtagaaggtaa tgt<u>acaggggtccggccttttcatttggcgccggtgagagcacaccctt</u>

<u>gtgacctgtttacggataatgccgccgcagggag</u>tacattacgcaccat tctaaagaataacagtgataaatttctgggttaaggcaatagcaatattt ctgcatataaatatttctgcatataaattgtaactgatgtaagaggttt catattgctaatagcagctacaatccagctaccattctgcttttatttt atggttgggataaggctggattattctgagtccaagctaggccctttg ctaatcatgttcatacctcttatcttcctcccacagCAAGGATATGGGC

TCACTGAGACTACATCAGCTATTCTGATTACACCCGAGGGGGATGATAA

ACCGGGCGCGGTCGGTAAAGTTGTTCCATTTTTTGAAGCGAAGGTTGTG

GATCTGGATACCGGGAAAACGCTGGGCGTTAATCAAAGAGGCGAACTGT

GTGTGAGAGGTCCTATGATTATGTCCGGTTATGTAAACAATCCGGAAGC

-continued

```
GACCAACGCCTTGATTGACAAGGATGGATGGCTACATTCTGGAGACATA

GCTTACTGGGACGAAGACGAACACTTCTTCATCGTTGACCGCCTGAAGT

CTCTGATTAAGTACAAAGGCTATCAGGTGGCTCCCGCTGAATTGGAATC

CATCTTGCTCCAACACCCCAACATCTTCGACGCAGGTGTCGCAGGTCTT

CCCGACGATGACGCCGGTGAACTTCCCGCCGCCGTTGTTGTTTTGGAGC

ACGGAAAGACGATGACGGAAAAAGAGATCGTGGATTACGTCGCCAGTCA

AGTAACAACCGCGAAAAAGTTGCGCGGAGGAGTTGTGTTTGTGGACGAA

GTACCGAAAGGTCTTACCGGAAAACTCGACGCAAGAAAAATCAGAGAGA

TCCTCATAAAGGCCAAGAAGGGCGGAAAGATCGCCGTGTAA
```

Animal study: Male Balb/c mice received a single tail vein injection of $1.0 \times 10^{11}$ or $2.5 \times 10^{11}$ genome copies of the receptive AAV2.8 viral particle. Twenty-eight days after AAV vector delivery, mice were treated intraperitoneally (IP.) with 50 mg/kg prosultiamine. Luciferase activity was measured the day prior to drug dosing, as well as 6 h, 24 h, 48 h and 72 h after drug dosing. After the first administration of prosultiamine, the mice were subjected to three additional rounds of dosing and imaging cycles as follows: Day 36 (after AAV administration):100 mg/kg; day 43: 200 mg/kg; and day 51: 400 mg/kg.

Noninvasive live animal bioluminescence imaging: Before imaging, mice were anesthetized with 2% isoflurane, and injected with 150 mg/kg body weight of luciferin. At the indicated time point post drug dosing, images were taken within 2 to 5 minutes after luciferin injection using a Bruker Xtreme system. Luciferase activity was expressed as mean photon/s±S.D. (n=5). The fold induction of luciferase gene expression was calculated as the quotient of photon/s obtained from mice treated with prosultiamine divided by the value obtained from mice the day before prosultiamine treatment.

Results:

To test the riboswitch in regulating gene expression in animals, AAV vectors harboring luciferase gene with or without riboswitch were delivered into mice intravenously. Mice were treated with prosultiamine intraperitoneally (IP.) 4 weeks after AAV injection. Six hours after a single dose of prosultiamine (50 mg/kg) treatment, luciferase activity was significantly increased in mice injected AAV vectors containing a luciferase gene comprising riboswitches 3H4 or 6B4, but not in the group of mice injected with the same dose of non-regulatable control vector Con1 (see FIGS. 8A-8E). Further, the increase in luciferase activity upon prosultiamine treatment was dose-dependent. In the group of mice that were treated with a single dose of 50 mg/kg or with two doses of 50 mg/kg and 100 mg/kg prosultiamine, respectively, the induced luciferase activity attenuated to the level before inducer treatment 24 hours after single dose treatment. However, in mice that were additionally treated with higher doses of the inducer prosultiamine (i.e., 200 mg/kg and 400 mg/kg) the induced luciferase activity remained for 48 h or longer.

These results demonstrate that riboswitches comprising re-engineered aptamer sequences selectively induce target gene expression upon treatment with a thiamine analog in a dose-dependent manner in vivo.

Examples 6 to 99: Thiamine Analog Riboswitch Regulates Gene Expression in Mammalian Cells in Response to Novel Thiamine Analogs Experimental Procedures Generation of Thiamine Analogs All solvents and reagents were obtained commercially and used as received. 1H NMR spectra were recorded on a Bruker instrument (300 MHz or 400 MHz) in the cited deuterated solvents. Chemical shifts are given in ppm, and coupling constants are in hertz. All final compounds were purified by flash chromatography using 220-400 mesh silica gel or reverse-phase HPLC with CH3CN/water as the solvents. Thin-layer chromatography was done on silica gel 60 F-254 (0.25-nm thickness) plates. Visualization was accomplished with UV light and/or 10% phosphomolybdic acid in ethanol. Nominal (low resolution) mass spectra were acquired on either a Waters LCT or an Applied Biosystems API 3000 mass spectrometer. High resolution mass spectra (HRMS) were acquired on either a Waters LCT or an Agilent TOF mass spectrometer. All other LC-MS experiments were done on an Agilent 1100 HPLC coupled with an Agilent single quadrupole mass spectrometer. Compound purity was determined by a LC-MS with 230 nM and 254 nM wavelengths. All final compounds reported here have purity ≥95%.

Example 6 (M19)

(((Z)-2-(N-((4-Amino-2-methylpyrimidin-5-yl)methyl)formamido)-5-hydroxypent-2-en-3-yl)thio)methyl (3r,5r,7r)-adamantane-1-carboxylate Step 1

(3r,5r,7r)-Adamantane-1-carbonyl chloride

A mixture of (3r,5r,7r)-adamantane-1-carboxylic acid (10.0 g, 55.4 mmol) and $SOCl_2$ (32.8 g, 275 mmol, 20.0 mL) was stirred at 25° C. for 1 h. TLC (dichloromethane: methanol=10: 1, bromocresol green, $R_f$=0.62) showed that the starting material was consumed completely. The mixture was concentrated to give the title compound (11.0 g, 99.7%)

as colorless crystal which was used directly for the next step reaction without further purification.

Step 2

Chloromethyl (3r,5r,7r)-adamantane-1-carboxylate

To a mixture of (3r,5r,7r)-adamantane-1-carboxylic acid (15 g, 83.2 mmol, 1 equiv), tetrabutylammonium bromide (TBAB) (2.68 g, 8.32 mmol, 0.1 equiv) and NaHCO$_3$ (21.0 g, 250.0 mmol, 3 equiv) in DCM (150 mL) and H$_2$O (150 mL) was added chloro(chlorosulfonyloxy)methane (16.5 g, 99.9 mmol, 1.2 equiv) drop-wise at 20° C. The mixture was stirred at 20° C. for 15 h (gas evolution). Upon standing, the mixture was separated into two layers and the aqueous layer was extracted with methylene dichloride (100 mL×2). The combined organic phases were dried with anhydrous Na$_2$SO$_4$, filtered, and concentrated to give a crude colorless oil. The crude product was diluted with petroleum ether (500 mL) and filtered through a pad of silica gel. The filtrate was concentrated to give the title compound (15.5 g, 81.4%) as a colorless oil. $^1$H NMR (400 MHz, DMSO-d$_6$) δ 5.72 (s, 2H), 2.05-1.92 (m, 6H), 1.74-1.70 (m, 2H).

Step 3

(((Z)-2-(N-((4-Amino-2-methylpyrimidin-5-yl) methyl)formamido)-5-hydroxypent-2-en-3-yl)thio) methyl (3r,5r,7r)-adamantane-1-carboxylate To a mixture of vitamin B1 (10 g, 33.2 mmol, 1 equiv) and KI (551.0 mg, 3.32 mmol, 0.1 equiv) in H$_2$O (150 mL) and THF (150 mL) was added NaOH (2.66 g, 66.5 mmol, 2 equiv) in portions and the mixture was stirred at 20° C. for 0.5 h. Chloromethyl (3r,5r,7r)-adamantane-1-carboxylate (15.2 g, 66.5 mmol, 2 equiv) was added drop-wise to the mixture and the resulting mixture was stirred at 20° C. for another 12 h. LCMS showed completion of the reaction. The reaction mixture separated into two layers. The aqueous layer was extracted with ethyl acetate (200 mL×3). The combined organic phases were dried with anhydrous Na$_2$SO$_4$, filtered, and concentrated to give a crude product (TLC: ethyl acetate/ethanol=10/1, product R$_f$=0.2). The crude product was purified by silica gel chromatography (methylene dichloride/methanol=10/1) to give a product as a yellow solid which was further purified by pre-HPLC (column: Waters Xbridge BEH C18 250×50 mm, 10 μm; mobile phase: water-acetonitrile with 0.05% ammonia hydroxide v/v, 20 min) to give the title compound (580.24 mg, 4%) as a white solid. $^1$H NMR (400 MHz, DMSO-d$_6$) δ 7.93 (s, 1H), 7.82 (s, 1H), 6.96 (br, 2H), 4.95 (s, 2H), 4.68 (t, J=5.2 Hz, 1H), 4.32 (s, 2H), 3.52-3.48 (m, 2H), 2.58 (m, 2H), 2.28 (s, 3H), 1.94 (s, 6H), 1.80-1.78 (m, 6H), 1.68-1.62 (m, 6H). MS (ES$^+$) m/e 475.2 (M+H)+.

Example 7 (M10)

(Z)-((2-(N-((4-Amino-2-methylpyrimidin-5-yl) methyl)formamido)-5-hydroxypent-2-en-3-yl)thio) methyl pivalate To a solution of vitamin B1 (1.00 g, 3.78 mmol, 1.00 equiv) in EtOH (10.0 mL) was added NaOEt (257 mg, 3.78 mmol, 1.00 equiv), chloromethyl pivalate (569 mg, 3.78 mmol, 547 μL, 1.00 equiv) and NaOH (45.4 mg, 1.13 mmol, 0.30 equiv). The mixture was stirred at 20° C. for 2 h. The reaction mixture was concentrated under reduced pressure to give a residue. The residue was purified by prep-HPLC to give the title compound (61.0 mg, 3.4%) as a light yellow solid. $^1$H NMR (400 MHz, DMSO-d$_6$) δ 7.93 (s, 1H), 7.83 (s, 1H), 6.71 (br d, J=0.9 Hz, 2H), 4.96 (s, 2H), 4.69 (t, J=5.5 Hz, 1H), 4.34 (br s, 2H), 3.60-3.42 (m, 2H), 2.59 (t, J=6.9 Hz, 2H), 2.28 (s, 3H), 1.96 (s, 3H), 1.12 (s, 9H). MS (ES$^+$) m/e 397.3 (M+H)$^+$.

Example 8 (M16)

(Z)-((2-(N-((4-Amino-2-methylpyrimidin-5-yl) methyl)formamido)-5-hydroxypent-2-en-3-yl)thio) methyl isobutyrate

Step 1

Sodium (Z)-2-(N-((4-Amino-2-methylpyrimidin-5-yl)methyl)formamido)-5-hydroxypent-2-ene-3-thiolate To a solution of vitamin B1 (40.0 g, 132 mmol) in EtOH (80.0 mL) was added NaOEt (40.0 g, 123 mmol) in EtOH at −10° C. The mixture was stirred at 10° C. for 30 min. The solid formed was collected by filtration and dried to give the title compound (36.0 g, 88.9%) as a yellow solid. $^1$H NMR (400 MHz, DMSO-$d_6$) δ 9.51 (s, 1H), 8.05 (s, 1H), 7.18 (s, 2H), 5.41 (s, 3H), 3.65-3.62 (m, 2H), 3.01-2.95 (m, 2H), 2.48 (s, 3H), 2.34 (s, 3H).

Step 2

(Z)-((2-(N-((4-Amino-2-methylpyrimidin-5-yl)methyl)formamido)-5-hydroxypent-2-en-3-yl)thio)methyl isobutyrate To a mixture of sodium (Z)-2-(N-((4-amino-2-methylpyrimidin-5-yl)methyl)formamido)-5-hydroxypent-2-ene-3-thiolate (3.00 g, 9.86 mmol) in EtOH (30.0 mL) was added NaOH (120 mg, 3.00 mmol) at 25° C. followed by chloromethyl isobutyrate (1.35 g, 9.88 mmol). The mixture was stirred at 25° C. for 1 h and was concentrated to give a residue. The residue was purified by prep-HPLC (basic condition) and lyophilized to give 150 mg of crude brown solid which was further purified by prep-HPLC (buffered with NH4HCO3) followed by lyophilization to provide the title compound (50.1 mg, 29%) as a yellow solid. $^1$H NMR (400 MHz, DMSO-$d_6$) δ 7.92 (s, 1H), 7.83 (s, 1H), 6.70 (br, 2H), 4.96 (s, 2H), 4.69 (t, J=5.2 Hz, 1H), 4.34 (s, 2H), 3.41-3.52 (m, 2H), 2.58 (t, J=6.8 Hz, 2H), 2.50-2.40 (m, 1H), 2.28 (s, 3H), 1.95 (s, 3H), 1.08 (d, J=7.2 Hz, 6H). MS (ES$^+$) m/e 383.3 (M+H)$^+$.

Example 9 (M18)

(Z)-1-((2-(N-((4-Amino-2-methylpyrimidin-5-yl)methyl)formamido)-5-hydroxypent-2-en-3-yl)thio) ethyl pivalate

Step 1

1-Chloroethyl pivalate

To a mixture of pivaloyl chloride (9.80 g, 81.2 mmol, 10.0 mL) and 2,4,6-trimethyl-1,3,5-trioxane (4.95 g, 37.4 mmol, 5.00 mL) was added ZnCl$_2$ (1 M, 2.50 mL) and the mixture was stirred at 90° C. for 1 h. The reaction mixture was cooled to room temperature and diluted with EtOAc (100 mL). The resulting organic solution was washed with ice-cooled NaHCO$_3$ (20.0 mL×3) solution and brine, dried over Na$_2$SO$_4$, filtered, and concentrated to give a residue. The residue was distilled at 90° C. (gage pressure: −0.09 MPa) to give the title compound (1.60 g) as a colorless oil. $^1$H NMR (400 MHz, CDCl$_3$) δ 6.52-6.56 (m, 1H), 1.80 (d, J=5.6 Hz, 3H), 1.22 (s, 9H).

Step 2

(Z)-1-((2-(N-((4-Amino-2-methylpyrimidin-5-yl)methyl)formamido)-5-hydroxypent-2-en-3-yl)thio) ethyl pivalate To a mixture of sodium (Z)-2-(N-((4-amino-2-methylpyrimidin-5-yl)methyl)formamido)-5-hydroxypent-2-ene-3-thiolate (3.00 g, 9.86 mmol) in EtOH (30.0 mL) was added NaOEt (3.20 g, 9.88 mmol) in EtOH at 25° C. followed by 1-chloroethyl pivalate (1.60 g, 9.72 mmol) and NaOH (120 mg, 3.00 mmol). The mixture was stirred at 25° C. for 12 h and was concentrated to give a residue. The residue was purified by prep-HPLC followed by lyophilization to give the title compound (60.0 mg, 2% yield) as a yellow solid. H NMR (400 MHz, DMSO-d$_6$) δ 7.92 (s, 1H), 7.85 (s, 1H), 6.48 (br, 2H), 5.74-5.79 (m, 1H), 4.46 (d, J=15.2 Hz, 1H), 4.37 (s, 1H), 4.28 (d, J=15.2 Hz, 1H), 3.53-3.55 (m, 2H), 2.52-2.57 (m, 2H), 2.30 (s, 3H), 1.95 (s, 3H), 1.29 (d, J=6.4 Hz, 3H), 1.33 (s, 9H). MS (ES$^+$) m/e 411.3 (M+H)$^+$.

Example 10 (M21)

(Z)-((2-(N-((4-Amino-2-methylpyrimidin-5-yl)methyl)formamido)-5-hydroxypent-2-en-3-yl)thio)methyl benzoate To a mixture of vitamin B1 (5 g, 16.6 mmol, 1 equiv) and KI (138.0 mg, 831.0 μmol, 0.05 equiv) in H$_2$O (25 mL) was added NaOH (1.33 g, 33.2 mmol, 2 equiv) in portions. The mixture was stirred at 20° C. for 0.5 h and then a solution of chloromethyl benzoate (2.84 g, 16.6 mmol, 1 equiv) in THE (25 mL) was added drop-wise. The reaction mixture was then stirred at 20° C. for another 10 h. LCMS showed a new product formed. The mixture was quenched by adding 5 mL of methanol and pH adjusted to ~7 with saturated sodium bicarbonate aqueous solution. The aqueous phase was then extracted with ethyl acetate (200 mL×2). The combined organic phases were dried by anhydrous Na$_2$SO$_4$, filtered, and concentrated to give a crude product which was triturated with ethyl acetate (50 mL) to provide the title compound (700 mg, 10%) as a white solid. $^1$H NMR (400 MHz, DMSO-d$_6$) δ 7.96-7.92 (m, 3H), 7.81 (s, 1H), 7.73-7.67 (m, 1H), 7.57-7.53 (m, 2H), 6.76 (brs, 2H), 5.28 (s, 2H), 4.74-4.70 (m, 1H), 4.32 (s, 2H), 3.54-3.48 (m, 2H), 2.69-2.66 (m, 2H), 2.26 (s, 3H), 1.96 (s, 3H). MS (ES$^+$) m/e 417.2 (M+H)$^+$.

Example 11 (M34)

(Z)—S-(2-(N-((4-Amino-2-methylpyrimidin-5-yl)methyl)formamido)-5-hydroxypent-2-en-3-yl) naphthalene-1-carbothioate To a mixture of vitamin B1 (9 g, 29.9 mmol, 1 equiv) and KI (497.0 mg, 2.99 mmol, 0.1 equiv) in H$_2$O (150 mL) and THE (150 mL) was added NaOH (2.39 g, 59.8 mmol, 2 equiv). The mixture was stirred at 20° C. for 0.5 h. 1-Naphthoyl chloride (11.1 g, 58.0 mmol, 8.71 mL, 1.94 equiv) was added drop-wise. The reaction mixture was stirred at 20° C. for another 12 h. LCMS showed completion of the reaction. The reaction mixture was extracted with ethyl acetate (100 mL×3). The aqueous phase was adjusted to pH 7-8 with saturated sodium bicarbonate solution and extracted with ethyl acetate (100 mL×3). The combined organic phases were dried with anhydrous Na$_2$SO$_4$, filtered and concentrated to give a crude product which was triturated with ethyl acetate (10 mL) to provide the title compound (420 mg, 962 μmol, 3% yield) as an off-white solid. $^1$H NMR (400 MHz, DMSO-d$_6$) δ 8.21-8.20 (m, 2H), 8.05-8.02 (m, 1H), 7.99 (s, 1H), 7.92-7.91 (m, 1H), 7.88 (s, 1H), 7.68-7.59 (m, 3H), 6.74 (brs, 2H), 4.70-4.68 (m, 1H), 4.44 (s, 2H), 3.53 (m, 2H), 2.70-2.68 (m, 2H), 2.19 (s, 3H), 2.13 (s, 3H). MS (ES$^+$) m/e 437.1 (M+H)$^+$.

Example 12 (M26)

(Z)—S-(2-(N-((4-Amino-2-methylpyrimidin-5-yl)methyl)formamido)-5-hydroxypent-2-en-3-yl) benzothioate To a solution of vitamin B1 (1.00 g, 3.32 mmol, 1.00 equiv) and NaOH (133.0 mg, 3.32 mmol, 1.00 equiv) in H$_2$O (50.0 mL) and THE (5.00 mL) was added benzoyl chloride (935.0 mg, 6.65 mmol, 772.0 μL, 2.00 equiv) at 0° C. The reaction mixture was stirred at 0° C. for 0.5 h. LCMS showed that the starting material was consumed and a product with the desired mass was detected. The reaction mixture was quenched with MeOH (5.00 mL) and adjusted to pH=7, and was extracted with 10:1 DCM:MeOH (25.0 mL×2). The combined organic layers were dried over Na$_2$SO$_4$, filtered and concentrated under a reduced pressure to give a crude product, which upon trituration with EtOAc/EtOH/DCM (2:2:1) provided the title compound (251 mg, 18.6%) as a white solid. $^1$H NMR (400 MHz, DMSO-d$_6$) δ 7.89 (s, 1H), 7.82 (s, 1H), 7.73 (d, J=7.2 Hz, 2H), 7.68 (t, J=7.6 Hz, 1H), 7.53 (t, J=7.6 Hz, 2H), 6.65 (brs, 2H), 4.64 (t, J=4.2 Hz, 1H), 4.39 (s, 2H), 3.46 (m, 2H), 2.57 (m, 2H), 2.16 (s, 3H), 2.14 (s, 3H). MS (ES$^+$) m/e 387.0 (M+H)$^+$.

Example 13 (M27)

(Z)—S-(2-(N-((4-Amino-2-methylpyrimidin-5-yl)
methyl)formamido)-5-hydroxypent-2-en-3-yl)
2-methylpropanethioate To a solution of vitamin B1 (1.00 g, 3.32 mmol, 1.00 equiv) and NaOH (266 mg, 6.65 mmol, 2.00 equiv) in H$_2$O (50.0 mL) and THE (5.00 mL) was added isobutyryl chloride (708 mg, 6.65 mmol, 695.0 µL, 2.00 equiv) at 0° C. The reaction mixture was stirred at 0° C. for 0.5 h, quenched with MeOH (5.00 mL), and adjusted to pH=7. The mixture was extracted with 10:1 DCM:MeOH (25.0 mL×2). The combined organic layers were dried over Na$_2$SO$_4$, filtered and concentrated under reduced pressure to give a crude product. The crude product was triturated with EtOAc/EtOH/DCM (2:2:1) to give the title compound (224.0 mg, 19.0%) as a white solid. $^1$H NMR (400 MHz, DMSO-d$_6$) δ 7.79 (s, 1H), 7.77 (s, 1H), 6.68 (brs, 2H), 4.61 (t, J=4.2 Hz, 1H), 4.35 (s, 2H), 3.40 (q, J=6.8 Hz, 2H), 2.60-2.50 (m, 1H), 2.44 (t, J=7.2 Hz, 1H), 2.26 (s, 3H), 2.07 (s, 3H), 1.02 (s, 3H), 1.00 (s, 3H). MS (ES$^+$) m/e 353.3 (M+H)$^+$.

Example 14 (M28)

(Z)—S-(2-(N-((4-Amino-2-methylpyrimidin-5-yl)
methyl)formamido)-5-hydroxypent-2-en-3-yl) 2,2-
dimethylpropanethioate To a mixture of sodium (Z)-2-(N-((4-amino-2-methylpyrimidin-5-yl)methyl)formamido)-5-hydroxypent-2-ene-3-thiolate (0.50 g, 1.64 mmol, 1.00 equiv) and NaOH (65.7 mg, 1.64 mmol, 1.00 equiv) in H$_2$O (5.00 mL) was added pivaloyl chloride (198 mg, 1.64 mmol, 202 µL, 1 equiv) at 0° C. and the resulting mixture was stirred at 0° C. for 1 h. The mixture was concentrated and purified by column chromatography (SiO$_2$, dichloromethane:methanol=100:1 to 10:1, TLC:dichloromethane:methanol=10:1, R$_f$=0.4) to give the title compound (110 mg, 18.2%) as a white solid. $^1$H NMR (400 MHz, DMSO-d$_6$) δ 7.79 (s, 1H) 7.75 (s, 1H) 6.70 (br s, 2H) 4.60 (t, J=5.6 Hz, 1H) 4.35 (br s, 2H) 3.39 (q, J=6.8 Hz, 2H) 2.42 (br t, J=6.8 Hz, 2H) 2.26 (s, 3H) 2.08 (s, 3H) 1.07 (s, 9 H). MS (ES$^+$) m/e 367.2 (M+H)$^+$.

Example 15 (M29)

(Z)—S-(2-(N-((4-Amino-2-methylpyrimidin-5-yl)
methyl)formamido)-5-hydroxypent-2-en-3-yl)
4-methoxybenzothioate To a mixture of sodium (Z)-2-(N-((4-amino-2-methylpyrimidin-5-yl)methyl)formamido)-5-hydroxypent-2-ene-3-thiolate (0.50 g, 1.64 mmol, 1.00 equiv) and NaOH (65.7 mg, 1.64 mmol, 1.00 equiv) in H$_2$O (4 mL) was added compound 4-methoxybenzoyl chloride (280 mg, 1.64 mmol, 226 µL, 1.00 equiv) at 0° C. and resulting mixture was stirred at 0° C. for 1 h. LCMS showed that the starting material was consumed and a product with the desired mass was detected. The mixture was then concentrated, and the residue was purified by silica gel column chromatography (100:0 to 20:1 dichloromethane:methanol) to give the title compound (60.0 mg, 9%) as a white solid. $^1$H NMR (400 MHz, DMSO-d$_6$) δ 7.87 (s, 1H), 7.81 (s, 1H), 7.72 (br d, J=8.8 Hz, 2H), 7.05 (br d, J=8.8 Hz, 2H), 6.64 (m, 2H), 4.64 (br s, 1H), 4.37 (br s, 2H), 3.84 (s, 3H), 3.46 (br d, J=4.0 Hz, 2H), 2.58 (m, 2H), 2.19 (s, 3H), 2.12 (s, 3H). MS (ES$^+$) m/e 417.1 (M+H)$^+$.

Example 16 (M30)

(Z)—S-(2-(N-((4-Amino-2-methylpyrimidin-5-yl)
methyl)formamido)-5-hydroxypent-2-en-3-yl) 2,6-
dichlorobenzothioate To a mixture of sodium (Z)-2-(N-((4-amino-2-methylpyrimidin-5-yl)methyl)formamido)-5-hydroxypent-2-ene-3-thiolate (0.50 g, 1.64 mmol, 1.00 equiv) and NaOH (65.7 mg, 1.64 mmol, 1.00 equiv) in H$_2$O (4.00 mL) was added 2,6-dichlorobenzoyl chloride (344 mg, 1.64 mmol, 235 µL, 1.00 equiv) at 0° C. The resulting mixture was stirred at 0° C. for 1 h and was then concentrated to provide a residue. The residue was purified by prep-HPLC to provide the title compound (150 mg, 20.1%) as a white solid. $^1$H NMR (400 MHz, DMSO-d$_6$) δ 7.96 (s, 1H), 7.84 (s, 1H), 7.60-7.54 (m, 3H), 6.68 (m, 2H), 4.68-4.75 (m, 1H), 4.41 (br s, 2H), 3.46-3.52 (m, 2H), 2.62-2.69 (m, 2H), 2.26 (s, 3H), 2.14 (s, 3H). MS (ES$^+$) m/e 455.1 (M+H)$^+$.

Example 17 (M31)

(Z)—S-(2-(N-((4-Amino-2-methylpyrimidin-5-yl) methyl)formamido)-5-(phosphonooxy)pent-2-en-3-yl) 2,2-dimethylpropanethioate

Step 1

3-((4-Amino-2-methylpyrimidin-5-yl)methyl)-4-methyl-5-(2-(phosphonooxy)ethyl)thiazol-3-ium chloride To a solution of polyphosphoric acid (150 g, 49.8 mmol, 1.00 equiv) at 130° C. was added vitamin B1 (15.0 g, 49.8 mmol, 1.00 equiv) in portions. The mixture was stirred at 100-130° C. for 2 h. Water (250 mL) was added, and the mixture was stirred at 100° C. for additional 2 h, cooled to 25° C., and extracted by trioctylamine/MTBE (1:1, 250 mL×2). The water layer was separated, diluted with 400 mL of EtOH, and stirred at 25° C. for 2 h. The white solid formed was collected by filtration and washed by EtOH (200 mL×2) and dried to provide the title compound (17.0 g, 98.7%).

Step 2

Sodium (Z)-4-(N-((4-amino-2-methylpyrimidin-5-yl)methyl)formamido)-3-sulfidopent-3-en-1-yl phosphate To a mixture of 3-((4-amino-2-methylpyrimidin-5-yl) methyl)-4-methyl-5-(2-(phosphonooxy)ethyl)thiazol-3-ium (2.00 g, 5.79 mmol, 1.00 equiv) in H$_2$O (20 mL) was added NaOH (5.64 g, 42.3 mmol, 7.30 equiv) slowly at 0-5° C. The mixture was stirred at 5-10° C. for 0.5 h and concentrated to provide the title compound (2.40 g, 97%) as a yellow solid which was used directly for the next step reaction without further purification.

Step 3

(Z)—S-(2-(N-((4-Amino-2-methylpyrimidin-5-yl) methyl)formamido)-5-(phosphonooxy)pent-2-en-3-yl) 2,2-dimethylpropanethioate To a mixture of sodium (Z)-4-(N-((4-amino-2-methylpyrimidin-5-yl)methyl)formamido)-3-sulfidopent-3-en-1-yl phosphate (0.800 g, 1.87 mmol, 1.00 equiv) in NaOH (1 M, 3.74 mL, 2.00 equiv) was added pivaloyl chloride (840 mg, 6.97 mmol, 857 μL, 3.73 equiv). The resulting mixture was stirred at 25° C. for 2 h. TLC (ethyl acetate:dichloromethane=2:1) showed the starting material was consumed and a new spot was formed. The reaction mixture was concentrated and purified by reversed-phase IPLC to give the title compound (132 mg, 15.7%) as a white solid. $^1$H NMR (400 MHz, MeOD) δ 7.99 (s, 1H), 7.79 (s, 1H), 3.93 (br d, J=5.6 Hz, 2H), 2.56 (s, 3H), 2.25 (s, 3H), 1.14 (s, 9H). MS (ES$^+$) m/e 447.1 (M+H)$^+$.

Example 18 (M32)

(Z)—S-(2-(N-((4-Amino-2-methylpyrimidin-5-yl)methyl)formamido)-5-(phosphonooxy)pent-2-en-3-yl) 4-methoxybenzothioate To a mixture of sodium (Z)-4-(N-((4-amino-2-methylpyrimidin-5-yl)methyl)formamido)-3-sulfidopent-3-en-1-yl phosphate (0.80 g, 1.87 mmol, 1.00 equiv) in NaOH (1 M, 3.74 mL, 2.00 equiv) was added 4-methoxybenzoyl chloride (1.19 g, 6.97 mmol, 958 μL, 3.73 equiv). The resulting mixture was stirred at 25° C. for 2 h. TLC (ethyl acetate:dichloromethane=2:1) showed the starting material was consumed, and a new spot formed. The mixture was concentrated and purified by reversed-phase HPLC to give the title compound (174 mg, 18.1%) as a white solid. $^{1}$H NMR (400 MHz, MeOD) δ 8.04 (s, 1H), 7.99 (s, 1H), 7.75 (d, J=8.8 Hz, 2H), 7.00 (d, J=8.8 Hz, 2H), 4.74-4.35 (m, 2H), 4.03 (q, J=5.6 Hz, 2H), 3.88 (s, 3H), 2.81 (m, 2H), 2.40 (s, 3H), 2.30 (s, 3H). MS (ES$^{+}$) m/e 497.1 (M+H)$^{+}$.

Example 19 (M33)

(Z)—S-(2-(N-((4-Amino-2-methylpyrimidin-5-yl)methyl)formamido)-5-(phosphonooxy)pent-2-en-3-yl) 2,6-dichlorobenzothioate To a mixture of sodium (Z)-4-(N-((4-amino-2-methylpyrimidin-5-yl)methyl)formamido)-3-sulfidopent-3-en-1-yl phosphate (0.800 g, 1.87 mmol, 1.00 equiv) in NaOH (1 M, 3.74 mL, 2.00 equiv) was added 2,6-dichlorobenzoyl chloride (391 mg, 1.87 mmol, 268 μL, 1.00 eq). The mixture was stirred at 25° C. for 2 h. TLC (ethyl acetate:dichloromethane=2:1) showed that the starting material was consumed, and a new spot formed. The mixture was concentrated and purified by reversed-phase HPLC to provide the title compound (72.0 mg, 7.20%) as a white solid. $^{1}$H NMR (400 MHz, MeOD) δ 8.06 (s, 1 H), 8.02 (s, 1H), 7.44 (s, 3H), 4.07-4.04 (m, 2H), 2.49 (s, 3H), 2.32 (s, 3H). MS (ES$^{+}$) m/e 535.0 (M+H)$^{+}$.

Examples 20 to 59: The following compounds were synthesized following the procedure for the preparation of M34 (Example 11) with appropriate starting material.

Example 20 (M37)

(Z)—S-(2-(N-((4-amino-2-methylpyrimidin-5-yl)methyl)formamido)-5-hydroxypent-2-en-3-yl) 4-methylnaphthalene-1-carbothioate $^{1}$H NMR (400 MHz, DMSO-d6) δ 8.30-8.25 (m, 1H), 8.13 (dd, J=3.2, 6.6 Hz, 1H), 7.98 (s, 1H), 7.88-7.80 (m, 2H), 7.69-7.64 (m, 2H), 7.47 (d, J=7.6 Hz, 1H), 6.71 (br s, 2H), 4.69 (br t, J=5.6 Hz, 1H), 4.43 (br s, 2H), 3.55-3.47 (m, 2H), 2.72 (s, 3H), 2.66 (br t, J=6.8 Hz, 2H), 2.18 (s, 3H), 2.13 (s, 3H). MS (ES$^{+}$) m/e 451 (M+H)$^{+}$.

Example 21 (M38)

(Z)—S-(2-(N-((4-amino-2-methylpyrimidin-5-yl)methyl)formamido)-5-hydroxypent-2-en-3-yl) 2-ethoxynaphthalene-1-carbothioate $^{1}$H NMR (400 MHz, DMSO-d6) δ 8.06-7.92 (m, 4H), 7.57-7.42 (m, 4H), 6.67 (br s, 2H), 4.73 (br t, J=4.8 Hz, 1H), 4.42 (br s, 2H), 4.23 (q, J=6.8 Hz, 2H), 3.62-3.51 (m, 2H), 2.73 (br s, 2H), 2.23 (s, 3H), 2.13 (s, 3H), 1.32 (br t, J=6.8 Hz, 3H). MS (ES$^{+}$) m/e 481 (M+H)$^{+}$.

79

Example 22 (M39)

(Z)—S-(2-(N-((4-amino-2-methylpyrimidin-5-yl)
methyl)formamido)-5-hydroxypent-2-en-3-yl) 4-bro-
monaphthalene-1-carbothioate <sup>1</sup>H NMR (400 MHz, DMSO-d6) δ 8.27-8.23 (m, 2H),
8.02-7.98 (m, 2H), 7.86-7.78 (m, 4H), 6.72 (br d, J=1.2 Hz,
2H), 4.71 (t, J=5.6 Hz, 1H), 4.44 (br s, 2H), 3.53 (q, J=6.4
Hz, 2H), 2.67 (br t, J=6.8 Hz, 2H), 2.19 (s, 3H), 2.08 (s, 3H).
MS (ES⁺) m/e 515 (M+H)⁺.

Example 23 (M40)

(Z)—S-(2-(N-((4-amino-2-methylpyrimidin-5-yl)
methyl)formamido)-5-hydroxypent-2-en-3-yl)
phenanthrene-9-carbothioate <sup>1</sup>H NMR (400 MHz, DMSO-d6) δ 8.92 (d, J=8.0 Hz, 1H),
8.88 (d, J=8.4 Hz, 1H), 8.26-8.19 (m, 3H), 8.03 (s, 1H), 7.90
(s, 1H), 7.80-7.75 (m, 1H), 7.80-7.77 (m, 2H), 7.74-7.72 (m,
1H), 6.80 (s, 2H), 4.74 (t, J=4.8 Hz, 1H), 4.47 (s, 2H), 4.11
(d, J=3.6 Hz, 2H), 3.58 (q, J=6.0 Hz, 2H), 3.17 (d, J=2.4 Hz,
2H), 2.72 (t, J=6.4 Hz, 2H), 2.21 (s, 3H), 2.09 (s, 3H). MS
(ES⁺) m/e 487 (M+H)⁺.

80

Example 24 (M43)

(Z)—S-(2-(N-((4-amino-2-methylpyrimidin-5-yl)
methyl)formamido)-5-hydroxypent-2-en-3-yl)
phenanthrene-9-carbothioate <sup>1</sup>H NMR (400 MHz, DMSO-d6) δ 7.88-7.83 (m, 2H),
7.32-7.20 (m, 3H), 6.73 (br d, J=1.2 Hz, 2H), 4.66 (t, J=5.6
Hz, 1H), 4.40 (br s, 2H), 3.47 (q, J=6.4 Hz, 2H), 2.75 (br s,
2H), 2.67 (br s, 2H), 2.58 (br t, J=6.8 Hz, 2H), 2.21 (s, 3H),
2.13 (s, 3H), 1.70 (m, 4H). MS (ES⁺) m/e 441 (M+H)⁺.

Example 25 (M44)

(Z)—S-(2-(N-((4-amino-2-methylpyrimidin-5-yl)
methyl)formamido)-5-hydroxypent-2-en-3-yl)
4-fluoronaphthalene-1-carbothioate <sup>1</sup>H NMR (400 MHz, DMSO-d6) δ 8.33 (br d, J=8.0 Hz,
1H), 8.16 (br d, J=7.6 Hz, 1H), 8.08-7.94 (m, 2H), 7.87 (s,
1H), 7.82-7.70 (m, 2H), 7.45 (dd, J=8.0, 10.1 Hz, 1H), 6.71
(br s, 2H), 4.69 (br t, J=5.2 Hz, 1H), 4.43 (br s, 2H),
3.66-3.47 (m, 2H), 2.66 (br t, J=6.8 Hz, 2H), 2.25-2.15 (m,
3H), 2.13-1.96 (m, 3H). MS (ES⁺) m/e 455 (M+H)⁺.

81

Example 26 (M45)

(Z)—S-(2-(N-((4-amino-2-methylpyrimidin-5-yl)
methyl)formamido)-5-hydroxypent-2-en-3-yl)
8-fluoronaphthalene-1-carbothioate $^1$H NMR (400 MHz, DMSO-d6) δ 8.20 (br d, J=8.4 Hz, 1H), 7.98 (s, 1H), 7.91-7.83 (m, 2H), 7.73-7.58 (m, 2H), 7.56-7.29 (m, 2H), 6.81 (br s, 2H), 4.73 (br s, 1H), 4.46 (br s, 2H), 3.55 (br s, 2H), 2.69 (br t, J=6.4 Hz, 2H), 2.20 (s, 3H), 2.18 (s, 3H). MS (ES$^+$) m/e 455 (M+H)$^+$.

Example 27 (M46)

(Z)—S-(2-(N-((4-amino-2-methylpyrimidin-5-yl)
methyl)formamido)-5-hydroxypent-2-en-3-yl)
8-methylnaphthalene-1-carbothioate $^1$H NMR (400 MHz, DMSO-d6) δ 8.14 (dd, J$_1$=1.6, J$_2$=8.0 Hz, 1H), 7.98 (s, 1H), 7.91-7.86 (m, 2H), 7.59-7.47 (m, 4H), 6.83 (br s, 2H), 4.75 (br t, J=5.2 Hz, 1H), 4.46 (br s, 2H), 3.54 (q, J=6.4 Hz, 2H), 2.70-2.64 (m, 2H), 2.48 (s, 3H), 2.19 (d, J=5.6 Hz, 6H). MS (ES$^+$) m/e 451 (M+H)$^+$.

Example 28 (M47)

(Z)—S-(2-(N-((4-amino-2-methylpyrimidin-5-yl)
methyl)formamido)-5-hydroxypent-2-en-3-yl)
4-methoxynaphthalene-1-carbothioate

82

$^1$H NMR (400 MHz, DMSO-d6) δ 8.42 (d, J=8.0 Hz, 1H), 8.26 (d, J=0.4 Hz, 1H), 8.05 (d, J=8.4 Hz, 1H), 7.96 (s, 1H), 7.87 (s, 1H), 7.68-7.65 (m, 1H), 7.65-7.61 (m, 1H), 7.08 (d, J=8.4 Hz, 1H), 6.71 (br s, 2H), 4.69 (br t, J=5.6 Hz, 1H), 4.43 (br s, 2H), 4.08 (s, 3H), 3.55-3.50 (m, 2H), 2.66-2.63 (m, 2H), 2.18 (s, 3H), 2.14 (s, 3H). MS (ES$^+$) m/e 467 (M+H)$^+$.

Example 29 (M49)

(Z)—S-(2-(N-((4-amino-2-methylpyrimidin-5-yl)
methyl)formamido)-5-hydroxypent-2-en-3-yl) naph-
thalene-2-carbothioate $^1$H NMR (400 MHz, DMSO-d6) δ 8.41 (s, 1H), 8.18 (br d, J=8.0 Hz, 1H), 8.06-8.02 (m, 2H), 7.95 (s, 1H), 7.85 (s, 1H), 7.76-7.64 (m, 3H), 6.64 (br s, 2H), 4.67 (br t, J=5.6 Hz, 1H), 4.41 (br s, 2H), 3.52 (q, J=6.4 Hz, 2H), 2.62 (br t, J=6.8 Hz, 2H), 2.18 (s, 3H), 2.14 (s, 3H). MS (ES$^+$) m/e 437 (M+H)$^+$.

Example 30 (M50)

(Z)—S-(2-(N-((4-amino-2-methylpyrimidin-5-yl)
methyl)formamido)-5-hydroxypent-2-en-3-yl) 5,5,8,
8-tetramethyl-5,6,7,8-tetrahydronaphthalene-2-car-
bothioate $^1$H NMR (400 MHz, DMSO-d6) δ 7.84 (d, J=14.4 Hz, 2H), 7.64 (s, 1H), 7.51-7.46 (m, 2H), 6.63 (s, 2H), 4.63 (t, J=4.2 Hz, 1H), 4.38 (s, 2H), 3.45 (d, J=5.6 Hz, 2H), 2.56 (t, J=6.4 Hz, 2H), 2.20 (s, 2H), 2.13 (s, 2H), 1.65 (s, 3H), 1.25 (s, 12H). MS (ES$^+$) m/e 497 (M+H)$^+$.

83

Example 31 (M51)

(Z)—S-(2-(N-((4-amino-2-methylpyrimidin-5-yl)
methyl)formamido)-5-hydroxypent-2-en-3-yl) 1-bro-
monaphthalene-2-carbothioate ¹H NMR (400 MHz, DMSO-d6) δ 8.28 (d, J=8.8 Hz, 2H),
8.12-8.09 (m, 2H), 7.98 (s, 1H), 7.88 (s, 1H), 7.80-7.76 (m,
1H), 7.74-7.72 (m, 1H), 7.46 (d, J=8.4 Hz, 2H), 6.75 (s, 2H),
4.72 (t, J=5.6 Hz, 1H), 4.45 (s, 2H), 3.55 (q, J=6.8 Hz, 2H),
2.68 (t, J=6.4 Hz, 2H), 2.20 (s, 3H), 2.17 (s, 3H). MS (ES⁺)
m/e 516 (M+H)⁺.

Example 32 (M52)

(Z)—S-(2-(N-((4-amino-2-methylpyrimidin-5-yl)
methyl)formamido)-5-hydroxypent-2-en-3-yl)
6-methoxynaphthalene-2-carbothioate ¹H NMR (400 MHz, DMSO-d6) δ 8.33 (d, J=1.2 Hz, 1H),
8.08 (d, J=8.8 Hz, 1H), 7.94-7.83 (m, 3H), 7.70 (dd, J₁=1.6,
J₂=8.4 Hz, 1H), 7.43 (d, J=2.0 Hz, 1H), 7.28 (dd, J₁=2.4,
J₂=8.8 Hz, 1H), 6.76-6.55 (m, 2H), 4.65 (t, J=5.6 Hz, 1H),
4.40 (br s, 2H), 3.92 (s, 3H), 3.53-3.46 (m, 2H), 2.60 (br t,
J=6.8 Hz, 2H), 2.16 (s, 3H), 2.14 (s, 3H). MS (ES⁺) m/e 467
(M+H)⁺.

84

Example 33 (M53)

S—((Z)-2-(N-((4-amino-2-methylpyrimidin-5-yl)
methyl)formamido)-5-hydroxypent-2-en-3-yl) (3r,5r,
7r)-adamantane-1-carbothioate ¹H NMR (400 MHz, DMSO-d6) δ 7.79 (s, 1H), 7.74 (s,
1H), 6.75 (br s, 2H), 4.60 (t, J=5.6 Hz, 1H), 4.35 (br s, 2H),
3.44-3.38 (m, 2H), 2.41 (t, J=6.8 Hz, 2H), 2.28 (s, 3H), 2.08
(s, 3H), 1.98 (br s, 3H), 1.84-1.75 (m, 1H), 1.71-1.62 (m,
11H). MS (ES⁺) m/e 445 (M+H)⁺.

Example 34 (M54)

(Z)—S-(2-(N-((4-amino-2-methylpyrimidin-5-yl)
methyl)formamido)-5-hydroxypent-2-en-3-yl)
2-phenylpropanethioate ¹H NMR (400 MHz, DMSO-d6) δ 7.77 (s, 1H), 7.73 (s,
1H), 7.34-7.24 (m, 5H), 6.64 (s, 2H), 4.55 (t, J=5.6 Hz, 1H),
4.40-4.24 (m, 2H), 3.82 (m, 1H), 3.29-3.28 (m, 2H), 2.48-
2.39 (m, 1H), 2.32-2.28 (m, 1H), 2.28 (s, 3H), 1.34-1.30 (d,
J=7.6 Hz, 3H). MS (ES⁺) m/e 415 (M+H)⁺.

Example 35 (M55)

(Z)—S-(2-(N-((4-amino-2-methylpyrimidin-5-yl)
methyl)formamido)-5-hydroxypent-2-en-3-yl) 2,2-
dimethyl-3-phenylpropanethioate ¹H NMR (400 MHz, DMSO-d6) δ 7.78 (s, 1H), 7.68 (s, 1H), 7.27-7.20 (m, 3H), 7.09 (m, 2H), 6.71 (s, 1H), 4.61 (t, J=5.6 Hz, 1H), 4.34 (s, 1H), 3.42-3.36 (m, 2H), 2.73 (s, 2H), 2.43 (t, J=6.8 Hz, 2H), 2.25 (s, 2H), 2.07 (s, 3H), 1.02 (s, 6H). MS (ES⁺) m/e 443 (M+H)⁺.

Example 36 (M57)

(Z)—S-(2-(N-((4-amino-2-methylpyrimidin-5-yl) methyl)formamido)-5-hydroxypent-2-en-3-yl) 1-methylcyclohexane-1-carbothioate ¹H NMR (400 MHz, DMSO-d6) δ 7.79 (s, 1H), 7.75 (s, 1H), 6.70 (s, 2H), 4.61 (t, J=5.6 Hz, 1H), 4.34 (s, 2H), 3.45-3.35 (m, 2H), 2.43 (br t, J=6.8 Hz, 2H), 2.27 (s, 3H), 2.08 (s, 3H), 1.78 (dd, J=6.8, 9.8 Hz, 2H), 1.49-1.24 (m, 8H), 1.05 (s, 3H). MS (ES⁺) m/e 407 (M+H)⁺.

Example 37 (M58)

(Z)—S-(2-(N-((4-amino-2-methylpyrimidin-5-yl) methyl)formamido)-5-hydroxypent-2-en-3-yl) 2,2-diphenylpropanethioate ¹H NMR (400 MHz, DMSO-d6) δ 7.77 (d, J=3.2 Hz, 2H), 7.35-7.25 (m, 6H), 7.16-7.08 (m, 4H), 6.73 (br s, 2H), 4.58 (t, J=5.6 Hz, 1H), 4.31 (br s, 2H), 3.32-3.28 (m, 2H), 2.41 (br t, J=6.8 Hz, 2H), 2.26 (s, 3H), 2.05 (s, 3H), 1.84 (s, 3H). MS (ES⁺) m/e 491 (M+H)⁺.

Example 38 (M59)

(Z)—S-(2-(N-((4-amino-2-methylpyrimidin-5-yl) methyl)formamido)-5-hydroxypent-2-en-3-yl) 3-methyl-2-phenylbutanethioate ¹H NMR (400 MHz, DMSO-d6) δ 7.77 (s, 1H), 7.73 (s, 1H), 7.35-7.30 (m, 2H), 7.29-7.21 (m, 3H), 6.64 (s, 2H), 4.55 (t, J=5.6 Hz, 1H), 4.25 (s, 2H), 3.45-3.41 (m, 1H), 3.29-3.17 (m, 2H), 2.48-2.39 (m, 1H), 2.27-2.20 (m, 5H), 1.99 (s, 3H), 0.92 (d, J=6.4 Hz, 3H), 0.61 (d, J=6.8 Hz, 3H). MS (ES⁺) m/e 443 (M+H)⁺.

Example 39 (M62)

(Z)—S-(2-(N-((4-amino-2-methylpyrimidin-5-yl) methyl)formamido)-5-hydroxypent-2-en-3-yl) 2-methyl-2,3-dihydro-1H-indene-2-carbothioate ¹H NMR (400 MHz, DMSO-d6) δ 7.79 (s, 2H), 7.21-7.13 (m, 4H), 6.72 (s, 2H), 4.62-4.59 (t, J=5.6 Hz, 1H), 4.35 (s, 1H), 3.43-3.38 (m, 2H), 3.20 (d, J=16.0 Hz, 2H), 2.73 (d, J=16.0 Hz, 2H), 2.44 (t, J=6.8 Hz, 2H), 2.22 (s, 3H), 2.09 (s, 3H), 1.21 (s, 3H). MS (ES⁺) m/e 441 (M+H)⁺.

Example 40 (M63)

(Z)—S-(2-(N-((4-amino-2-methylpyrimidin-5-yl)
methyl)formamido)-5-hydroxypent-2-en-3-yl)
2-methyl-2-(naphthalen-2-yl)propanethioate $^1$H NMR (400 MHz, DMSO-d6) δ 7.90-7.89 (m, 1H), 7.88-7.85 (m, 3H), 7.77 (s, 1H), 7.73 (s, 1H), 7.53-7.51 (m, 2H), 7.35-7.33 (m, 1H), 6.71 (s, 2H), 4.50 (t, J=5.6 Hz, 1H), 4.31 (s, 2H), 3.26 (q, J=5.6 Hz, 2H), 2.38 (t, J=6.8 Hz, 2H), 2.22 (s, 3H), 2.04 (s, 3H), 1.53 (s, 6H). MS (ES$^+$) m/e 479 (M+H)$^+$.

Example 41 (M64)

(Z)—S-(2-(N-((4-amino-2-methylpyrimidin-5-yl)
methyl)formamido)-5-hydroxypent-2-en-3-yl) 2,2-
diphenylethanethioate $^1$H NMR (400 MHz, DMSO-d6) δ 7.77 (d, J=3.2 Hz, 2H), 7.39-7.23 (m, 12H), 6.78-6.57 (m, 2H), 5.29 (s, 1H), 4.63-4.51 (m, 1H), 4.31 (br s, 2H), 2.21 (s, 3H), 2.02 (s, 3H). MS (ES$^+$) m/e 477 (M+H)$^+$.

Example 42 (M65)

(Z)—S-(2-(N-((4-amino-2-methylpyrimidin-5-yl)
methyl)formamido)-5-hydroxypent-2-en-3-yl) 1-(3-
bromophenyl)cyclopropane-1-carbothioate $^1$H NMR (400 MHz, DMSO-d6) δ 7.74 (s, 1H), 7.71 (s, 1H), 7.55-7.52 (m, 2H), 7.39-7.37 (m, 2H), 6.71 (s, 2H), 4.55-4.52 (m, 1H), 4.31 (s, 2H), 3.37-3.35 (m, 1H), 2.41-2.34 (m, 2H), 2.37 (s, 3H), 2.04 (s, 3H), 1.40-1.37 (m, 2H), 1.22-1.19 (s, 2H). MS (ES$^+$) m/e 506 (M+H)$^+$.

Example 43 (M66)

(Z)—S-(2-(N-((4-amino-2-methylpyrimidin-5-yl)
methyl)formamido)-5-hydroxypent-2-en-3-yl) 3,5-
dichloro-[1,1'-biphenyl]-4-carbothioate $^1$H NMR (400 MHz, DMSO-d6) δ 7.98 (s, 1H), 7.89 (s, 3H), 7.78 (dd, J$_1$=1.6, J$_2$=8.0 Hz, 2H), 7.58-7.45 (m, 3H), 6.92 (m, 2H), 4.74 (t, J=5.6 Hz, 1H), 4.43 (br s, 2H), 3.55-3.48 (m, 2H), 2.67 (br d, J=1.6 Hz, 2H), 2.22 (s, 3H), 2.15 (s, 3H). MS (ES$^+$) m/e 532 (M+H)$^+$.

89

Example 44 (M67)

(Z)—S-(2-(N-((4-amino-2-methylpyrimidin-5-yl)
methyl)formamido)-5-hydroxypent-2-en-3-yl)
4-(tert-butyl)-2,6-dimethylbenzothioate ¹H NMR (400 MHz, DMSO-d6) δ 7.95 (s, 1H), 7.83 (s, 1H), 7.13-7.08 (m, 2H), 6.75 (s, 2H), 4.75-4.72 (m, 1H), 4.40 (s, 2H), 3.49-3.44 (m, 2H), 2.68 (m, 1H), 2.26 (s, 3H), 2.20 (s, 6H), 2.15 (s, 3H), 1.24 (s, 9H). MS (ES⁺) m/e 471 (M+H)⁺.

Example 45 (M68)

(Z)—S-(2-(N-((4-amino-2-methylpyrimidin-5-yl)
methyl)formamido)-5-hydroxypent-2-en-3-yl)
3-chloro-[1,1'-biphenyl]-4-carbothioate ¹H NMR (400 MHz, DMSO-d6) δ 7.92 (s, 1H), 7.90-7.84 (m, 2H), 7.80-7.73 (m, 3H), 7.65 (d, J=8.0 Hz, 1H), 7.57-7.45 (m, 3H), 6.96-6.56 (m, 2H), 4.70 (t, J=5.6 Hz, 1H), 4.43 (br s, 2H), 3.53-3.46 (m, 2H), 2.61 (br t, J=6.8 Hz, 2H), 2.21 (s, 3H), 2.16 (s, 3H). MS (ES⁺) m/e 498 (M+H)⁺.

90

Example 46 (M70)

(Z)—S-(2-(N-((4-amino-2-methylpyrimidin-5-yl)
methyl)formamido)-5-hydroxypent-2-en-3-yl) 3,5-
di-tert-butylbenzothioate ¹H NMR (400 MHz, DMSO-d6) δ 7.88 (s, 1H), 7.83 (s, 1H), 7.74 (t, J=2.0 Hz, 1H), 7.55 (d, J=2.0 Hz, 1H), 6.60 (s, 2H), 4.65 (t, J=5.6 Hz, 1H), 4.39 (s, 2H), 3.57-3.42 (m, 2H), 2.57 (t, J=6.8 Hz, 2H), 2.20 (s, 3H), 2.15 (s, 3H), 1.32 (s, 18H). MS (ES⁺) m/e 499 (M+H)⁺.

Example 47 (M72)

(Z)—S-(2-(N-((4-amino-2-methylpyrimidin-5-yl)
methyl)formamido)-5-hydroxypent-2-en-3-yl) [1,1'-
biphenyl]-3-carbothioate ¹H NMR (400 MHz, DMSO-d6) δ 7.98 (m, 1H), 7.93 (s, 1H), 7.91-7.90 (m, 1H), 7.84 (s, 1H), 7.73-7.71 (m, 3H), 7.63 (m, 1H), 7.55-7.51 (m, 2H), 7.44 (m, 1H), 6.64 (s, 2H), 4.64-4.65 (m, 2H), 4.40 (s, 2H), 3.52-3.48 (m, 2H), 2.61-2.51 (m, 2H), 2.21 (s, 3H), 2.13 (s, 3H). MS (ES⁺) m/e 463 (M+H)⁺.

91

Example 48 (M73)

(Z)—S-(2-(N-((4-amino-2-methylpyrimidin-5-yl)
methyl)formamido)-5-hydroxypent-2-en-3-yl)
4-phenoxybenzothioate ¹H NMR (400 MHz, DMSO-d6) δ 7.87 (s, 1H), 7.82 (s, 1H), 7.77 (s, 1H), 7.75 (s, 1H), 7.50-7.46 (m, 2H), 7.27 (m, 1H), 7.15 (d, J=8 Hz, 2H), 7.04 (d, J=8 Hz, 2H), 6.64 (s, 2H), 4.64-4.61 (m, 2H), 4.38 (s, 2H), 3.48-3.43 (m, 2H), 2.58-2.52 (m, 2H), 2.18 (s, 3H), 2.13 (s, 3H). MS (ES⁺) m/e 463 (M+H)⁺.

Example 49 (M76)

(Z)—S-(2-(N-((4-amino-2-methylpyrimidin-5-yl)
methyl)formamido)-5-hydroxypent-2-en-3-yl)
dibenzo[b,d]furan-2-carbothioate ¹H NMR (400 MHz, DMSO-d6) δ 8.57 (s, 1H), 8.35-8.34 (d, J=4 Hz, 1H), 7.96-7.90 (m, 5H), 7.79-7.77 (m, 1H), 7.61-7.48 (m, 1H), 6.65 (m, 2H), 4.70 (m, 1H), 4.41 (s, 1H), 3.54 (m, 2H), 2.63 (m, 2H), 2.17 (s, 3H), 2.16 (s, 6H). MS (ES⁺) m/e 477 (M+H)⁺.

92

Example 50 (M79)

(Z)—S-(2-(N-((4-amino-2-methylpyrimidin-5-yl)
methyl)formamido)-5-hydroxypent-2-en-3-yl) benzo
[b]thiophene-5-carbothioate ¹H NMR (400 MHz, DMSO-d6) δ 8.31 (s, 1 H), 8.15 (d, J=8.4 Hz, 1H), 7.94-7.93 (m, 2H), 7.84 (s, 1H), 7.67-7.65 (m, 2H), 6.63 (s, 2H), 4.67-4.64 (m, 2H), 4.40 (s, 2H), 3.51-3.47 (m, 2H), 2.67-2.58 (m, 2H), 2.16 (s, 3H), 2.14 (s, 3H). MS (ES⁺) m/e 443 (M+H)⁺.

Example 51 (M82)

(Z)—S-(2-(N-((4-amino-2-methylpyrimidin-5-yl)
methyl)formamido)-5-hydroxypent-2-en-3-yl) 4-(2-
methoxyethoxy)benzothioate ¹H NMR (400 MHz, DMSO-d6) δ 7.88 (s, 1H), 7.83 (s, 1H), 7.73-7.69 (m, 2H), 7.08-7.04 (m, 2H), 6.64 (s, 2H), 4.66-4.63 (m, 2H), 4.38 (s, 2H), 4.21-4.18 (m, 2H), 3.69-3.68 (m, 2H), 3.47 (m, 2H), 3.34 (s, 3H), 2.56 (m, 2H), 2.25 (s, 3H), 2.20 (s, 3H). MS (ES⁺) m/e 461 (M+H)⁺.

Example 52 (M88)

S—((Z)-2-(N-((4-amino-2-methylpyrimidin-5-yl)
methyl)formamido)-5-hydroxypent-2-en-3-yl) (E)-3-
(naphthalen-2-yl)prop-2-enethioate $^1$H NMR (400 MHz, DMSO-d6) δ 8.26 (s, 1H), 8.00-7.94 (m, 4H), 7.90 (s, 1H), 7.84 (s, 1H), 7.59-7.56 (m, 3H), 6.95 (d, J=15.6 Hz, 1H), 6.68 (s, 2H), 4.69 (s, 1H), 4.39 (s, 2H), 3.48 (t, J=7.2 Hz, 2H), 2.57 (t, J=6.4 Hz, 2H), 2.22 (s, 3H), 2.12 (s, 3H). MS (ES$^+$) m/e 463 (M+H)$^+$.

Example 53 (M108)

(Z)—S-(2-(N-((4-amino-2-methylpyrimidin-5-yl) methyl)formamido)-5-hydroxypent-2-en-3-yl) 6-methoxynaphthalene-1-carbothioate $^1$H NMR (400 MHz, DMSO-d6) δ 8.13 (d, J=9.6 Hz, 1H), 8.09 (d, J=8.4 Hz, 1H), 7.97 (s, 1H), 7.87 (s, 1H), 7.74 (d, J=6.8 Hz, 1H), 7.55 (t, J=6.8 Hz, 1H), 7.45 (d, J=2.4 Hz, 1H), 7.29 (dd, J$_1$=2.8 Hz, J$_2$=9.2 Hz, 1H), 6.73 (s, 2H), 4.71 (s, 1H), 4.43 (s, 2H), 3.89 (s, 3H), 3.52 (s, 2H), 2.66 (t, J=6.8 Hz, 2H), 2.18 (s, 3H), 2.13 (s, 3H). MS (ES$^+$) m/e 467 (M+H)$^+$.

Example 54 (M109)

(Z)—S-(2-(N-((4-amino-2-methylpyrimidin-5-yl) methyl)formamido)-5-hydroxypent-2-en-3-yl) 4-ethoxynaphthalene-1-carbothioate $^1$H NMR (400 MHz, DMSO-d6) δ 8.42 (d, J=8.4 Hz, 1H), 8.26 (d, J=8.0 Hz, 1H), 8.03 (d, J=8.4 Hz, 1H), 7.96 (s, 1H), 7.87 (s, 1H), 7.67 (t, J=1.2 Hz, 1H), 7.65-7.60 (m, 1H), 7.05 (d, J=8.4 Hz, 1H), 6.70 (s, 2H), 4.68 (t, J=9.2 Hz, 1H), 4.42 (s, 1H), 4.32 (q, J=7.2 Hz, 2H), 3.51 (q, J=6.4 Hz, 2H), 2.64 (t, J=6.8 Hz, 2H), 2.17 (s, 3H), 2.13 (s, 3H), 1.50 (t, J=6.8 Hz, 3H). MS (ES$^+$) m/e 481 (M+H)$^+$.

Example 55 (M110)

(Z)—S-(2-(N-((4-amino-2-methylpyrimidin-5-yl) methyl)formamido)-5-hydroxypent-2-en-3-yl) 4-ethylnaphthalene-1-carbothioate $^1$H NMR (400 MHz, DMSO-d6) δ 8.28-8.26 (m, 1H), 8.19-8.18 (m, 1H), 7.97 (s, 1H), 7.87-7.85 (m, 1H), 7.67-7.64 (m, 1H), 7.48 (d, J=7.6 Hz, 1H), 6.74 (s, 2H), 4.70 (t, J=5.6 Hz, 1H), 4.43 (s, 1H), 3.52 (q, J=6.0 Hz, 2H), 3.14 (q, J=7.2 Hz, 2H), 2.66 (t, J=6.8 Hz, 2H), 2.18 (s, 3H), 2.14 (s, 3H), 1.31 (t, J=7.6 Hz, 3H). MS (ES$^+$) m/e 465 (M+H)$^+$.

Example 56 (M111)

(Z)—S-(2-(N-((4-amino-2-methylpyrimidin-5-yl) methyl)formamido)-5-hydroxypent-2-en-3-yl) 5-bromonaphthalene-1-carbothioate $^1$H NMR (400 MHz, DMSO-d6) δ 8.44 (d, J=8.8 Hz, 1H), 8.20 (d, J=8.8 Hz, 1H), 8.06-7.95 (m, 3H), 7.88 (s, 1H), 7.79 (dd, J$_1$=7.2, J$_2$=8.4 Hz, 1H), 7.58 (dd, J$_1$=7.6, J2=8.4 Hz, 1H), 6.74 (br s, 2H), 4.70 (t, J=5.6 Hz, 1H), 4.45 (br s, 2H), 3.56-3.49 (m, 2H), 2.68 (br t, J=6.8 Hz, 2H), 2.21-2.16 (m, 3H), 2.11 (s, 3H). MS (ES$^+$) m/e 516 (M+H)$^+$.

Example 57 (M114)

(Z)—S-(2-(N-((4-amino-2-methylpyrimidin-5-yl)
methyl)formamido)-5-hydroxypent-2-en-3-yl)
4-(tert-butyl)benzothioate <sup>1</sup>H NMR (400 MHz, DMSO-d6) δ 7.90-7.82 (m, 2H), 7.68 (d, J=8.4 Hz, 2H), 7.59-7.52 (m, 2H), 6.84-6.54 (m, 2H), 4.67 (br s, 1H), 4.38 (br s, 2H), 4.03 (q, J=7.2 Hz, 1H), 3.45 (br s, 2H), 2.56 (br t, J=6.8 Hz, 2H), 2.27-2.07 (m, 6H), 1.30 (s, 9H). MS (ES⁺) m/e 443 (M+H)⁺.

Example 58 (M115)

(Z)—S-(2-(N-((4-amino-2-methylpyrimidin-5-yl)
methyl)formamido)-5-hydroxypent-2-en-3-yl)
4-(tert-butyl)-2-ethoxybenzothioate <sup>1</sup>H NMR (400 MHz, DMSO-d6) δ 7.83-7.82 (m, 2H), 7.52 (d, J=8.0 Hz, 1H), 7.06-7.03 (m, 2H), 6.68 (s, 2H), 4.62 (t, J=5.6 Hz, 1H), 4.36 (s, 1H), 4.17 (q, J=7.2 Hz, 2H), 3.44 (q, J=5.6 Hz, 2H), 2.54-2.52 (m, 2H), 2.20 (s, 3H), 2.10 (s, 3H), 1.32 (t, J=6.8 Hz, 3H), 1.28 (s, 9H). MS (ES⁺) m/e 487 (M+H)⁺.

Example 59 (M148)

(Z)—S-(2-(N-((4-amino-2-methylpyrimidin-5-yl)
methyl)formamido)-5-hydroxypent-2-en-3-yl)
dibenzo[b,d]furan-4-carbothioate <sup>1</sup>H NMR (400 MHz, DMSO-d6) δ 8.47 (d, J=6.80 Hz, 1H), 8.22 (d, J=7.60 Hz, 1H), 7.95 (s, 1H), 7.90-7.86 (m, 3H), 7.62 (t, J=8.00 Hz, 1H), 7.58-7.47 (m, 2H), 6.64 (s, 2H), 4.67 (t, J=5.60 Hz, 1H), 4.42 (s, 2H), 3.54-3.48 (m, 2H), 2.65 (t, J=6.80 Hz, 2H), 2.18 (s, 3H), 2.13 (s, 3H). MS (ES⁺) m/e 477 (M+H)⁺.

Examples 60 to 68: The following compounds were synthesized following the procedure for the preparation of M19 (example 6) with appropriate starting material.

Example 60 (M97)

(Z)-((2-(N-((4-amino-2-methylpyrimidin-5-yl)
methyl)formamido)-5-hydroxypent-2-en-3-yl)thio)
methyl 1-naphthoate <sup>1</sup>H NMR (400 MHz, DMSO-d6) δ 8.75 (d, 1H), 8.29-8.22 (m, 1H), 8.14-8.12 (m, 1H), 8.12-8.05 (m, 1H), 7.94 (s, 1H), 7.81 (s, 1H), 7.69-7.63 (m, 3H), 6.74-6.71 (m, 2H), 5.37 (s, 2H), 4.73 (t, J=5.6 Hz, 1H), 4.34 (br s, 2H), 3.57-3.52 (m, 2H), 2.73-2.69 (m, 2H), 2.25 (s, 3H), 1.95 (s, 3H). MS (ES⁺) m/e 467 (M+H)⁺.

Example 61 (M98)

(Z)-((2-(N-((4-amino-2-methylpyrimidin-5-yl)
methyl)formamido)-5-hydroxypent-2-en-3-yl)thio)
methyl phenanthrene-9-carboxylate $^1$H NMR (400 MHz, DMSO-d6) δ 8.97-8.87 (m, 2H), 8.77-8.70 (m, 1H), 8.52 (s, 1H), 8.19 (d, J=8.0 Hz, 1H), 7.98 (s, 1H), 7.90-7.81 (m, 2H), 7.80-7.73 (m, 3H), 6.74 (br s, 2H), 5.41 (s, 2H), 4.78 (t, J=5.6 Hz, 1H), 4.35 (br s, 2H), 3.63-3.50 (m, 2H), 2.74 (br t, J=7.2 Hz, 2H), 2.24 (s, 3H), 1.98 (s, 3H). MS (ES$^+$) m/e 517 (M+H)$^+$.

Example 62 (M99)

(Z)-((2-(N-((4-amino-2-methylpyrimidin-5-yl)
methyl)formamido)-5-hydroxypent-2-en-3-yl)thio)
methyl 5,5,8,8-tetramethyl-5,6,7,8-tetrahydronaph-
thalene-2-carboxylate $^1$H NMR (400 MHz, DMSO-d6) δ 7.93 (s, 1H), 7.89-7.85 (m, 1H), 7.77 (s, 1H), 7.66 (dd, J$_1$=2.0, 1H), 7.51-7.46 (m, 1H), 6.73 (m, 2H), 5.24 (s, 2H), 4.69 (t, J=5.6 Hz, 1H), 4.44-4.18 (m, 2H), 3.57-3.44 (m, 2H), 2.67 (br t, J=6.8 Hz, 2H), 2.29-2.24 (m, 3H), 1.94 (s, 3H), 1.66 (s, 4H), 1.25 (s, 12H). MS (ES$^+$) m/e 527 (M+H)$^+$.

Example 63 (M100)

(Z)-((2-(N-((4-amino-2-methylpyrimidin-5-yl)
methyl)formamido)-5-hydroxypent-2-en-3-yl)thio)
methyl 2-ethoxy-1-naphthoate $^1$H NMR (400 MHz, DMSO-d6) δ 8.07 (d, J=8.8 Hz, 1H), 7.95-7.90 (m, 2H), 7.80 (s, 1H), 7.62-7.49 (m, 3H), 7.43 (m, 1H), 6.73 (br s, 2H), 5.33 (s, 2H), 4.65 (t, J=5.6 Hz, 1H), 4.35 (br s, 2H), 4.27-4.21 (m, 2H), 3.55-3.44 (m, 2H), 2.61 (br t, J=6.8 Hz, 2H), 2.28 (s, 3H), 1.95 (s, 3H), 1.31 (t, J=7.2 Hz, 3H). MS (ES$^+$) m/e 511 (M+H)$^+$.

Example 64 (M101)

(Z)-((2-(N-((4-amino-2-methylpyrimidin-5-yl)
methyl)formamido)-5-hydroxypent-2-en-3-yl)thio)
methyl 2,2-dimethyl-3-(naphthalen-2-yl)propanoate $^1$H NMR (400 MHz, DMSO-d6) δ 7.90 (s, 1H), 7.88-7.78 (m, 4H), 7.64-7.58 (m, 1H), 7.51-7.44 (m, 2H), 7.28-7.19 (m, 1H), 6.78 (m, 2H), 4.95 (br s, 2H), 4.66 (t, J=5.6 Hz, 1H), 4.33 (br s, 2H), 3.50-3.41 (m, 2H), 3.01-2.92 (m, 2H), 2.48 (br s, 2H), 2.28 (m, 3H), 1.91 (s, 3H), 1.16-1.12 (m, 6H). MS (ES$^+$) m/e 523 (M+H)$^+$.

Example 65 (M103)

Example 67 (M107)

(Z)-((2-(N-((4-amino-2-methylpyrimidin-5-yl)
methyl)formamido)-5-hydroxypent-2-en-3-yl)thio)
methyl 2,2-diphenylpropanoate (Z)-((2-(N-((4-amino-2-methylpyrimidin-5-yl)
methyl)formamido)-5-hydroxypent-2-en-3-yl)thio)
methyl 2-methyl-2-(naphthalen-2-yl)propanoate <sup>1</sup>H NMR (400 MHz, DMSO-d6) δ 7.92-7.82 (m, 4H), 7.76 (s, 1H), 7.70-7.64 (m, 1H), 7.53-7.46 (m, 2H), 7.44-7.37 (m, 1H), 6.69 (br d, J=12.4 Hz, 2H), 4.96 (s, 2H), 4.59 (t, J=5.6 Hz, 1H), 4.35-4.12 (m, 2H), 3.32-3.25 (m, 2H), 2.34 (br t, J=6.8 Hz, 2H), 2.29-2.20 (m, 3H), 1.77 (s, 3H), 1.64-1.57 (m, 6H). MS (ES⁺) m/e 509 (M+H)⁺.

<sup>1</sup>H NMR (400 MHz, DMSO-d6) δ 7.78 (s, 1H), 7.64 (s, 1H), 7.28-7.34 (m, 6H), 7.12-7.36 (m, 4H), 6.72-6.70 (m, 2H), 5.04 (br s, 2H), 4.60 (t, J=5.6 Hz, 1H), 4.27 (br s, 2H), 3.28-3.32 (m, 2H), 2.38-2.35 (m, 2H), 2.27 (s, 3H), 1.88-1.85 (m, 6H). MS (ES⁺) m/e 521 (M+H)⁺.

Example 68 (M126)

Example 66 (M105)

(Z)—S-(2-(N-((4-amino-2-methylpyrimidin-5-yl)
methyl)formamido)-5-hydroxypent-2-en-3-yl)
2-fluoro-6-phenoxybenzothioate (Z)-((2-(N-((4-amino-2-methylpyrimidin-5-yl)
methyl)formamido)-5-hydroxypent-2-en-3-yl)thio)
methyl 2,2,2-triphenylacetate Step 1. 2-Fluoro-6-phenoxybenzoic acid To a solution of 2-bromo-6-fluorobenzoic acid (5.00 g, 22.8 mmol, 1.00 eq) and phenol (3.87 g, 41.1 mmol, 3.61 mL, 1.80 eq) in DMF (100 mL) was added CuI (434 mg, 2.28 mmol, 0.10 eq) and Cs₂CO₃ (22.3 g, 68.5 mmol, 3.00 eq). The mixture was stirred at 100° C. for 10 hrs under N₂, cooled to rt, diluted with water (300 mL) and washed with ethyl acetate (200 mL×2). The aqueous phase was adjusted <sup>1</sup>H NMR (400 MHz, DMSO-d6) δ 7.89 (s, 1H), 7.80 (s, 1H), 7.34-7.28 (m, 11H), 7.11-7.09 (m, 7H), 6.77-6.72 (m, 2H), 5.39 (br s, 2H), 4.56 (t, J=5.6 Hz, 1H), 4.33 (br s, 2H), 3.20-3.19 (m, 2H), 2.28 (s, 3H), 2.08-1.99 (m, 2H), 1.89 (s, 3H). MS (ES⁺) m/e 583 (M+H)⁺.

pH ~1 with HCl (2 M) and extracted with ethyl acetate (300 mL×2). The combined organic phase was washed with brine (100 mL×2), dried over Na$_2$SO$_4$, filtered and concentrated under vacuum to give crude product which was purified by reversed-phase HPLC (5%~55% acetonitrile in water, 0.1% HCl) and concentrated under vacuum to remove acetonitrile. The residue was extracted with ethyl acetate (300 mL×2). The combined organic phase was washed with brine (100 mL×2), dried over Na$_2$SO$_4$, filtered and concentrated under vacuum to give the title compound (1.10 g, 4.74 mmol, 21% yield) as yellow solid. $^1$H NMR (400 MHz, DMSO-d6) δ 7.47-7.36 (m, 3H), 7.20-7.16 (m, 1H), 7.13-7.06 (m, 1H), 7.03 (dd, J$_1$=0.80 Hz, J$_2$=8.80 Hz, 2H), 6.74 (d, J=8.40 Hz, 1H). MS (ES$^+$) m/e 233 (M+H)$^+$.

Step 2. 2-Fluoro-6-phenoxybenzoyl chloride

To a solution of 2-fluoro-6-phenoxybenzoic acid (500 mg, 2.15 mmol, 1.00 eq) in DCM (10.0 mL) and DMF (1.57 mg, 21.5 umol, 1.66 uL, 0.01 eq) was added (COCl)$_2$ (328 mg, 2.58 mmol, 226 μL, 1.20 eq) drop-wise at 25° C. The reaction mixture was stirred at 25° C. for 0.5 hr. The reaction was quenched with anhydrous MeOH and concentrated under reduced pressure to give the title compound (540 mg, crude) as yellow oil was directly used for next step without further purification.

Step 3. (Z)—S-(2-(N-((4-Amino-2-methylpyrimi-din-5-yl)methyl)formamido)-5-hydroxypent-2-en-3-yl) 2-fluoro-6-phenoxybenzothioate $^1$H NMR (400 MHz, DMSO-d6) δ 7.93 (s, 1H), 7.83 (s, 1H), 7.58-7.48 (m, 1H), 7.46-7. 39 (m, 1H), 7.24-7.17 (m, 1H), 7.13-7.02 (m, 1H), 6.78 (d, J=8.40 Hz, 1H), 6.42 (s, 2H), 4.47-4.25 (m, 1H), 3.47 (br d, J=5.20 Hz, 1H), 2.58 (br t, J=6.80 Hz, 1H), 2.29 (s, 3H), 2.05 (s, 1H). MS (ES$^+$) m/e 497 (M+H)$^+$.

Examples 69 to 99: The following compounds were synthesized using essentially the same procedure for the preparation of M126 and appropriate starting material.

Example 69 (M113)

(Z)—S-(2-(N-((4-amino-2-methylpyrimidin-5-yl) methyl)formamido)-5-hydroxypent-2-en-3-yl) 2-phenoxybenzothioate $^1$H NMR (400 MHz, DMSO-d6) δ 7.83 (s, 1H), 7.79 (s, 1H), 7.66-7.56 (m, 2H), 7.43-7.36 (m, 2H), 7.27 (dt, J$_1$=0.8, J$_2$=7.6 Hz, 1H), 7.19-7.12 (m, 1H), 7.01-6.95 (m, 3H), 6.78-6.59 (m, 2H), 4.57 (t, J=5.6 Hz, 1H), 4.34 (br s, 2H), 3.36 (br d, J=6.0 Hz, 2H), 2.43 (t, J=6.4 Hz, 2H), 2.16 (s, 3H), 2.08 (s, 3H). MS (ES$^+$) m/e 479 (M+H)$^+$.

Example 70 (M127)

(Z)—S-(2-(N-((4-amino-2-methylpyrimidin-5-yl) methyl)formamido)-5-hydroxypent-2-en-3-yl) 2-chloro-6-phenoxybenzothioate $^1$H NMR (400 MHz, DMSO-d6) δ 7.91 (s, 1H), 7.81 (s, 1H), 7.53-7.45 (m, 1H), 7.44-7.37 (m, 2H), 7.33 (br d, J=8.00 Hz, 1H), 7.19 (br t, J=8.00 Hz, 1H), 7.08-6.97 (m, 2H), 6.90 (br d, J=8.40 Hz, 1H), 6.83-6.58 (m, 2H), 4.62 (br t, J=5.20 Hz, 1H), 4.35 (br s, 2H), 3.41-3.37 (m, 2H), 2.59-2.54 (m, 2H), 2.27 (s, 3H), 2.07 (s, 3H). MS (ES$^+$) m/e 514 (M+H)$^+$.

Example 71 (M128)

(Z)—S-(2-(N-((4-amino-2-methylpyrimidin-5-yl)
methyl)formamido)-5-hydroxypent-2-en-3-yl)
2-methyl-6-phenoxybenzothioate $^1$H NMR (400 MHz, DMSO-d6) δ 7.91 (s, 1H), 7.79 (s, 1H), 7.40-7.31 (m, 3H), 7.16-7.05 (m, 2H), 6.98-6.92 (m, 2H), 6.80-6.60 (m, 3H), 4.57 (t, J=5.20 Hz, 1H), 4.34 (br s, 2H), 3.37-3.33 (m, 2H), 2.53-2.51 (m, 2H), 2.26 (s, 3H), 2.24 (s, 3H), 2.06 (s, 3H). MS (ES$^+$) m/e 493 (M+H)$^+$.

Example 72 (M129)

(Z)—S-(2-(N-((4-amino-2-methylpyrimidin-5-yl)
methyl)formamido)-5-hydroxypent-2-en-3-yl)
2-(benzyloxy)-6-fluorobenzothioate $^1$H NMR (400 MHz, DMSO-d6) δ 7.91 (s, 1H), 7.80 (s, 1H), 7.50-7.25 (m, 7H), 7.04 (d, J=8.40 Hz, 1H), 6.89 (t, J=8.80 Hz, 1H), 6.77-6.52 (m, 2H), 5.21 (s, 2H), 4.63 (t, J=5.60 Hz, 1H), 4.33 (s, 2H), 3.43-3.38 (m, 2H), 2.59-2.55 (m, 2H), 2.26 (s, 3H), 2.05 (s, 3H). MS (ES$^+$) m/e 511 (M+H)$^+$.

Example 73 (M130)

(Z)—S-(2-(N-((4-amino-2-methylpyrimidin-5-yl)
methyl)formamido)-5-hydroxypent-2-en-3-yl) 2-(3-
chlorophenoxy)-6-fluorobenzothioate $^1$H NMR (400 MHz, DMSO-d6) δ 7.86 (s, 1H), 7.80 (s, 1H), 7.63-7.55 (m, 1H), 7.46-7.40 (m, 1H), 7.28-7.18 (m, 2H), 7.13 (t, J=2.00 Hz, 1H), 6.98 (dd, J$_1$=2.00 Hz, J$_2$=8.40 Hz, 1H), 6.92 (d, J=8.40 Hz, 1H), 6.73-6.57 (m, 2H), 4.64 (t, J=5.60 Hz, 1H), 4.34 (s, 2H), 3.40 (br s, 2H), 2.60-2.58 (m, 2H), 2.26 (s, 3H), 2.06 (s, 3H). MS (ES$^+$) m/e 532 (M+H)$^+$.

Example 74 (M131)

(Z)—S-(2-(N-((4-amino-2-methylpyrimidin-5-yl)
methyl)formamido)-5-hydroxypent-2-en-3-yl)
5-chloro-2-phenoxybenzothioate $^1$H NMR (400 MHz, DMSO-d6) δ 7.85 (s, 1H), 7.80 (s, 1H), 7.61 (dd, J=12.0 Hz, 1H), 7.58 (d, J=4.00 Hz, 1H), 7.45-7.39 (m, 2H), 7.22-7.16 (m, 1H), 7.04 (d, J=7.60 Hz, 2H), 6.97 (d, J=8.80 Hz, 1H), 6.76-6.73 (m, 2H), 4.61-4.56 (m, 1H), 4.35 (s, 2H), 3.43-3.38 (m, 2H), 2.49-2.45 (m, 2H), 2.17 (s, 3H), 2.10 (s, 3H). MS (ES$^+$) m/e 514 (M+H)$^+$.

Example 75 (M133)

(Z)—S-(2-(N-((4-amino-2-methylpyrimidin-5-yl)
methyl)formamido)-5-hydroxypent-2-en-3-yl) 2-(2-
chlorophenoxy)-4-methylbenzothioate <sup>1</sup>H NMR (400 MHz, DMSO-d6) δ 7.82 (s, 1H), 7.78 (s, 1H), 7.60-7.54 (m, 2H), 7.35 (dt, J$_1$=1.60 Hz, J$_2$=7.8 Hz, 1H), 7.21 (dt, J=1.60 Hz, J$_2$=8.00 Hz, 1H), 7.10 (d, J=8.00 Hz, 1H), 6.99 (dd, J$_1$=1.60 Hz, J$_2$=8.00 Hz, 1H), 6.70-6.60 (m, 3H), 4.57 (t, J=5.60 Hz, 1H), 4.33 (br s, 2H), 3.43-3.37 (m, 2H), 2.45-2.41 (m, 2H), 2.28 (s, 3H), 2.16 (s, 3H), 2.06 (s, 3H). MS (ES$^+$) m/e 528 (M+H)$^+$.

Example 76 (M134)

(Z)—S-(2-(N-((4-amino-2-methylpyrimidin-5-yl)
methyl)formamido)-5-hydroxypent-2-en-3-yl)
5-chloro-2-(4-fluorophenoxy)benzothioate <sup>1</sup>H NMR (400 MHz, DMSO-d6) δ 7.84 (s, 1H), 7.79 (s, 1H), 7.65-7.63 (m, 2H), 7.29-7.24 (m, 2H), 7.13-7.11 (m, 2H), 6.66 (d, J=7.20 Hz, 1H), 6.64 (br s, 2H), 5.60 (t, J=5.60 Hz, 1H), 4.35 (s, 2H), 3.42-3.39 (m, 2H), 2.56-2.55 (m, 2H), 2.15 (s, 3H), 2.11 (s, 3H). MS (ES$^+$) m/e 532 (M+H)$^+$.

Example 77 (M135)

(Z)—S-(2-(N-((4-amino-2-methylpyrimidin-5-yl)
methyl)formamido)-5-hydroxypent-2-en-3-yl) 2-(3-
cyanophenoxy)benzothioate <sup>1</sup>H NMR (400 MHz, DMSO-d6) δ 7.81 (s, 1H), 7.78 (s, 1H), 7.72-7.62 (m, 2H), 7.61-7.54 (m, 2H), 7.46-7.35 (m, 2H), 7.28-7.20 (m, 1H), 7.14 (d, J=7.60 Hz, 1H), 6.69 (br s, 2H), 4.58 (t, J=5.60 Hz, 1H), 4.34 (br s, 2H), 3.45-3.38 (m, 2H), 2.42-2.35 (m, 2H), 2.15 (s, 3H), 2.08 (s, 3H). MS (ES$^+$) m/e 504 (M+H)$^+$.

Example 78 (M136)

(Z)—S-(2-(N-((4-amino-2-methylpyrimidin-5-yl)
methyl)formamido)-5-hydroxypent-2-en-3-yl) 2-(2-
chlorophenoxy)benzothioate <sup>1</sup>H NMR (400 MHz, DMSO-d6) δ 7.85 (s, 1H), 7.80 (s, 1H), 7.64 (dd, J$_1$=1.60 Hz, J$_2$=7.60 Hz, 1H), 7.61-7.55 (m, 2H), 7.40-7.33 (m, 1H), 7.31-7.25 (m, 1H), 7.24-7.19 (m, 1H), 7.06-7.00 (m, 1H), 6.86 (d, J=7.60 Hz, 1H), 6.67 (br s, 2H), 4.59 (t, J=5.60 Hz, 1H), 4.35 (br s, 2H), 3.42-3.35 (m, 2H), 2.46-2.44 (m, 2H), 2.16 (s, 3H), 2.08 (s, 3H). MS (ES$^+$) m/e 514 (M+H)$^+$.

Example 79 (M137)

(Z)—S-(2-(N-((4-amino-2-methylpyrimidin-5-yl)methyl)formamido)-5-hydroxypent-2-en-3-yl) 2-(2-bromophenoxy)benzothioate $^1$H NMR (400 MHz, DMSO-d6) δ 7.85 (s, 1H), 7.80 (s, 1H), 7.73 (dd, $J_1$=1.60 Hz, $J_2$=8.00 Hz, 1H), 7.64 (dd, $J_1$=1.60 Hz, $J_2$=8.00 Hz, 1H), 7.60-7.54 (m, 1H), 7.44-7.37 (m, 1H), 7.28 (t, J=7.60 Hz, 1H), 7.18-7.12 (m, 1H), 7.00 (dd, $J_1$=1.60 Hz, $J_2$=8.00 Hz, 1H), 6.84 (d, J=8.40 Hz, 1H), 6.75-6.60 (m, 2H), 4.59 (t, J=6.00 Hz, 1H), 4.35 (br s, 2H), 3.40 (q, J=6.80 Hz, 2H), 2.47-2.43 (m, 2H), 2.16 (s, 3H), 2.08 (s, 3H). MS (ES$^+$) m/e 558 (M+H)$^+$.

Example 80 (M138)

(Z)—S-(2-(N-((4-amino-2-methylpyrimidin-5-yl)methyl)formamido)-5-hydroxypent-2-en-3-yl) 2-(2,6-dichlorophenoxy)benzothioate $^1$H NMR (400 MHz, DMSO-d6) δ 8.30-8.25 (m, 1H), 8.13 (dd, $J_1$=3.20 Hz, $J_2$=6.4 Hz, 1H), 7.98 (s, 1H), 7.88-7.80 (m, 2H), 7.69-7.64 (m, 2H), 7.47 (d, J=7.60 Hz, 1H), 6.71 (br s, 2H), 4.69 (br t, J=5.60 Hz, 1H), 4.43 (br s, 2H), 3.55-3.47 (m, 2H), 2.72 (s, 3H), 2.66 (br t, J=6.80 Hz, 2H), 2.18 (s, 3H), 2.13 (s, 3H). MS (ES$^+$) m/e 457 (M+H)$^+$.

Example 81 (M139)

(Z)—S-(2-(N-((4-amino-2-methylpyrimidin-5-yl)methyl)formamido)-5-hydroxypent-2-en-3-yl) 2-(3-(tert-butyl)phenoxy)benzothioate $^1$H NMR (400 MHz, DMSO-d6) δ 7.86 (s, 1H), 7.80 (s, 1H), 7.66-7.54 (m, 2H), 7.34-7.23 (m, 2H), 7.19 (br d, J=8.00 Hz, 1H), 7.05-6.93 (m, 2H), 6.79-6.56 (m, 3H), 4.58 (t, J=5.60 Hz, 1H), 4.34 (br s, 2H), 3.40-3.37 (m, 2H), 2.44 (br t, J=6.80 Hz, 2H), 2.17 (s, 3H), 2.07 (s, 3H), 1.26 (s, 9H). MS (ES$^+$) m/e 535 (M+H)$^+$.

Example 82 (M140)

(Z)—S-(2-(N-((4-amino-2-methylpyrimidin-5-yl)methyl)formamido)-5-hydroxypent-2-en-3-yl) 2-(naphthalen-2-yloxy)benzothioate $^1$H NMR (400 MHz, DMSO-d6) δ 7.97 (d, J=8.80 Hz, 1H), 7.91 (d, J=7.60 Hz, 1H), 7.86-7.81 (m, 2H), 7.77 (s, 1H), 7.72-7.65 (m, 1H), 7.65-7.58 (m, 1H), 7.54-7.41 (m, 2H), 7.37-7.29 (m, 2H), 7.26 (dd, $J_1$=2.40 Hz, $J_2$=8.80 Hz, 1H), 7.10 (d, J=8.40 Hz, 1H), 6.70 (br s, 2H), 4.50 (t, J=5.60 Hz, 1H), 4.32 (br s, 2H), 3.23 (q, J=6.40 Hz, 2H), 2.35 (br t, J=6.40 Hz, 2H), 2.14 (s, 3H), 2.05 (s, 3H). MS (ES$^+$) m/e 529 (M+H)$^+$.

Example 83 (M141)

(Z)—S-(2-(N-((4-amino-2-methylpyrimidin-5-yl)
methyl)formamido)-5-hydroxypent-2-en-3-yl)
2-(quinolin-8-yloxy)benzothioate $^1$H NMR (400 MHz, DMSO-d6) δ 7.86 (s, 1H), 7.84-7.72 (m, 2H), 7.68-7.59 (m, 1H), 7.49-7.32 (m, 3H), 7.32-7.17 (m, 2H), 7.11-6.84 (m, 1H), 6.83-6.47 (m, 3H), 6.44-6.06 (m, 1H), 4.64-4.40 (m, 2H), 4.13-3.95 (m, 1H), 3.56-3.48 (m, 2H), 2.80-2.70 (m, 2H), 2.28 (s, 3H), 1.83 (br s, 3H). MS (ES$^+$) m/e 530 (M+H)$^+$.

Example 84 (M142)

(Z)—S-(2-(N-((4-amino-2-methylpyrimidin-5-yl)
methyl)formamido)-5-hydroxypent-2-en-3-yl) 2-(2-
chlorophenoxy)-6-fluorobenzothioate $^1$H NMR (400 MHz, DMSO-d6) δ 7.89 (s, 1H), 7.80 (s, 1H), 7.58 (dd, J$_1$=1.60 Hz, J$_2$=8.00 Hz, 1H), 7.51-7.45 (m, 1H), 7.41-7.36 (m, 1H), 7.29-7.23 (m, 1H), 7.18-7.08 (m, 2H), 6.87-6.61 (m, 2H), 6.55 (d, J=8.40 Hz, 1H), 4.61 (t, J=5.60 Hz, 1H), 4.33 (s, 2H), 3.42-3.38 (m, 2H), 2.57-2.55 (m, 2H), 2.27 (s, 3H), 2.06 (d, J=1.60 Hz, 3H). MS (ES$^+$) m/e 532 (M+H)$^+$.

Example 85 (M143)

(Z)—S-(2-(N-((4-amino-2-methylpyrimidin-5-yl)
methyl)formamido)-5-hydroxypent-2-en-3-yl)
4-ethoxy-2-(3-fluorophenoxy)benzothioate $^1$H NMR (400 MHz, DMSO-d6) δ 7.79 (s, 1H), 7.77 (s, 1H), 7.69 (d, J=8.80 Hz, 1H), 7.44-7.36 (m, 1H), 6.98 (dt, J$_1$=2.40 Hz, J$_2$=8.40 Hz, 1H), 6.91-6.85 (m, 1H), 6.76 (dd, J$_1$=2.00 Hz, J$_2$=8.00 Hz, 1H), 6.65 (br d, J=2.00 Hz, 2H), 6.54 (d, J=2.40 Hz, 1H), 4.55 (t, J=5.60 Hz, 1H), 4.31 (br s, 2H), 4.06 (q, J=7.20 Hz, 2H), 3.37-3.33 (m, 2H), 2.40 (br t, J=6.80 Hz, 1H), 2.17 (s, 3H), 2.06 (s, 3H), 1.30 (t, J=6.80 Hz, 3H). MS (ES$^+$) m/e 541 (M+H)$^+$.

Example 86 (M145)

(Z)—S-(2-(N-((4-amino-2-methylpyrimidin-5-yl)
methyl)formamido)-5-hydroxypent-2-en-3-yl)
4-(tert-butyl)-2-phenoxybenzothioate $^1$H NMR (400 MHz, DMSO-d6) δ 7.89 (s, 1H), 7.83 (s, 1H), 7.64 (br d, J=8.40 Hz, 1H), 7.40-7.36 (m, 2H), 7.32 (br d, J=7.20 Hz, 1H), 7.19-7.08 (m, 1H), 7.01 (s, 1H), 6.96 (d, J=8.40 Hz, 2H), 6.30 (br s, 2H), 4.35 (s, 2H), 4.21-4.06 (m, 1H), 3.50-3.43 (m, 2H), 2.55 (br s, 2H), 2.25 (s, 3H), 2.06 (s, 3H), 1.26 (s, 9H). MS (ES$^+$) m/e 535 (M+H)$^+$.

Example 87 (M146)

(Z)—S-(2-(N-((4-amino-2-methylpyrimidin-5-yl)
methyl)formamido)-5-hydroxypent-2-en-3-yl) 2-((6-
(trifluoromethyl)pyridin-3-yl)oxy)benzothioate $^1$H NMR (400 MHz, DMSO-d6) δ 8.50 (d, J=2.40 Hz,
1H), 7.89 (d, J=8.80 Hz, 1H), 7.85-7.63 (m, 4H), 7.50-7.40
(m, 2H), 7.39-7.27 (m, 1H), 6.71 (br s, 2H), 4.59 (t, J=5.60
Hz, 1H), 4.35 (br s, 2H), 2.59 (br d, J=6.80 Hz, 2H), 2.40 (br
t, J=6.40 Hz, 2H), 2.16 (s, 3H), 2.09 (s, 3H). MS (ES$^+$) m/e
548 (M+H)$^+$.

Example 88 (M147)

(Z)—S-(2-(N-((4-amino-2-methylpyrimidin-5-yl)
methyl)formamido)-5-hydroxypent-2-en-3-yl) 2-((2,
3-dihydrobenzo[b][1,4]dioxin-6-yl)oxy)benzothioate $^1$H NMR (400 MHz, DMSO-d6) δ 7.85 (s, 1H), 7.80 (s,
1H), 7.65-7.51 (m, 2H), 7.22 (t, J=7.60 Hz, 1H), 6.93 (d,
J=8.40 Hz, 1H), 6.87 (d, J=8.80 Hz, 1H), 6.67 (br s, 2H),
6.56 (d, J=2.40 Hz, 1H), 6.48 (dd, J$_1$=2.80 Hz, J$_2$=8.80 Hz,
1H), 4.67-4.54 (m, 1H), 4.35 (br s, 2H), 4.25-4.23 (br d,
J=2.40 Hz, 4H), 3.41 (q, J=6.40 Hz, 2H), 2.48-4.46 (m, 2H),
2.16 (s, 3H), 2.09 (s, 3H). MS (ES$^+$) m/e 537 (M+H)$^+$.

Example 89 (M149)

(Z)—S-(2-(N-((4-amino-2-methylpyrimidin-5-yl)
methyl)formamido)-5-hydroxypent-2-en-3-yl)
2-chloro-4-phenoxybenzothioate $^1$H NMR (400 MHz, DMSO-d6) δ 7.88 (s, 1H), 7.84 (s,
1H), 7.61 (d, J=8.80 Hz, 1H), 7.50 (t, J=8.00 Hz, 2H),
7.33-7.28 (m, 1H), 7.22-7.15 (m, 3H), 6.98 (dd, J$_1$=2.40 Hz,
J$_2$=8.80 Hz, 1H), 6.79-6.68 (m, 2H), 4.67 (t, J=5.60 Hz, 1H),
4.45-4.41 (m, 2H), 3.49-3.45 (m, 2H), 2.60-2.58 (m, 2H),
2.20 (s, 3H), 2.15 (s, 3H). MS (ES$^+$) m/e 514 (M+H)$^+$.

Example 90 (M150)

(Z)—S-(2-(N-((4-amino-2-methylpyrimidin-5-yl)
methyl)formamido)-5-hydroxypent-2-en-3-yl)
2-fluoro-6-methyl-4-phenoxybenzothioate $^1$H NMR (400 MHz, DMSO-d6) δ 7.91 (s, 1H), 7.83 (s,
1H), 7.49-7.42 (m, 2H), 7.29-7.22 (m, 1H), 7.14 (d, J=8.00
Hz, 2H), 6.79-6.57 (m, 4H), 4.71 (t, J=5.20 Hz, 1H), 4.39 (br
s, 2H), 3.49-3.43 (m, 2H), 2.60 (br s, 2H), 2.26 (m, 3H), 2.19
(s, 3H), 2.12 (s, 3H). MS (ES$^+$) m/e 511 (M+H)$^+$.

Example 91 (M151)

(Z)—S-(2-(N-((4-amino-2-methylpyrimidin-5-yl)
methyl)formamido)-5-hydroxypent-2-en-3-yl) 4-(3-
chlorophenoxy)-2-methylbenzothioate $^1$H NMR (400 MHz, DMSO-d6) δ 7.88 (s, 1H), 7.83 (s, 1H), 7.67 (d, J=8.40 Hz, 1H), 7.47 (t, J=8.00 Hz, 1H), 7.30 (dd, J$_1$=0.80 Hz, J$_2$=8.00 Hz, 1H), 7.23 (t, J=2.00 Hz, 1H), 7.09 (dd, J$_1$=2.00 Hz, J$_2$=8.00 Hz, 1H), 7.00 (br d, J=2.00 Hz, 1H), 6.90 (br dd, J=2.40 Hz, J$_2$=8.80 Hz, 1H), 6.82-6.59 (m, 2H), 4.65 (br t, J=5.60 Hz, 1H), 4.40 (br s, 2H), 3.46 (q, J=6.40 Hz, 2H), 2.58-2.55 (m, 2H), 2.32 (s, 3H), 2.19 (s, 3H), 2.14 (s, 3H). MS (ES$^+$) m/e 528 (M+H)$^+$.

Example 92 (M152)

(Z)—S-(2-(N-((4-amino-2-methylpyrimidin-5-yl)methyl)formamido)-5-hydroxypent-2-en-3-yl) 2,4-diphenoxybenzothioate $^1$H NMR (400 MHz, DMSO-d6) δ 8.13 (s, 1H), 7.93 (s, 1H), 7.71 (d, J=8.80 Hz, 1H), 7.43-7.41 (m, 5H), 7.28-7.18 (m, 2H), 7.09 (m, 5H), 6.79-6.77 (m, 1H), 6.38 (d, J=2.40 Hz, 1H), 4.70 (s, 1H), 4.48 (s, 2H), 3.42 (t, J=6.00 Hz, 2H), 2.448-2.44 (m, 2H), 2.20 (s, 3H), 2.16 (s, 3H). MS (ES$^+$) m/e 571 (M+H)$^+$.

Example 93 (M153)

(Z)—S-(2-(N-((4-amino-2-methylpyrimidin-5-yl)methyl)formamido)-5-hydroxypent-2-en-3-yl) 2-(phenylthio)benzothioate $^1$H NMR (400 MHz, DMSO-d6) δ 7.92 (s, 1H), 7.85 (s, 1H), 7.69 (dd, J$_1$=1.20 Hz, J$_2$=8.00 Hz, 1H), 7.53-7.40 (m, 7H), 7.34-7.28 (m, 1H), 6.90 (d, J=8.00 Hz, 1H), 6.86-6.60 (m, 2H), 4.67 (t, J=5.60 Hz, 1H), 4.44-4.33 (m, 2H), 3.49-3.44 (m, 2H), 2.62-2.55 (m, 2H), 2.20 (s, 3H), 2.14 (s, 3H). MS (ES$^+$) m/e 495 (M+H)$^+$.

Example 94 (M155)

(Z)—S-(2-(N-((4-amino-2-methylpyrimidin-5-yl)methyl)formamido)-5-hydroxypent-2-en-3-yl) 2-(4-(2-oxopyrrolidin-1-yl)phenoxy)benzothioate $^1$H NMR (400 MHz, DMSO-d6) δ 7.84 (s, 1H), 7.79 (s, 1H), 7.69-7.63 (m, 3H), 7.62-7.54 (m, 1H), 7.31-7.22 (m, 1H), 7.04-6.99 (m, 2H), 6.96 (d, J=8.40 Hz, 1H), 6.69 (br s, 2H), 4.59 (t, J=5.60 Hz, 1H), 4.34 (br s, 2H), 3.82 (t, J=7.20 Hz, 2H), 3.42-3.37 (m, 2H), 2.49-2.44 (m, 4H), 2.17 (s, 3H), 2.11-2.02 (m, 5H). MS (ES$^+$) m/e 562 (M+H)$^+$.

Example 95 (M156)

(Z)—S-(2-(N-((4-amino-2-methylpyrimidin-5-yl)methyl)formamido)-5-hydroxypent-2-en-3-yl) 4-(tert-butyl)-2-(3-(tert-butyl)phenoxy)benzothioate $^1$H NMR (400 MHz, DMSO-d6) δ 7.83 (s, 1H), 7.79 (s, 1H), 7.60 (d, J=8.00 Hz, 1H), 7.39-7.30 (m, 2H), 7.16 (d, J=7.20 Hz, 1H), 6.99 (s, 2H), 6.74-6.66 (m, 3H), 4.62-4.54 (m, 1H), 4.42-4.39 (s, 2H), 2.45-2.40 (m, 3H), 2.17 (s, 3H), 2.06 (s, 3H), 1.24 (s, 9H), 1.21 (s, 9H). MS (ES$^+$) m/e 591 (M+H)$^+$.

Example 96 (M157)

(Z)—S-(2-(N-((4-amino-2-methylpyrimidin-5-yl)
methyl)formamido)-5-hydroxypent-2-en-3-yl)
2-(naphthalen-1-yloxy)benzothioate $^1$H NMR (400 MHz, DMSO-d6) δ 8.09-8.04 (m, 1H), 8.01-7.96 (m, 1H), 7.84 (s, 1H), 7.80-7.71 (m, 2H), 7.68 (dd, $J_1$=1.60 Hz, $J_2$=8.00 Hz, 1H), 7.62-7.52 (m, 3H), 7.47 (t, J=8.00 Hz, 1H), 7.32-7.24 (m, 1H), 6.97-6.88 (m, 2H), 6.69 (br s, 2H), 4.52 (t, J=5.60 Hz, 1H), 4.33 (br s, 2H), 3.29-3.26 (m, 2H), 2.39 (br t, J=6.40 Hz, 2H), 2.15 (s, 3H), 2.05 (s, 3H). MS (ES$^+$) m/e 529 (M+H)$^+$.

Example 97 (M158)

(Z)—S-(2-(N-((4-amino-2-methylpyrimidin-5-yl)
methyl)formamido)-5-hydroxypent-2-en-3-yl)
5-chloro-2-(2-chlorophenoxy)benzothioate $^1$H NMR (400 MHz, DMSO-d6) δ 7.87 (s, 1H), 7.81 (s, 1H), 7.64-7.58 (m, 3H), 7.39 (t, J=7.20 Hz, 1H), 7.27 (t, J=7.20 Hz, 1H), 7.14 (t, J=8.00 Hz, 1H), 6.86 (d, J=8.40 Hz, 1H), 6.63 (s, 2H), 4.63-4.59 (m, 1H), 4.35 (s, 2H), 3.46-3.41 (m, 2H), 2.46-2.44 (m, 2H), 2.17 (s, 3H), 2.10 (s, 3H). MS (ES$^+$) m/e 548 (M+H)$^+$.

Example 98 (M159)

(Z)—S-(2-(N-((4-amino-2-methylpyrimidin-5-yl)
methyl)formamido)-5-hydroxypent-2-en-3-yl) 2-(2-
bromophenoxy)-5-chlorobenzothioate $^1$H NMR (400 MHz, DMSO-d6) δ 7.87 (s, 1H), 7.81 (s, 1H), 7.78-7.74 (m, 1H), 7.65-7.58 (m, 2H), 7.48-7.42 (m, 1H), 7.25-7.18 (m, 1H), 7.16-7.13 (m, 1H), 6.86 (d, J=8.40 Hz, 1H), 6.63 (s, 2H), 4.62-4.58 (m, 1H), 4.35 (s, 2H), 3.45-3.40 (m, 2H), 2.46-2.42 (s, 2H), 2.17 (s, 3H), 2.10 (s, 3H). MS (ES$^+$) m/e 592 (M+H)$^+$.

Example 99 (M160)

(Z)—S-(2-(N-((4-amino-2-methylpyrimidin-5-yl)
methyl)formamido)-5-hydroxypent-2-en-3-yl) 2-(2-
bromophenoxy)-6-fluorobenzothioate $^1$H NMR (400 MHz, DMSO-d6) δ 7.89 (s, 1H), 7.81 (s, 1H), 7.75 (dd, $J_1$=1.20 Hz, $J_2$=7.60 Hz, 1H), 7.56-7.41 (m, 2H), 7.23-7.19 (m, 1H), 7.18-7.08 (m, 2H), 6.63-6.61 (m, 2H), 6.56 (d, J=8.80 Hz, 1H), 4.64-4.61 (m, 1H), 4.35 (s, 2H), 3.47-3.36 (m, 2H), 2.06 (s, 3H). MS (ES$^+$) m/e 576 (M+H)$^+$.

Example 100: Results

To identify compounds that are more potent in turning on these thiamine analog riboswitches in mammalian cells, and/or have other characteristics such as improved pharmacokenic parameters, additional compounds (e.g., compounds of Formulas IV-VIII) were made and tested for their activity in regulating thiamine analog riboswitches using a luciferase construct harboring 15D10 riboswitch (Luci-15D10, SEQ ID NO:93).

SEQ ID NO: 93 was obtained by inserting the 15D10 riboswitch into the luciferase reporter gene. Capital letters indicate the luciferase encoding sequence. Lower case letters indicate the intron/alternative exon/intron and ribo-switch sequence. The 15D10 aptamer encoding sequence (SEQ ID NO:26) is underlined.

SEQ ID NO: 93:
ATGGAAGACGCCAAAAACATAAAGAAAGGCCCGGCGCCATTCTATCCG

CTGGAAGATGGAACCGCTGGAGAGCAACTGCATAAGGCTATGAAGAGA

TACGCCCTGGTTCCTGGAACAATTGCTTTTACAGATGCACATATCGAG

GTGGACATCACTTACGCTGAGTACTTCGAAATGTCCGTTCGGTTGGCA

GAAGCTATGAAACGATATGGGCTGAATACAAATCACAGAATCGTCGTA

TGCAGTGAAAACTCTCTTCAATTCTTTATGCCGGTGTTGGGCGCGTTA

TTTATCGGAGTTGCAGTTGCGCCCGCGAACGACATTTATAATGAACGT

GAATTGCTCAACAGTATGGGCATTTCGCAGCCTACCGTGGTGTTCGTT

TCCAAAAAGGGGTTGCAAAAATTTTGAACGTGCAAAAAAAGCTCCCA

ATCATCCAAAAAATTATTATCATGGATTCTAAAACGGATTACCAGGGA

TTTCAGTCGATGTACACGTTCGTCACATCTCATCTACCTCCCGGTTTT

AATGAATACGATTTTGTGCCAGAGTCCTTCGATAGGGACAAGACAATT

GCACTGATCATGAACTCCTCTGGATCTACTGGTCTGCCTAAAGGTGTC

GCTCTGCCTCATAGAACTGCCTGCGTGAGATTCTCGCATGCCAGAGAT

CCTATTTTTGGCAATCAAATCATTCCGGATACTGCGATTTTAAGTGTT

GTTCCATTCCATCACGGTTTTGGAATGTTTACTACACTCGGATATTTG

ATATGTGGATTTCGAGTCGTCTTAATGTATAGATTTGAAGAAGAGCTG

TTTCTGAGGAGCCTTCAGGATTACAAGATTCAAAGTGCGCTGCTGGTG

CCAACCCTATTCTCCTTCTTCGCCAAAAGCACTCTGATTGACAAATAC

GATTTATCTAATTTACACGAAATTGCTTCTGGTGGCGCTCCCCTCTCT

AAGGAAGTCGGGGAAGCGGTTGCCAAGAGGTTCCATCTGCCAGGTATC

AGGgtgagtctatgggacccttgatgtttctttccccttcttttcta tggttaagttcatgtcataggaaggggagaagtaacagggtacacata ttgaccaaatcagggtaattttgcatttgtaattttaaaaaatgcttt cttcttttaatatactttttgtttatcttatttctaatactttccct aatctctttctttcagggcaataatgatacaatgtatcatgccgagta acgctgtttctctaacttgtaggaatgaattcagatatttccagagaa tgaaaaaaatcttcagtagaaggtaatgt<u>acaggggtccggccttt catttggcaccggtgagaacataccctt</u>cggacctgttcacggataat <u>gccgctgcagggagt</u>acattacgcaccattctaaagaataacagtgat aatttctgggttaaggcaatagcaatatttctgcatataaatatttct gcatataaattgtaactgatgtaagaggtttcatattgctaatagcag ctacaatccagctaccattctgcttttattttatggttgggataaggc tggattattctgagtccaagctaggccctttttgctaatcatgttcata cctcttatcttcctcccacagCAAGGATATGGGCTCACTGAGACTACA

TCAGCTATTCTGATTACACCCGAGGGGGATGATAAACCGGGCGCGGTC

GGTAAAGTTGTTCCATTTTTTGAAGCGAAGGTTGTGGATCTGGATACC

GGGAAAACGCTGGGCGTTAATCAAAGAGGCGAACTGTGTGTGAGAGGT

-continued

CCTATGATTATGTCCGGTTATGTAAACAATCCGGAAGCGACCAACGCC

TTGATTGACAAGGATGGATGGCTACATTCTGGAGACATAGCTTACTGG

GACGAAGACGAACACTTCTTCATCGTTGACCGCCTGAAGTCTCTGATT

AAGTACAAAGGCTATCAGGTGGCTCCCGCTGAATTGGAATCCATCTTG

CTCCAACACCCCAACATCTTCGACGCAGGTGTCGCAGGTCTTCCCGAC

GATGACGCCGGTGAACTTCCCGCCGCCGTTGTTGTTTTGGAGCACGGA

AAGACGATGACGGAAAAAGAGATCGTGGATTACGTCGCCAGTCAAGTA

ACAACCGCGAAAAAGTTGCGCGGAGGAGTTGTGTTTGTGGACGAAGTA

CCGAAAGGTCTTACCGGAAAACTCGACGCAAGAAAAATCAGAGAGATC

CTCATAAAGGCCAAGAAGGGCGGAAAGATCGCCGTGTAA

Figure 9A:
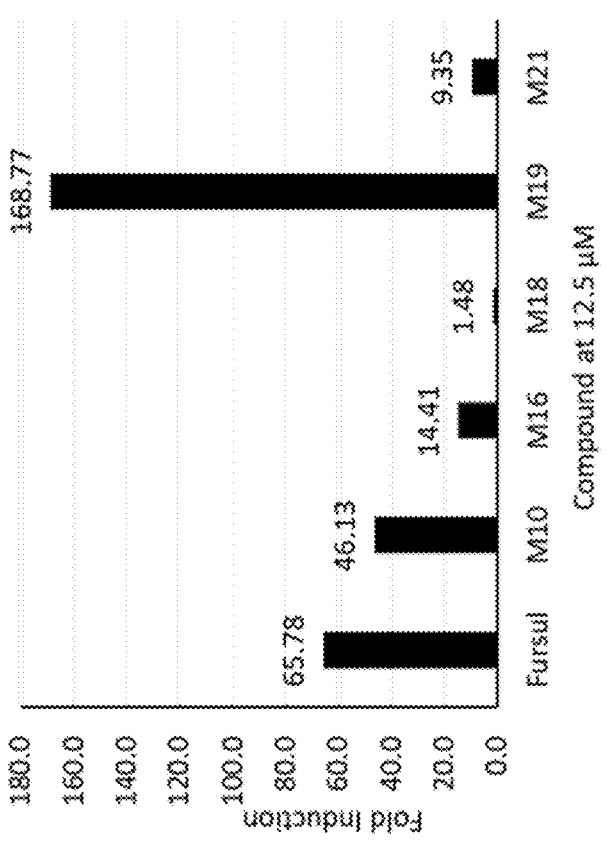
FIG. 9 shows induction of luciferase target gene expression in response to fursultiamine or benfotiamine compared to additional thiamine analogs of Formulas IV, V, and VI. The luciferase target gene contained a sequence encoding a riboswitch comprising the 15D10 aptamer. Group IV compounds were tested for their ability to induce luciferase expression in HEK 293 (FIG. 9A) and AML 12 (FIG. 9B) cells. Group V and Group VI compounds were tested for their ability to induce luciferase expression in HEK 293 (FIG. 9C) and AML 12 (FIG. 9D) cells. The most potent compounds were further tested for their ability to induce luciferase expression in ARPE-19 (FIG. 9E) and Hep G2 (FIG. 9F) cells.
Figure 9A:
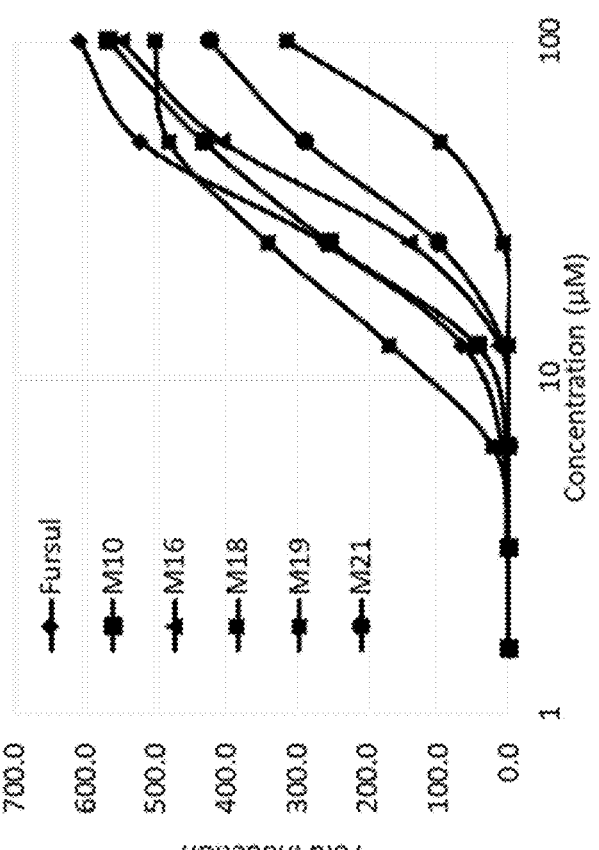
Figure 9B:
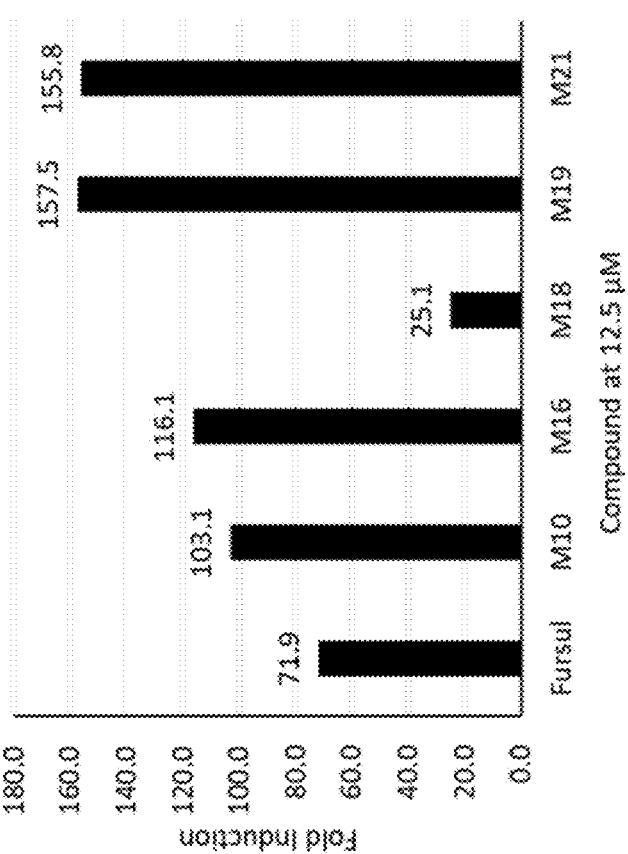
Figure 9B:
Figure 9B:
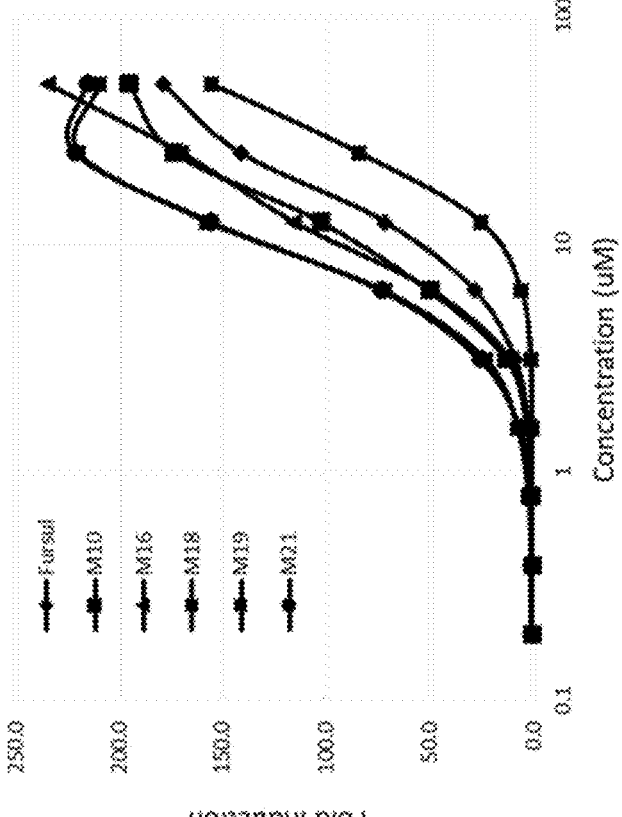

Compounds of Formula IV were first tested in HEK 293 cells. As shown in FIG. 9A, luciferase gene expression was increased upon treatment with compound M10, M16, M18, M19 or M21, in a dose-dependent manner in HEK 293 cells. In comparison with the activity of fursultiamine, M19 is more potent in inducing luciferase expression, generating 168.7-fold increase in luciferase expression at 12.5 $\mu M$ concentration in HEK 293 cells. Further, these new compounds were tested in mouse liver cell line AML 12 cells. As shown in FIG. 9B, consistent with the observation from HEK 293 cells, all the compounds increased the luciferase expression from construct harboring 15D10 riboswitch in a dose dependent manner. In comparison with the activity of fursultiamine on the riboswitch 15D10, compounds M10, M16, M19 and M21 are more potent than fursultiamine. M19 and M21 are equally potent in inducing riboswitch 15D10 regulated luciferase expression in this type of cell.

Figure 9C:
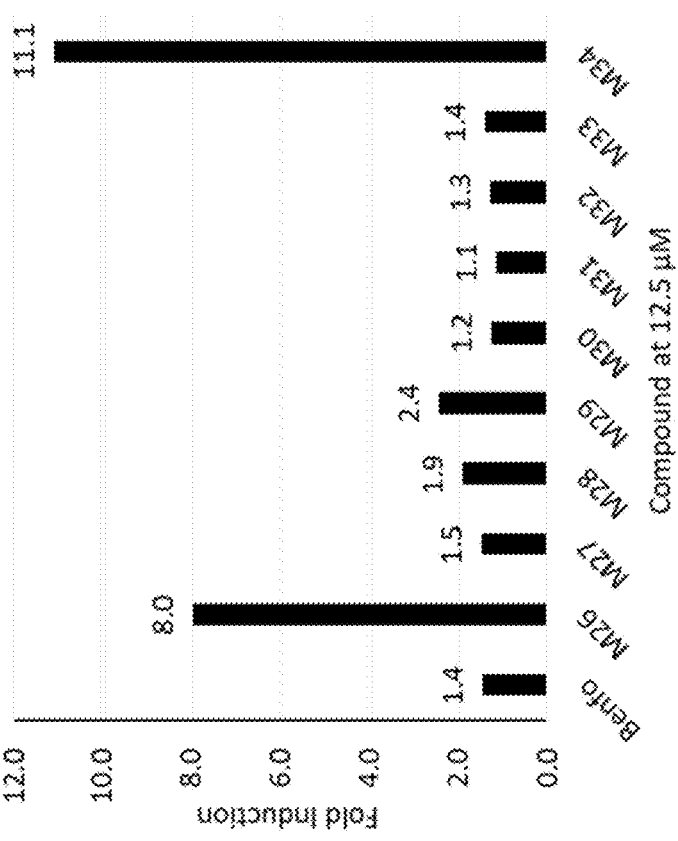
Figure 9C:
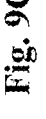
Figure 9C:
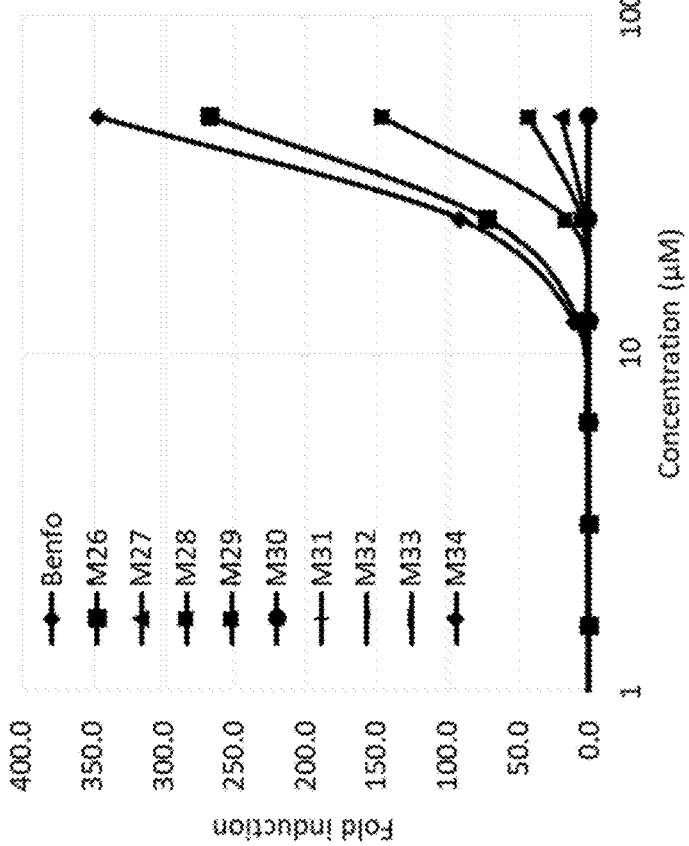
Figure 9D:
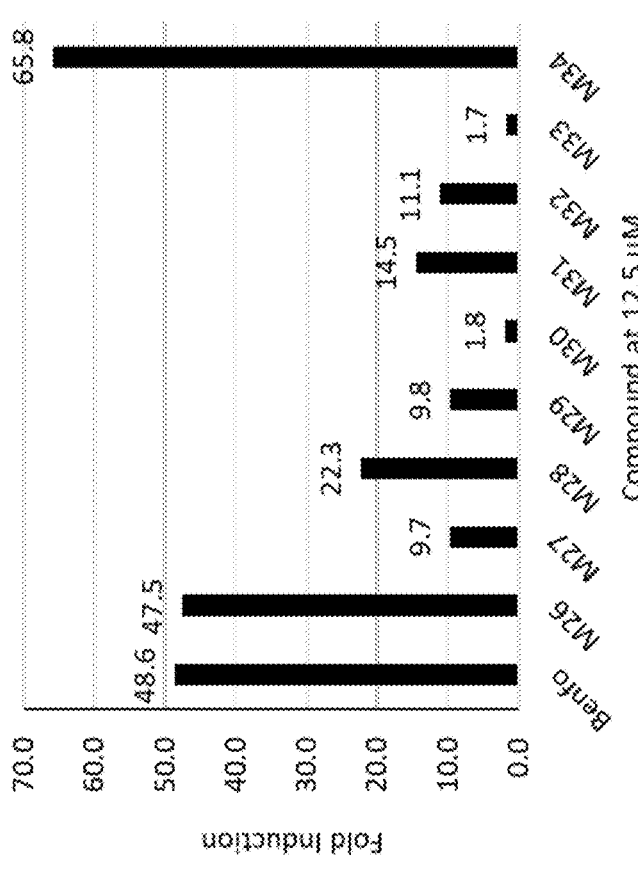
Figure 9D:
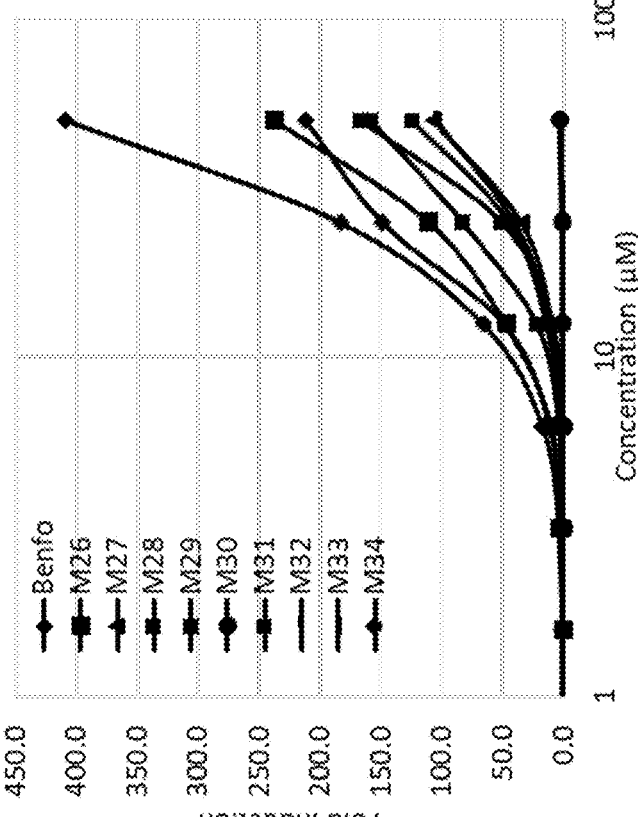

Compounds of Formulas V and VI together with benfotiamine as control compound were tested in both HEK 293 and AML 12 cells. As shown in FIG. 9C, compound M30, M31 M32 and M33, as well as benfotiamine had no effect on luciferase expression, while M26, M27, M28, M29 and M34 increased luciferase expression from the Luci-15D10 construct, with M34 being the most potent compound in HEK 293 cells. In contrast, in AML 12 cells, all the compounds except M30 and M33, increased luciferase expression from Luci-15D10 construct. Consistently within these two cell types, M34 is the most potent inducer among these two groups of compounds in turning on the riboswitch (FIG. 9D).

Figure 9E:
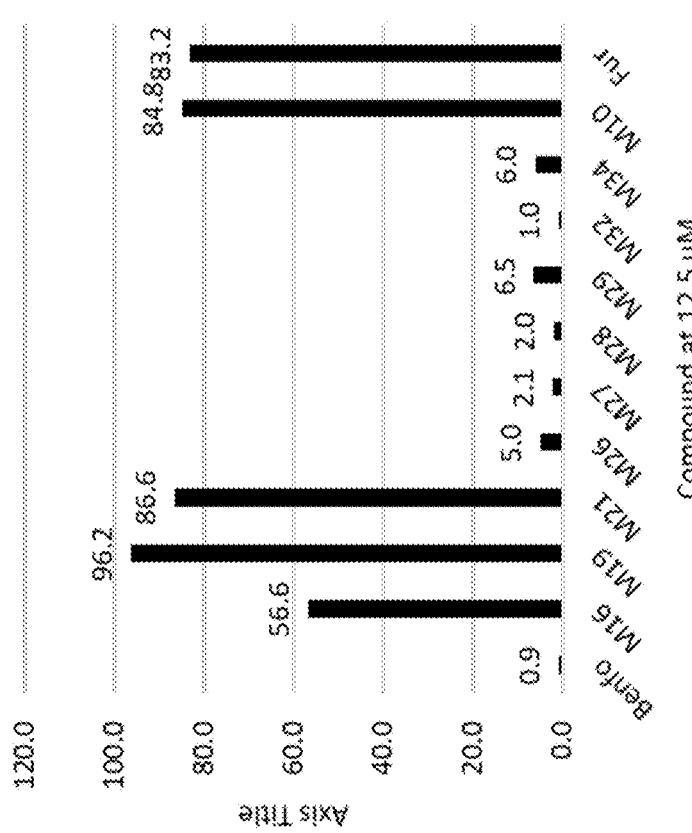
Figure 9E:
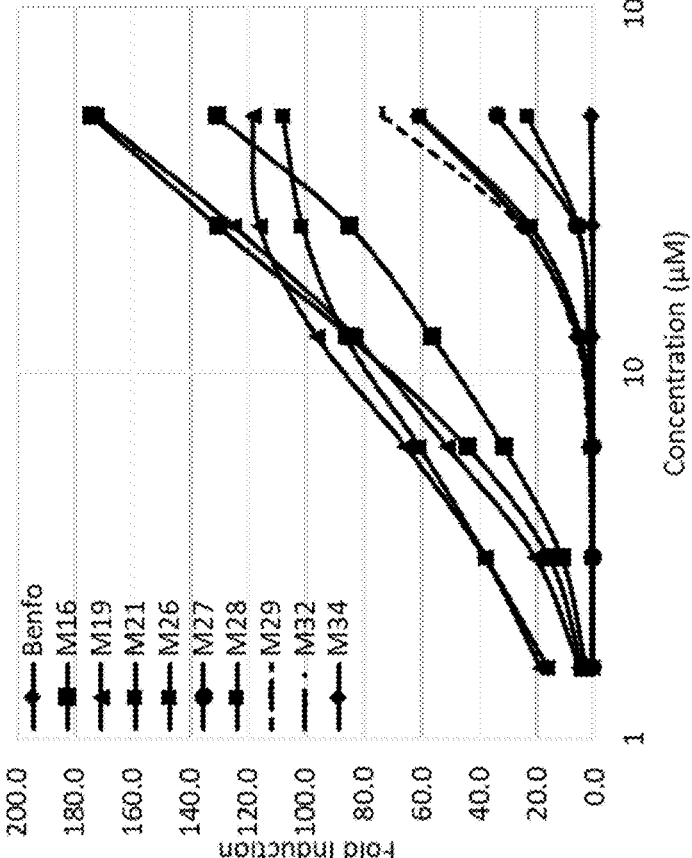
Figure 9F:
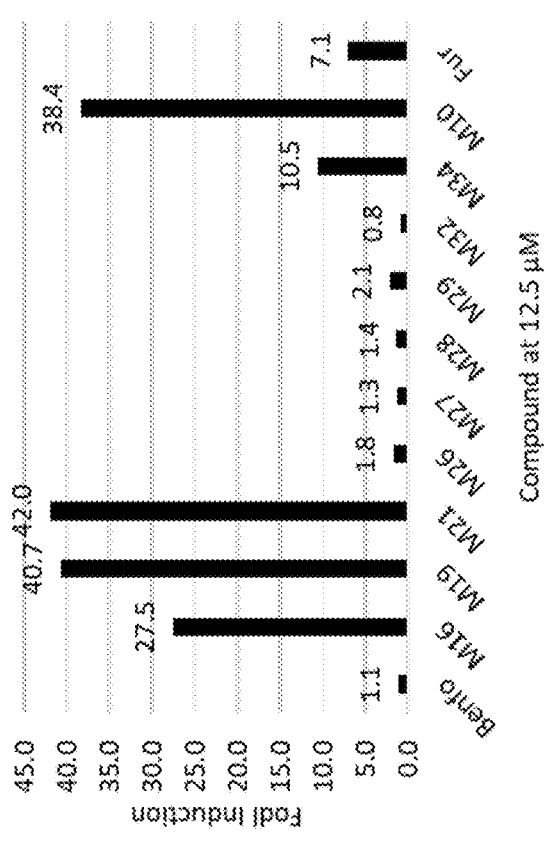
Figure 9F:
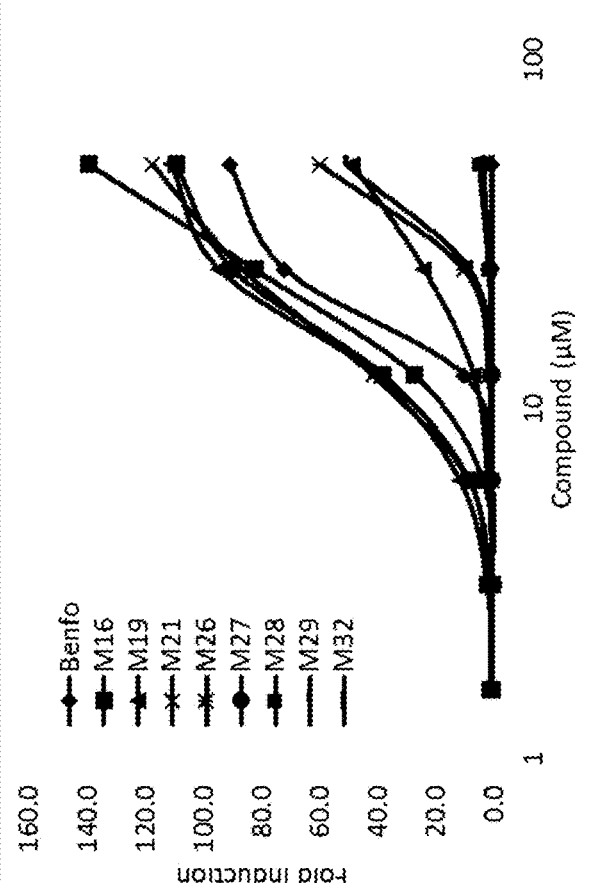

The relatively more potent compounds were further tested for their activity in regulating riboswitch in additional human cell lines. As shown in FIG. 9E in human ARPE-19 cells, both benfotiamine and M32 showed no activity in increasing riboswitch 15D10-regulated luciferase expression, whereas M10, M19 and M21 have equivalent potency to fursultaimine in increasing luciferase expression from Luci-15D10 construct. Similarly, benfotiamine and M32 have no activity in Hep G2 cells, while M19, M21 and M10 have similar potency at 12.5 $\mu M$ concentration (FIG. 9F).

Compounds M34 to M123 and compounds M126 to M160, with fursultiamine as a control compound, were tested in both HEK 293 and AML 12 cells for their activity in regulating thiamine analog riboswitches using a luciferase construct harboring 15D10 riboswitch (Luci-15D10, SEQ ID NO:93). Increases for the luciferase expression from the Luci-15D10 construct in response to these compounds are shown in Tables 2 and 3.

TABLE 2

Fold increase in riboswitch 15D10-regulated luciferase expression for compounds M34 to M123 at 50 μM (calculated as the ratio of the luciferase signal from cells treated with the identified compound divided by luciferase signal from untreated cells).

| # | HEK | AML |
|---|-----|-----|
| M19 | 676.3 | 329.5 |
| M21 | 618.3 | 228.6 |
| M34 | 163.5 | 290.6 |
| M37 | 76.2 | 134.3 |
| M38 | 1.2 | 1.0 |
| M39 | 102.7 | 127.2 |
| M40 | 83.1 | 206.0 |
| M43 | 10.2 | 95.3 |
| M44 | 176.8 | 314.1 |
| M45 | 1.3 | 2.9 |
| M46 | 1.3 | 6.0 |
| M47 | 25.3 | 85.1 |
| M49 | 414.0 | 202.3 |
| M50 | 93.5 | 141.8 |
| M51 | 392.5 | 188.6 |
| M52 | 363.9 | 195.1 |
| M53 | 2.4 | 57.0 |
| M54 | 3.0 | 13.9 |
| M55 | 2.1 | 9.0 |
| M57 | 1.2 | 24.4 |
| M58 | 1.1 | 1.5 |
| M59 | 1.1 | 1.0 |
| M62 | 49.0 | 109.9 |
| M63 | 1.7 | 19.0 |
| M64 | 2.0 | 3.9 |
| M65 | 3.2 | 67.1 |
| M66 | 1.1 | 0.4 |
| M67 | 2.1 | 0.9 |
| M68 | 303.0 | 209.0 |
| M70 | 51.0 | 235.9 |
| M72 | 235.9 | 295.1 |
| M73 | 205.1 | 200.3 |
| M76 | 60.7 | 134.3 |
| M79 | 352.8 | 358.2 |
| M82 | 89.2 | 73.9 |
| M88 | 215.7 | 355.2 |
| M91 | 13.1 | 150.3 |
| M92 | 0.9 | 23.7 |
| M97 | 298.9 | 126.2 |
| M98 | 13.6 | 57.7 |
| M99 | 0.2 | 0.4 |
| M100 | 1.1 | 0.4 |
| M101 | 88.6 | 128.0 |
| M103 | 0.9 | 0.5 |
| M105 | 0.2 | 0.2 |
| M106 | 1.2 | 294.4 |
| M107 | 26.0 | 40.2 |
| M108 | 75.8 | 129.2 |
| M109 | 22.6 | 87.3 |
| M110 | 65.7 | 145.6 |
| M111 | 180.7 | 174.7 |
| M113 | 212.9 | 272.5 |
| M114 | 50.1 | 88.8 |
| M115 | 19.9 | 52.1 |
| M116 | 1.3 | 0.8 |
| M117 | 0.8 | 3.4 |
| M118 | 9.3 | 140.3 |
| M119 | 0.9 | 0.7 |

TABLE 2-continued

Fold increase in riboswitch 15D10-regulated luciferase expression for compounds M34 to M123 at 50 μM (calculated as the ratio of the luciferase signal from cells treated with the identified compound divided by luciferase signal from untreated cells).

| # | HEK | AML |
|---|-----|-----|
| M120 | 0.5 | 30.5 |
| M121 | 0.9 | 0.5 |
| M122 | 1.3 | 0.5 |
| M123 | 0.4 | 0.6 |
| Ctrl. | 446.2 | 314.6 |

\# = Compound number.
HEK = HEK 293 cells.
AML = AML12 cells.
Ctrl. = fursultiamine.

TABLE 3

Fold increase in riboswitch 15D10-regulated luciferase expression for compounds M126 to M160 at 50 μM (calculated as the ratio of the luciferase signal from cells treated with the identified compound divided by luciferase signal from untreated cells.

| # | HEK | AML |
|---|-----|-----|
| M113 | 265.00 | 348.35 |
| M126 | 147.00 | 305.39 |
| M127 | 0.46 | 7.39 |
| M128 | 0.56 | 7.87 |
| M129 | 10.91 | 167.48 |
| M130 | 110.40 | 328.65 |
| M131 | 740.64 | 508.85 |
| M133 | 99.97 | 273.22 |
| M134 | 556.94 | 407.79 |
| M135 | 87.55 | 44.49 |
| M136 | 132.20 | 262.53 |
| M137 | 139.56 | 287.66 |
| M138 | 227.96 | 195.26 |
| M139 | 37.02 | 188.39 |
| M140 | 174.69 | 192.16 |
| M141 | 1.61 | 3.46 |
| M142 | 85.27 | 183.85 |
| M143 | 138.05 | 299.80 |
| M145 | 156.06 | 60.62 |
| M146 | 53.27 | 96.56 |
| M147 | 193.36 | 266.56 |
| M148 | 152.89 | 288.05 |
| M149 | 175.93 | 382.94 |
| M150 | 12.27 | 11.96 |
| M151 | 20.51 | 231.00 |
| M152 | 68.89 | 36.62 |
| M153 | 441.91 | 534.59 |
| M155 | 7.71 | 117.46 |
| M156 | 0.06 | 10.13 |
| M157 | 117.52 | 315.57 |
| M158 | 96.94 | 235.31 |
| M159 | 85.50 | 205.55 |
| M160 | 79.51 | 131.03 |

\# = Compound number.
HEK = HEK 293 cells.
AML = AML12 cells.

We claim:

1. A polynucleotide cassette for regulating the expression of a target gene, wherein the polynucleotide cassette comprises a sequence encoding an aptamer that binds to a small molecule, wherein the aptamer encoding sequence comprises ACX$_1$GGGGTCCGGCX$_2$TX$_3$TTCATTTGGCX$_4$CCGGTGAGAX$_5$X$_6$AX$_7$ACCCTTX$_8$X$_9$X$_{10}$X$_{11}$CCTGTTX$_{12}$ACGGATAATGCCGCX$_{13}$GCAGGGAGT (SEQ ID NO:1), and wherein:

X$_1$ is A or G;

X$_2$ is C or no nucleotide;

X$_3$ is T or no nucleotide;

X$_4$ is A or G;

X$_5$ is any nucleotide;

X$_6$ is any nucleotide;

X$_7$ is any nucleotide;

X$_8$ is any nucleotide;

X$_9$ is C, G, or T;

X$_{10}$ is any nucleotide;

X$_{11}$ is A or T;

X$_{12}$ is C or T; and

X$_{13}$ is C or T.

2. The polynucleotide cassette of claim 1, wherein the aptamer encoding sequence comprises ACX$_1$GGGGTCCGGCX$_2$TX$_3$TTCATTTGGCGCCGGTGAGAX$_5$X$_6$AX$_7$ACCCTTX$_8$X$_9$ X$_{10}$X$_{11}$CCTGTTX$_{12}$ACGGATAATGCCGCX$_{13}$GCAGGGAGT (SEQ ID NO:2) and wherein:

X$_1$ is A or G;

X$_2$ is C or no nucleotide;

X$_3$ is T or no nucleotide;

X$_5$ is G or T;

X$_6$ is C or T;

X$_7$ is C or T;

X$_8$ is any nucleotide;

X$_9$ is G or T;

X$_{10}$ is A, G, or T;

X$_{11}$ is A or T;

X$_{12}$ is C or T; and

X$_{13}$ is C or T.

3. The polynucleotide cassette of claim 1, wherein the aptamer encoding sequence comprises ACAGGGGTCCGGCCTTTTCATTTGGCGCCGGTGAGAGCACACCCTTTGAACCT GTTX$_{12}$ACGGATAATGCCGCX$_{13}$GCAGGGAGT (SEQ ID NO:3) and wherein:

X$_{12}$ is C or T; and

X$_{13}$ is C or T.

4. The polynucleotide cassette of claim 1, wherein the aptamer encoding sequence comprises ACX$_1$GGGGTCCGGCCTTTTCATTTGGCGCCGGTGAGAGCACACCCTTX$_8$X$_9$ X$_{10}$X$_{11}$CCTGTTTACGGATAATGCCGCCGCAGGGAGT (SEQ ID NO:4) and wherein X$_1$ is A or G;

X$_8$ is any nucleotide;

X$_9$ is G or T;

X$_{10}$ is A, G, or T; and

X$_{11}$ is A or T.

5. The polynucleotide cassette of claim 1, wherein the aptamer encoding sequence comprises ACAGGGGTCCG-GCCTTTTCATTTGGCGCCGGTGAGAX$_5$X$_6$AX$_7$ACC-CTTTGAAC CTGTTTACGGATAATGCCGCCGCAGG-GAGT (SEQ ID NO:5) and wherein:

X$_5$ is G or T;

X$_6$ is C or T; and

X$_7$ is C or T.

6. The polynucleotide cassette of claim 1, wherein the aptamer encoding sequence comprises ACAGGGGTCCGGCCTTTTCATTTGGCX$_4$CCGGTGA-GAX$_5$X$_6$AX$_7$ACCCTTX$_8$ X$_9$X$_{10}$ACCTGTTCACGGATA-ATGCCGCTGCAGGGAGT (SEQ ID NO:6) and wherein:

X$_4$ is A or G;

X$_5$ is any nucleotide;

X$_6$ is any nucleotide;

X$_7$ is any nucleotide;

X$_8$ is any nucleotide;

X$_9$ is C or G; and

X$_{10}$ is any nucleotide.

7. The polynucleotide cassette of claim 1, wherein the aptamer encoding sequence comprises a sequence that is at least 95% identical to a sequence selected from the group consisting of SEQ ID NOs:7-36.

8. The polynucleotide cassette of claim 7, wherein the aptamer encoding sequence is selected from the group consisting of SEQ ID NOs:7-36.

9. The polynucleotide cassette of claim 8, wherein the aptamer encoding sequence is selected from the group consisting of SEQ ID NOs:8, 9, 14-18, 21, 25, 26, and 30.

10. The polynucleotide cassette of claim 9, wherein the aptamer encoding sequence comprises a sequence selected from the group consisting of SEQ ID NOs: 9, 14, and 26.

11. A nucleic acid sequence encoding an aptamer that binds to a small molecule, wherein the aptamer encoding sequence comprises ACX$_1$GGGGTCCGGCX$_2$TX$_3$TTC-ATTTGGCX$_4$CCGGTGAGAX$_5$X$_6$AX$_7$ACCCTTX$_8$X$_9$ X$_{10}$X$_{11}$CCTGTTX$_{12}$ACGGATAATGCCGCX$_{13}$GCAGG-GAGT (SEQ ID NO:1) and wherein:

X$_1$ is A or G;

X$_2$ is C or no nucleotide;

X$_3$ is T or no nucleotide;

X$_4$ is A or G;

X$_5$ is any nucleotide;

X$_6$ is any nucleotide;

X$_7$ is any nucleotide;

X$_8$ is any nucleotide;

X$_9$ is C, G, or T;

X$_{10}$ is any nucleotide;

X$_{11}$ is A or T;

X$_{12}$ is C or T; and

X$_{13}$ is C or T, wherein the aptamer encoding sequence has one or more of the following properties: X$_1$ is not A; X$_2$ is not C; X$_3$ is not T; X$_4$ is not G; X$_5$ is not G; X$_6$ is not C; X$_7$ is not C; X$_8$ is not T; X$_9$ is not G; X$_{10}$ is not A; X$_{11}$ is not A; X$_{12}$ is not T; and X$_{13}$ is not C.

12. The nucleic acid sequence of claim 11, wherein all of the following are not simultaneously present in the aptamer encoding sequence: X$_1$ is A; X$_2$ is C; X$_3$ is T; X$_4$ is G; X$_5$ is G; X$_6$ is C; X$_7$ is C; X$_8$ is T; X$_9$ is G; X$_{10}$ is A; X$_{11}$ is A; X$_{12}$ is T; and X$_{13}$ is C.

13. The nucleic acid sequence of claim 11, wherein the aptamer encoding sequence comprises ACX$_1$GGGGTCCGGCX$_2$TX$_3$TTCATTTGGCGCCGGT- GAGAX$_5$X$_6$AX$_7$ACCCTTX$_8$X$_9$ X$_{10}$X$_{11}$CCTGTTX$_{12}$ ACGGATAATGCCGCX$_{13}$GCAGGGAGT (SEQ ID NO:2) and wherein:

X$_1$ is A or G;

X$_2$ is C or no nucleotide;

X$_3$ is T or no nucleotide;

X$_5$ is G or T;

X$_6$ is C or T;

X$_7$ is C or T;

X$_8$ is any nucleotide;

X$_9$ is G or T;

X$_{10}$ is A, G, or T;

X$_{11}$ is A or T;

X$_{12}$ is C or T; and

X$_{13}$ is C or T.

14. The nucleic acid sequence of claim 13, wherein the aptamer encoding sequence has one or more of the following properties: X$_1$ is not A; X$_2$ is not C;

X$_3$ is not T; X$_5$ is not G; X$_6$ is not C; X$_7$ is not C; X$_8$ is not T; X$_9$ is not G; X$_{10}$ is not A;

X$_{11}$ is not A; X$_{12}$ is not T; and X$_{13}$ is not C.

15. The nucleic acid sequence of claim 13, wherein all of the following are not simultaneously present in the aptamer encoding sequence: X$_1$ is A; X$_2$ is C; X$_3$ is T; X$_5$ is G; X$_6$ is C; X$_7$ is C; X$_8$ is T; X$_9$ is G; X$_{10}$ is A; X$_{11}$ is A; X$_{12}$ is T; and X$_{13}$ is C.

16. The nucleic acid sequence of claim 11, wherein the aptamer encoding sequence comprises ACAGGGGTCCGGCCTTTTCATTTGGCGCCGGT-GAGAGCACACCCTTTGAACCT GTTX$_{12}$ACGG-ATAATGCCGCX$_{13}$GCAGGGAGT (SEQ ID NO:3) and wherein:

X$_{12}$ is C or T; and

X$_{13}$ is C or T.

17. The nucleic acid sequence of claim 16, wherein the aptamer encoding sequence has one or more of the following properties: X$_{12}$ is not T; and X$_{13}$ is not C.

18. The nucleic acid sequence of claim 16, wherein all of the following are not simultaneously present in the aptamer encoding sequence: X$_{12}$ is T and X$_{13}$ is C.

19. The nucleic acid sequence of claim 11, wherein the aptamer encoding sequence comprises ACX$_1$GGGGTCCGGCCTTTTCATTTGGCGCCGGTGA-GAGCACACCCTTX$_8$X$_9$ X$_{10}$X$_{11}$CCTGTTTACGGATAA-TGCCGCCGCAGGGAGT (SEQ ID NO:4) and wherein:

X$_1$ is A or G;

X$_8$ is any nucleotide;

X$_9$ is G or T;

X$_{10}$ is A, G, or T; and

X$_{11}$ is A or T.

20. The nucleic acid sequence of claim 19, wherein the aptamer encoding sequence has one or more of the following properties: X$_1$ is not A; X$_8$ is not T; X$_9$ is not G; X$_{10}$ is not A; X$_{11}$ is not A.

21. The nucleic acid sequence of claim 19, wherein all of the following are not simultaneously present in the aptamer encoding sequence: X$_1$ is A; X$_8$ is T; X$_9$ is G; X$_{10}$ is A; and X$_{11}$ is A.

22. The nucleic acid sequence of claim 11, wherein the aptamer encoding sequence comprises ACAGGGGTCCGGCCTTTTCATTTGGCGCCGGTGA-GAX$_5$X$_6$AX$_7$ACCCTTTGAACCTGTTTACGGATAATG-CCGCCGCAGGGAGT (SEQ ID NO:5) and wherein:

X$_5$ is G or T;

X$_6$ is C or T; and

X$_7$ is C or T.

23. The nucleic acid sequence of claim 22, wherein the aptamer encoding sequence has one or more of the following properties: $X_5$ is not G; $X_6$ is not C; and $X_7$ is not C.

24. The nucleic acid sequence of claim 22, wherein all of the following are not simultaneously present in the aptamer encoding sequence: $X_5$ is G; $X_6$ is C; and $X_7$ is C.

25. The nucleic acid sequence of claim 11, wherein the aptamer encoding sequence comprises ACAGGGGTCCGGCCTTTTCATTTGGCX$_4$CCGGTG-AGAX$_5$X$_6$AX$_7$ACCCTTX$_8$ X$_9$X$_{10}$ACCTGTTCACGGAT-AATGCCGCTGCAGGGAGT (SEQ ID NO:6) and wherein:

$X_4$ is A or G;

$X_5$ is any nucleotide;

$X_6$ is any nucleotide;

$X_7$ is any nucleotide;

$X_8$ is any nucleotide;

$X_9$ is C or G; and $X_{10}$ is any nucleotide.

26. The nucleic acid sequence of claim 11, wherein the aptamer encoding sequence comprises a sequence that is at least 95% identical to a sequence selected from the group consisting of SEQ ID NOs:7-36.

27. The nucleic acid sequence of claim 26, wherein the aptamer encoding sequence is selected from the group consisting of SEQ ID NOs:7-36.

28. The nucleic acid sequence of claim 27, wherein the aptamer encoding sequence is selected from the group consisting of SEQ ID NOs:8, 9, 14-18, 21, 25, 26, and 30.

29. The nucleic acid sequence of claim 28, wherein the aptamer encoding sequence comprises a sequence selected from the group consisting of SEQ ID NOs: 9, 14, and 26.

30. The polynucleotide cassette of claim 1, wherein the aptamer is in the context of a riboswitch encoded as part of a polynucleotide cassette for regulating the expression of a target gene.

31. A riboswitch for the regulation of target gene expression in response to a small molecule, wherein the riboswitch comprises the aptamer of claim 1.

32. The riboswitch of claim 31, wherein the riboswitch comprises the sequence of SEQ ID NO:37.

33. A polynucleotide cassette for the regulation of the expression of a target gene in response to a small molecule, the polynucleotide cassette comprising:

(a) a riboswitch; and (b) an alternatively-spliced exon, flanked by a 5' intron and a 3' intron, wherein the riboswitch comprises (i) an effector region comprising a stem that includes the 5' splice site sequence of the 3' intron, and (ii) the aptamer of claim 1; and wherein the alternatively-spliced exon comprises a stop codon that is in-frame with the target gene when the alternatively-spliced exon is spliced into the target gene mRNA.

34. The polynucleotide cassette of claim 33, wherein the riboswitch comprises the sequence of SEQ ID NO:37.

35. A vector comprising the polynucleotide cassette of claim 1.

36. The vector of claim 35, wherein the vector is a viral vector.

37. The vector of claim 36, wherein the viral vector is selected from the group consisting of an adenoviral vector, an adeno-associated virus vector, and a lentiviral vector.

* * * * *